US011535856B2

(12) United States Patent
Medina-Bolivar et al.

(10) Patent No.: US 11,535,856 B2
(45) Date of Patent: Dec. 27, 2022

(54) STILBENOID PRENYLTRANSFERASES FROM PLANTS

(71) Applicant: Arkansas State University—Jonesboro, State University, AR (US)

(72) Inventors: Luis Fabricio Medina-Bolivar, Memphis, TN (US); Tianhong Yang, Jonesboro, AR (US); Keithanne Mockaitis, Indianapolis, IN (US)

(73) Assignees: ARKANSAS STATE UNIVERSITY—JONESBORO, Jonesboro, AR (US); INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 16/921,540

(22) Filed: Jul. 6, 2020

(65) Prior Publication Data
US 2020/0332308 A1  Oct. 22, 2020

Related U.S. Application Data

(63) Continuation of application No. 15/625,450, filed on Jun. 16, 2017, now Pat. No. 10,704,052.

(60) Provisional application No. 62/351,117, filed on Jun. 16, 2016.

(51) Int. Cl.
*C12N 15/82* (2006.01)
*C12N 15/81* (2006.01)

(52) U.S. Cl.
CPC ......... *C12N 15/8243* (2013.01); *C12N 15/81* (2013.01)

(58) Field of Classification Search
None
See application file for complete search history.

(56) References Cited

U.S. PATENT DOCUMENTS 9,765,308 B2 * 9/2017 Page .................... C12P 7/42

OTHER PUBLICATIONS

Deng et al. Transgenic peanut plants obtained by particle bombardment via somatic embryogenesis regeneration system. Cell Res. Jun. 2001;11(2):156-60. (Year: 2001).*
Yang et al. Stilbenoid prenyltransferases define key steps in the diversification of peanut phytoalexins. J. Biol. Chem. Jan. 5, 2018; 293(1):28-46. Epub Nov. 20, 2017. (Year: 2018).*
Li. Bringing Bioactive Compounds into Membranes: The UbiA Superfamily of Intramembrane Aromatic Prenyltransferases. Trends Biochem Sci. Apr. 2016;41(4):356-370. Epub Feb. 24, 2016. (Year: 2016).*

* cited by examiner

*Primary Examiner* — Cynthia E Collins
(74) *Attorney, Agent, or Firm* — Schrantz Law Firm, PLLC; Stephen D. Schrantz

(57) ABSTRACT

The process and system led to the identification of prenyltransferase genes from elicitor-treated peanut hairy roots. One of the prenyltransferases, AhR4DT-1 catalyzes a key reaction involved in the biosynthesis of prenylated stilbenoids, in which resveratrol is prenylated at its C-4 position to form arachidin-2, while another, AhR3'DT-1, was able to add the prenyl group to C-3' of resveratrol. Each of these prenyltransferases has a high specificity for stilbenoid substrates, and their subcellular location in the plastid was confirmed by fluorescence microscopy. Structure analysis of the prenylated stilbenoids suggest that these two prenyltransferase activities represent the first committed steps in the biosynthesis of a large number of prenylated stilbenoids and their derivatives in peanut.

20 Claims, 95 Drawing Sheets

Specification includes a Sequence Listing.

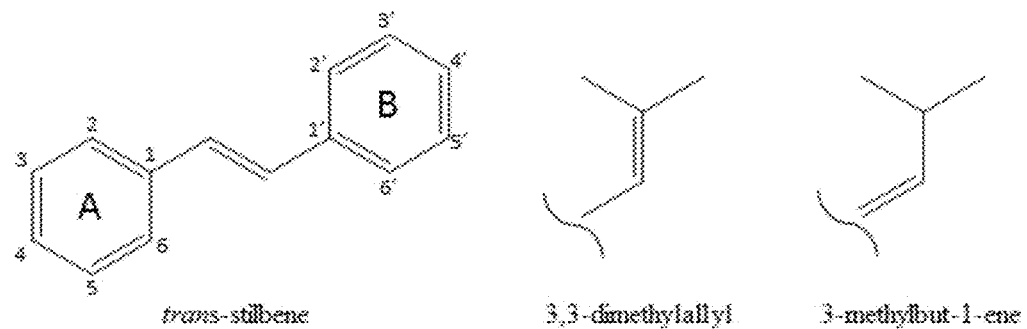
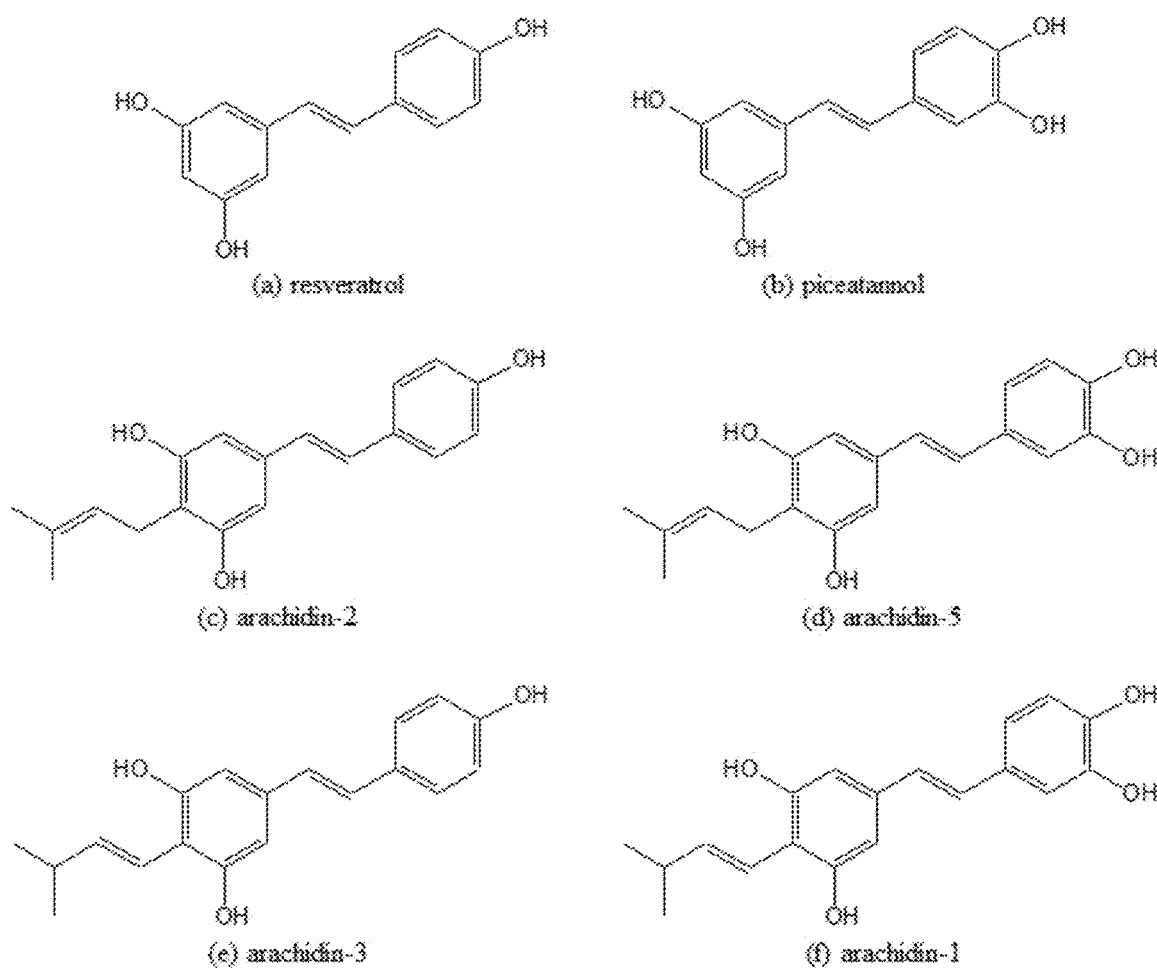
FIG. 1

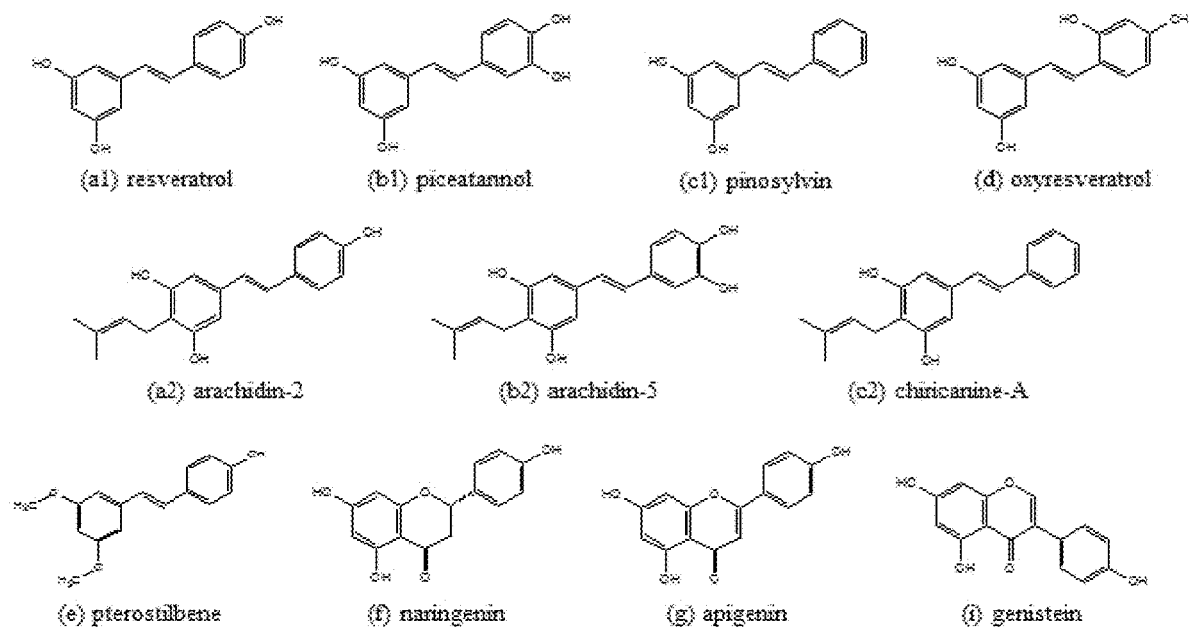
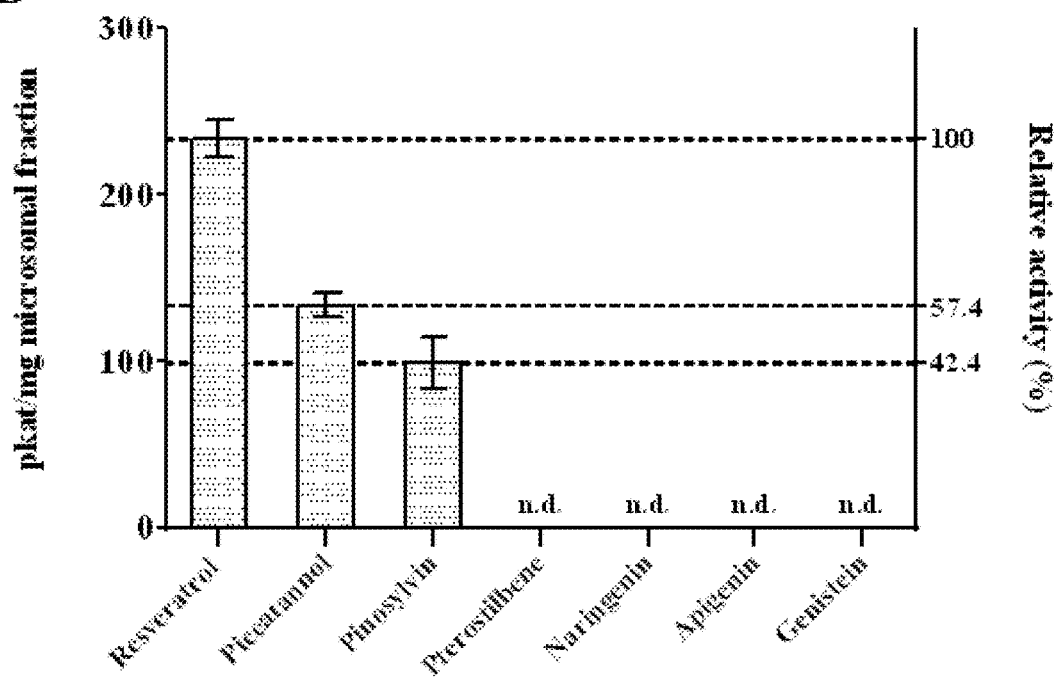
FIG. 6

| No | Analyte | Rt (min)[a] | UV (nm) | [M+H]$^+$ (m/z) | MS$^2$ ions | MS$^3$ ions |
|----|---------|-------------|---------|-----------------|-------------|-------------|
| 1 | Piceatannol | 5.41 | 240, 324 | 245 | 227, 199, 135[b] | 107 |
| 2 | Resveratrol | 6.08 | 237, 306, 317 | 229 | 211, 183 | 107 |
| 3 | Arachidin-5 | 10.29 | 240, 327 | 313 | 257 | 239, 229, 211 |
| 4 | Arachidin-5 derivative | 10.62 | 240, 355 | 311 | 283, 201, 135 | 241, 173, 135 |
| 5 | Arachidin-1 | 11.87 | 243, 341 | 313 | 257 | 239, 229, 211 |
| 6 | Arachidin-2 | 12.29 | 239, 311, 323 | 297 | 241 | 223, 213, 195 |
| 7 | Arachidin-2 derivative | 13.38 | 238, 350 | 295 | 267, 253, 201 | 239, 225, 172 |
| 8 | Arachidin-3 | 15.11 | 243, 335 | 297 | 241 | 223, 213, 195 | a, Rt: HPLC retention time
b, MS$^2$ ions in bold were the most abundant ions and were subjected to MS$^3$ fragmentation

FIG. 7

Table 2. Resveratrol prenyltransferase activity from peanut hairy root protein fractions. Preparation of fractions and resveratrol prenyltransferase assay are described in Materials and Methods. Values are the mean ± standard deviation for two replicates.

| Enzyme Solution | Total Activity | Total Protein | Specific Activity |
|---|---|---|---|
| | $pkat \cdot g \text{ of root tissue}^{-1}$ | $mg \cdot g \text{ of root tissue}^{-1}$ | $pkat \cdot mg \text{ of protein}^{-1}$ |
| Crude cell-free extracts | 147.95 ± 16.71 | 3.27 ± 0.06 | 45.27 ± 4.35 |
| 156,000 g supernatant | 23.48 ± 4.65 | 3.00 ± 0.22 | 7.80 ± 0.97 |
| Microsomal fraction | 50.38 ± 6.66 | 0.12 ± 0.01 | 421.16 ± 16.25 |

FIG. 8

Stilbenoid Prenyltransferase Genes and Protein Sequences:

>AhR4DT-9b13 (renamed as AhR4DT-1; GenBank accession No. KY565244)　SEQ ID NO:3

ATGGCTTTTGGGCATTTGGTGTTAATTCCCAGATCAACTTCTTCCATTGCCACTACTG
CTGCAAGCTGCTGGAAGAGTAAAAAATTCGCCGACAATTACTATGCAAATTCTTATG
GAAGAAGAGCTTTATGGCAGAGTGATAGGAATCTCACAAAAGATCACAGCATCAAG
ACATCTTTGCAGCACAACATTTCAAAGCTTCATTACAATCCCATTGAAAGAGGATCT
AGATGCAATAAAATTGAGAAACATACTTAACAAATGCATCATCTTCTGCACAATCA
CATGAATCTGAACCAGAAGTGCATGAATCACCAAAAGCTTTAGAGTCTATTAAAAAG
GGACTCGTTATGTTTCTCCAATTTTGCAGACTTTATGCATTCCTTGGCATGATACCAG
CAGGACTTTCTTCATCACTTCTTGCCGTAGATAATTTTCAGAAATATCTCCATTATTA
TTTTTAAAAGGAGTCTTGCAGTATATAGTAACTTTCTTCTTCACGTCTCAATTTGTTAT
GGGAGTGAATCAATTATCCGATGTGGAAATAGACAAGATTAATAAGCCAGATCTTCC
TTTGGCATCCGGAGAATATTCCTTCACTTCTGGAGTTATACTTGTGACATCGTTTTTA
CTTGCGGGTTTTGGAGTTGCATGGATGTTAGGATCACAACCATTAATTTGGAGTGTTG
TTGTTACTGCTGCGCTAATGGGAGCATATTCAGTTAATTTCCCTTTATTAAGATGGAA
GAGATCTATAATCCTCACATCACTATCTAATGCAATTGCTATGTTGGCATCATTTCAT
ATAGGACCTTTTCTTCACATGAAGACCTTTGTGCTAAAAAAGGCAGCTACCTTTCCAA
GATCTATGATTCTTGGTTGTGTGGTCATAGGTTTGTTCTACACAATAATAACATTAAC
AAAGGATTTAGGGGATGTTGAAGGAGACAAAGCAGCAGGTTTGAAAACTTTGCCAA
TACGCTTGGGTGTTAAGCCGGTATTTGGTTATGTGTATCACTTATTCAAATGGCTTA
TGGAATTGCTATTACAATGGGAGCATTATCTCCTGTTCTATGGAGCAAAATTGTTACG
GTTGTGGCACATGCCTTCATGGTTTTCTACGTGTGGAACCATGCTCTTAATTCAGTAG
ACTTATCAAGCAAAGATTCGTTACATTCCTTTCATTTGTTTATGTTTAAGCTTGTAACT
GTGGAAGGCATCCTTATACAATTTGTTCGTTGA

>AhR4DT-9b13 (renamed as AhR4DT-1)　SEQ ID NO:2

MAFGHLVLIPRSTSSIATTAASCWKSKKFADNYYANSYGRRALWQSDRNLTKDHSIKTS
LQHNISKLHYNPIERGSRCNKIEKTYLTNASSSAQSHESEPEVHESPKALESIKKGLVMFL
QFCRLYAFLGMIPAGLSSSLLAVDNFSEISPLLFLKGVLQYIVTFFFTSQFVMGVNQLSDV
EIDKINKPDLPLASGEYSFTSGVILVTSFLLAGFGVAWMLGSQPLIWSVVVTAALMGAYS
VNFPLLRWKRSIILTSLSNAIAMLASFHIGPFLHMKTFVLKKAATFPRSMILGCVVIGLFYT
IITLTKDLGDVEGDKAAGLKTLPIRLGVKPVFWLCVSLIQMAYGIAITMGALSPVLWSKI
VTVVAHAFMVFYVWNHALNSVDLSSKDSLHSFHLFMFKLVTVEGILIQFVR*

FIG. 12

>AhRPT-4e1 (Renamed as AhR3'DT-2; GenBank Accession No. KY565246)   SEQ ID NO:6

ATGCCTTTCGGACTCTCCGCCTCATTTCTCAAATCTCGCTCCTTCCACCACCACGGTA
CAAGAAGAGCCTTATGGAACAACAATGGGAAACTATCAAAAGAATATTGTATCAAG
ATGCAGCATAATTATTGGAAGAATCATTGCACCAACCTTAAAGGAGGATCTATGATG
AGTGATGATAAATTTGAGAAAAATACTTGGTGAATGCAACCTCAAAAAATTCACAT
GATGAACCAAAAAAATCACAACCTATTTTGGAGTTTATCAAAGATGGCATGGATACT
TTTCGCCAGTTTTCCAGATTATACGCATTCTTTAGCTTCATATCAAGTGGACTTTCTTC
ATCACTCCTTGCGGTGGACAATTTATCAAATATATCTCCAAAAATGTTCTTAATAGGC
TTCTTGCAGTTTCTGATACCTAACTGCATCATGTTTCAATATATTGTTGGTGTGAATC
AATTAGCCGATATTGAAATAGACAAGATTAACAAACCATATCTTCCATTGGCATCCG
GGAAATATTCCTTAAGAAATGCAATAATAATTGTCGCATCATCTCTTCTAATGGGCTT
TGGATCTGCGTGGGTGTTAGGATCAAGGCCAATGTTTTGGTGTTAGTCATCAGTACT
ATGCTCATGACTGCTTATTCAGTTAATTTGCCCTTGTTGAGATGGAAAAGATCCACAA
TCCTTGCAACATTATCTCTTGCAAGTTCTATGACAATTGGACAACATATTGCACCATT
TCTTCACATGAAGACTGTGCTCAAGAAGGCACTTAACTATCCGAGATCACTAGTTTTT
ACTGTTGTGGTCGTCAGCCTTTTCTATACAGTTATATCCTTGGCAAAGGATATACCTG
ACATTGAAGGAGATAAAGCAGCAGGTCACAAAACCTTGGCAATACATTTGGGTCCTA
GACGAGTATTTTGGTTTTGCATTTCGCTCCTTCAAATGACATATGGAATTGCTATTAT
AATGGGAGCATTATCTCCTATCCTATGGAGCAAAATTTTTACGGTTGTGACACATTTC
ATCATGTCCATAATCCTTTGGTATCGTGCAAATTCCGTAGATTTATCGAACAATGATT
CGTTACAATCCTTTTATATGGCTATCTTTGTGTTTCTTTCTGTGGAAAACTTCCTTGTA
CTTTTTGTTCGATGA

>AhRPT-4e1 (Renamed as AhR3'DT-2)   SEQ ID NO:5

MPFGLSASFLKSRSFHHHGTRRALWNNNGKLSKEYCIKMQHNYWKNHCTNLKGGSMM
SDDKFEKKYLVNATSKNSHDEPKKSQPILEFIKDGMDTFRQFSRLYAFFSFISSGLSSSLLA
VDNLSNISPKMFLIGFLQFLIPNCIMFQYIVGVNQLADIEIDKINKPYLPLASGKYSLRNAIII
VASSLLMGFGSAWVLGSRPMFWCLVISTMLMTAYSVNLPLLRWKRSTILATLSLASSMT
IGQHIAPFLHMKTVLKKALNYPRSLVFTVVVSLFYTVISLAKDIPDIEGDKAAGHKTLAI
HLGPRRVFWFCISLLQMTYGIAIMGALSPILWSKIFTVVTHFIMSIILWYRANSVDLSNND
SLQSFYMAIFVFLSVENFLVLFVR*

FIG. 13

>AhRPT-4e10 (Renamed as AhR3'DT-3; GenBank Accession No. KY565247)    SEQ ID NO:9

ATGCCTTTCGGACTCTCCGCCTCATTTCTCAAATCTCGCTCCCTCCACCACCACGGGT
GGAAGTTTCTGAAAGAGCGAGAAATTCACAAACAACCACTACGCAATACAAGAAGA
GCCTTATGGAACAACAATGGGAAACTATCAAAGAATATTGTATCAAGATGCAGCAT
AATTATTGGAAGAATCATTGCACCAACCTTAAAGGAGGATCTATGATGAGTGATGAT
AAATTTGAGAAAAATACTTGGTGAATGCAACCTCAAAAAATTCACATGATGAACCA
AAAAAATCACAACCTATTTTGGAGTTTATCAAAGATGGCATGGATACTTTCGCCAG
TTTTCCAGATTATACGCATTCTTTAGCTTCATATCAAGTGGACTTTCTTCATCACTCCT
TGCGGTGGACAATTTATCAAATATATCTCCAAAAATGTTCTTAATAGGCTTCTTGCAG
TTTCTGATACCTAACTGCATCATGTTTCAATATATTGTTGGTGTGAATCAATTAGCCG
ATATTGAAATAGACAAGATTAACAAACCATATCTTCCATTGGCATCCGGGAAATATT
CCTTAAGAAATGCAATAATAATTGTCGCATCATCTCTTATAATGGGCTTTGGATCTGC
GTGGGTGTTAGGATCAAGGCCAATGTTTTGGTGTTTAGTCATCAGTACTATGCTCATG
ACTGCTTATTCAGTTAATTTGCCCTTGTTGAGATGGAAAAGATCCACAATCCTTGCAA
CATTATCTCTTGCAAGTTCTATGACAATTGGACAACATATTGCACCATTTCTTCACAT
GAAGACTGTGCTCAAGAAGGCACTTAACTATCCGAGATCACTAGTTTTACTGTTGT
GGTCGTCAGCCTTTTCTATACAGTTATATCCTTGGCAAAGGATATACCTGACATTGAA
GGAGATAAAGCAGCAGGTCACAAAACCTTGGCAATACATTTGGGTCCTAGACGAGT
ATTTTGGTTTTGCATTTCGCTCCTTCAAATGACATATGGAATTGCTATTATAATGGGA
GCATTATCTCCTATCCTATGGAGCAAAATTTTACGGTTGTGACACATTTCATCATGT
CCATAATCCTTTGGTATCGTGCAAATTCCGTAGATTTATCGAACAATGATTCGTTACA
ATCCTTTTATATGGCTATCTTTGTGTTCTTTCTGTGGAAAACTTCCTTGTACTTTTGT
TCGATGA

>AhRPT-4e10 (Renamed as AhR3'DT-3)    SEQ ID NO:8

MPFGLSASFLKSRSLHHHGWKFLKEREIHKQPLRNTRRALWNNNGKLSKEYCIKMQHN
YWKNHCTNLKGGSMMSDDKFEKKYLVNATSKNSHDEPKKSQPILEFIKDGMDTFRQFS
RLYAFFSFISSGLSSSLLAVDNLSNISPKMFLIGFLQFLIPNCIMFQYIVGVNQLADIEIDKIN
KPYLPLASGKYSLRNAIIIVASSLIMGFGSAWVLGSRPMFWCLVISTMLMTAYSVNLPLL
RWKRSTILATLSLASSMTIGQHIAPFLHMKTVLKKALNYPRSLVFTVVVSLFYTVISLAK
DIPDIEGDKAAGHKTLAIHLGPRRVFWFCISLLQMTYGIAIIMGALSPILWSKIFTVVTHFI
MSIILWYRANSVDLSNNDSLQSFYMAIFVFLSVENFLVLFVR*

FIG. 14

>AhRPT-5m3 (Renamed as AhR3'DT-4; GenBank Accesion No. KY565248) SEQ ID NO:12

ATGGCTTCCACTTCCAGGCTGCTGCTTCATGCCTCATTGCCTCCTCCCACTACATCCA
TTTCCAAAACCAATTCTGGTTCACATGCAGTGATCAGAAGCATATGGCATAATAATG
GGAAATATCCAAAAGAAAAAACTTGCATTGAGACGCCATTATTATTGCAGCATAATC
AGAAGCATCATTATACATGTGATCAAATTAAGAGAAAACACTTTGTGAAAGCAACTC
ATGCACAATCGAAGAATGAACCTGAACCGCAAGCTGATTCTGCAAACCCATTTGGA
ATTCTATCAAAGATGTTATGCATACTATCCAAAAGTTTAGCGTATTCTATGCGTTAAT
TGGCCTGTTATCGGGCATACTTTCTTCATCACTCCTTGCAGTAGAAAAATTATCAGAT
TTATCTCCAACATTTTTTATTTCCATGTTACAGTTTATGGCAGCTTATAGCTCTATGCA
ATTGTATACTACTGGCGTGAATCAATTAGCCGATATTGAAATAGACAAGATTAATAA
GCCATACCGTCCATTGGCATCATCGAAAATTTCTTTTGGAGGTGGACTCGCTATTGTT
GCAGCATCTTTATTTATGAGCTTTGGACTTGCGCTGATGATAGGATCAAAGCCTTTGC
TTTGGGGTCTCATATTAATTTTTATACTGATGACTGCTTATTCAGTGAACTTACCCTTT
TTAAGATGGAAGAAATCTACAATTCTTACATTACTGTCTGGCGTACCAACTATTCTCA
CTGCATATAATTTGGCACCATATCTTCACATGAAGACCTTTGTGCTGAAGAAGCCATT
TATATTTACAAGATCACTAGCTTTTACCACTGTGGTCATGACCTTCTTCTATGTAGTT
ATATCATTGTTCAAGGACATTCCCGACATTGAAGGAGATAAAAAGAAGGTCTTCAA
ACTTTGTCTATTCGCTTGGGTCCTAAACGAGTATTTGGTTGTGTATTTCACTTCTTGA
GATGACTTATGGAATTGCCATTATAATGGATTAACATCTCCATTCCTATGGAGCAA
AATCTTCACGGTTATGGCACATGCCATCAATGCTTGGATTTTGTGGTTTCGTGCTAAT
TCTGTAGATTTAAAGAGCAAAGAAGATTTCCAATCCTTTTATATGTTTATCTTTAAGC
TCCTTTACTTGGAGAATGTCCTTGTGCTTTTGTGAGATAA

>AhRPT-5m3 (Renamed as AhR3'DT-4) SEQ ID NO:11

MASTSRLLLHASLPPPTTSISKTNSGSHAVIRSIWHNNGKYPKEKTCIETPLLLQHNQKHH
YTCDQIKRKHFVKATHAQSKNEPEPQADSAKPIWNSIKDVMHTIQKFSVFYALIGLLSGIL
SSSLLAVEKLSDLSPTFFISMLQFMAAYSSMQLYTTGVNQLADIEIDKINKPYRPLASSKIS
FGGGLAIVAASLFMSFGLALMIGSKPLLWGLILIFILMTAYSVNLPFLRWKKSTILTLLSG
VPTILTAYNLAPYLHMKTFVLKKPFIFTRSLAFTTVVMTFFYVVISLFKDIPDIEGDKKEGL
QTLSIRLGPKRVFWLCISLLEMTYGIAIIMGLTSPFLWSKIFTVMAHAINAWILWFRANSV
DLKSKEDFQSFYMFIFKLLYLENVLVLFVR*

FIG. 15

>AhRPT-10k1 (AC1) (Renamed as AhR3'DT-1; GenBank Accesion No. KY565245) SEQ ID NO:15

ATGGCTTTTGGTGTTGTTGCTGCCTCATTTTCAAGAGCTCCCTCCATTGTCACCACCA
GAGGTTGTTATGTAACAAGAGCTTCATTGCCTAATAAGAGTCTCAAATTCTCAAAAG
AATATAATTTGAAGACATCTCTGCAGCATAATTGGAAGCACAATTCCAGAAGCATTT
TTGAAAGAGGATCTACAATTACAACATGTGATAAATATGATGAAAGAAGTACCTTA
TGAATGTGACACAATCACATGAAGCTGAACCACATTCACAAAGCATCTTGAAGTCCA
TCATTGATGCTTTAGATGCTTTCCGCAAGTTTAGCAGATTTTACGCATTCATTGCCAT
GGTAGTGGGTTCACTTTCCACATCGCTTCTTGCAGTGGACAATTTAACAGAATTATAT
CCAGCATTTTTTAATGGCTTTTTGCAATGTATGGCAGCTTACTTCTTCATGCATTTGTA
CATTGTTGGAATAAATCAATTAGCGGATCTTGAAATAGACAAGATTAACAAGCCATA
TCTTCCTTTGGCATCAGGGAACTATTCCTTCAGAACTGCAGTTATAACTGTGACGTCA
TTTTTATTTACGGGCTTTGGAATTGCATGGATCATAGGATCAAAGCCGTTGCTTTGGA
CTATTTTTGCCAGTTTTGTTCTAATGACTGCTTATTCAGTTAATTTGCCCTTATTGAGA
TGGAAGAAATCTACAATACTTACAGTGATGGGTAACACACTTTCTATGGTGATATCA
TTTAATCTTGGTCCCTTTTATCACATGAAGACTCATGTGCTCAAGAAGGCAGCTACCT
TTCCAAGATCCCTACTTTTTGCTGTTGTGGTCATGAGCATGTACTATATCGTTATAGC
ATTGACAAAGGATATACCTGATATCGAAGGAGACAAAGAAGCCGGCCTCCAAACTT
TGGCCATACGCTTGGGTCCTAAGACGGTATTTTGGTCTAGTGTTGCACTTCTTGAAAT
GGCTTATGGAGCTGCTATTATAATTGGAGCATCCTCTCCTTTTCTTTGGAGCAAAATC
TCTGTGGTTCTTTCCCATGCTATCTTGGCTTTGTTCGTATGGTATCGCTCCACTCTTGT
AGATTTATCCAACAAAGATTCATTGCAAGCTTTTTATATGCTTATCTTTAAGCTTTTT
CTGTGGAAAATATTCTTATGCTTTTGTTAGATGA

>AhRPT-10k1 (AC1) (Renamed as AhR3'DT-1) SEQ ID NO:14

MAFGVVAASFSRAPSIVTTRGCYVTRASLPNKSLKFSKEYNLKTSLQHNWKHNSRSIFER
GSTITTCDKYDEKKYLMNVTQSHEAEPHSQSILKSIIDALDAFRKFSRFYAFIAMVVGSLS
TSLLAVDNLTELYPAFFNGFLQCMAAYFFMHLYIVGINQLADLEIDKINKPYLPLASGNY
SFRTAVITVTSFLFTGFGIAWIIGSKPLLWTIFASFVLMTAYSVNLPLLRWKKSTILTVMGN
TLSMVISFNLGPFYHMKTHVLKKAATFPRSLLFAVVVMSMYYIVIALTKDIPDIEGDKEA
GLQTLAIRLGPKTVFWSSVALLEMAYGAAIIIGASSPFLWSKISVVLSHAILALFVWYRST
LVDLSNKDSLQAFYMLIFKLFSVENILMLFVR*

FIG. 16

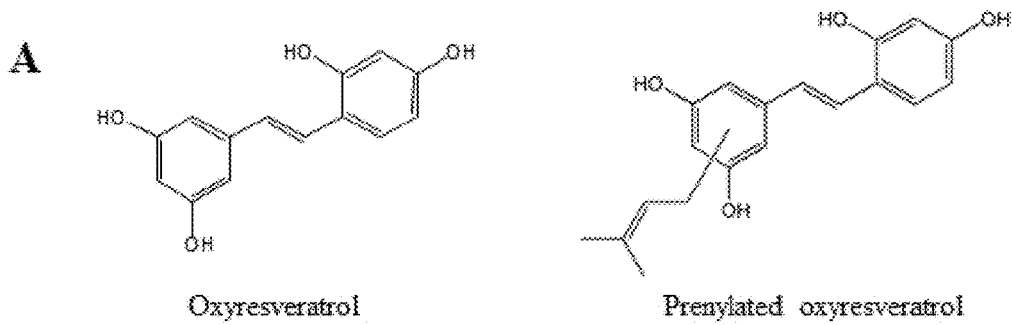
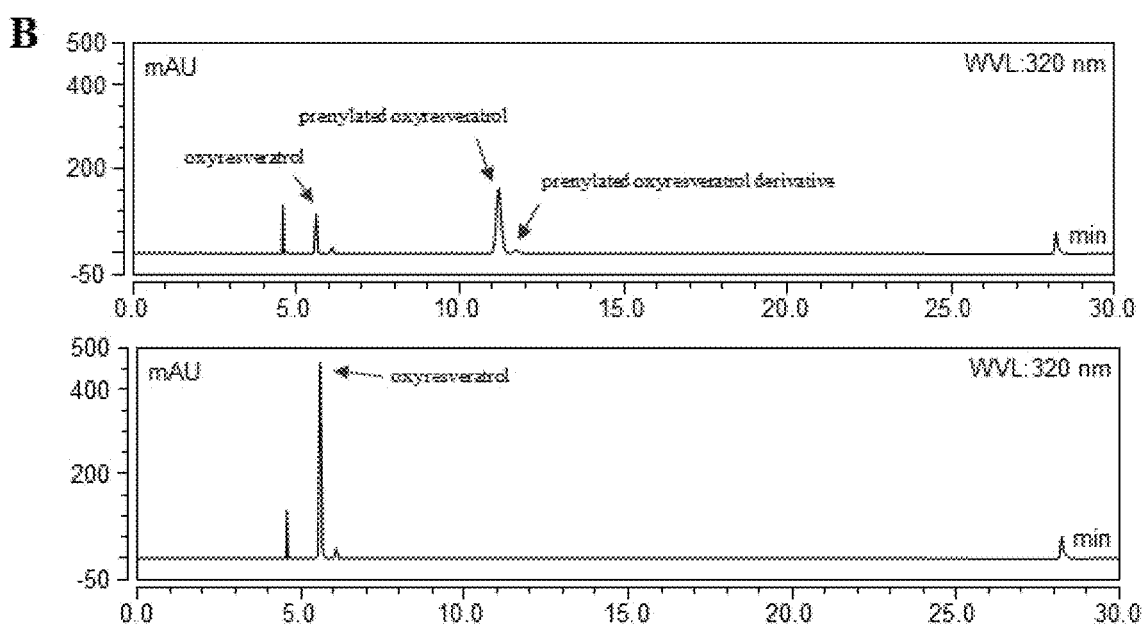
FIG. 32

FIG. 36

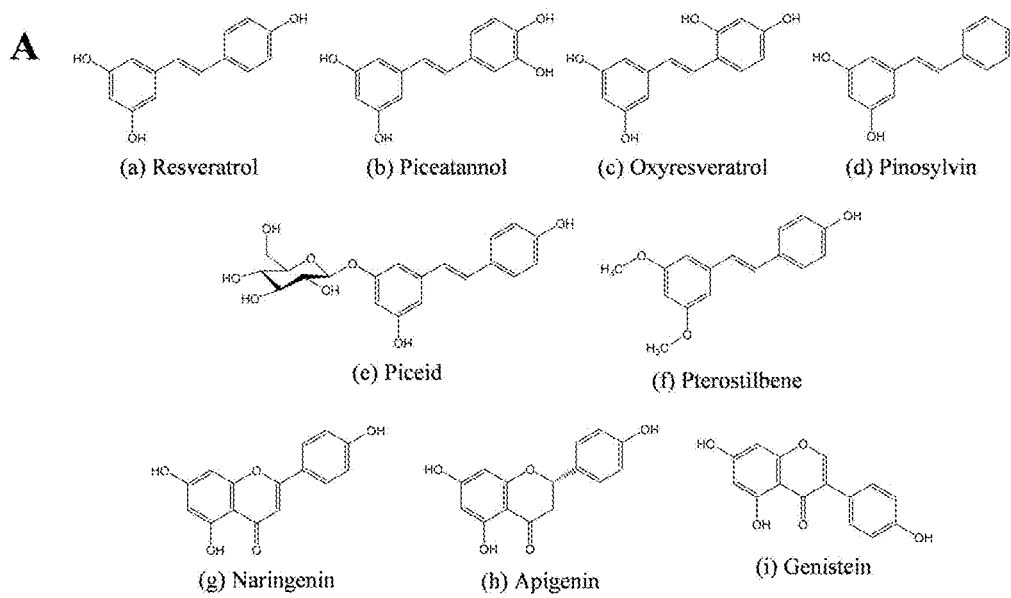
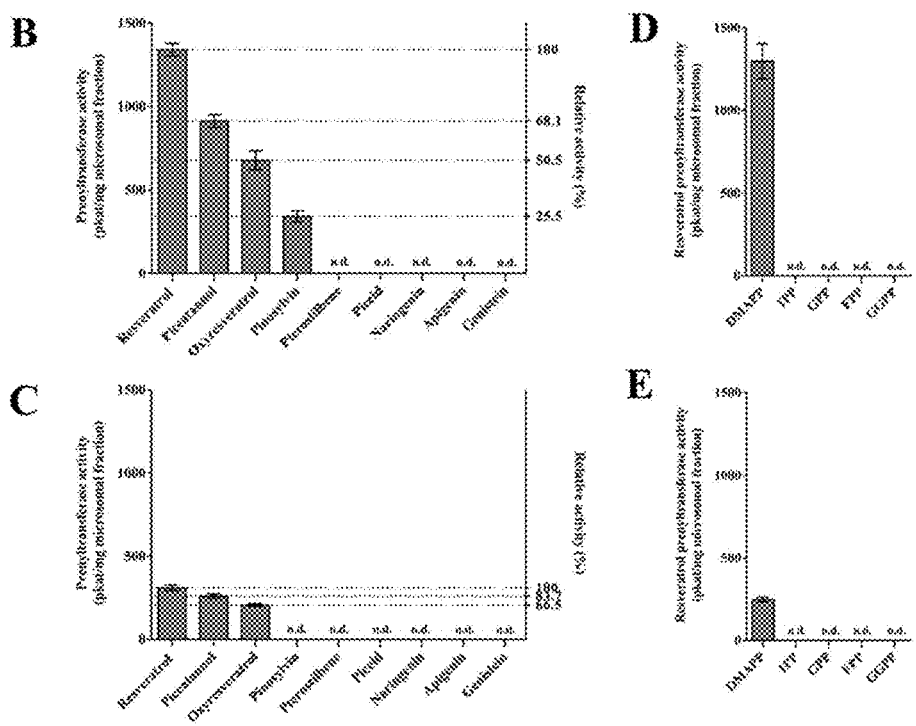
FIG. 38

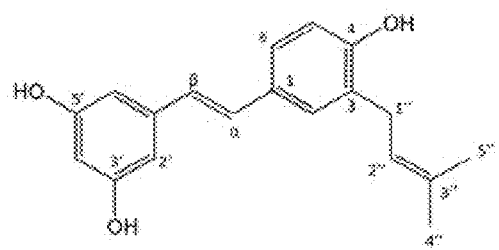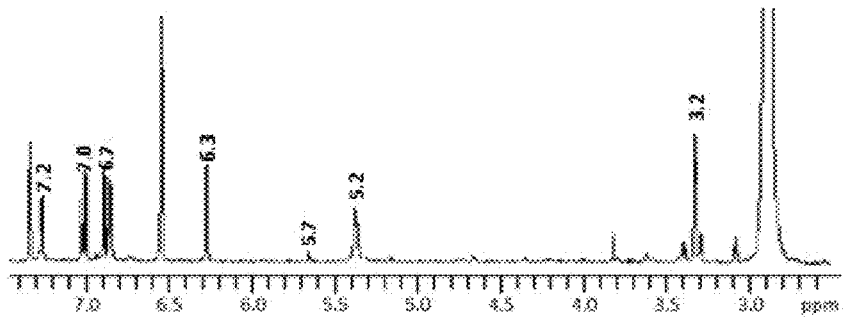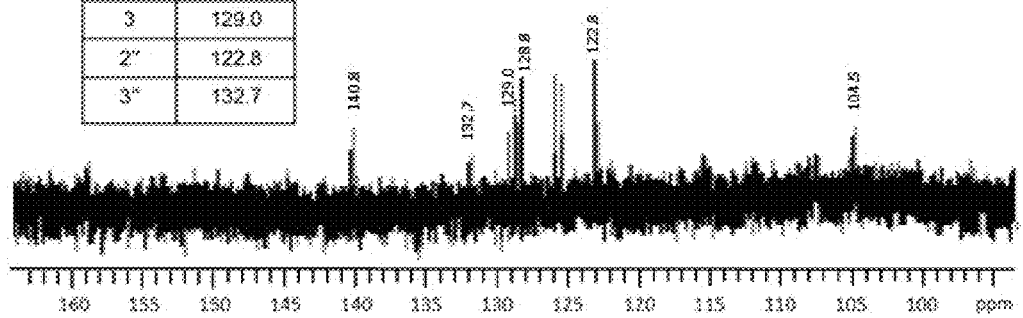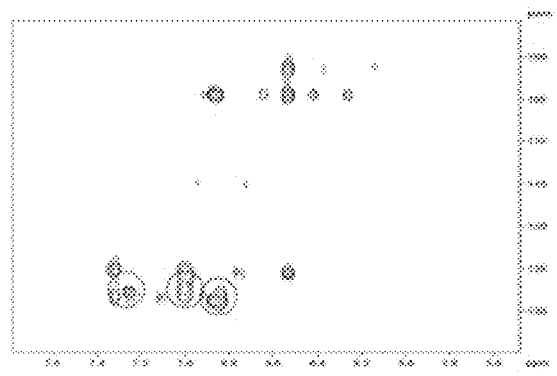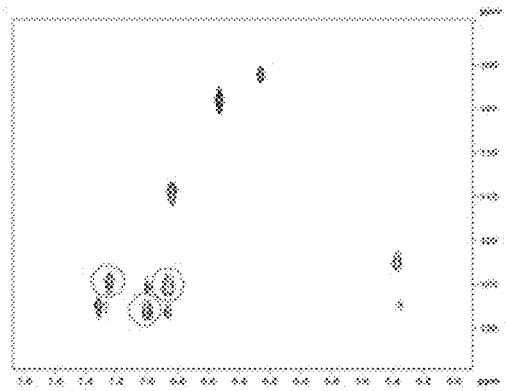
FIG. 43

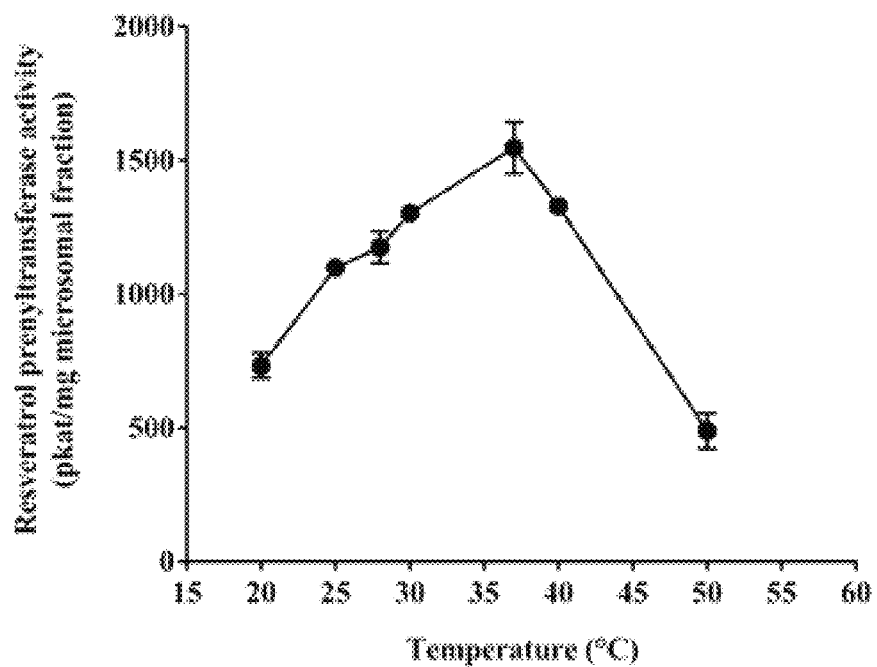
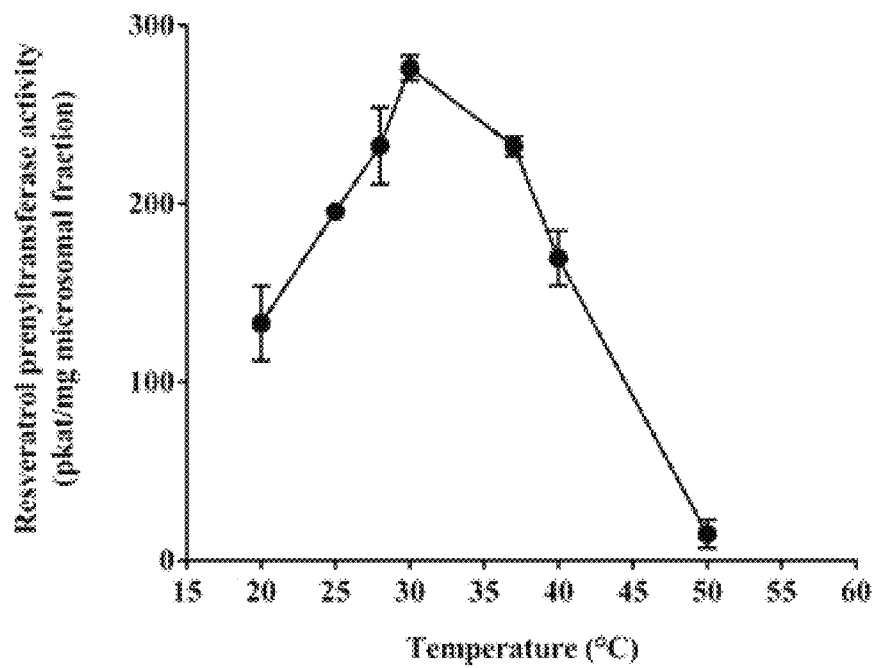
FIG. 49

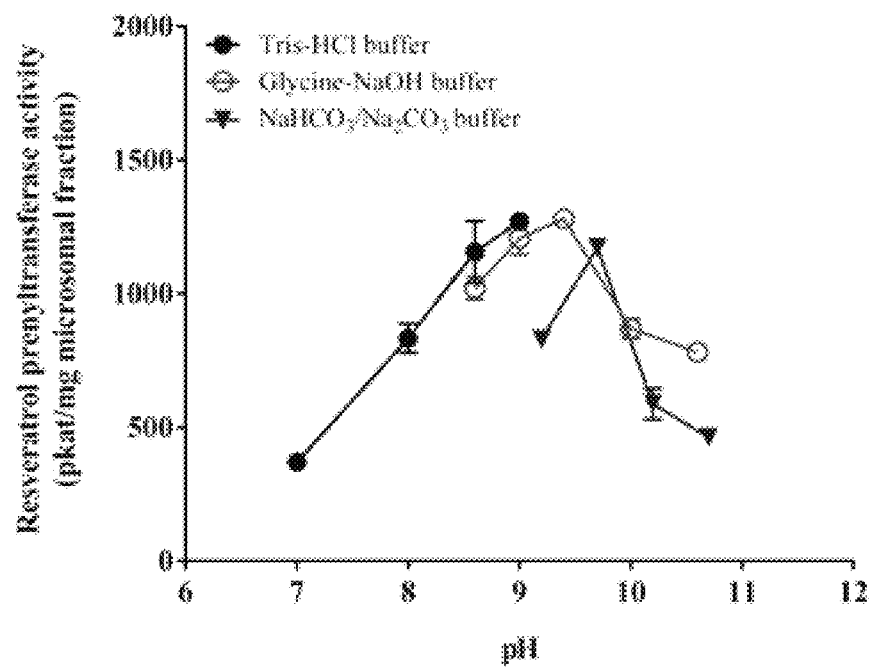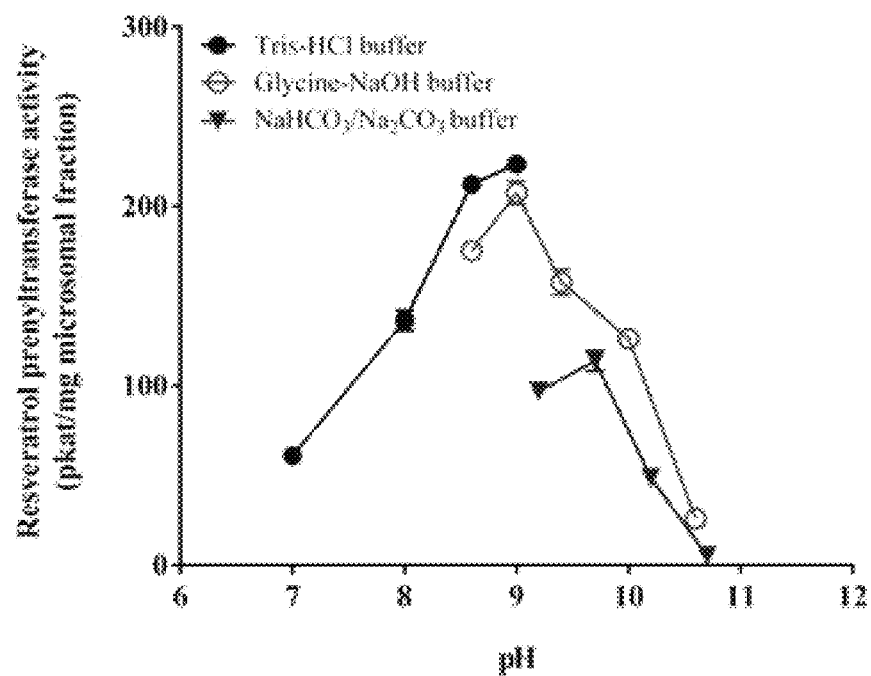
FIG. 51

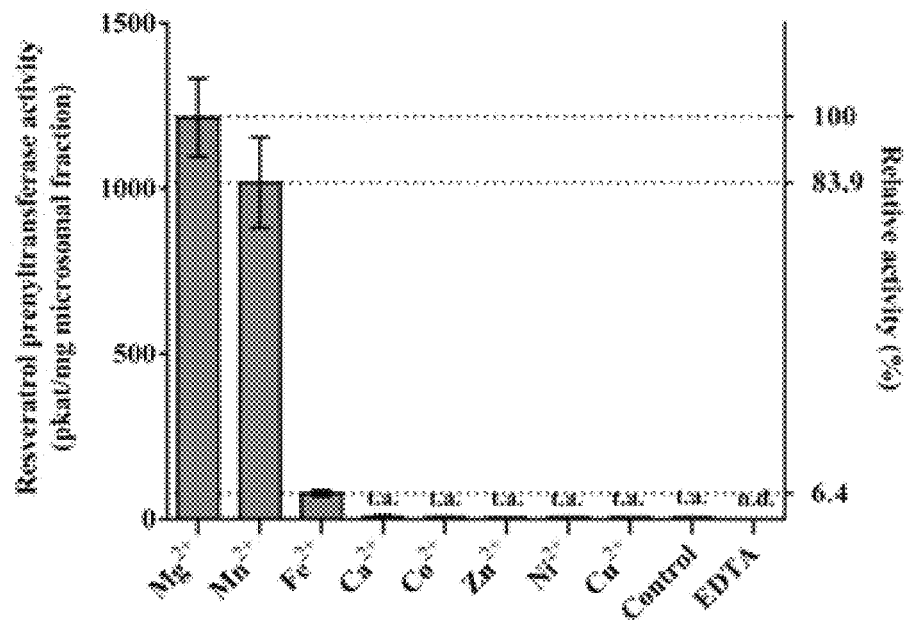
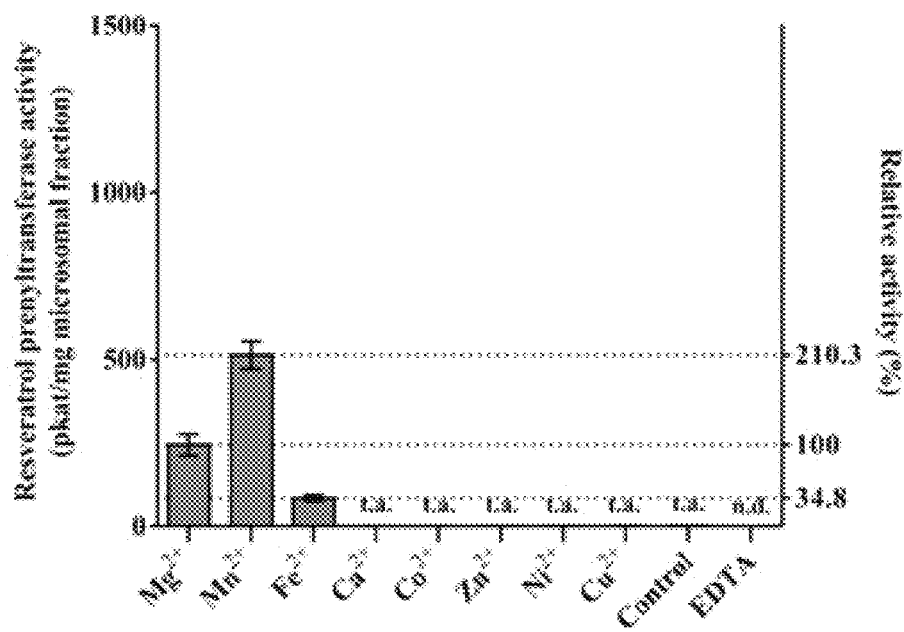
FIG. 52

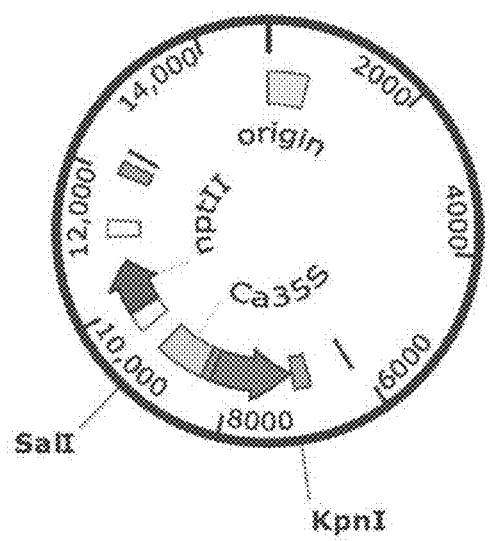
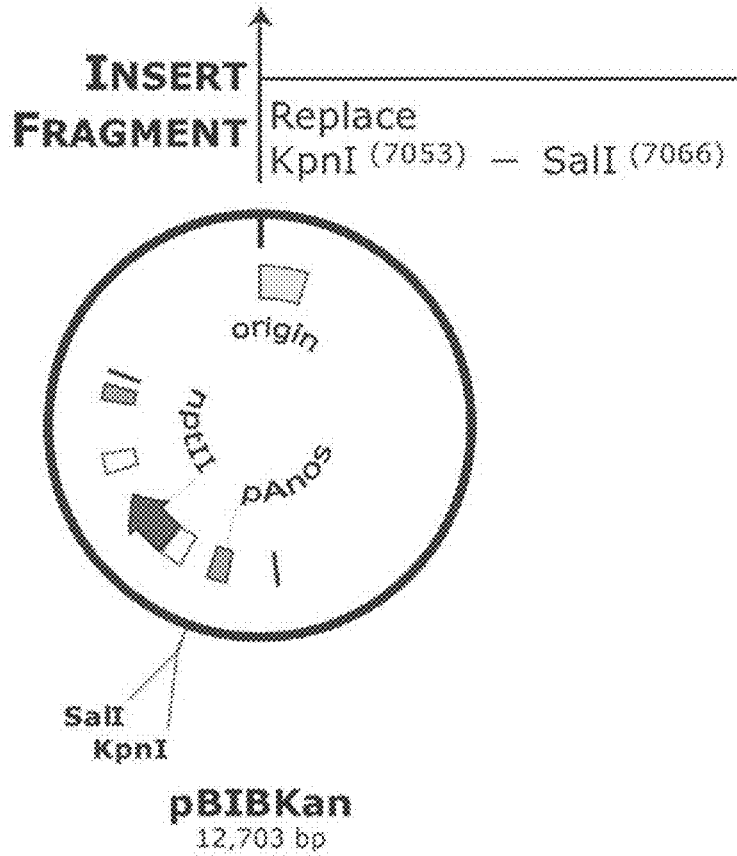
FIG. 59A

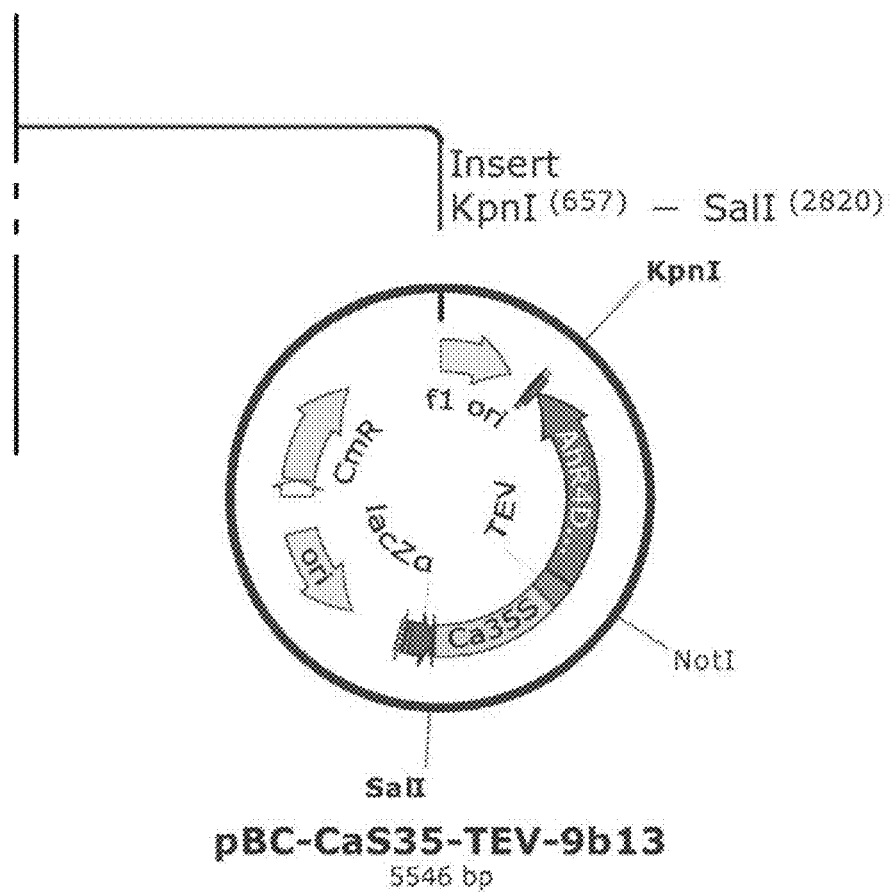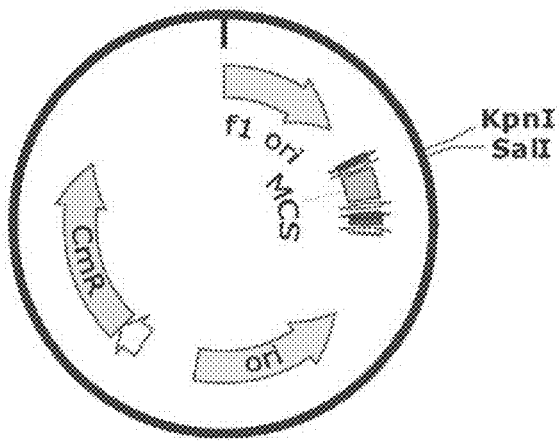
FIG. 59B

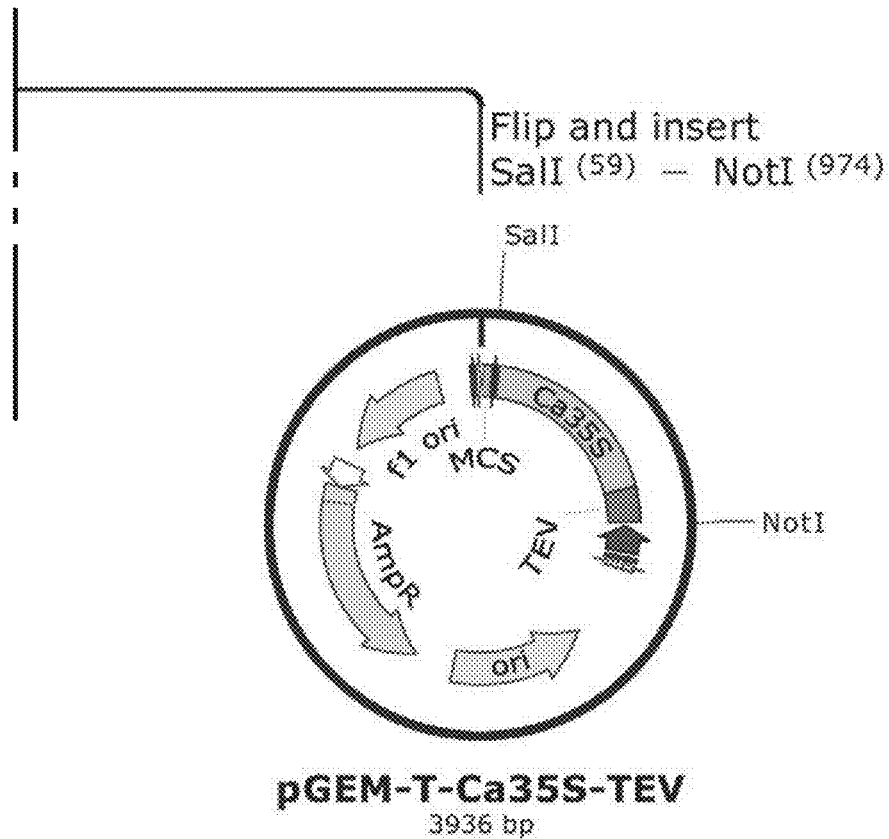
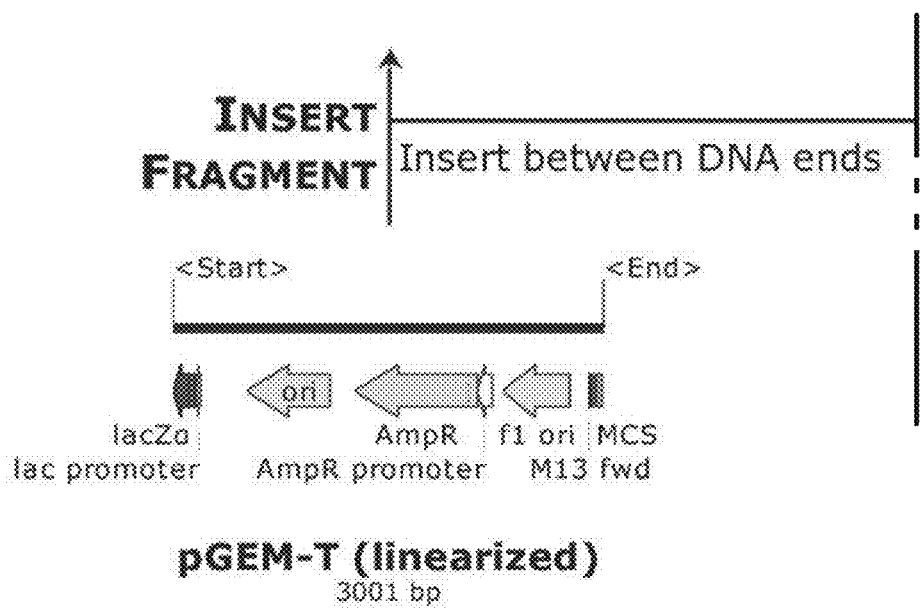
FIG. 59F

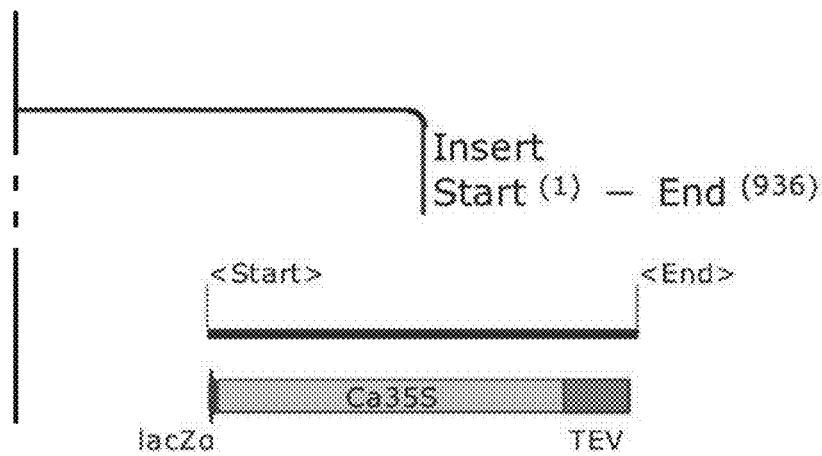
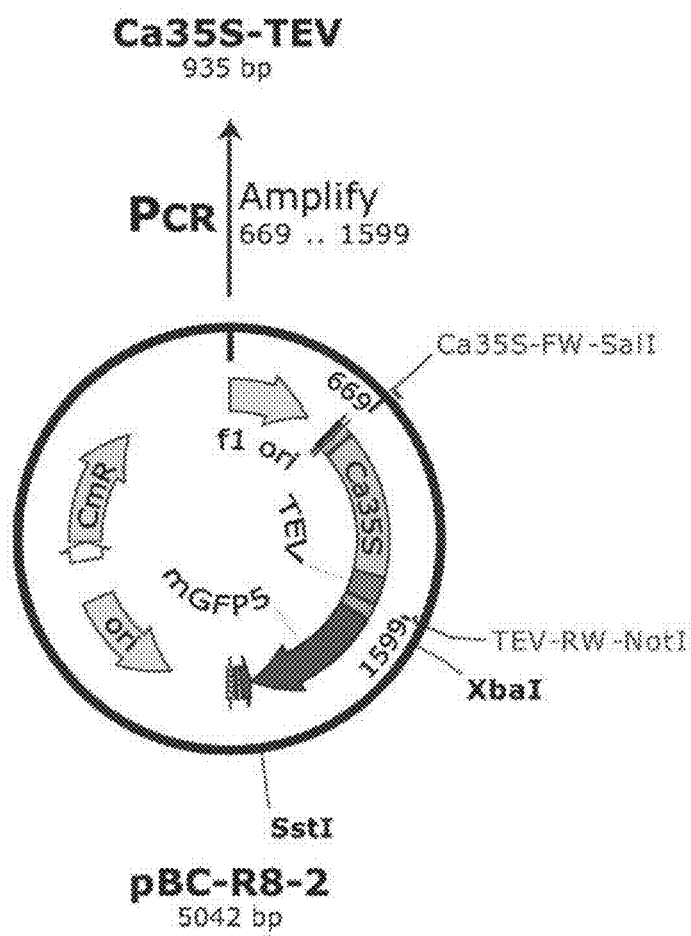
(History Hidden)
FIG. 59G

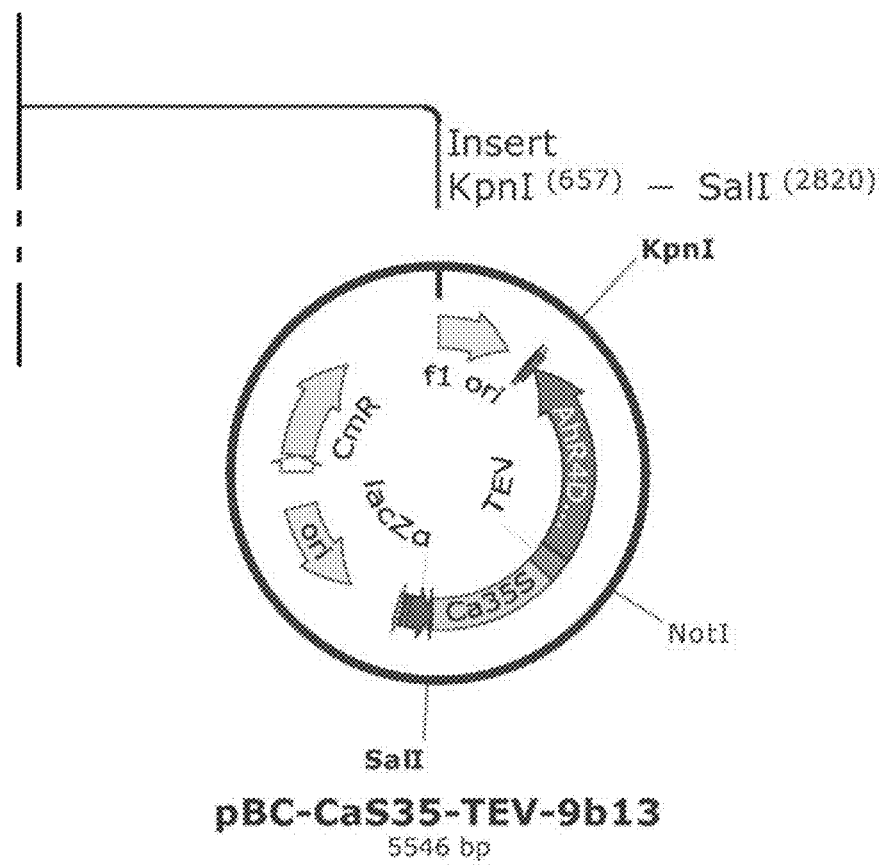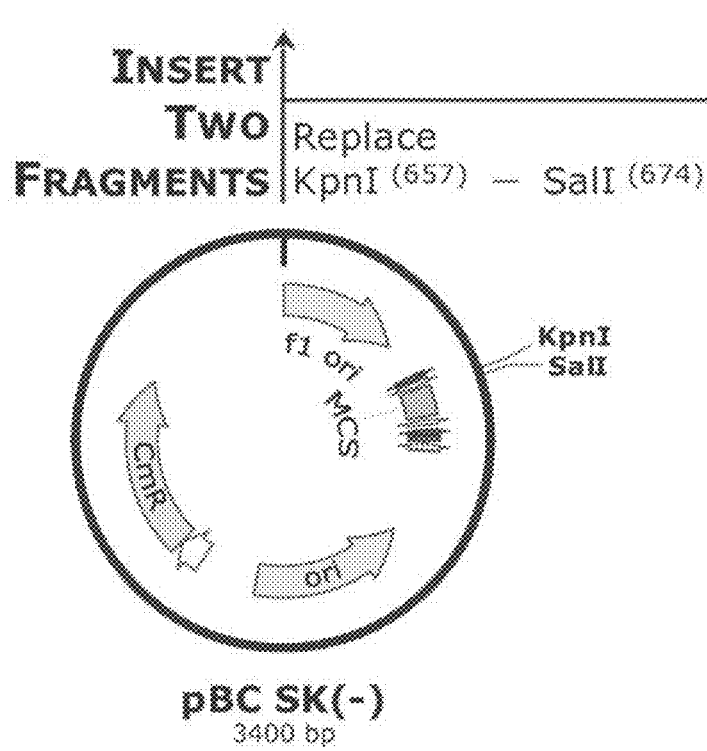
FIG. 60B

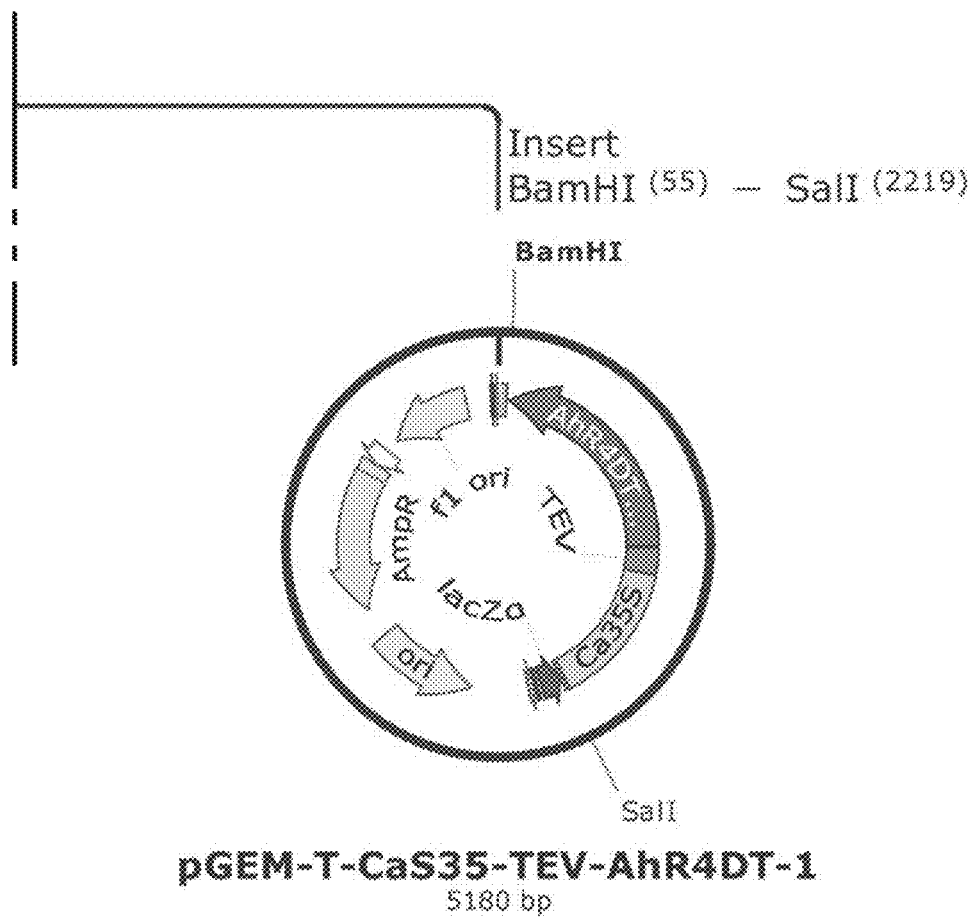
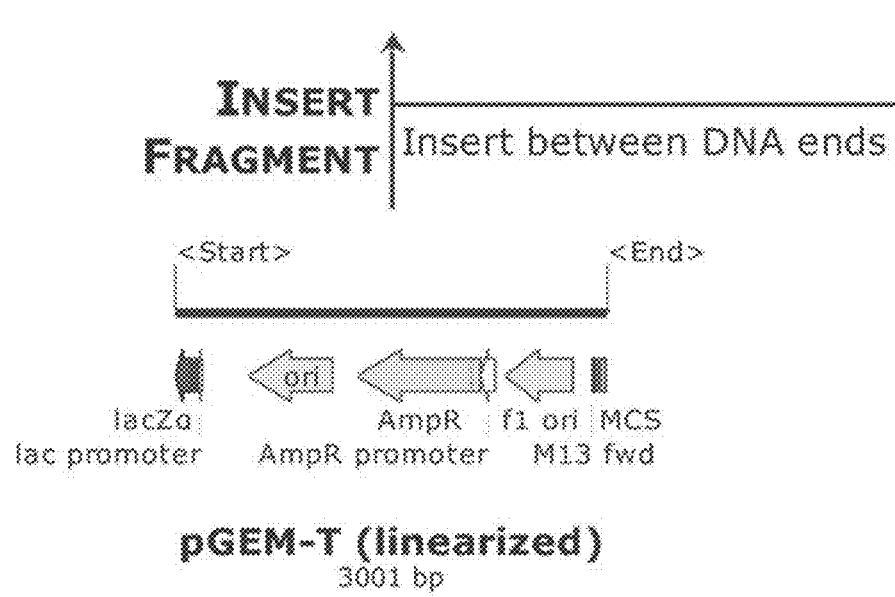
FIG. 60F

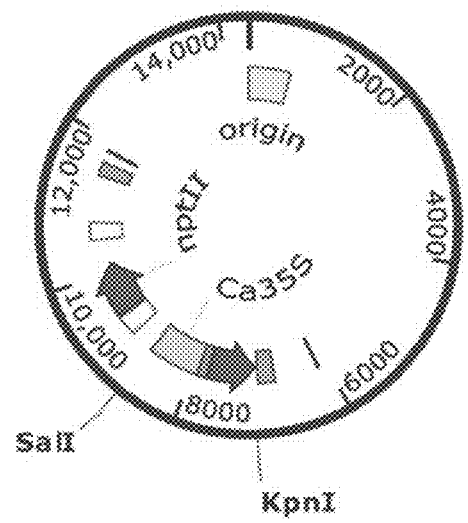
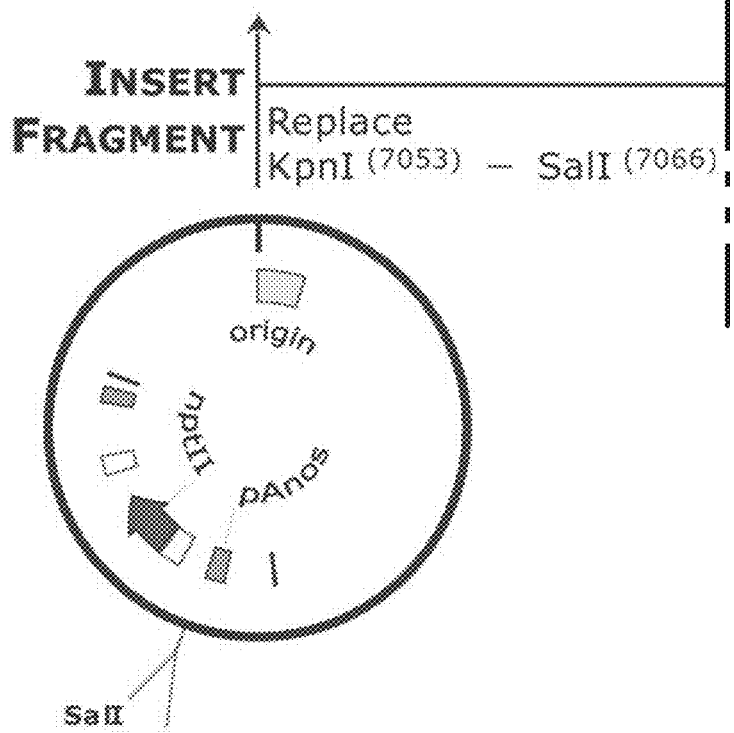
FIG. 61A

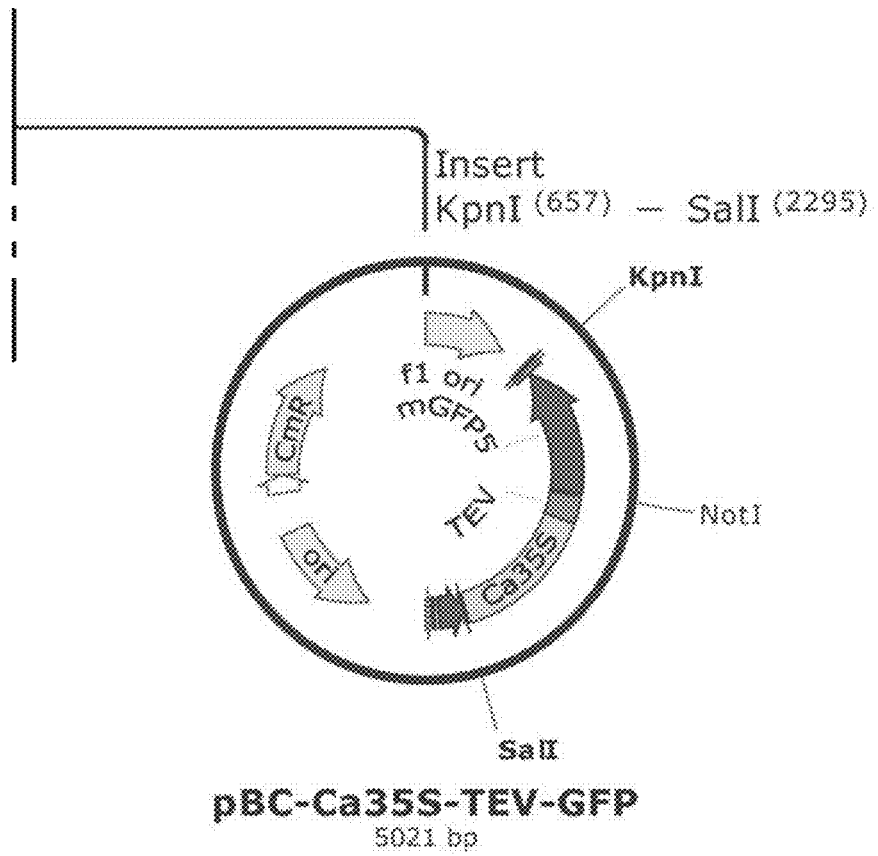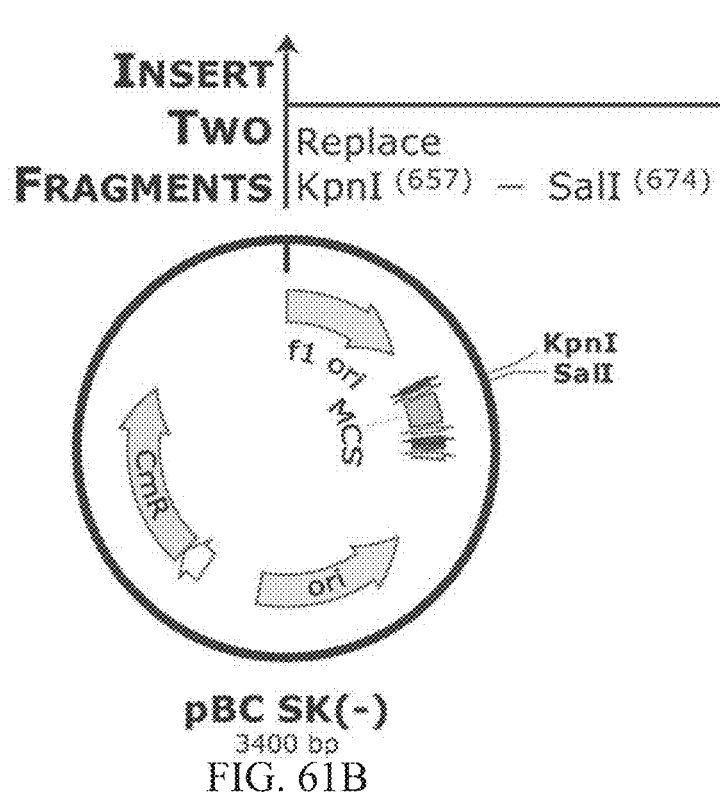
FIG. 61B

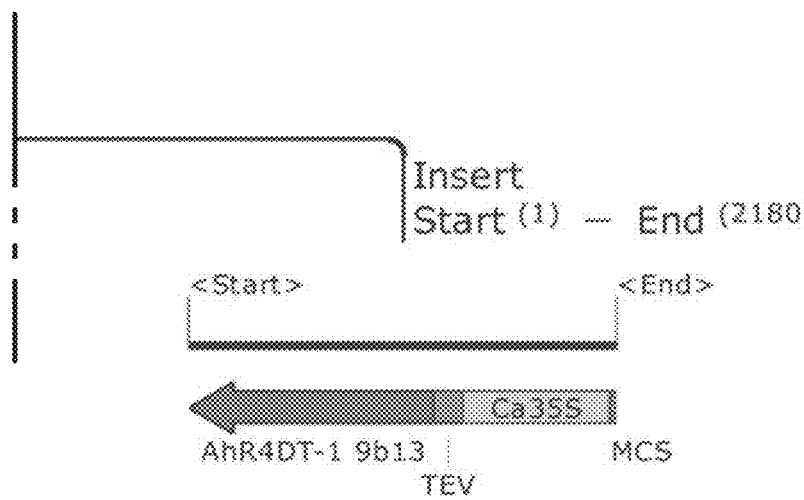
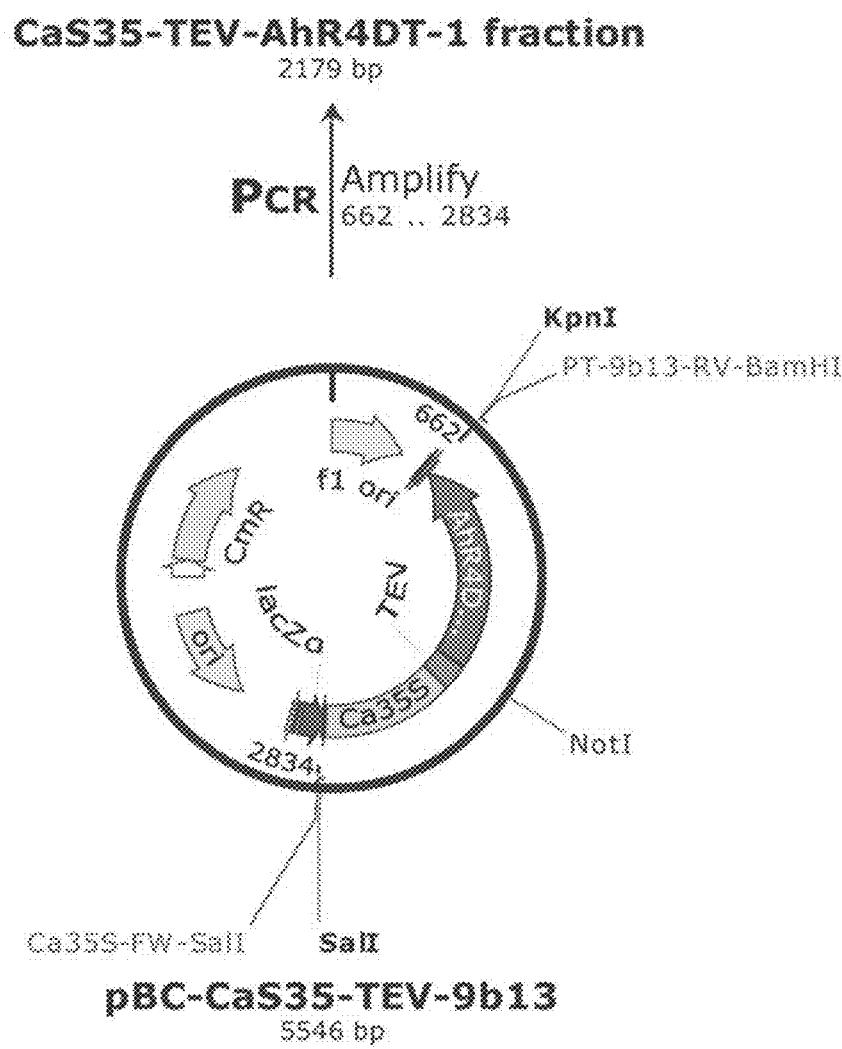
FIG. 61G

| cDNA clone | GenBank Accession | Activity* (percentage relative activity) | Product | Alignment to proxy genome |
|---|---|---|---|---|
| AhR4DT-1 | KY565244 | 1352.84 (100%) | arachidin-2 | *A. duranensis* A08, 40225499-40234019, - 8520 bp |
| AhRPT-9i2 | - | n.d.** | - | - |
| AhR3'DT-1 | KY565245 | 236.56 (100%) | 3-methyl-2-butenyl-3'-resveratrol | *A. ipaensis* B08, 114687148-114693743, - 6595 bp |
| AhRPT-10a4 | - | n.d. | - | - |
| AhRPT-10l4 | - | n.d. | - | - |
| AhR3'DT-2 | KY565246 | 42.58 (18%) | 3-methyl-2-butenyl-3'-resveratrol | *A. ipaensis* B08, 119033572-119042841, + 9269 bp |
| AhR3'DT-3 | KY565247 | 40.22 (17%) | 3-methyl-2-butenyl-3'-resveratrol | |
| AhR3'DT-4 | KY565248 | 11.83 (5%) | 3-methyl-2-butenyl-3'-resveratrol | *A. duranensis* A01, 2413393-2427986, - 14.5 Kbp |

*Resveratrol dimethylallyltransferase activity determined as pkat mg$^{-1}$ protein of microsomal fraction in *N. benthamiana* transient assay.

**n.d., Not detected

FIG. 63

| Enzyme solution | AhR4DT-1 | AhR3'DT-1 |
|---|---|---|
| | pkat mg$^{-1}$ protein | pkat mg$^{-1}$ protein |
| Crude cell-free extracts | 151.39 ± 7.15 | 16.97 ± 5.92 |
| 156,000 ×g supernatant | 16.81 ± 4.21 | 2.02 ± 1.15 |
| Microsomal fraction | 1352.84 ± 68.31 | 236.56 ± 26.29 |

FIG. 64

| | AhR4DT-1 | | AhR3'DT-1 | | Prenyltransferase from peanut hairy root | |
|---|---|---|---|---|---|---|
| | $K_m$ (μM) | $V_{max}$ (pkat/mg) | $K_m$ (μM) | $V_{max}$ (pkat/mg) | $K_m$ (μM) | $V_{max}$ (pkat/mg) |
| Resveratrol | 99.52±15.11 | 2948±151.1 | 17.67±1.61 | 296.3±5.7 | 111.1±40.4 | 709.9±90.0 |
| Piceatannol | 311.4±54.83 | 2580±217.2 | 50.32±5.51 | 372.5±11.5 | - | - |
| DMAPP | 153.7±27.28 | 3378±229.5 | 691.45±48.46 | 572.8±24.7 | 91.9±7.0 | 686.6±17.4 |

FIG. 65

| SEQ ID NO | Name | Sequence (5'-3') | Reference |
|---|---|---|---|
| | First screening for prenyltransferase gene | | |
| SEQ ID NO:21 | PT-10-FW-NotI | TAGCGGCCGCATGGCTTTGGTGTTGTGCTGC | This study |
| SEQ ID NO:22 | PT-a-RV-KpnI | ATCGATGGTACCTATTTTTAAGAAGTTTTTACTGC | This study |
| SEQ ID NO:23 | PT-d-RV-KpnI | ATCGATGAGGTACCTCATGGAAATAGTTGAACAGAGAG | This study |
| SEQ ID NO:24 | PT-k-RV-KpnI | CGATGGTACCTCATCTAACAAAAGCATAAGAATATTTC | This study |
| | Second screening for prenyltransferase gene | | |
| SEQ ID NO:25 | PT-4-FW-NotI | TAGCGGCCGCATGCCTTTCGGACTCTCCGC | This study |
| SEQ ID NO:26 | PT-5-FW-NotI | TAGCGGCCGCATGGCTTCCACTTCCAGGCT | This study |
| SEQ ID NO:27 | PT-6-FW-NotI | TAGCGGCCGCATGGCTTTTAGGCTTCTAGGATC | This study |
| SEQ ID NO:28 | PT-8-FW-NotI | TAGCGGCCGCATGGCTTTTGGGCATTGGTGT | This study |
| SEQ ID NO:29 | PT-b-RV-KpnI | CTGAGGTACCTCAACGAACAAATTGTATAAGGATG | This study |
| SEQ ID NO:30 | PT-c-RV-KpnI | CTGAGGTACCCTATCTCACGAAAAGTATAAGGATG | This study |
| SEQ ID NO:31 | PT-e-RV-KpnI | CTGAGGTACCTCATCGAACAAAAGTACAAGGAAG | This study |
| SEQ ID NO:32 | PT-i-RV-KpnI | CTGAGGTACCTTAGTTATTGGTTACCTTAAACATA | This study |
| SEQ ID NO:33 | PT-m-RV-KpnI | CTGAGGTACCTTATCTCACAAAAGCACAAGGACA | This study |
| | Promoter cloning | | |
| SEQ ID NO:34 | Ca35S-FW-SalI-1 | ATCGATGTCGACAAGCTTGCATGCCTG | This study |
| SEQ ID NO:35 | TEV-RW-NotI | ATCGATGCGGCCGCTATCGTTCGTAAATGGTGA | This study |
| | GFP fusion protein cloning | | |
| SEQ ID NO:36 | mgfp5-FW-BamHI | ATCGATGGATCCATGGCTAGTAAAGGAGAAGAACTTTTC | This study |
| SEQ ID NO:37 | mgfp5-FW-NotI | ATCGATGCGGCCGCATGGCTAGTAAAGGAGAAGAACTTTT | This study |
| SEQ ID NO:38 | mgfp5-RW-KpnI | ATCGATGGTACCTCATTTGTATAGTTCATCCAT | This study |
| SEQ ID NO:39 | PT-10k1-RV-BamHI | ATCGATGGATCCTCTAACAAAAGCATAAGAA | This study |
| SEQ ID NO:40 | PT-9b13-RV-BamHI | ATGGATCCACGAACAAATTGTATAAGGATG | This study |

FIG 66A

| | | | |
|---|---|---|---|
| SEQ ID NO:41 | Ca35S-FW-*SalI*-2 | GATACCGTCGACAAGCTTGCATG | This study |
| Real time-quantitative PCR | | | |
| SEQ ID NO:42 | AHR4DT-1-FW | ACTTCTGGAGTTATACTTGTG | This study |
| SEQ ID NO:43 | AHR4DT-1-RV | TAGATAGTGATGTGAGGATTATAG | This study |
| SEQ ID NO:44 | AHR3'DT-1-FW | GCAGCATAATTGGAAGCA | This study |
| SEQ ID NO:45 | AHR3'DT-1-RV | GGAAAGCATCTAAAGCATCA | This study |
| SEQ ID NO:46 | JC1-FW | TATGTATTTAACAGAAGAAATAC | (Condori et al., 2009) |
| SEQ ID NO:47 | JC1-RV | AGTTGCAGCCTCTTTTCCAACT | (Condori et al., 2009) |
| SEQ ID NO:48 | ACT7-FW | ATGTATGTAGCCATCCAAG | (Condori et al., 2011) |
| SEQ ID NO:49 | ACT7-RV | ACCAGAGTCCAGAACAATA | (Condori et al., 2011) |
| SEQ ID NO:50 | EF1α-FW | GGTGTCAAGCAGAGATGATT | (Condori et al., 2011) |
| SEQ ID NO:51 | EF1α-RV | ACTTCCTTCACGATTTCA | (Condori et al., 2011) |

FIG 66B

| No | Analyte | $t_R$ (min) | UV (nm) | $[M+H]^+$ (m/z) | $MS^2$ ions | $MS^3$ ions |
|---|---|---|---|---|---|---|
| 1 | Oxyresveratrol | 5.74 | 243, 302, 328 | 245 | 227 | 209, 199, 157 |
| 2 | Piceatannol | 5.79 | 240, 324 | 245 | 227, 199, 135[a] | 107 |
| 3 | Resveratrol | 6.50 | 237, 306, 317 | 229 | 211, 183 | 107 |
| 4 | Prenylated oxyresveratrol by AhR3'DT-1 | 9.8R | 22R, 32R | 313 | 2RT | 239 |
| R | Prenylated oxyresveratrol by AhR4DT-1 | 10.63 | 22R, 304, 329 | 313 | 2RT | 239 |
| 6 | Arachidin-R | 11.01 | 240, 32T | 313 | 257 | 239, 229, 211 |
| 7 | Pinosylvin | 12.42 | 229, 300, 307 | 213 | 135 | 107 |
| 8 | Arachidin-2 | 13.84 | 239, 311, 323 | 297 | 241 | 223, 213, 195 |
| 9 | Prenylated piceatannol by AhR3'DT-1 | 14.44 | 228, 32R | 313 | 2RT | 239, 211 |
| 10 | 3-methyl-2-butenyl-3'-resveratrol | 16.99 | 230, 320 | 29T | 241 | 223 |
| 11 | Chiricanine A | 2R.02 | 209, 314 | 281 | 22R | 179, 207 |

FIG. 67

| Name | Description | Reference |
|---|---|---|
| pBC KS(-) | Phagemid vector derived from pBluescript II KS(-) | (Becker, 1990) |
| pBIB-Kan | Binary vector | (Medina-Bolivar and Cramer, 2004) |
| pR8-2 | *CaMV35S::TEV::pat::mGFP5* in pBC KS(-) | |
| Prenyltransferase Characterization | | |
| pGEM-CaMV35S-TEV | *CaMV35S::TEV* in pGEM-T | This study |
| pBC-CaMV35S-TEV-9b13 | *CaMV35S::TEV::AhR4DT-1* in pBC KS(-) | This study |
| pBC-CaMV35S-TEV-10k1 | *CaMV35S::TEV::AhR3'DT-1* in pBC KS(-) | This study |
| pBIB-Kan-AhR4DT-1 | *CaMV35S::TEV::AhR4DT-1* in pBIB-Kan | This study |
| pBIB-Kan-AhR3'DT-1 | *CaMV35S::TEV::AhR3'DT-1* in pBIB-Kan | This study |
| pBIB-Kan-AhR3'DT-2 | *CaMV35S::TEV::AhR3'DT-2* in pBIB-Kan | This study |
| pBIB-Kan-AhR3'DT-3 | *CaMV35S::TEV::AhR3'DT-3* in pBIB-Kan | This study |
| pBIB-Kan-AhR3'DT-4 | *CaMV35S::TEV::AhR3'DT-4* in pBIB-Kan | This study |
| Subcellular Localization | | |
| pt-rk | *CaMV35S::RS-TP-mCherry* in pBIN20 | (Nelson et al., 2007) |
| pGEM-mGFP5-1 | *mGFP5* with BamHI/KpnI sites in pGEM-T | This study |
| pGEM-mGFP5-2 | *mGFP5* with NotI/KpnI sites in pGEM-T | This study |
| pGEM-CaMV35S-TEV-AhR4DT-1-GFP | *CaMV35S::TEV::AhR4DT-1::mGFP5* in pGEM-T | This study |
| pGEM-CaMV35S-TEV-AhR3'DT-1-GFP | *CaMV35S::TEV::AhR3'DT-1::mGFP5* in pGEM-T | This study |
| pBC-CaMV35S-TEV-GFP | *CaMV35S::TEV::mGFP5* in pBC KS(-) | This study |
| pBIB-Kan-AhR4DT-1-GFP | *CaMV35S::TEV::AhR4DT-1::mGFP5* in pBIB-Kan | This study |
| pBIB-Kan-AhR3'DT-1-GFP | *CaMV35S::TEV::AhR3'DT-1::mGFP5* in pBIB-Kan | This study |
| pBIB-Kan-GFP | *CaMV35S::TEV::mGFP5* in pBIB-Kan | This study |

FIG. 68

| Protein name | Accession number | Description | Organism |
|---|---|---|---|
| AaVTE2-1 | ABB70124.1 | homogentisate phytyltransferase VTE2-1 | *Allium ampeloprasum* |
| AhR4DT-1 | AQM74172.1 | resveratrol-4-dimethylallyltransferase | *Arachis hypogaea* |
| AhR3'DT-1 | AQM74173.1 | resveratrol-3'-dimethylallyltransferase | *Arachis hypogaea* |
| AhR3'DT-2 | AQM74174.1 | resveratrol-3'-dimethylallyltransferase | *Arachis hypogaea* |
| AhR3'DT-3 | AQM74175.1 | resveratrol-3'-dimethylallyltransferase | *Arachis hypogaea* |
| AhR3'DT-4 | AQM74176.1 | resveratrol-3'-dimethylallyltransferase | *Arachis hypogaea* |
| AtHPT1 | AAM10489.1 | homogentisate phytylprenyltransferase | *Arabidopsis thaliana* |
| AtPPT1 | BAB20818.2 | p-hydroxybenzoate polyprenyltransferase | *Arabidopsis thaliana* |
| AtVTE2-2 | ABB70127.1 | homogentisate phytyltransferase VTE2-2 | *Arabidopsis thaliana* |
| ClPT1a | BAP27988.1 | umbelliferone 8-geranyltransferase | *Citrus limon* |
| CpVTE2-1 | ABB70125.1 | homogentisate phytyltransferase VTE2-1 | *Cuphea pulcherrima* |
| CrVTE2-2 | CAL01105.1 | homogentisate prenyltransferase | *Chlamydomonas reinhardtii* |
| CtIDT | AJD80983.1 | isoliquiritigenin 3'-dimethylallyltransferase | *Cudrania tricuspidata* |
| GmG4DT | BAH22520.1 | pterocarpan 4-dimethylallyltransferase | *Glycine max* |
| GmVTE2-1 | ABB70126.1 | homogentisate phytyltransferase VTE2-1 | *Glycine max* |
| GmVTE2-2 | ABB70128.1 | homogentisate phytyltransferase VTE2-2 | *Glycine max* |
| GuA6DT | AIT11912.1 | flavone prenyltransferase | *Glycyrrhiza uralensis* |
| HlPT-1 | BAJ61049.1 | aromatic prenyltransferase | *Humulus lupulus* |
| HvHGGT | AAP43911.1 | homogentisic acid geranylgeranyl transferase | *Hordeum vulgare* |
| LaPT-1 | AER35706.1 | genistein 3'-dimethylallyltransferase | *Lupinus albus* |
| LePGT-1 | BAB84122.1 | 4-hydroxybenzoate geranyltransferase | *Lithospermum erythrorhizon* |
| LePGT-2 | BAB84123.1 | 4-hydroxybenzoate geranyltransferase | *Lithospermum erythrorhizon* |
| MaIDT | AJD80982.1 | isoliquiritigenin 3'-dimethylallyltransferase | *Morus alba* |
| OsHGGT | AAP43913.1 | homogentisic acid geranylgeranyl transferase | *Oryza sativa* |
| OsPPT1 | BAE96574.1 | p-hydroxybenzoate polyprenyltransferase | *Oryza sativa* |
| | | umbelliferone 6- | |

FIG. 69A

| | | | |
|---|---|---|---|
| PcPT | BAO31627.1 | dimethylallyltransferase | *Petroselinum crispum* |
| SfG6DT | BAK52291.1 | genistein 6-dimethylallyltransferase | *Sophora flavescens* |
| SfiLDT | BAK52290.1 | isoliquiritigenin dimethylallyltransferase | *Sophora flavescens* |
| SfN8DT-1 | BAG12671.1 | naringenin 8-dimethylallyltransferase | *Sophora flavescens* |
| SfN8DT-2 | BAG12673.1 | naringenin 8-dimethylallyltransferase | *Sophora flavescens* |
| SfN8DT-3 | BAK52289.1 | naringenin 8-dimethylallyltransferase | *Sophora flavescens* |
| TaHGGT | AAP43912.1 | homogentisic acid geranylgeranyl transferase | *Triticum aestivum* |
| TaVTE2-1 | ABB70123.1 | homogentisate phytyltransferase VTE2-1 | *Triticum aestivum* |
| ZmVTE2-1 | ABB70122.1 | homogentisate phytyltransferase VTE2-1 | *Zea mays* |

FIG. 69B

STILBENOID PRENYLTRANSFERASES FROM PLANTS

CROSS-REFERENCE TO RELATED APPLICATIONS

This application claims priority to and is a continuation of U.S. patent application Ser. No. 15/625,450 filed on Jun. 16, 2017 entitled "STILBENOID PRENYLTRANSFERASES FROM PLANTS" which is a continuation in part of U.S. Patent Application No. 62/351,117 filed on Jun. 16, 2016 entitled "STILBENOID PRENYLTRANSFERASES FROM PEANUT."

STATEMENT REGARDING FEDERALLY SPONSORED RESEARCH OR DEVELOPMENT

This work was supported by USDA-NIFA Grant 2014-67014-21701, National Sciences Foundation-EPSCoR Grant EPS 0701890 (Center for Plant-Powered Production-P3), the National Science Foundation Division of Biological Infrastructure Grant ABI-1062432 to Indiana University (National Center for Genome Analysis Support), the Arkansas ASSET Initiative, the Arkansas Science & Technology Authority, and the Arkansas Biosciences Institute.

REFERENCE TO SEQUENCE LISTING SUBMITTED VIA EFS-WEB

The official copy of the sequence listing is submitted electronically via EFS-WEB as an ASCII (.txt) formatted sequence listing with a file named 20044_4-6-22_SEQ_ST25.txt, created on Apr. 7, 2022 and having a size of 72 KB and accompanies this specification. The sequence listing contained in this ASCII formatted document is part of the specification and is herein incorporated by reference in its entirety and includes no new matter.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

The present invention relates generally to prenylated stilbenoids and the production of prenylated stilbenoids.

II. Description of the Known Art

A substantial part of non-host defense responses in many plants is the pathogen-induced production of secondary metabolites, generally termed phytoalexins, that locally restrict disease progression due to bioactivities toxic to the pathogen (reviewed in Ahuja et al., 2012). Peanut or groundnut (*Arachis hypogaea*) tissues mount a defense against infection by the soil fungus *Aspergillus flavus* and other pathogens by overproducing stilbene derivatives around sites of wounding and elicitor perception (Sobolev, 2013).

SUMMARY OF THE INVENTION

The present invention is related to prenylated stilbenoids and a method of producing the prenylated stilbenoids. Harnessing the inducible bioproduction capabilities of the peanut hairy root culture system, we have newly produced a prenylated stilbenoid, i.e., arachidin-5, and have demonstrated that the prenyl moiety on peanut prenylated stilbenoids is derived from a plastidic biosynthesis pathway. We have characterized for the first time plant membrane-bound stilbenoid-specific prenyltransferase activity from the microsomal fraction of peanut hairy roots. With multidisciplinary approaches, we have isolated stilbenoid prenyltransferase genes and comprehensively characterized their functionality as stilbenoid prenyltransferase via a transient expression system in *Nicotiana benthamiana* and stable expression in tobacco plants and hairy roots. Moreover, we have observed the enzymatic degradation of exogenous resveratrol by peanut hairy root tissue, an observation that will lead to elucidation of further mechanisms governing phytoalexin accumulation in plants.

Prenylated stilbenoids synthesized in some legumes exhibit plant pathogen defense properties and pharmacological activities with potential benefits to human health. Despite their importance, the biosynthetic pathways of these compounds remain to be elucidated. Peanut (*Arachis hypogaea*) hairy root cultures produce a diverse array of prenylated stilbenoids upon treatment with elicitors. Using metabolic inhibitors of the plastidic and cytosolic isoprenoid biosynthetic pathways, we demonstrated that the prenyl moiety on the prenylated stilbenoids derives from a plastidic pathway. We further characterized for the first time a membrane-bound stilbenoid-specific prenyltransferase from the microsomal fraction of peanut hairy roots. This microsomal fraction-derived prenyltransferase utilizes 3,3-dimethylallyl pyrophosphate as a prenyl donor. The microsomal fraction also prenylates pinosylvin to chiricanine A and piceatannol to arachidin-5, a prenylated stilbenoid produced for the first time in this study. Using a transcriptomics and targeted metabolomics approach, we have isolated stilbenoid prenyltransferase genes from peanut and confirmed their functionality as stilbenoid prenyltransferase via a transient expression system in *Nicotiana benthamiana* and stable expression in tobacco plants and hairy roots.

Defense responses of peanut (*Arachis hypogaea*) include the synthesis of prenylated stilbenoids as phytoalexins in response to biotic and abiotic stresses. Despite their importance, the biosynthetic pathways of prenylated stilbenoids remain to be elucidated and genes encoding stilbenoid-specific prenyltransferases have yet to be identified in any plant species. In this study, we combined targeted transcriptome and metabolome analyses to discover prenyltransferase genes from elicitor-treated peanut hairy roots. Transcripts encoding five enzymes were identified, and two of these were functionally characterized in a transient expression system of *Agrobacterium*-infiltrated leaves of *Nicotiana benthamiana*. One of the prenyltransferases, AhR4DT-1, catalyzes a key reaction involved in the biosynthesis of prenylated stilbenoids, in which resveratrol is prenylated at its C-4 position to form arachidin-2, while another, AhR3'DT-1, was able to add the prenyl group to C-3' of resveratrol. Each of these prenyltransferases has a high specificity for stilbenoid substrates, and their subcellular location in the plastid was confirmed by fluorescence microscopy. Structure analysis of the prenylated stilbenoids suggest that these two prenyltransferase activities represent the first committed steps in the biosynthesis of a large number of prenylated stilbenoids and their derivatives in peanut.

Stilbenoids are phenylpropanoid compounds that accumulate in response to biotic and abiotic stresses in a small number of higher plant families including grape (Vitaceae), pine (Pinaceae) and peanut (Fabaceae). These compounds serve as phytoalexins and provide protection to the host plant against various microbial pathogens (Ahuja et al., 2012). Resveratrol (3,5,4'-trihydroxy-trans-stilbene), as the most studied compound in the stilbene family has attracted great attention in the scientific community, not only because of its important role for disease defense in plants (Ahuja et al., 2012), but also because of numerous bioactivities including anticancer, cardioprotective, antioxidant, anti-inflammatory and neuroprotective properties in human cell culture and in vivo, although the extent of its bioavailability has been questioned (Gambini et al., 2015; Tomé-Carneiro et al., 2013; Baur and Sinclair, 2006).

Interestingly, resveratrol is synthesized in peanut, along with stilbenoids conjugated to a prenyl group, a modification not common in other stilbene-producing plants (Aguamah et al., 1981; Cooksey et al., 1988; Sobolev et al., 2006). The prenylation of the stilbene backbone is the primary feature that contributes to the diversity of these peanut secondary metabolites. Differences occur in the position of prenylation as well as in subsequent modifications of the prenyl moiety, such as cyclization and hydroxylation. To date, more than 45 prenylated stilbenoids and their derivatives have been detected in peanut tissues subjected to biotic or abiotic stress (Wu et al., 2011; Sobolev, 2013; Sobolev et al., 2010, 2009, 2006, 2016). The prenylation of stilbenoids increases their lipophilicities and membrane permeabilities, and may have additional impacts on bioactivities. Prenylated stilbenoids have shown equivalent or enhanced bioactivities relative to non-prenylated forms, such as resveratrol, in in vitro studies (Huang et al., 2010; Chang et al., 2006; Sobolev et al., 2011). The prenylated stilbenoids arachidin-1 and arachidin-3 showed favorable metabolic profiles when compared to their non-prenylated analogs piceatannol and resveratrol (Brents et al., 2012). Furthermore, arachidin-1 and arachidin-3 exhibited specific bioactivities not found in their non-prenylated forms, such as inhibiting the replication of rotavirus in HT29.f8 cells (Ball et al., 2015). Also, prenylated stilbenoids showed higher affinity to human cannabinoid receptors when compared to non-prenylated stilbenoids (Brents et al., 2012).

Prenyltransferase(s) responsible for these stilbenoid modifications is/are crucial for the biosynthesis of peanut bioactive compounds of interest. To date however, no gene encoding a stilbenoid prenyltransferase has been identified in plants. Previously, we developed a peanut hairy root culture system to serve as a platform for sustainable production of prenylated stilbenoids (Yang et al., 2015; Condori et al., 2010). Leveraging this system more recently, we characterized biochemically the first stilbenoid-specific prenyltransferase activity from the microsomal fraction of these elicited cultures (Yang et al., 2016). This prenyltransferase utilizes plastid-derived dimethylallyl pyrophosphate (DMAPP) to prenylate resveratrol or piceatannol into arachidin-2 or arachidin-5, respectively, and shares several features in common with flavonoid prenyltransferases reported in other legume species. For instance, all identified flavonoid and stilbenoid prenyltransferase enzymatic reactions require divalent cations as cofactors, and show maximum activity at basic pH (Sasaki et al., 2008; Akashi et al., 2008; Sasaki et al., 2011; Shen et al., 2012; Li et al., 2014; Chen et al., 2013; Yang et al., 2016). These characteristics and others guided cloning of the peanut prenyltransferase genes described here. We took a dual approach, combining parallel targeted transcriptome and metabolome analyses to isolate prenyltransferase activities. We generated extensive RNAseq data assemblies designed to capture elicitor-induced mRNAs, and used these sequences to clone potential prenyltransferase cDNAs. Here we describe the first transcripts to be identified as encoding stilbenoid-specific prenyltransferase enzymes. These catalyze two distinct dimethylallylation reactions in the biosynthesis of prenylated stilbenoids. Functionalities of the enzymes are uncovered using a transient expression system of *Agrobacterium*-infiltrated *Nicotiana benthamiana* leaves, and their subcellular location is proposed from fluorescence microscopy imaging in particle-bombarded onion epidermal cells. We further use available genome assemblies of the two diploid progenitors of *A. hypogaea* to align the prenyltransferase transcripts and estimate their genomic structure.

It is an object of the present invention to isolate or purify nucleic acid molecules comprising a gene sequence that encodes a polypeptide having stilbenoid prenyltranferase activity.

It is another object of the present invention to produce a prenylated stilbenoid in an organism, cell or tissue, said method comprising the expression or over-expression of a gene that encodes for a stilbenoid prenyltransferase.

It is another object of the present invention to produce a prenylated stilbenoid in an organism wherein the organism is peanut, tobacco, grape, muscadine, *Polygonum*, pine, or yeast.

It is another object of the present invention to produce a prenylated stilbenoid in an organism wherein the method comprises expressing a gene sequence that encodes a polypeptide having stilbenoid prenyltransferase activity in an organism, including but not limited to, peanut, tobacco, grape, muscadine, *Polygonum*, pine, or yeast.

It is another object of the present invention to provide a new prenylated stilbenoid.

It is another object of the present invention to provide an improved method of producing a prenylated stilbenoid.

It is another object of the present invention to provide a method of producing the improved stilbenoid.

It is another object of the present invention to produce the stilbenoid in greater quantities.

It is another object of the present invention to provide a more effective stilbenoid.

It is another object of the present invention to provide a method of producing the more effective stilbenoid.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 1 shows A, Structure of stilbene backbone and main prenylation patterns found on peanut prenylated stilbenoids. B, Chemical structures of stilbenoids identified in elicited peanut hairy roots: (a) resveratrol; (b) piceatannol; (c)

arachidin-2; (d) arachidin-5; (e) arachidin-3; (f) arachidin-1. All compounds are shown in their trans isomers.

Figure 2:
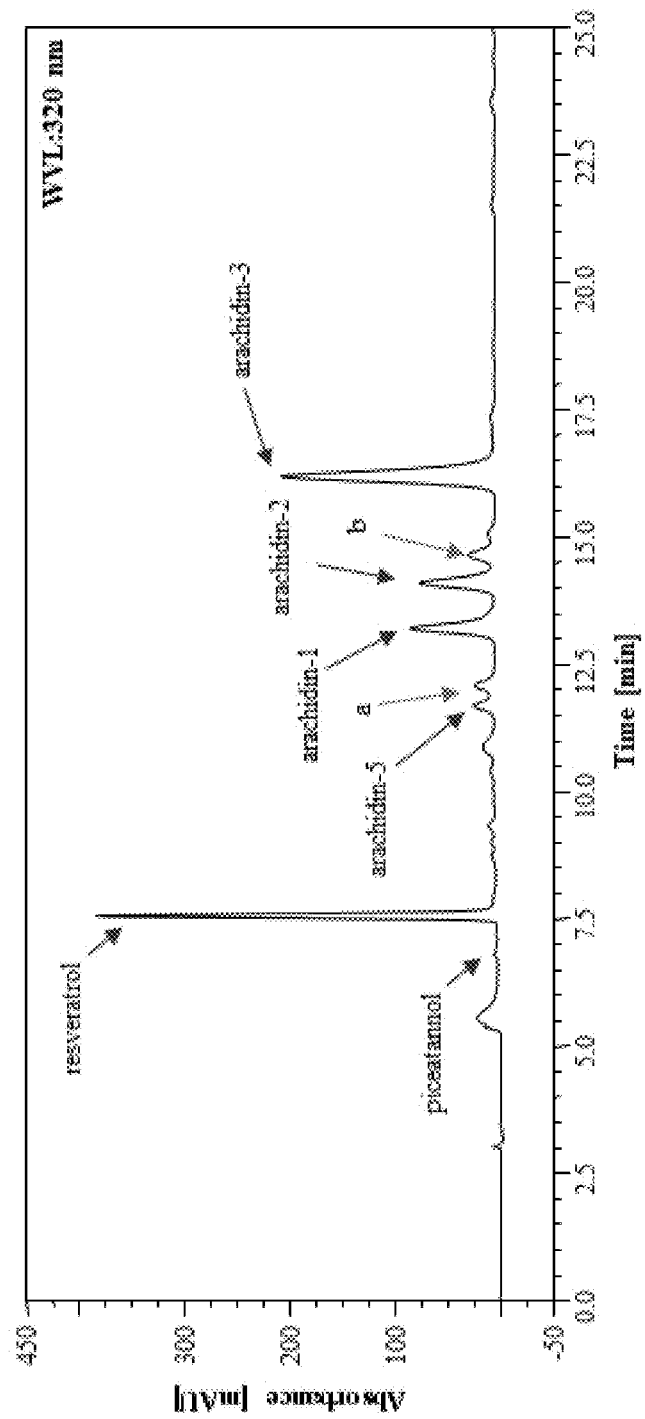

FIG. 2 shows a HPLC chromatogram (UV 320 nm) of ethyl acetate extract from peanut hairy root culture medium after 72 h post treatment with 100 μM methyl jasmonate and 9 g/L methyl-β-cyclodextrin. a, arachidin-5 derivative; b, arachidin-2 derivative.

Figure 3:
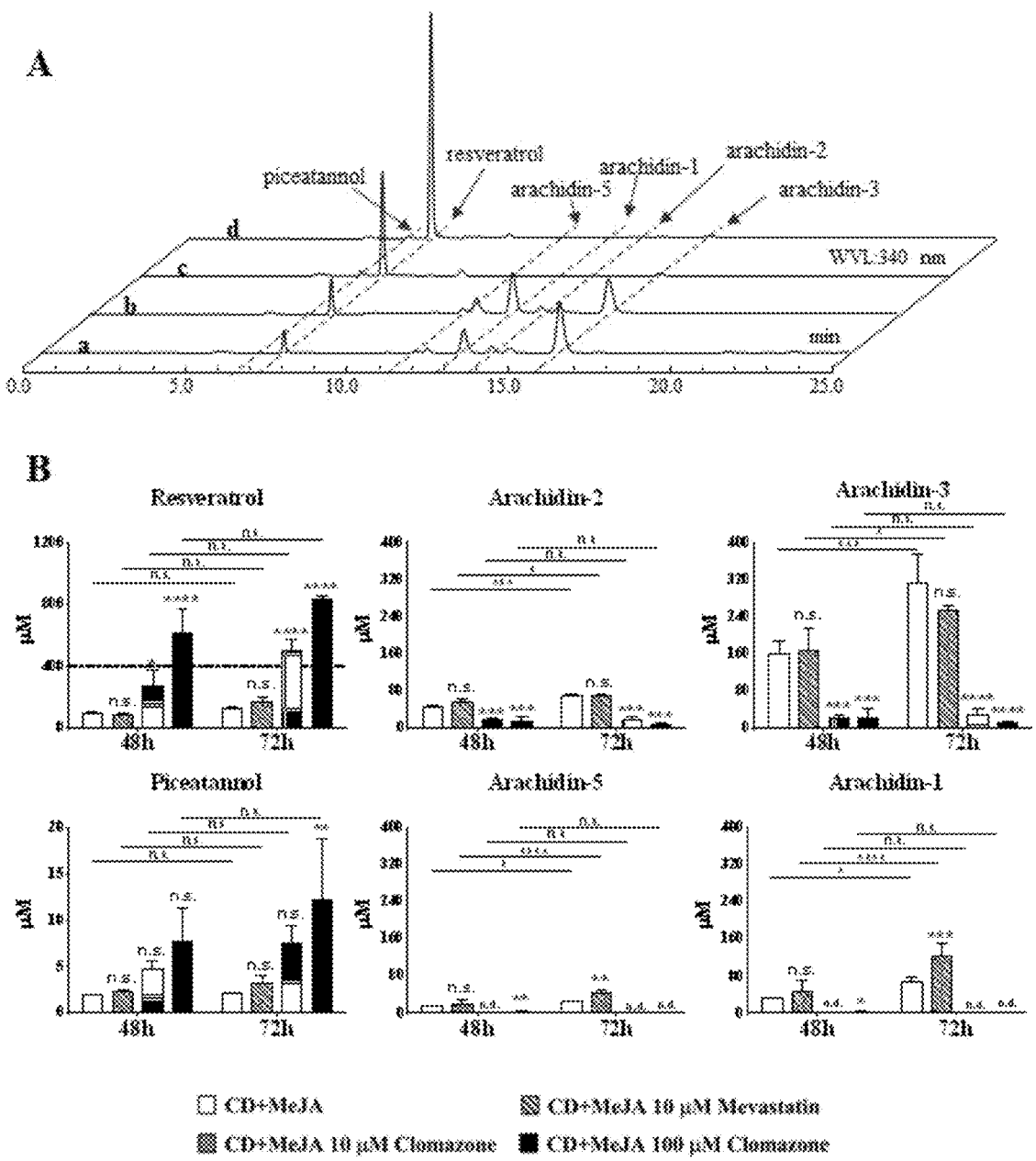

FIG. 3 shows effects of mevastatin and clomazone on the production of stilbenoids in elicited peanut hairy root culture. A, HPLC chromatograms (UV 340 nm) of ethyl acetate extracts from peanut hairy root cultures after 48-hour treatment with (a) 100 μM methyl jasmonate (MeJA) and 9 g/L methyl-β-cyclodextrin (CD); (b) 100 μM MeJA, 9 g/L CD, and 10 μM mevastatin; (c) 100 μM MeJA, 9 g/L CD, and 10 μM clomazone and (d) 100 μM MeJA, 9 g/L CD, and 100 μM clomazone. B, Yields of resveratrol, arachidin-2, arachidin-3, piceatannol, arachidin-5, and arachidin-1 after 48 hour and 72 hour co-treatment of 10 μM mevastatin, 10 μM or 100 μM clomazone with elicitors (CD+MeJA). Values shown are the average mM yield of three replicates and error bars represent standard deviation. The asterisks above bars represent significant difference when compared to the group treated with MeJA and CD alone (*, $p<0.05$; , $p<0.01$; *, $p<0.001$; ****, $p<0.0001$; n.s., not significant; n.d., not detected); and the asterisks above the connecting line represent significant difference between 48 hour and 72 hour treatments (*, $p<0.05$; *, $p<0.001$; **, $p<0.0001$; n.s., not significant). Statistical analyses were performed by two-way ANOVA with Dunnett's and Sidak's multiple-comparisons test respectively.

Figure 4:
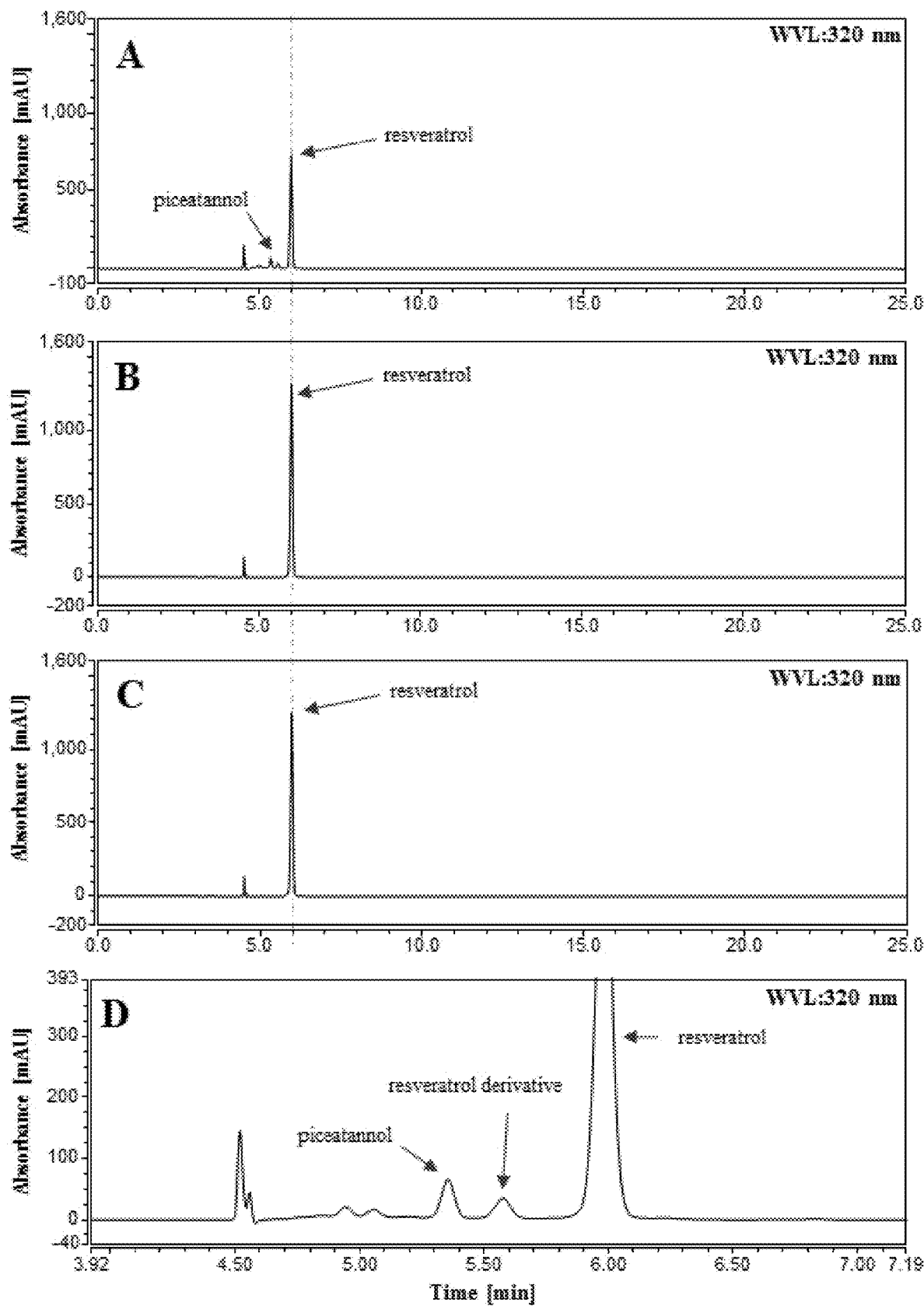

FIG. 4 shows enzymatic degradation of resveratrol by crude cell-free protein extract from non-elicited peanut hairy root. HPLC chromatograms (UV 320 nm) of ethyl acetate extracts from the incubation mixtures contained 1 mM resveratrol with (A) 50 μg crude cell-free protein extract for 30 min; (B) 50 μg heat-denatured crude cell-free protein extract for 30 min; (C) 50 μg crude cell-free protein extract and additional 5 mM DTT for 120 min. All reactions were done in a pH 7.6 Tris-HCl buffer. (D) Close-up (3.92-7.19 min) of chromatogram shown in (A).

Figure 5:
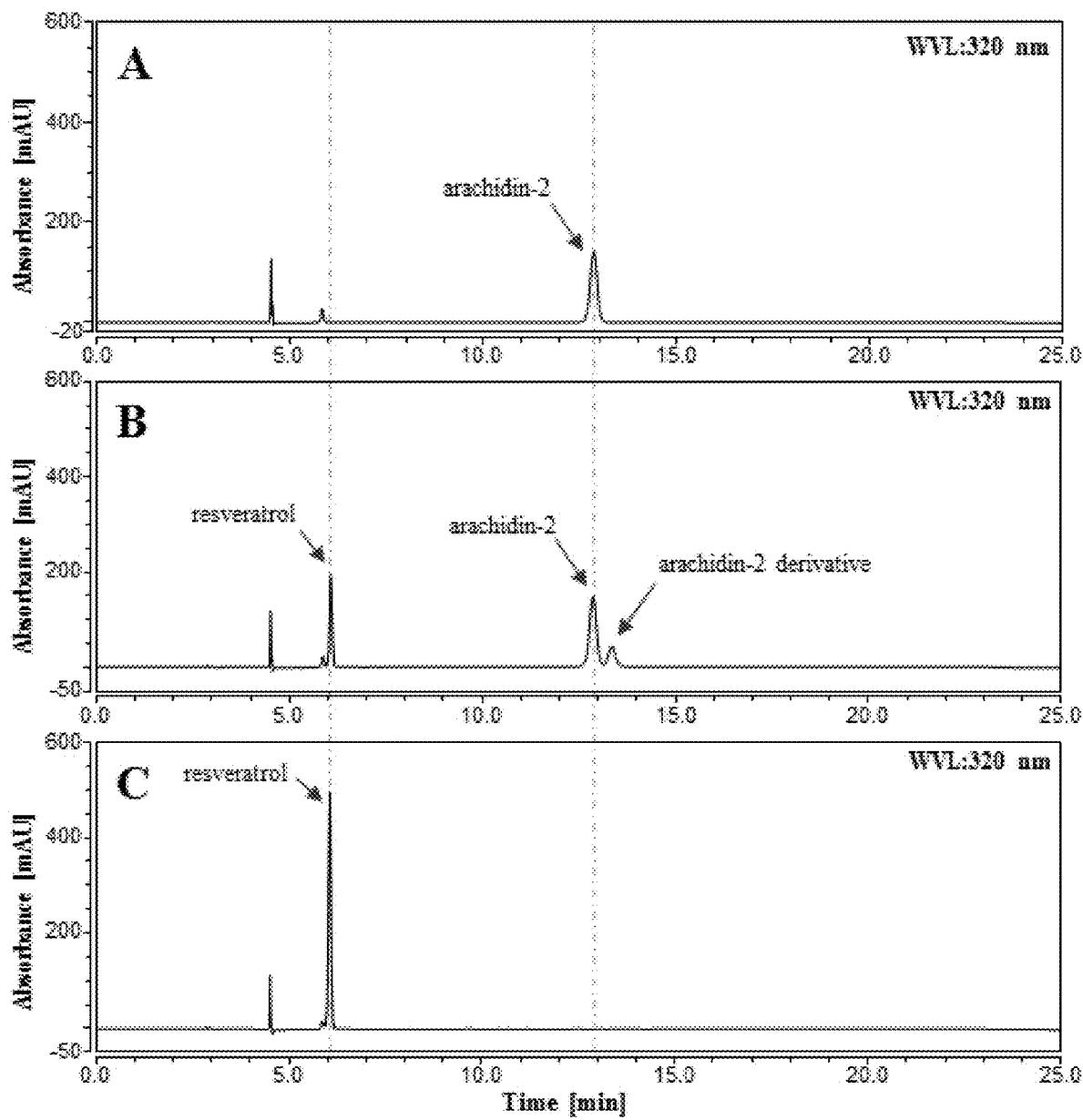

FIG. 5 shows resveratrol prenyltransferase activity in microsomal fraction of elicited peanut hairy root. HPLC chromatograms (UV 320 nm) of (A) purified arachidin-2; (B) ethyl acetate extract of 500 μl reaction mixture containing 30 μg microsomal fraction, 100 μM resveratrol, 300 μM DMAPP, 10 mM $MgCl_2$ and 5 mM DTT (C) ethyl acetate extract of 500 μl reaction mixture containing heat-denatured 30 μg microsomal fraction, 100 μM resveratrol, 300 μM DMAPP, 10 mM $MgCl_2$ and 5 mM DTT. All reactions were done for 60 min in a pH 9.2 Tris-HCl buffer.

FIG. 6 shows substrate specificity of resveratrol prenyltransferase in microsomal fraction of elicited peanut hairy root. A, Chemical structures of prenyl acceptors used for substrate specificity analysis and their prenylated products: stilbenoids (a1, resveratrol, a2 arachidin-2; b1, piceatannol, b2, arachidin-5; c1, pinosylvin, c2, chiricanine-A, d, oxyresveratrol and e, pterostilbene), flavanone (e, naringenin), flavone (f, apigenin) and isoflavone (g, genistein). B, Prenylation activity of microsomal fraction with various prenyl acceptors. Values are the average of 2 replicates and error bars represent standard deviation (n.d., not detected).

FIG. 7 shows a table of detected stilbenoids.

FIG. 8 shows a table of resveratrol prenyltransferase activity.

Figure 9:
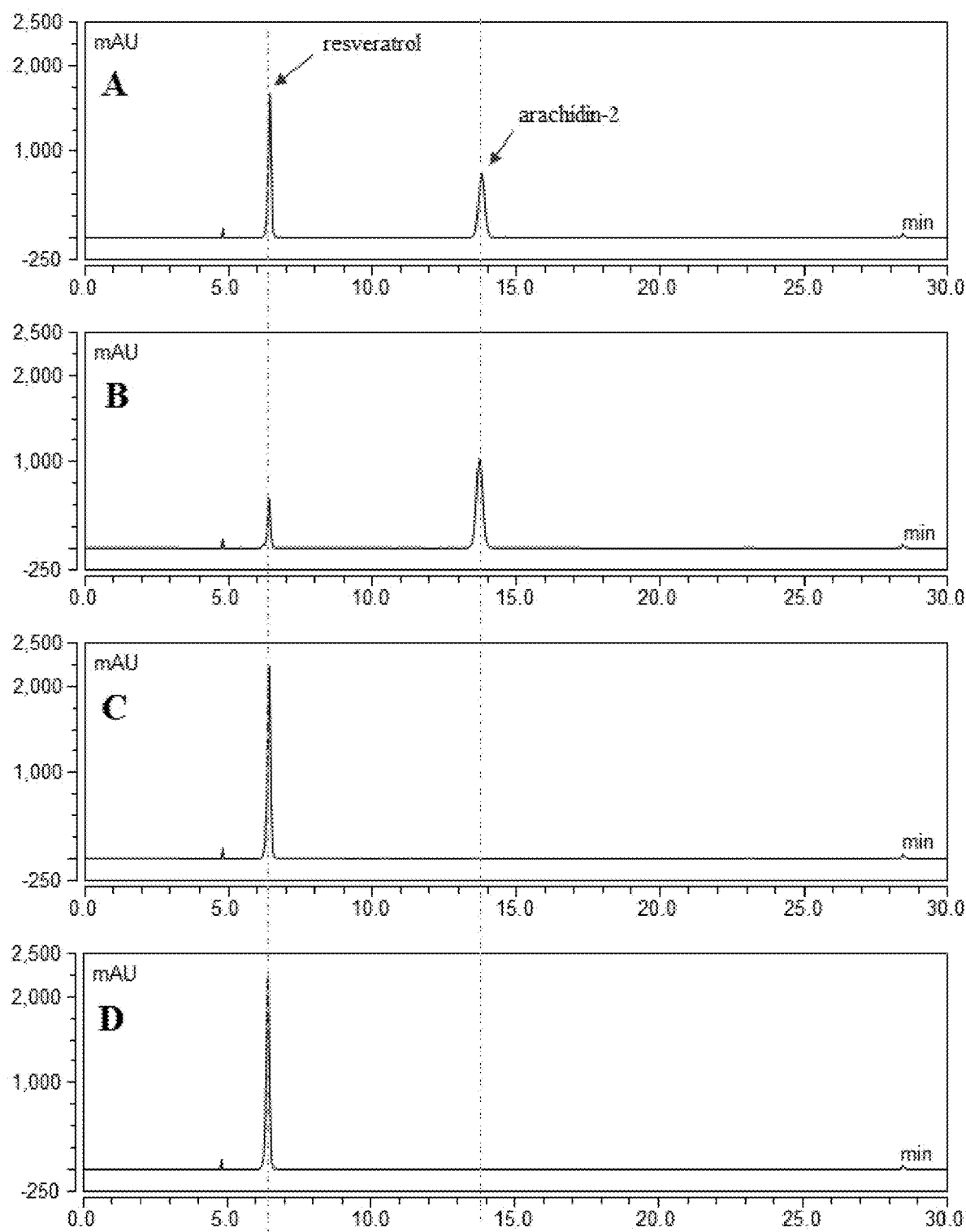

FIG. 9 shows enzymatic characterization of AhR4DT transiently expressed in Nicotiana benthamiana leaf HPLC chromatograms (UV 320 nm) of ethyl acetate extraction of 1000 μl reaction mixture of 200 μM resveratrol, 600 μM DMAPP, 10 mM $MgCl_2$ and 10 mM DTT incubated with 50 μl crude protein of Nicotiana benthamiana leaf after vacuum infiltration with Agrobacterium tumefaciens LBA4404 harboring pBIBKan-9b13 binary vector for (A) 48 hours and (B) 72 hours in a pH 9.2 Tris-HCl buffer for 40 min. Chromatograms of the reactions with (C) heated denatured protein) and (D) no DMAPP added for control.

Figure 10:
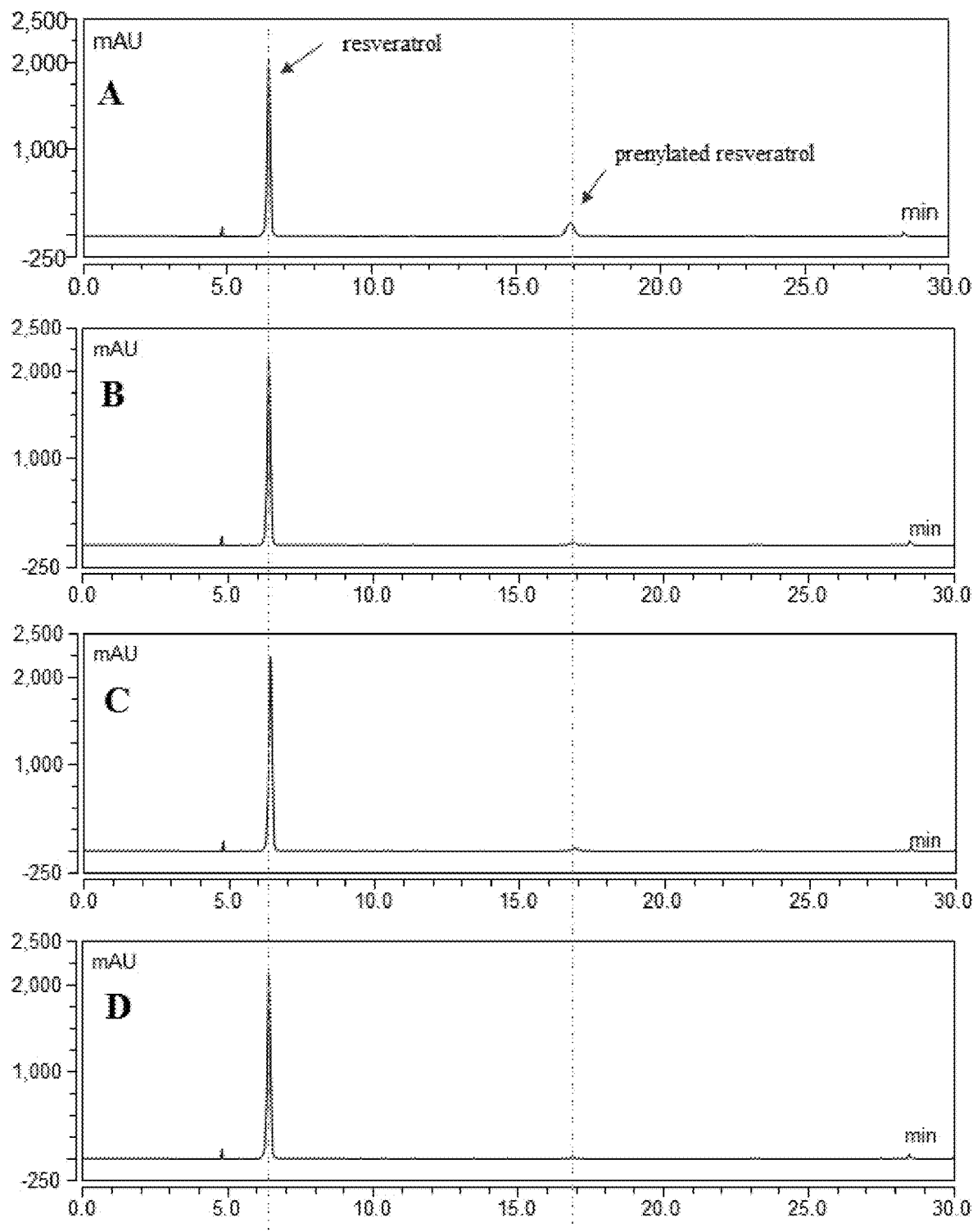

FIG. 10 shows enzymatic characterization of resveratrol prenyltransferase transiently expressed in Nicotiana benthamiana leaf HPLC chromatograms (UV 320 nm) of ethyl acetate extraction of 1000 μl reaction mixture of 200 μM resveratrol, 600 μM DMAPP, 10 mM $MgCl_2$ and 10 mM DTT incubated with 50 μl crude protein of Nicotiana benthamiana leaf after vacuum infiltration with Agrobacterium tumefaciens LBA4404 harboring (A) pBIBKan-10k1; (B) pBIBKan-4e1; (C) pBIBKan-4e10 and (D) pBIBKan-5m3 binary vectors in a pH 9.2 Tris-HCl buffer for 40 min.

Figure 11:
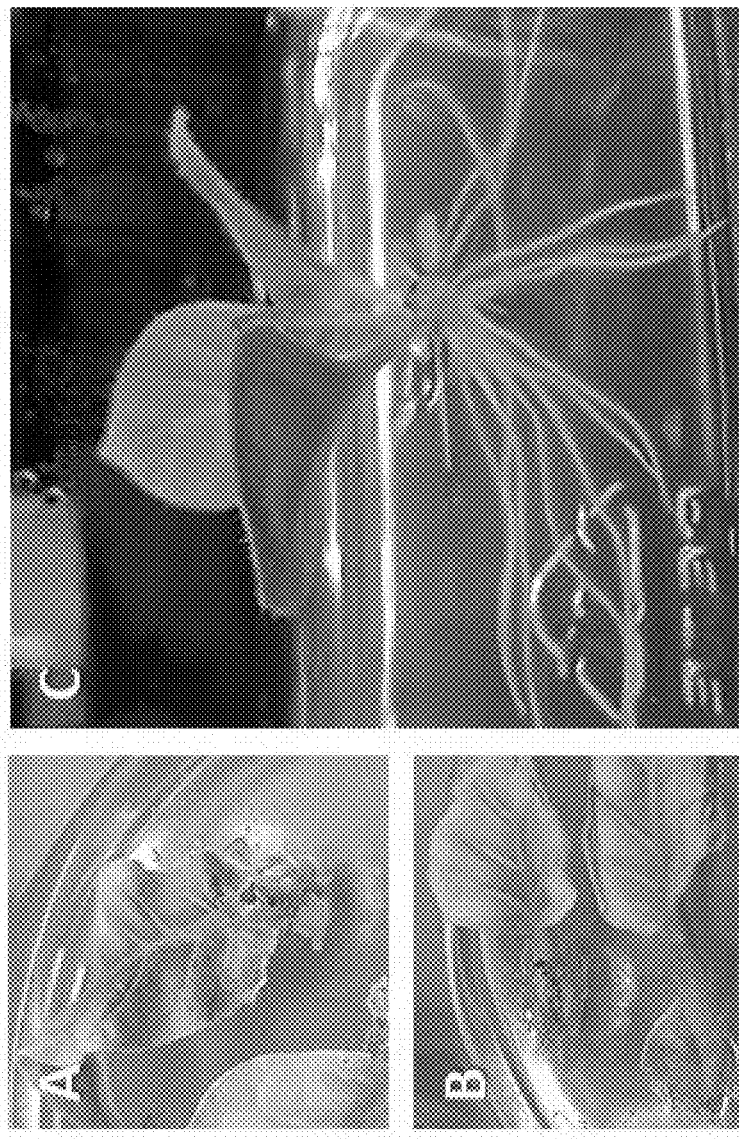

FIG. 11 shows the development of transgenic tobacco plants expressing a stilbenoid-specific prenyltransferase from peanut. A, B: Regenerated shoots from the Agrobacterium inoculation sites. C: Rooting of transgenic tobacco plant.

FIG. 12 shows a sequence view of the nucleotide sequence (SEQ ID NO:3) and amino acid sequence (SEQ ID NO:2) of stilbenoid-specific prenyltransferase AhR4DT-9b13 (renamed as AhR4DT-1; GenBank accession No. KY565244) (SEQ ID NO:1) involved in the biosynthesis of arachidin-2.

FIG. 13 shows a sequence view of the nucleotide sequence (SEQ ID NO:6) and amino acid sequence (SEQ ID NO:5) of stilbenoid prenyltransferase AhRPT-4e1 (Renamed as AhR3'DT-2; GenBank Accession No. KY565246) (SEQ ID NO:4).

FIG. 14 shows a sequence view of the nucleotide sequence (SEQ ID NO:9) and amino acid sequence (SEQ ID NO:8) of stilbenoid prenyltransferase AhRPT-4e10 (Renamed as AhR3'DT-3; GenBank Accession No. KY565247).

FIG. 15 shows a sequence view of the nucleotide sequence (SEQ ID NO:12) and amino acid sequence (SEQ ID NO:11) of stilbenoid prenyltransferase AhRPT-5m3 (Renamed as AhR3'DT-4; GenBank Accesion No. KY565248) (SEQ ID NO:10).

FIG. 16 shows a sequence view of the nucleotide sequence (SEQ ID NO:15) and amino acid sequence (SEQ ID NO:14) of stilbenoid prenyltransferase AhRPT-10k1 (AC1) (Renamed as AhR3'DT-1; GenBank Accesion No. KY565245) (SEQ ID NO:13).

Figure 17:
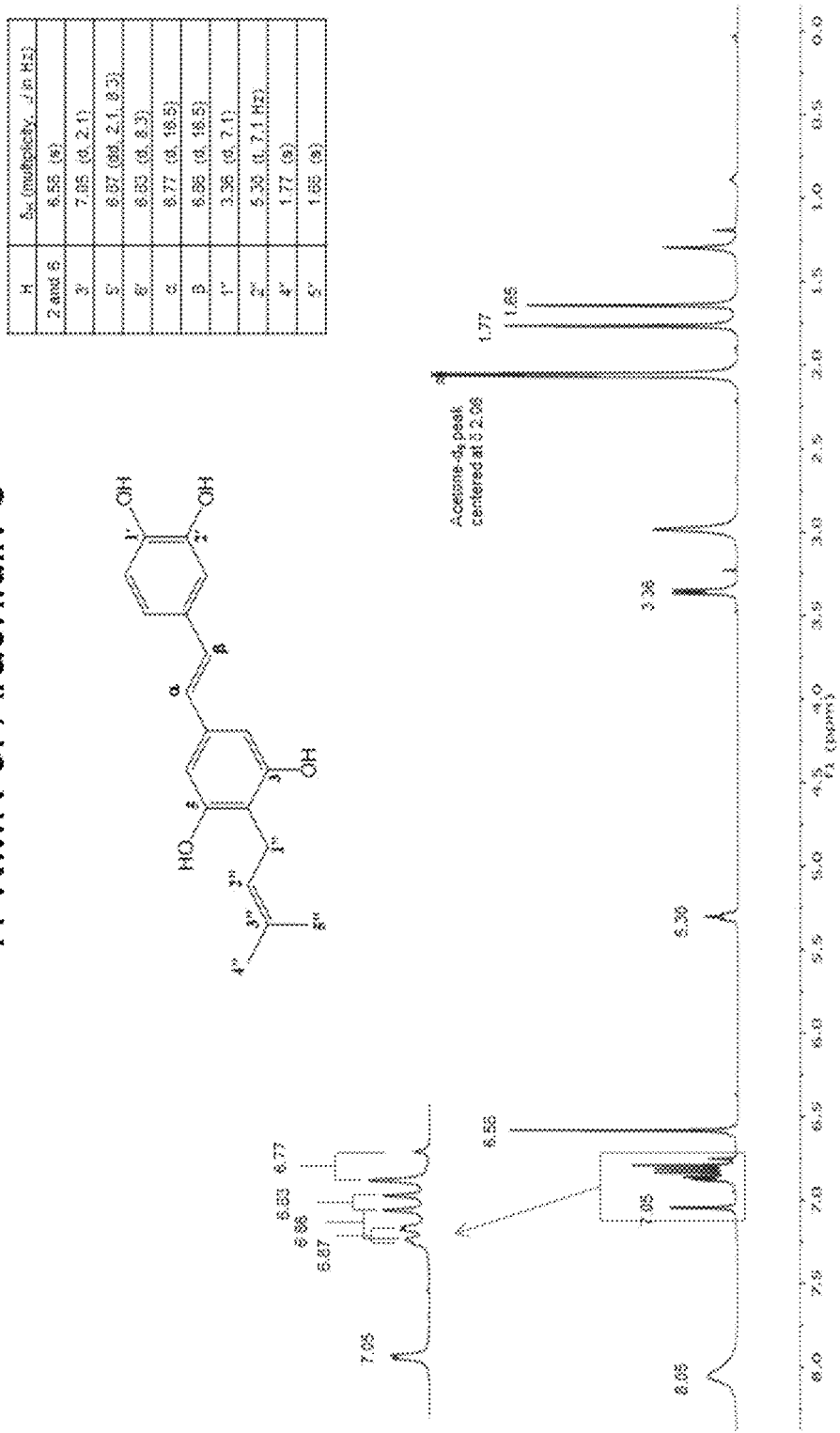

FIG. 17 shows $^1H$ NMR analysis of arachidin-5. $^1H$ NMR was recorded at 400 MHz in acetone-$d_6$ on a Bruker AV-400 NMR spectrometer.

Figure 18:
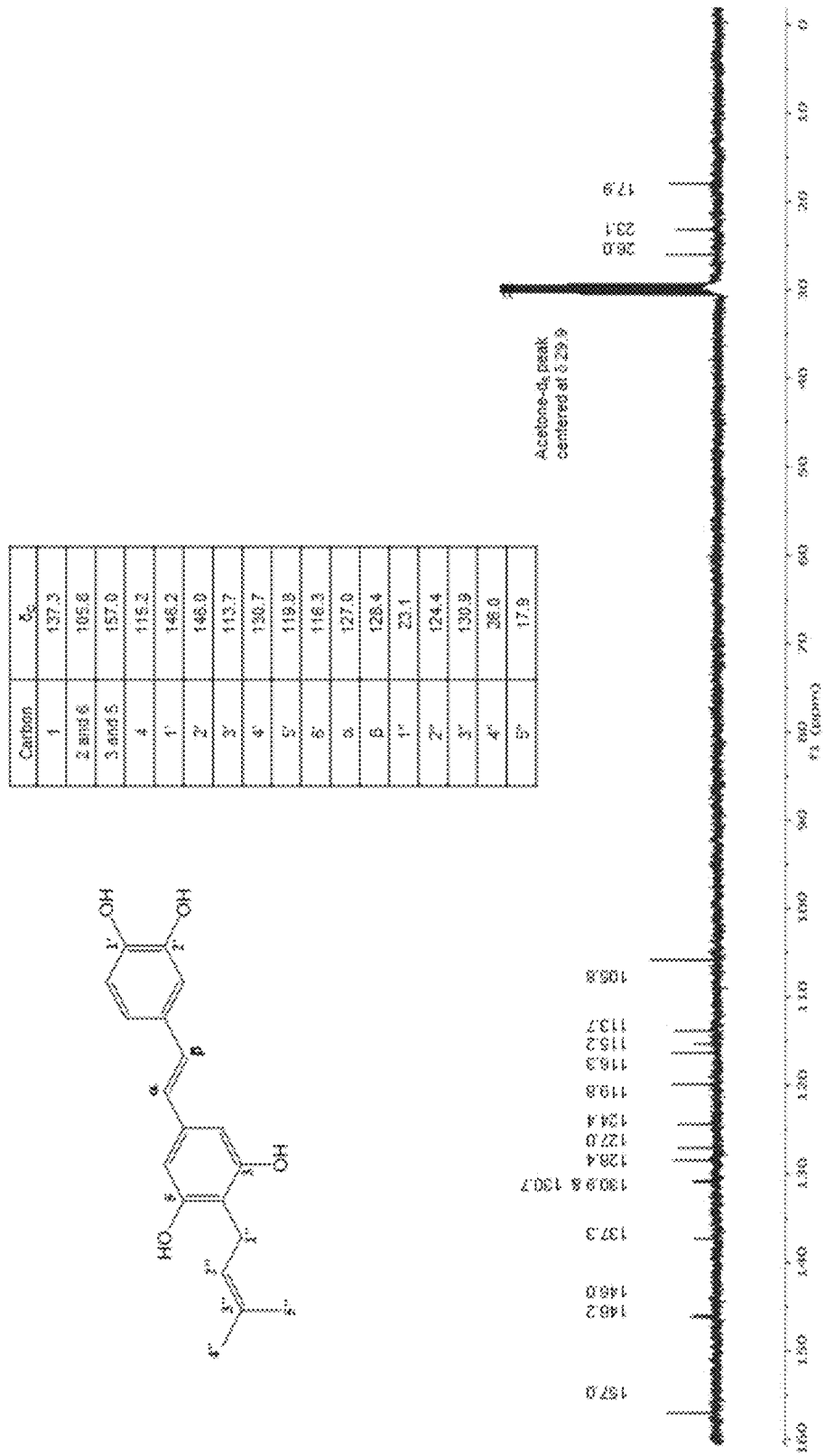

FIG. 18 shows $^{13}C$ NMR analysis of arachidin-5. $^{13}C$ NMR was recorded at 100 MHz in acetone-$d_6$ on a Bruker AV-400 NMR spectrometer.

Figure 19:
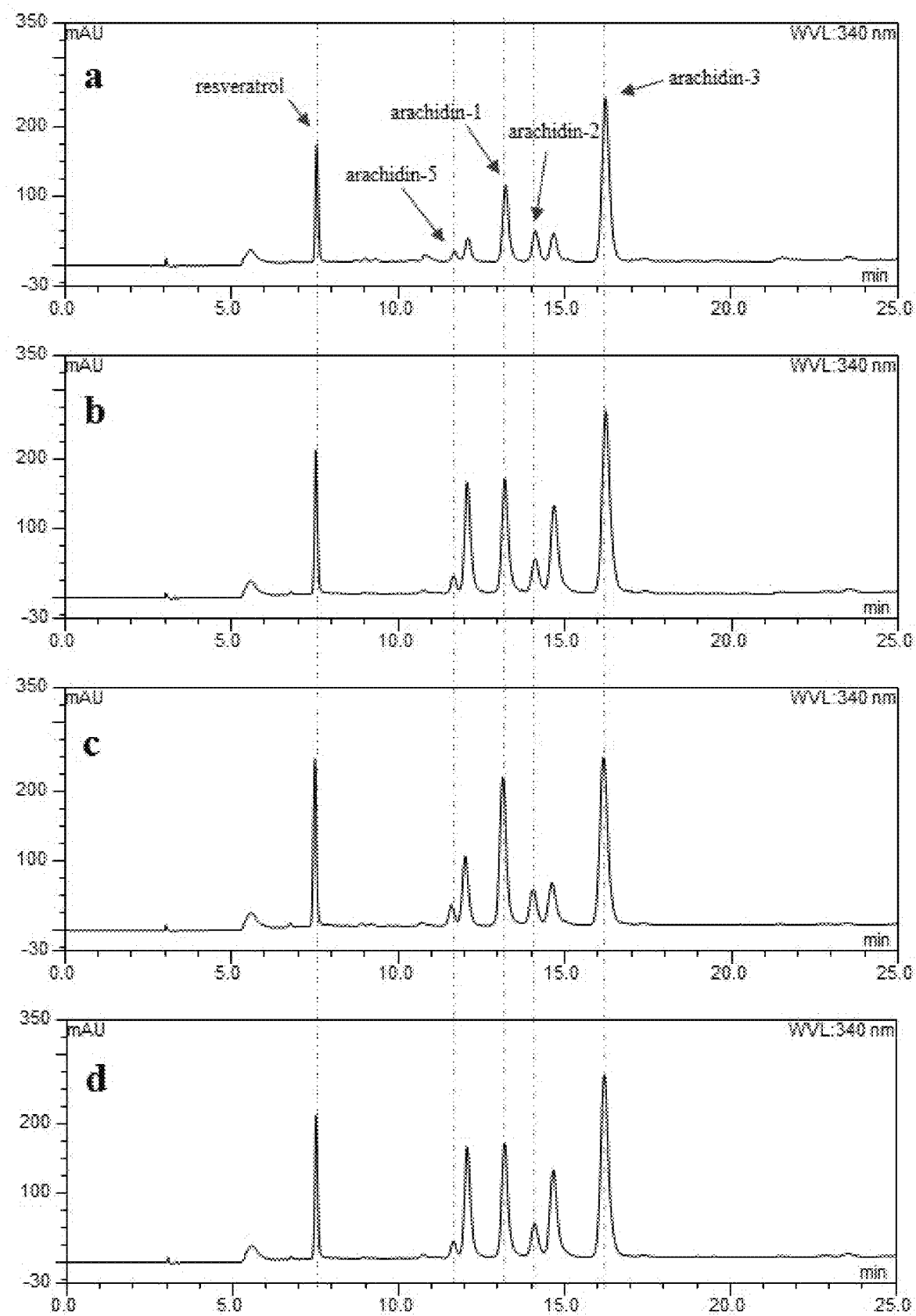

FIG. 19 shows effect of mevastatin on the production of stilbenoids in elicited peanut hairy root culture. HPLC chromatograms (UV 340 nm) of ethyl acetate extracts from peanut hairy root cultures after 48-hour treatment with (A) 100 μM methyl jasmonate (MeJA) and 9 g/L methyl-β-cyclodextrin (CD); (B) 100 μM MeJA, 9 g/L CD, and 1 μM mevastatin; (C) 100 μM MeJA, 9 g/L CD, and 10 μM mevastatin and (D) 100 μM MeJA, 9 g/L CD, and 100 μM mevastatin.

Figure 20:
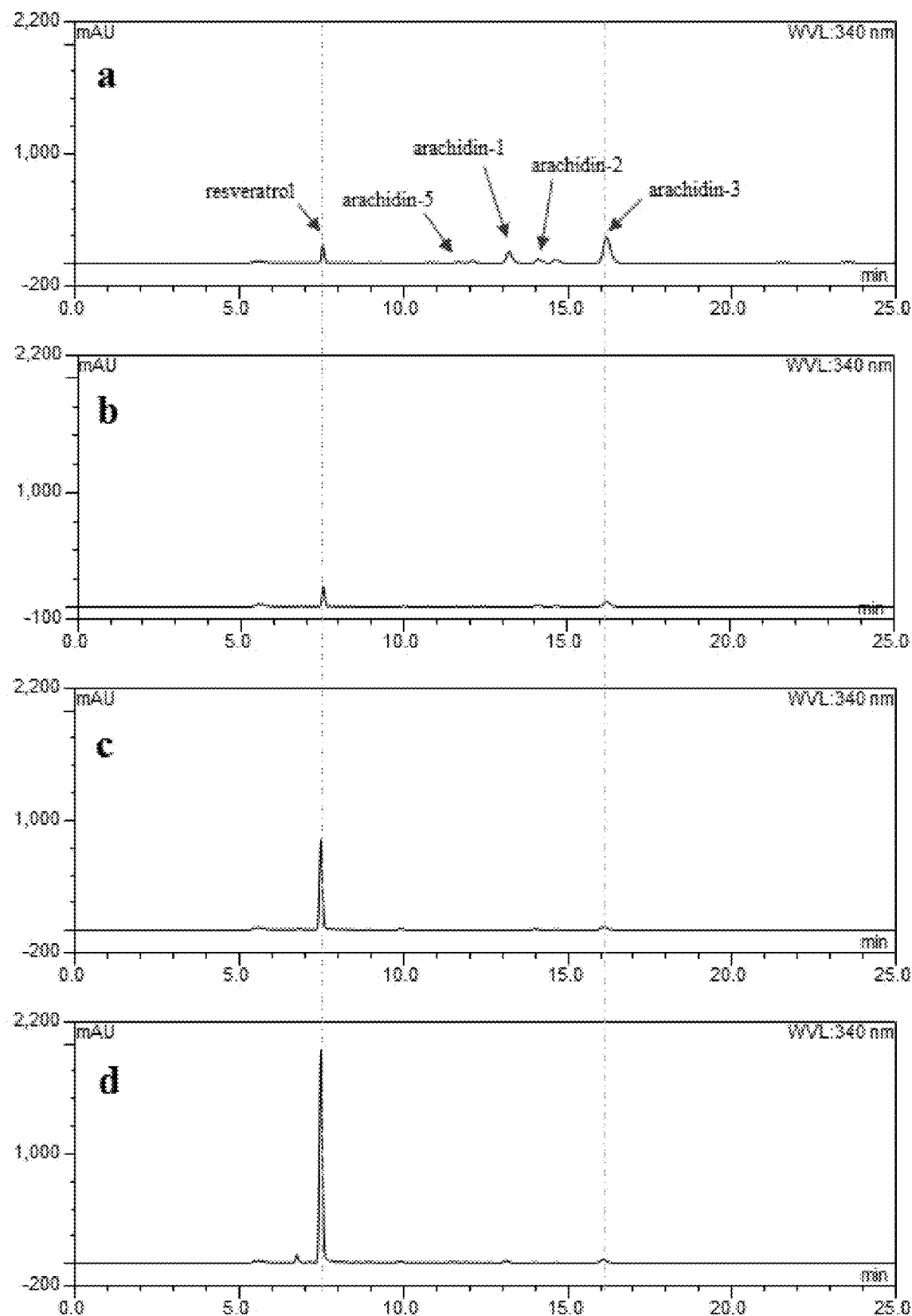

FIG. 20 shows effect of clomazone on the production of stilbenoids in elicited peanut hairy root culture. HPLC chromatograms (UV 340 nm) of ethyl acetate extracts from peanut hairy root cultures after 48-hour treatment with (A)

100 μM methyl jasmonate (MeJA) and 9 g/L methyl-β-cyclodextrin (CD); (B) 100 μM MeJA, 9 g/L CD, and 1 μM clomazone; (C) 100 μM MeJA, 9 g/L CD, and 10 μM clomazone and (D) 100 μM MeJA, 9 g/L CD, and 100 μM clomazone.

Figure 21:
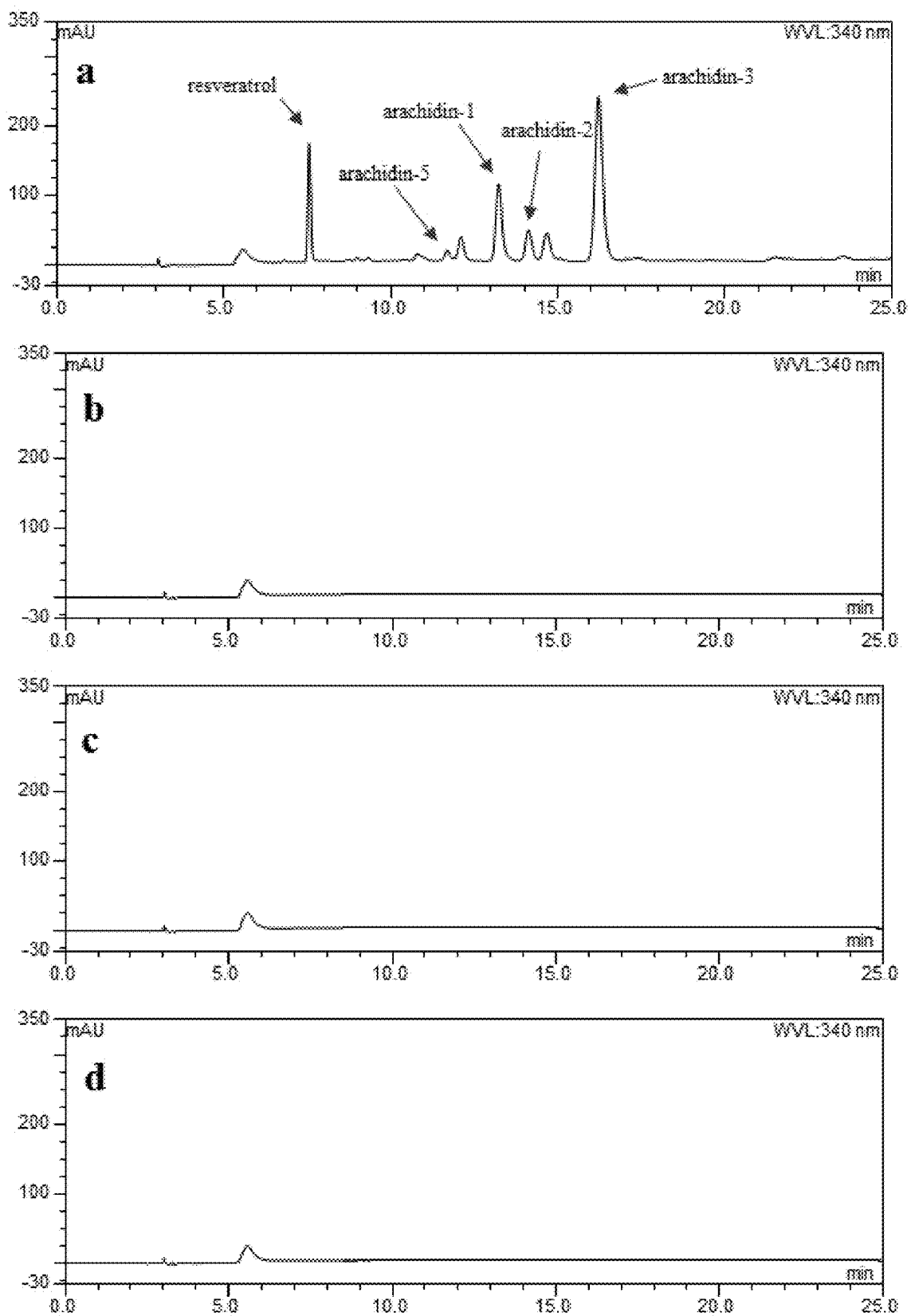

FIG. 21 shows effect of clomazone on the production of stilbenoids in non-elicited peanut hairy root culture. HPLC chromatograms (UV 340 nm) of ethyl acetate extracts from peanut hairy root cultures after 48-hour treatment with (A) 100 μM methyl jasmonate and 9 g/L methyl-β-cyclodextrin; (B) 10 μM clomazone; (C) 50 μM clomazone and (D) 100 μM clomazone.

Figure 22:
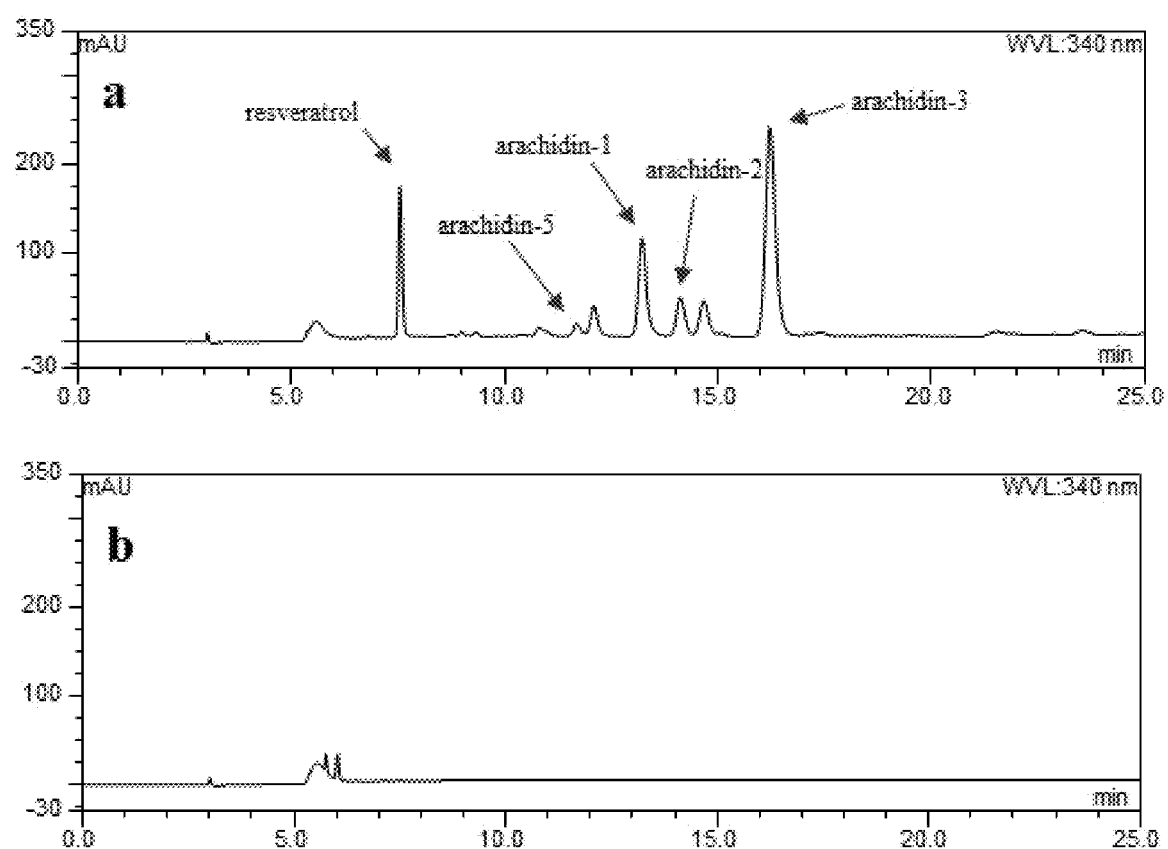

FIG. 22 shows comparison of stilbenoid yields from the culture medium and root tissue. Ethyl acetate extracts were prepared from elicited peanut hairy root cultures. HPLC chromatograms (UV 340 nm) of ethyl acetate extract from (A) culture medium and (B) lyophilized root tissue. Cultures were elicited for 48 hours with 100 μM methyl jasmonate and 9 g/L methyl-β-cyclodextrin.

Figure 23:
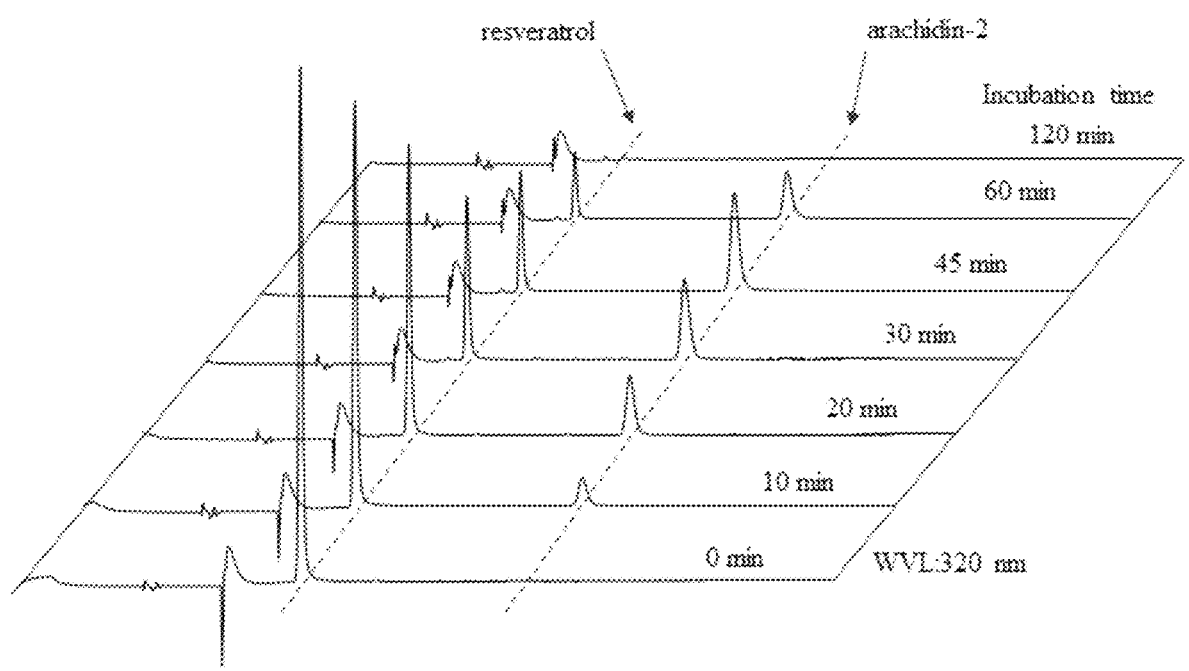

FIG. 23 shows time course of resveratrol prenyltransferase assay without DTT and subsequent degradation of resveratrol and arachidin-2 in the reaction. Assays were done for 0 to 120 min. HPLC chromatograms (UV 320 nm) of ethyl acetate extracts from the reaction mixture of 30 μg microsomal fraction, 100 μM resveratrol, 300 μM DMAPP, and 10 mM $MgCl_2$. Assays were done for 0, 10, 20, 30, 45, 60 or 120 min in a pH 9.2 Tris-HCl buffer.

Figure 24:
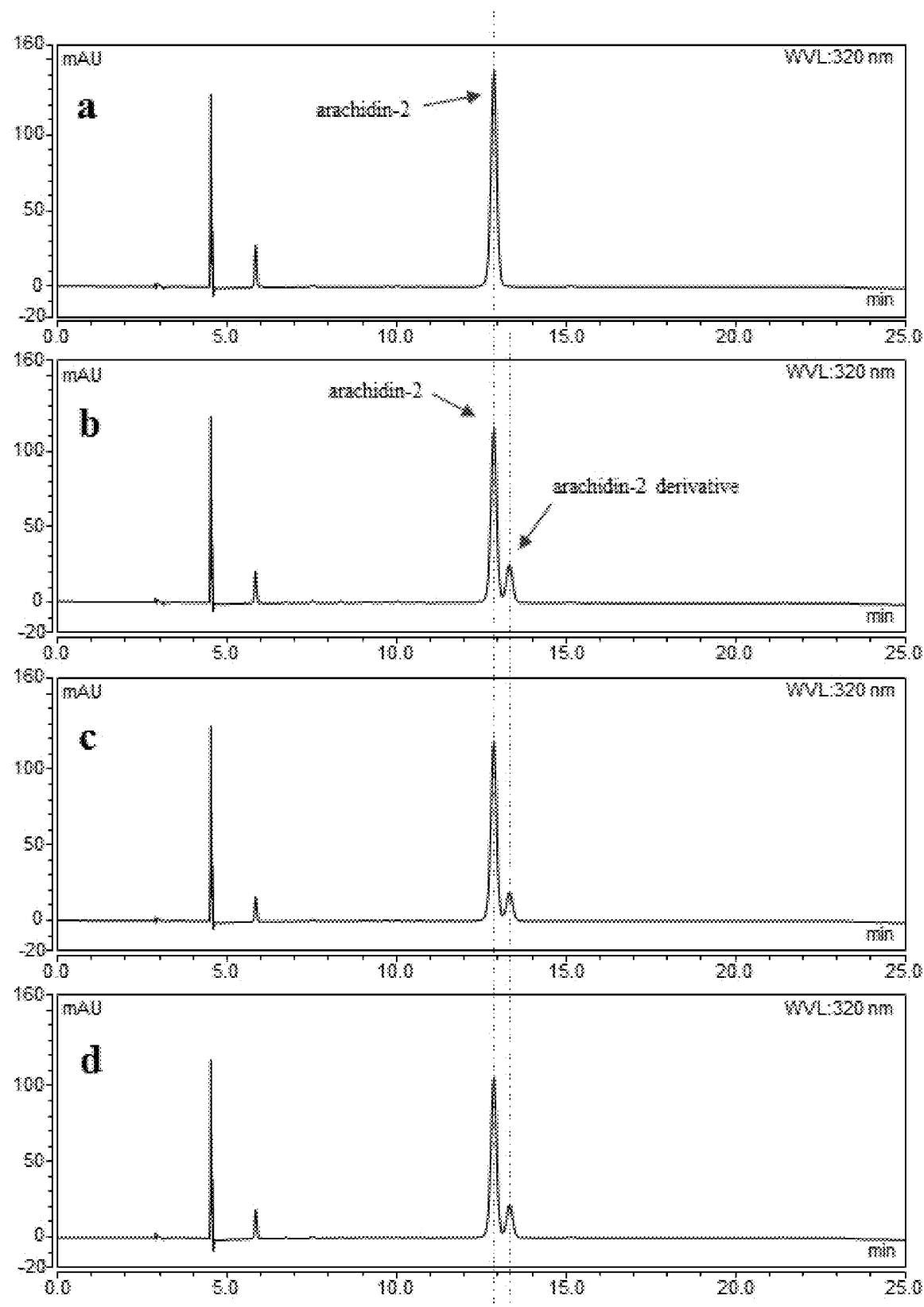

FIG. 24 shows biotransformation of arachidin-2 by protein extracts from elicited peanut hairy root culture. HPLC chromatograms (UV 320 nm) of ethyl acetate extracts from the 60 min reaction contained (a) 100 μM arachidin-2 with 30 μg heat-denatured crude cell-free protein extract as control; (b) 30 μg crude cell-free protein extract; (c) 30 μg microsomal fraction and (d) 30 μg 156,000 g supernatant. All reactions were done in a pH 9.2 Tris-HCl buffer.

Figure 25:
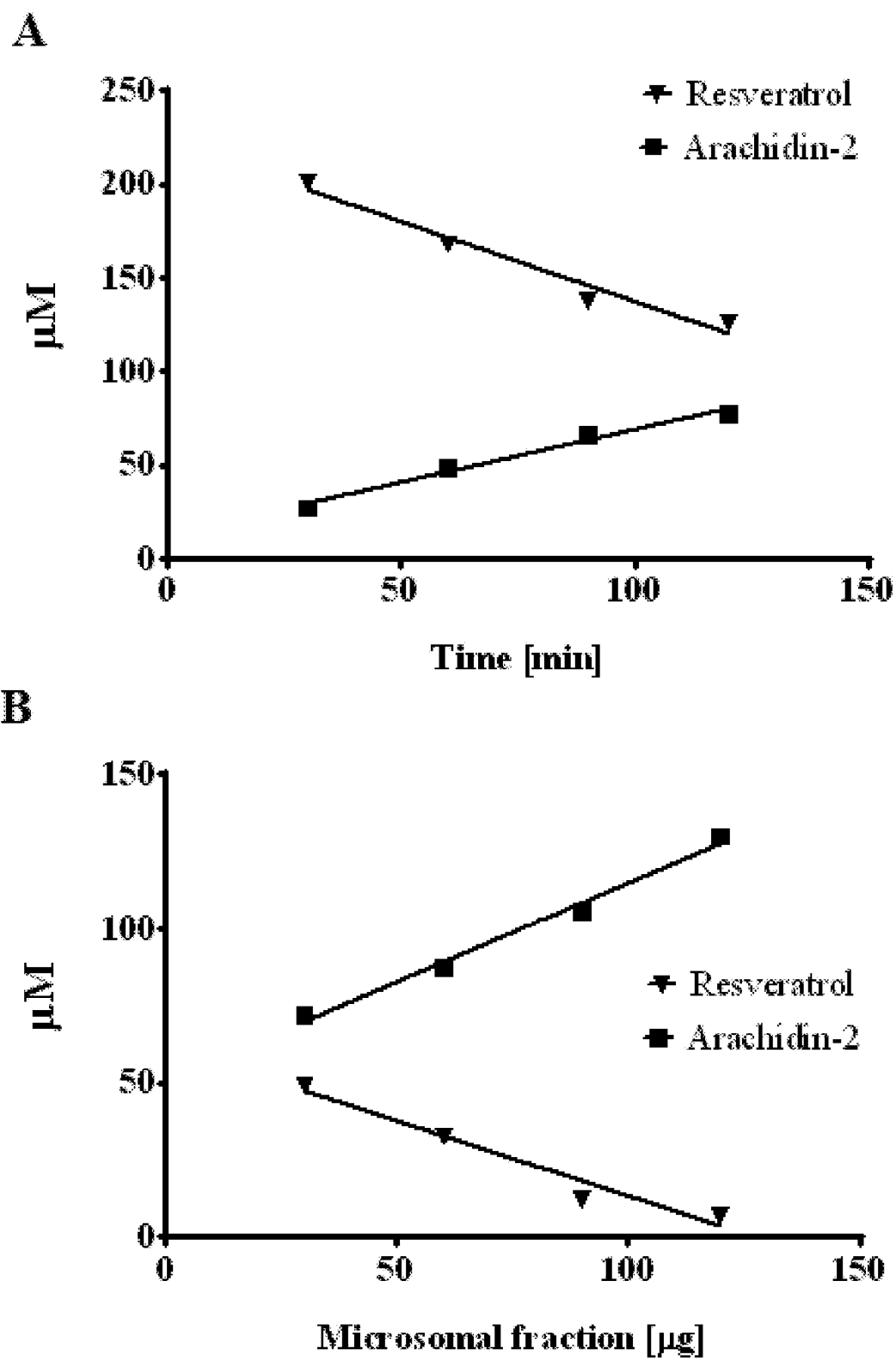

FIG. 25 shows resveratrol prenyltransferase activity. A, Concentrations of remaining resveratrol and generated arachidin-2 from the reaction mixtures with varying incubation times (30, 60, 90 and 120 min) were measured by HPLC. B, Concentrations of remaining resveratrol and generated arachidin-2 from the reaction mixtures with varying amounts of microsomal fraction (30, 60, 90 and 120 μg) were measured by HPLC.

Figure 26:
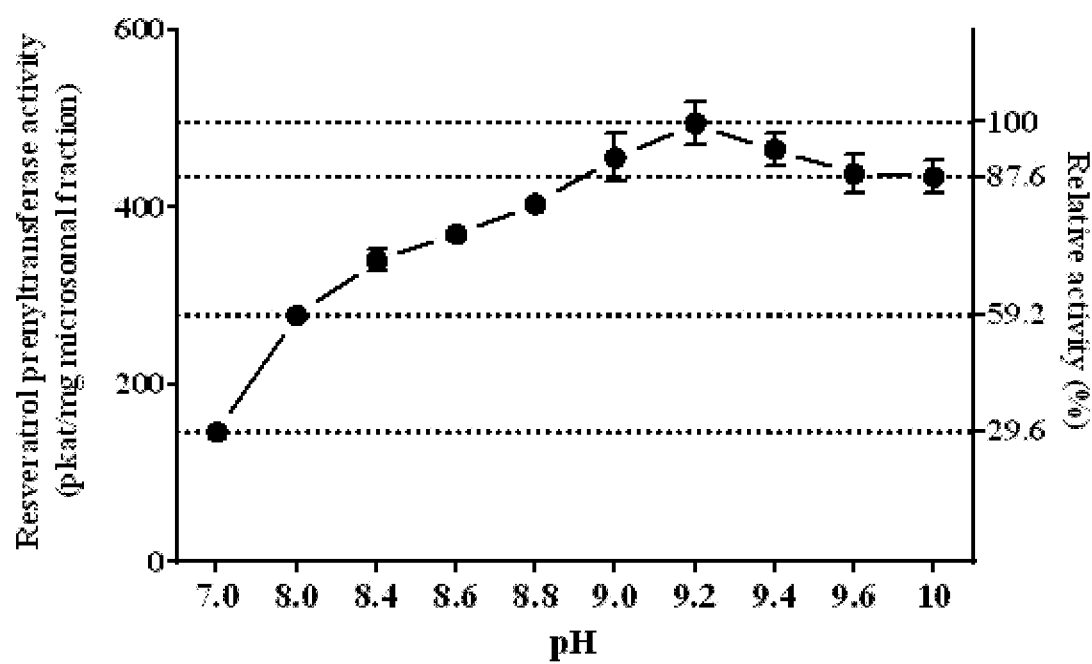

FIG. 26 shows pH dependency of resveratrol prenyltransferase activity. Resveratrol prenyltransferase activity at various pH values was measured using 100 mM Tris-HCl buffer at pH 7.0, 8.0, 8.4, 8.6, 8.8, 9.0, 9.2, 9.4, 9.6 and 10.

Figure 27:
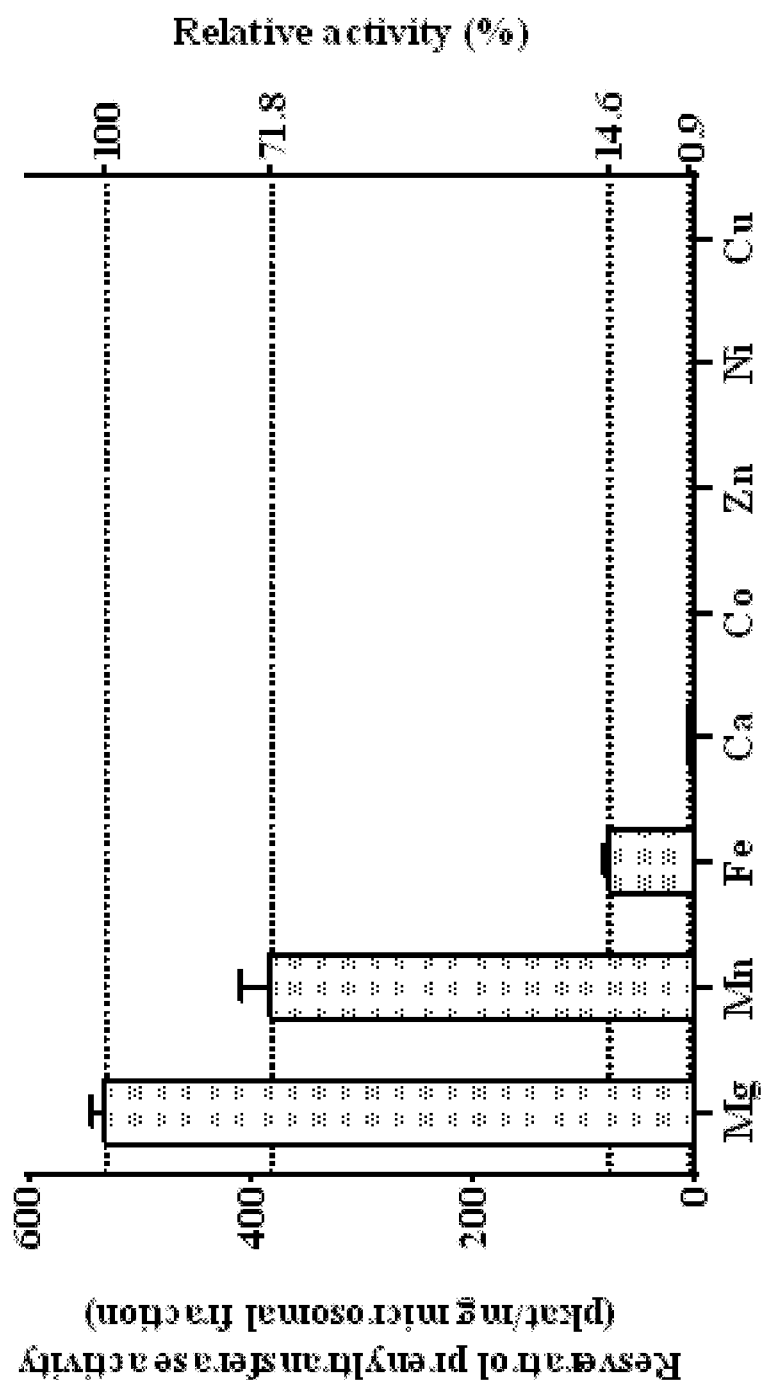

FIG. 27 shows divalent cation requirement for resveratrol prenyltransferase activity. Resveratrol prenyltransferase activity was compared in the presence of various divalent cations: $Mg^{2+}$, $Mn^{2+}$, $Fe^{2+}$, $Ca^{2+}$, $Co^{2+}$, $Zn^{2+}$, $Ni^{2+}$ and $Cu^{2+}$. The activity in the presence of $Mg^{2+}$ is shown as 100%.

Figure 28:
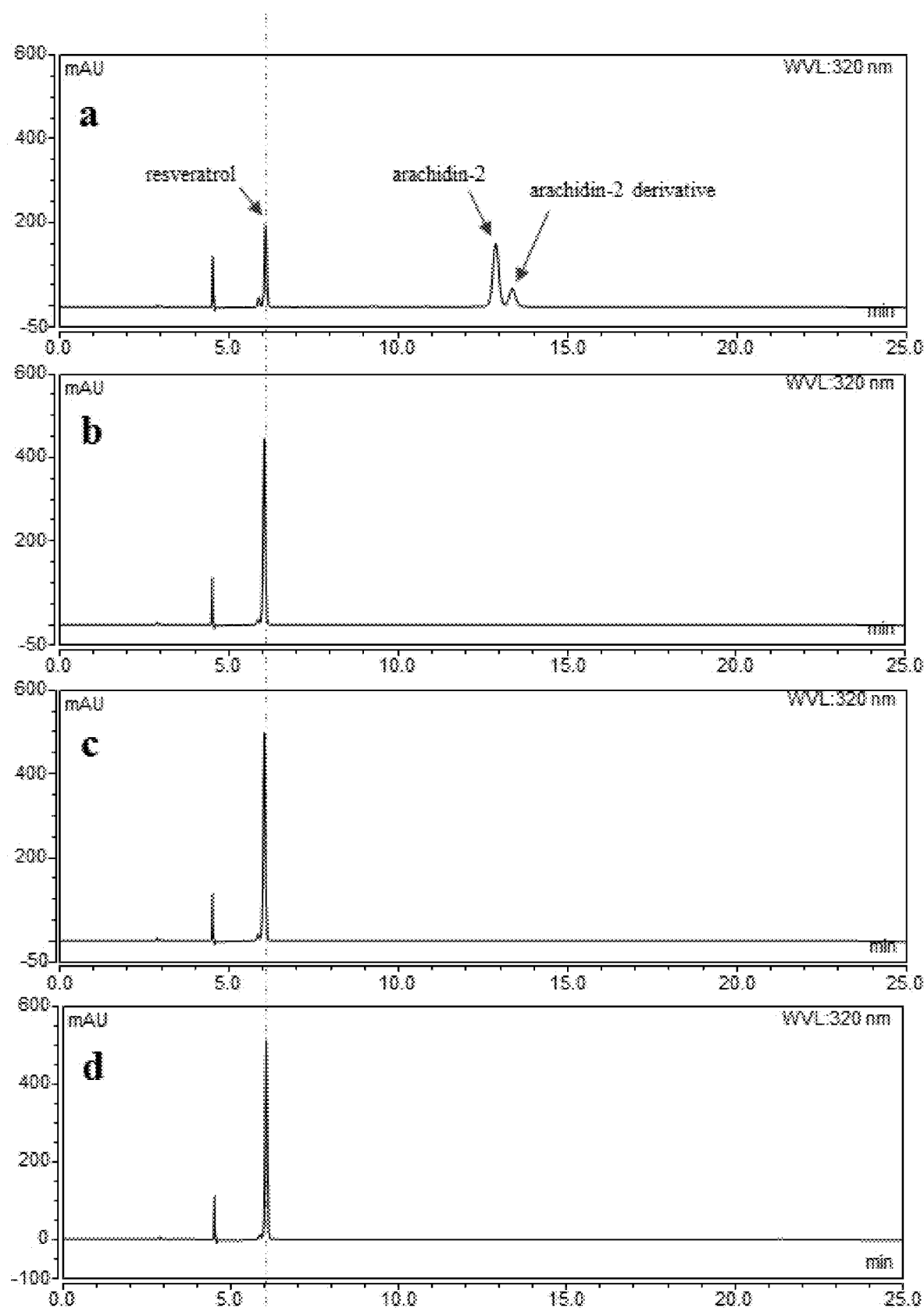

FIG. 28 shows biochemical characterization of resveratrol prenyltransferase in microsomal fraction of elicited peanut hairy root. HPLC chromatogram (UV 320 nm) of ethyl acetate extract of a 60 min incubation mixture containing (A) standard reaction (30 μg microsomal fraction, 100 μM resveratrol, 300 μM DMAPP, 10 mM $MgCl_2$ and 5 mM DTT in a pH 9.2 Tris-HCl buffer); (B) standard reaction without divalent cation added; (C) standard reaction with 300 μM IPP instead of DMAPP and (D) standard reaction with 30 μg microsomal fraction isolated from non-elicited peanut hairy root instead of 30 μg microsomal fraction isolated from elicited peanut hairy root.

Figure 29:
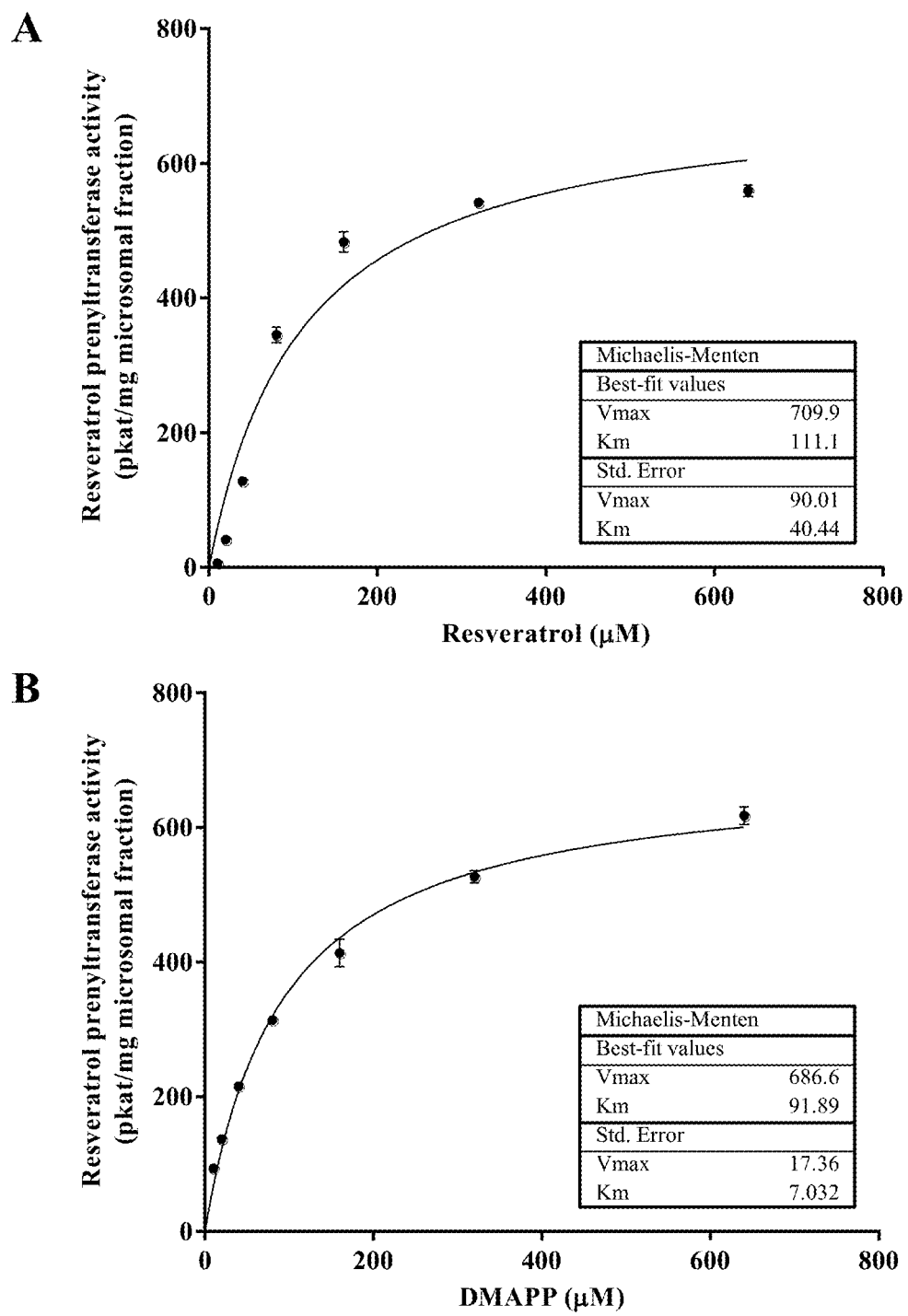

FIG. 29 shows effects of (A) resveratrol and (B) DMAPP concentrations on resveratrol prenyltransferase activity. Enzymatic activity was measured with a microsomal fraction from peanut hairy roots. The apparent $K_m$ and $V_{max}$ values for resveratrol and DMAPP were determined with varying concentrations of resveratrol (10-640 μM) and of DMAPP (10-640 μM) respectively and calculated via non-linear regression analysis with Michaelis-Menten equation by Graphpad Prism 6 software.

Figure 30:
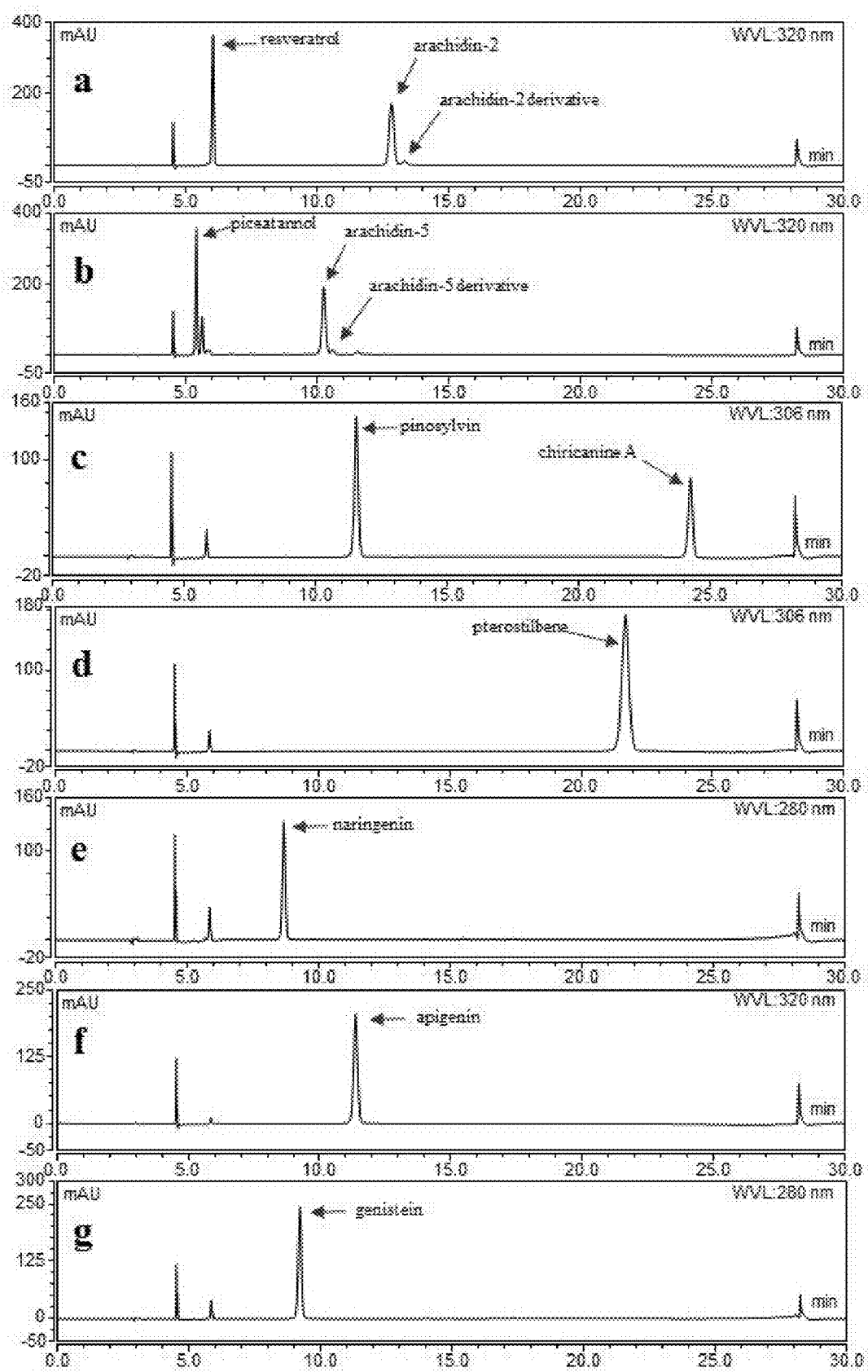

FIG. 30 shows substrate specificity of resveratrol prenyltransferase in microsomal fraction of elicited peanut hairy root. HPLC chromatograms (UV 320 nm) of ethyl acetate extracts of a 60 min incubation mixture containing 30 μg microsomal fraction with 300 μM DMAPP, 10 mM $MgCl_2$ and 5 mM DTT, and 100 μM prenyl acceptors (A, resveratrol; B, piceatannol; C, pinosylvin; D, pterostilbene; E, naringenin; F, apigenin and G, genistein) in a pH 9.2 Tris-HCl buffer.

Figure 31:
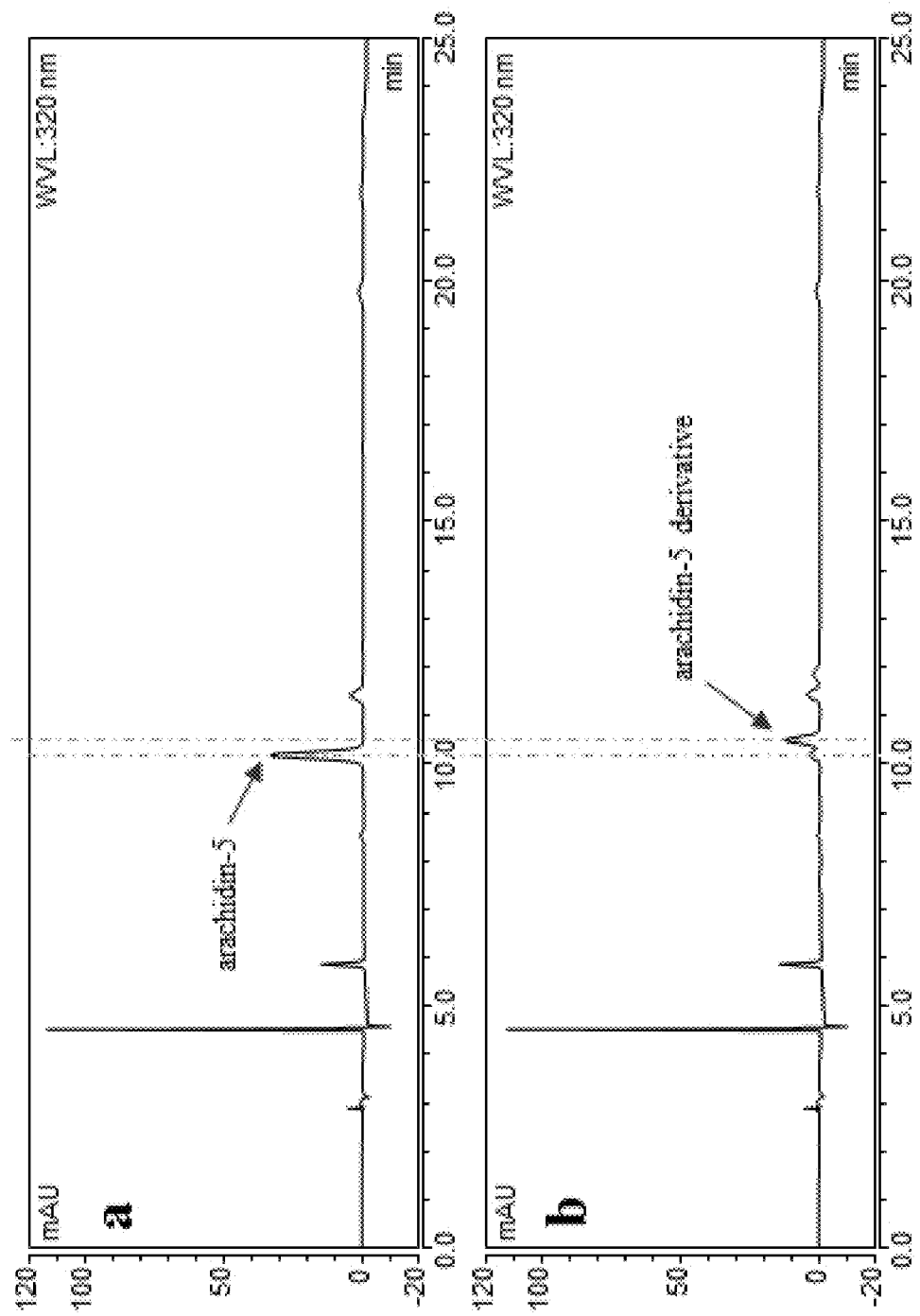

FIG. 31 shows biotransformation of arachidin-5 by protein fractions from elicited peanut hairy root culture. HPLC chromatograms (UV 320 nm) of ethyl acetate extracts from the 60 min incubation mixtures contained 40 μM arachidin-5 with (A) 30 μg heated microsomal fraction as control and (B) 30 μg microsomal fraction. All reactions were done in a pH 9.2 Tris-HCl buffer.

FIG. 32 shows substrate specificity of resveratrol prenyltransferase in microsomal fraction of elicited peanut hairy root. A, Chemical structures of oxyresveratrol and its prenylated product. B, HPLC chromatograms (UV 320 nm) of ethyl acetate extraction of reaction mixtures contained 100 μM oxyresveratrol, 300 μM DMAPP, 10 mM $MgCl_2$, 5 mM DTT and 30 μg microsomal fraction (above); heated denatured microsomal fraction (below) in a pH 9.2 Tris-HCl buffer for 60 min. C, HPLC-PDA-ESI-$MS^3$ analysis of oxyresveratrol, prenylated oxyresveratrol and its derivative.

Figure 33:
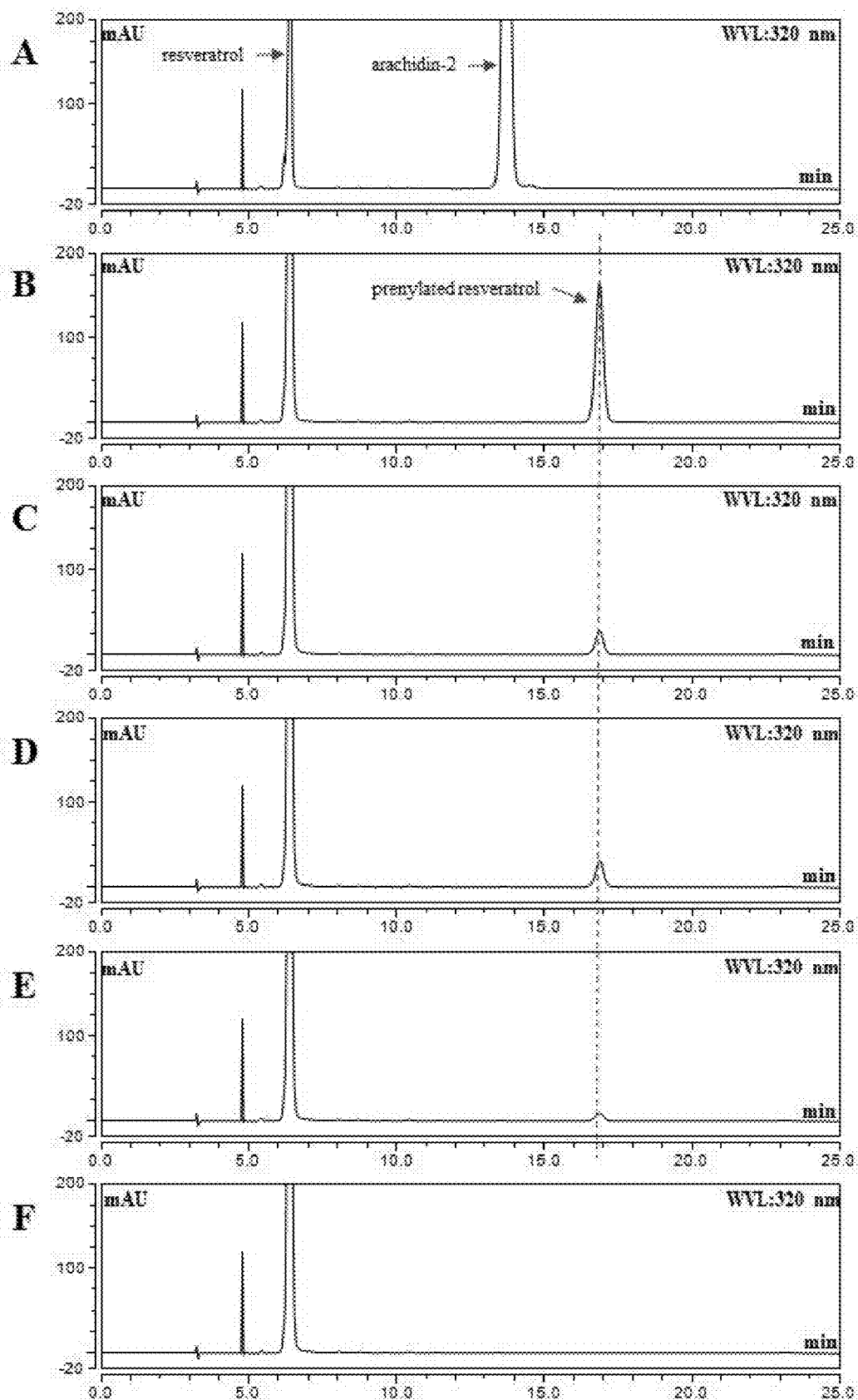

FIG. 33 shows enzymatic characterization of stilbenoid prenyltransferase genes (AhR4DT-9b13, AhRPT-10k1, AhRPT-4e1, AhRPT-4e10, and AhRPT5m3) transiently expressed in Nicotiana benthamiana leaf HPLC chromatograms (UV 320 nm) of ethyl acetate extraction of 1000 μl reaction mixture of 200 μM resveratrol, 600 μM DMAPP, 10 mM $MgCl_2$ and 10 mM DTT incubated with 50 μl crude protein of Nicotiana benthamiana leaf after vacuum infiltration with Agrobacterium tumefaciens LBA4404 harboring pBIBKan-9b13 (A); pBIBKan-10k1 (B); pBIBKan-4e1 (C); pBIBKan-4e10 (D); pBIBKan-5m3 (E) and pBIBKan (F) binary vectors in a pH 9.2 Tris-HCl buffer for 40 min.

Figure 34:
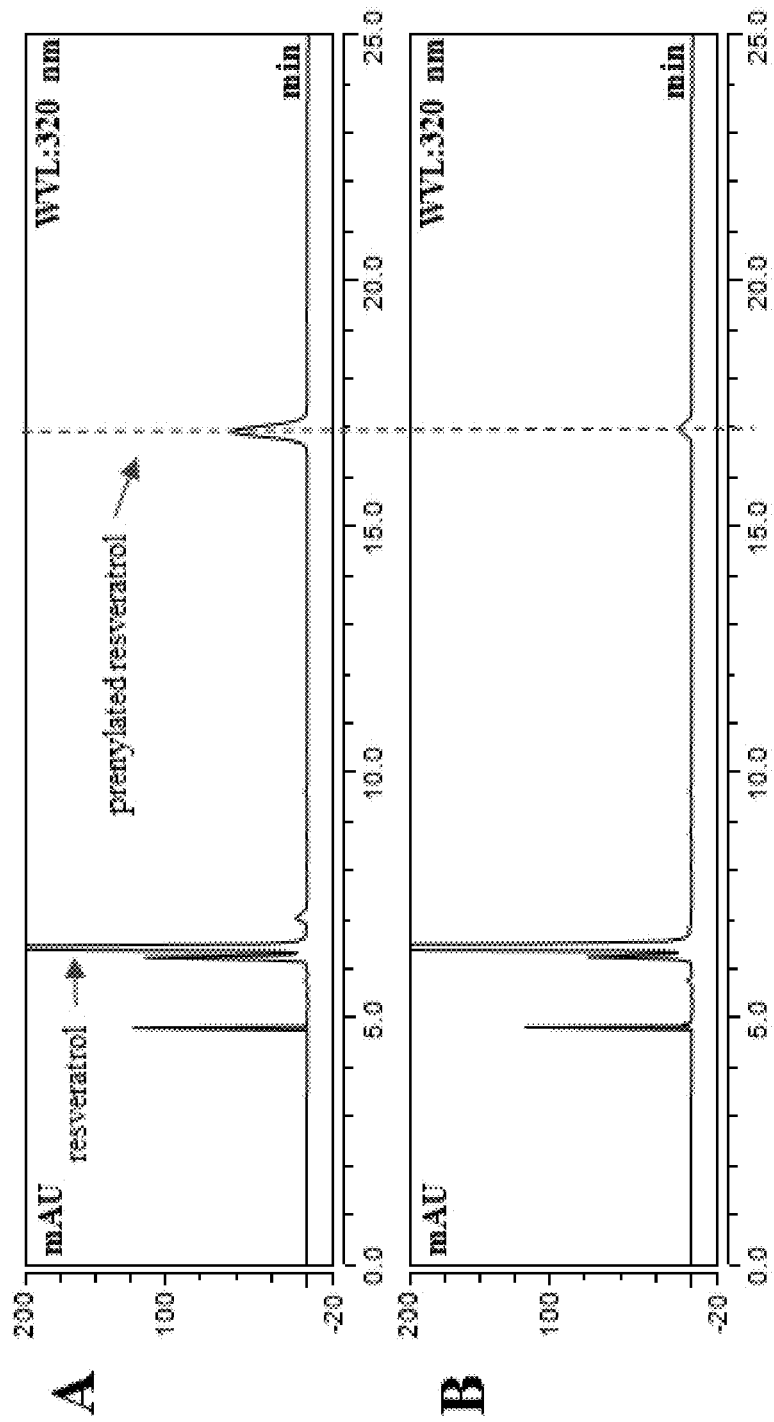

FIG. 34 shows resveratrol prenyltransferase activities in transgenic tobacco (Nicotiana tabacum) expressing AhRPT-10k1 gene cloned from peanut hairy roots. HPLC chromatograms (UV 320 nm) of ethyl acetate extraction of 500 μl reaction mixture of 200 μM resveratrol, 300 μM DMAPP, 10 mM $MgCl_2$ and 10 mM DTT incubated with 50 μg crude protein of transgenic N. tabacum leaf expressed 10k1 gene (A) and 50 μg of microsomal fraction of transgenic N. tabacum hairy roots expressed 10k1 gene (B) for 2 hours.

Figure 35:
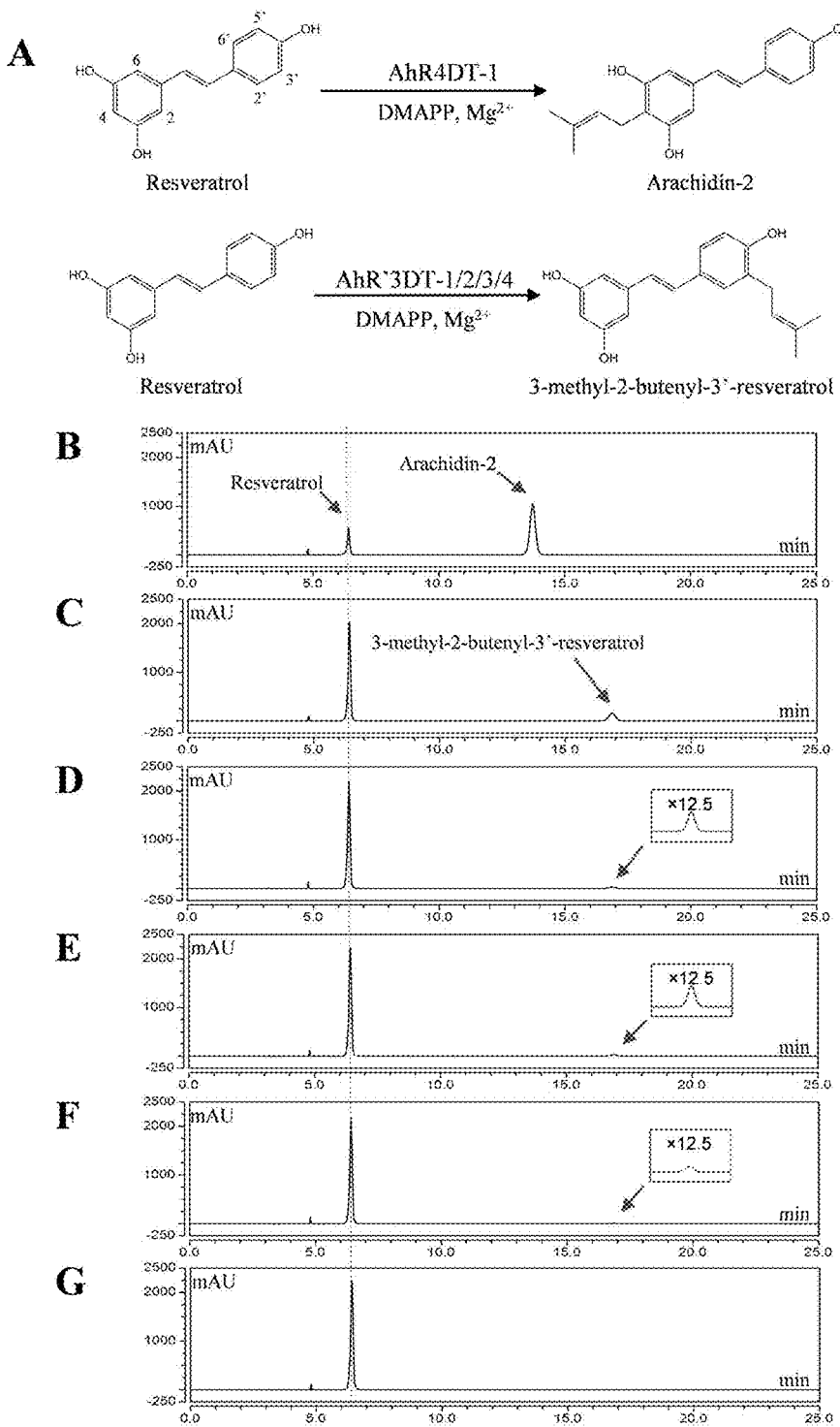

FIG. 35 shows the enzymatic characterization of recombinant stilbenoid prenyltransferases expressed in Nicotiana benthamiana. (A) AhR4DT-1 and AhR'3DT-1/2/3/4 from peanut catalyzes the 4 and 3'-prenylation of resveratrol, respectively. (B) Enzymatic characterization of resveratrol prenyltransferase transiently expressed in Nicotiana benthamiana leaf. HPLC chromatograms (UV 320 nm) of ethyl acetate extract of 1 mL reaction mixture of 100 μM resveratrol, 300 μM DMAPP, 10 mM $MgCl_2$ and 10 mM DTT incubated with 5 mg crude protein of N. benthamiana leaf after vacuum infiltration with Agrobacterium tumefaciens LBA4404 harboring (B) pBIB-Kan-AhR4DT-1; (C) pBIB-Kan-AhR3'DT-1; (D) pBIB-Kan-AhR3'DT-2; (E) pBIB- Kan-AhR3'DT-3; (F) pBIB-Kan-AhR3'DT-4 and (G) pBIB-Kan binary vectors in a pH 9.0 Tris-HCl buffer for 40 min.

Figure 36:
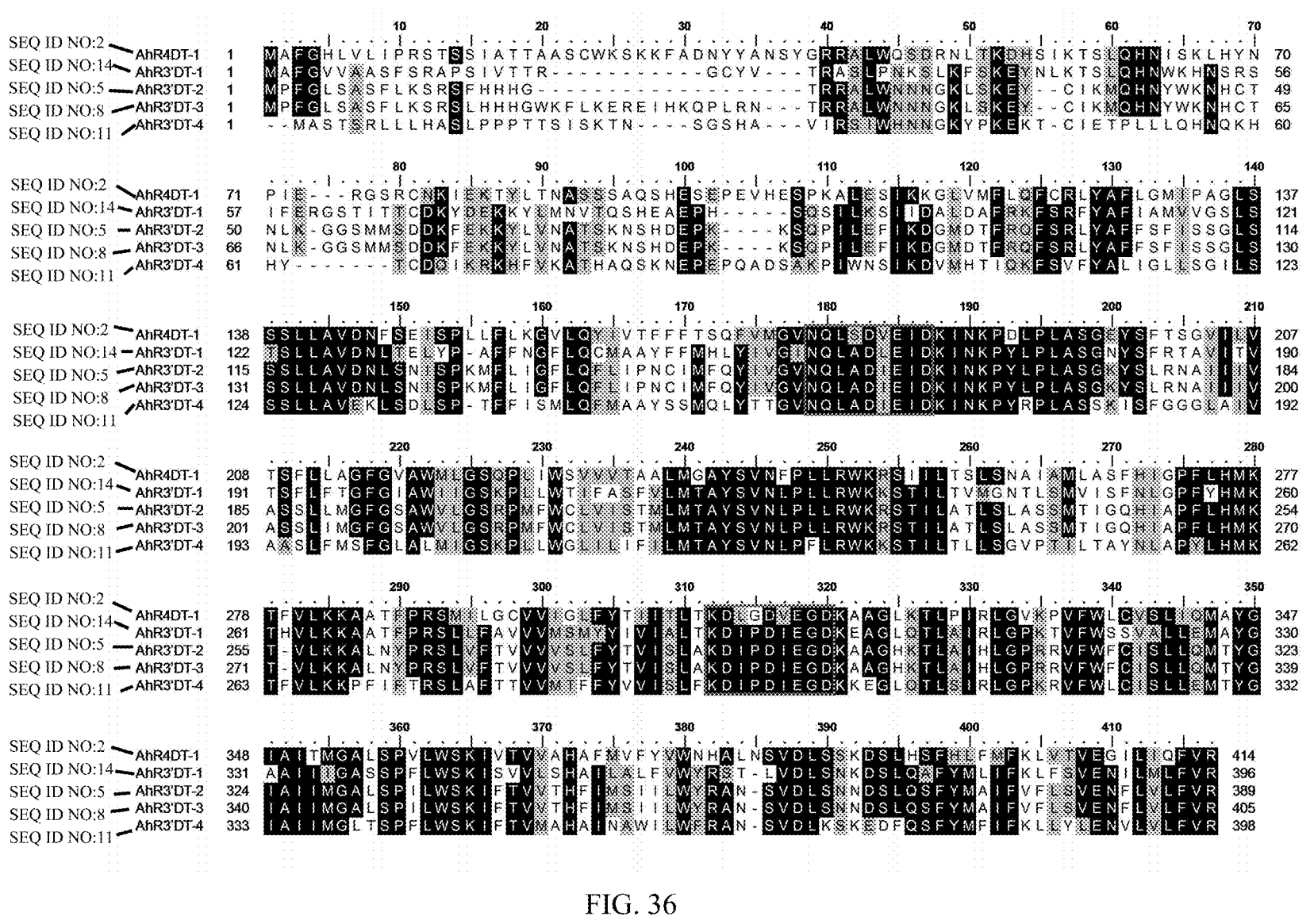

FIG. 36 shows the primary structures of stilbenoid prenyltransferases. Two conserved NQXXDXXXD (SEQ ID NO:16) and KDXXDXEGD (SEQ ID NO:17) motifs are boxed.

Figure 37:
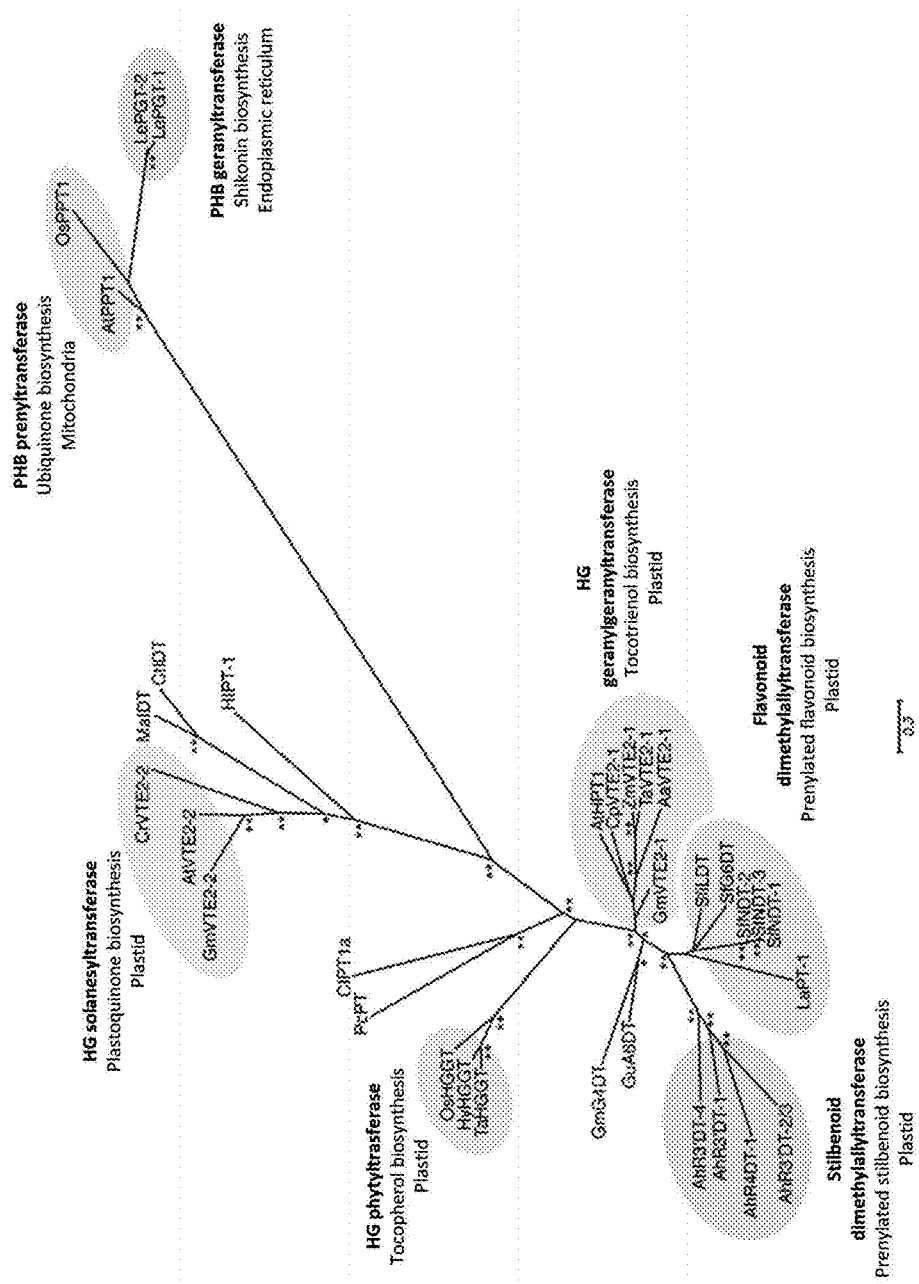

FIG. 37 shows the phylogenetic relationship between peanut stilbenoid prenyltransferases and related prenyltransferases accepting aromatic substrates. Species abbreviations are: Aa, *Allium ampeloprasum*; Ah, *Arachis hypogaea*; At, *Arabidopsis thaliana*; Cl, *Citrus limon*; Cp, *Cuphea avigera* var *pulcherrima*; Cr, *Chlamydomonas reinhardtii*; Ct, *Cudrania tricuspidata*; Gm, *Glycine max*; Hl, *Humulus lupulus*; Hv, *Hordeum vulgare*; La, *Lupinus albus*; Le, *Lithospermum erythrorhizon*; Ma, *Morus alba*; Os, *Oryza sativa*; Pc, *Petroselinum crispum*; Sf, *Sophora flavescens*; Ta, *Triticum aestivum*; Zm, *Zea mays*. Homogentisate phytyltransferases (VTE2-1s) and homogentisate geranylgeranyltransferases (HGGTs), homogentisate solanesyltransferases (VTE2-2s), p-hydroxybenzoate geranyltransferase (PGT) and p-hydroxybenzoate polyprenyltransferases (PPTs) are involved in the biosynthesis of vitamin E, plastoquinone, shikonin and ubiquinone, respectively. IDT is isoliquiritigenin dimethylallyltransferase. Accession numbers of these proteins are listed in FIG. 69.

FIG. 38 shows the substrate specificity of AhR4DT-1 and AhR3'DT-1. A, Chemical structures of prenyl acceptors used for substrate specificity analysis and their prenylated products: stilbenoids (a, resveratrol, b, piceatannol, c, oxyresveratrol, d, pinosylvin, e, piceid and f, pterostilbene), flavanone (g, naringenin), flavone (h, apigenin) and isoflavone (i, genistein). B, Relative prenylation activity of AhR4DT-1 (B) and AhR3'DT-1 (C) with various prenyl acceptors were compared with that of resveratrol. The prenyl donor specificity of AhR4DT-1 (D) and AhR3'DT-1 (E) were tested using DMAPP, IPP, GPP, FPP, GGPP with resveratrol as a prenyl acceptor. All these reactions were performed in 100 mM Tric-HCl buffer (pH 9.0) at 28° C. for 40 mins. Values are the average of triplicate and error bars represent standard deviation (n.d., not detected).

Figure 39:
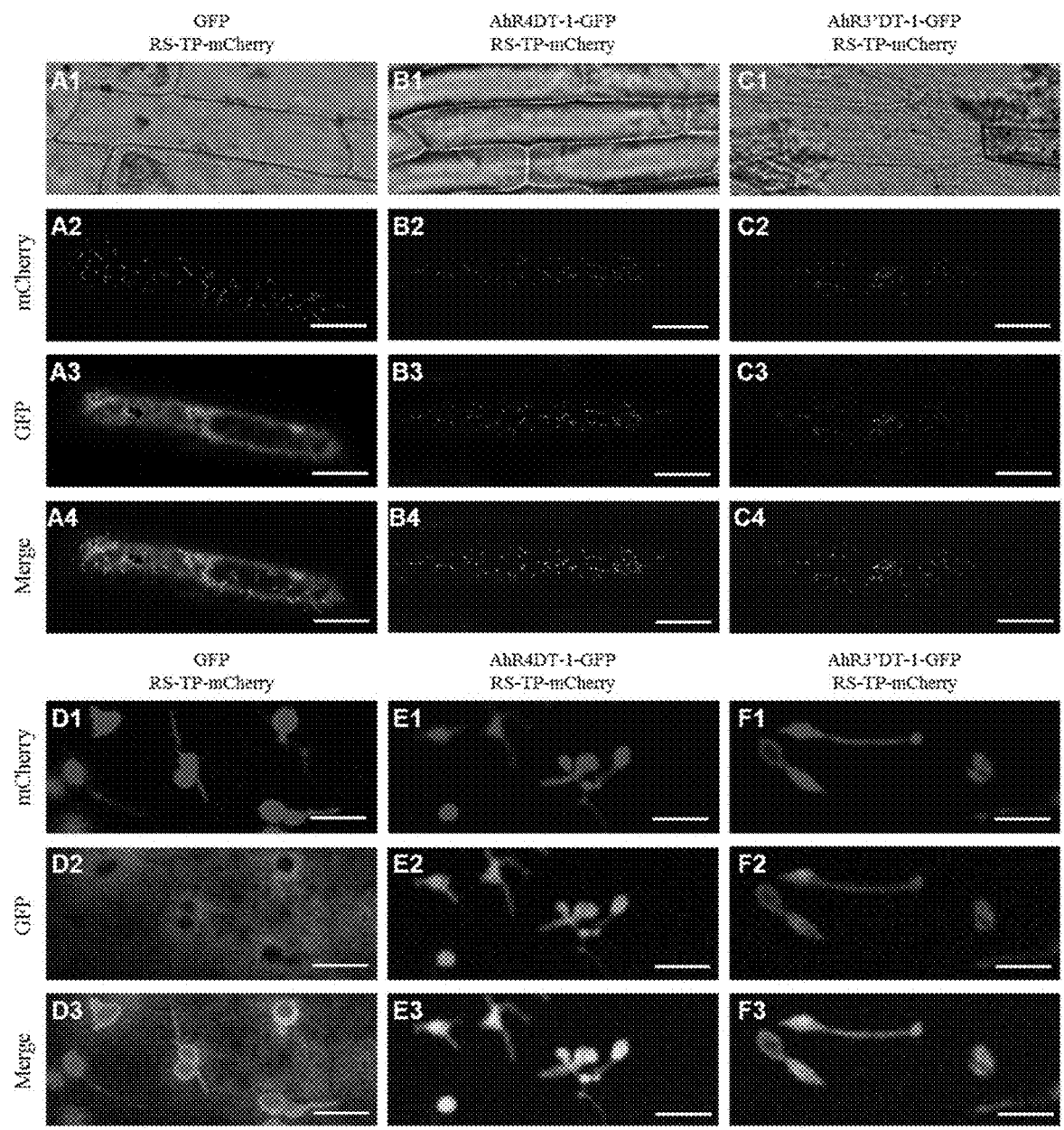

FIG. 39 shows the microscopic analysis of subcellular localization of AhR4DT-1 and AhR3'DT-1 fused with GFP in onion epidermal cells upon particle bombardment. (A, D) Plasmids containing CaMV735S-TEV-GFP and RS-TP-mCherry, (B, E) AhR4DT-1-GFP and RS-TP-mCherry or (C, F) AhR3'DT-1-GFP and RS-TP-mCherry were mixed and introduced into onion epidermal cells by particle bombardment.

Magnification: 20×; Scale bars in A, B and C equal 100 μm.
A1, B1, C1: Bright field images of onion cells.
A2, B2, C2: Expression pattern of mCherry from construct CaMV35S-RS-TP-mCherry
A3: Expression pattern of GFP from construct CaMV35S-TEV-GFP
B3: Expression pattern of GFP from construct AhR4DT-1-GFP
C3: Expression pattern of GFP from construct AhR3'DT-1-GFP
A4: Merge of A2 and A3
B4: Merge of B2 and B3
C4: Merge of C2 and C3
Close up of the same cells shown. Scale bars in D, E and F equal 10 μm
D1, E1, F1: Expression pattern of mCherry from construct CaMV35S-RS-TP-mCherry
D2: Expression pattern of GFP from construct CaMV35S-TEV-GFP
E2: Expression pattern of GFP from construct AhR4DT-1-GFP
F2: Expression pattern of GFP from construct AhR3'DT-1-GFP
D3: Merge of D1 and D2
E3: Merge of E1 and E2
F3: Merge of F1 and F2
CaMV35S: cauliflower mosaic virus 35S promoter; TEV: tobacco etch virus translational enhancer; GFP: green fluorescent protein; RS-TP: rubisco small subunit transit peptide.

Figure 40:
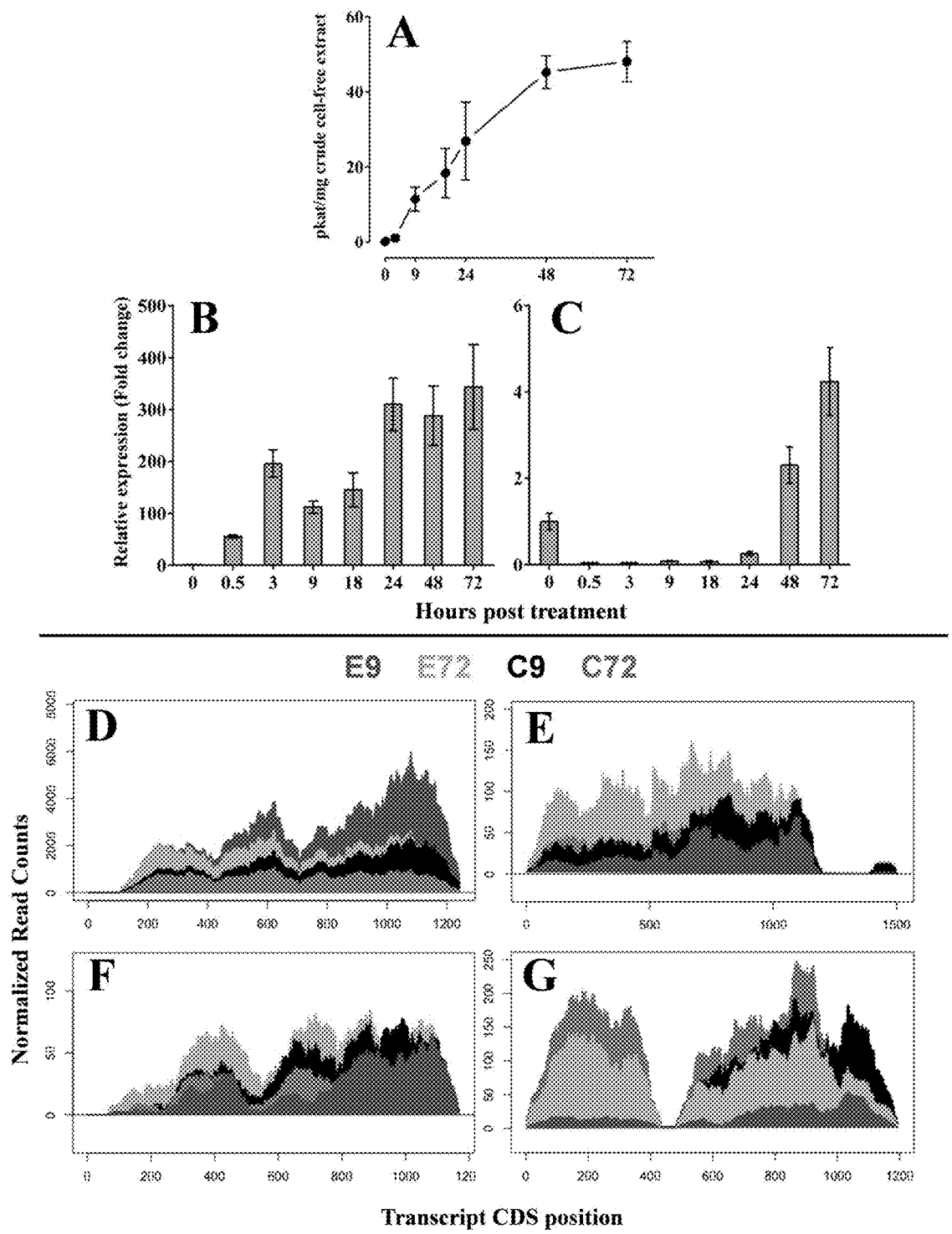

FIG. 40 shows the enzyme activities and transcript coexpression during elicitation time course in peanut hairy root cultures. (A) Prenyltransferase activities from crude cell-free extracts. (B) Relative transcript accumulation of AhR4DT-1 and (C) AhR3'DT-1 as determined by RT-qPCR. (D) Uniquely mapped RNA-Seq reads coverage over reference *A. hypogaea* transcripts AhR4DT-1, (E) AhR3'DT-1, (F) AhR3'DT-2/3 and (G) AhR3'DT-4 as described. E9 and E72, 9 h and 72 h MeJA+CD treatment; C9 and C72, 9 h and 72 h control treatments.

Figure 41:
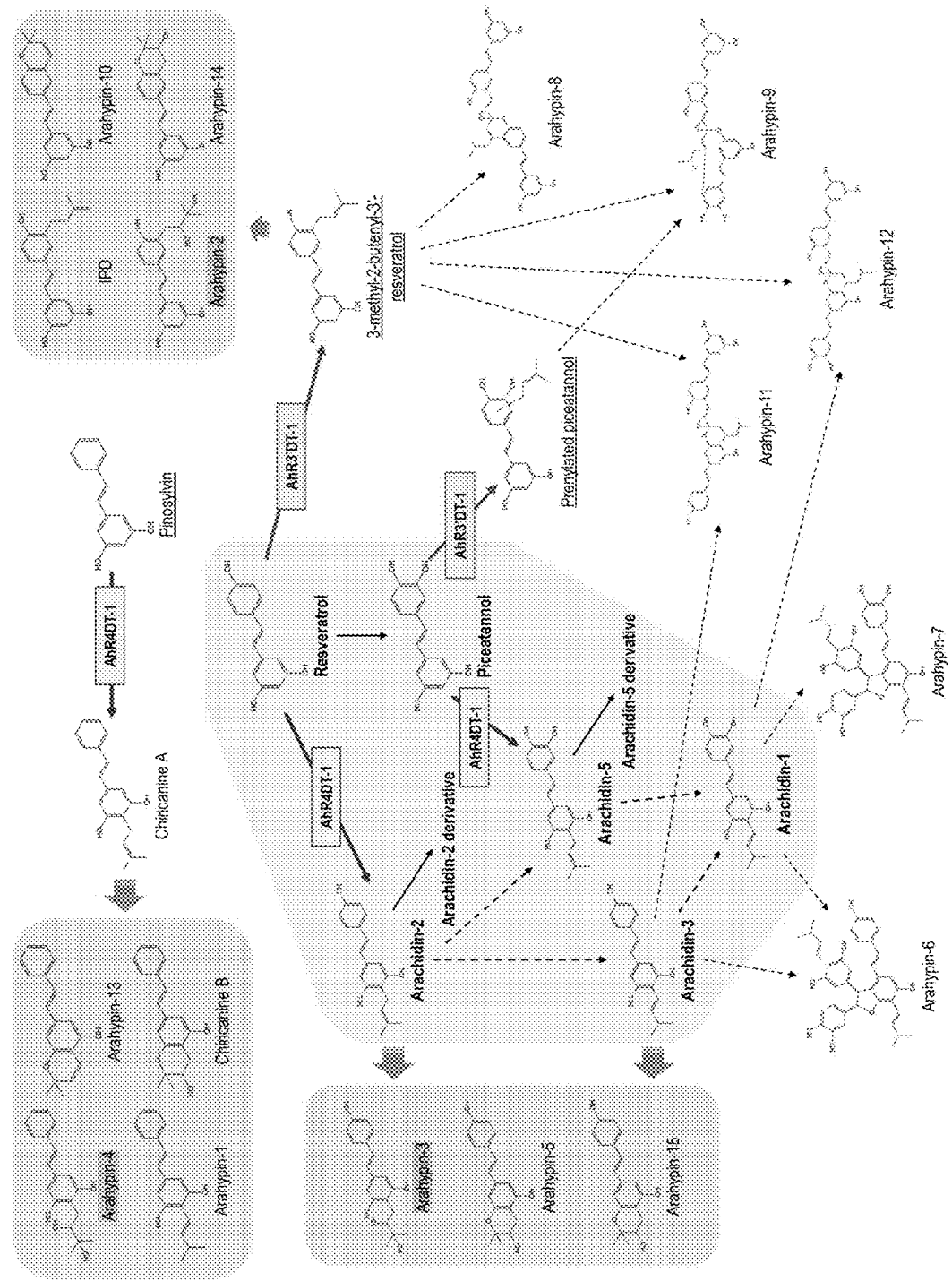

FIG. 41 shows the proposed pathway of prenylated stilbenoids in peanut. Stilbenoids identified from the medium of peanut hairy root culture upon elicitors treatment are bolded and their proposed pathway is highlighted in yellow. Other prenylated stilbenoids identified in fungal-challenged peanut seeds are divided into three groups based on the prenyl unit and hydroxyl groups on their stilbene backbone. Prenylation reactions catalyzed by AhR4DT-1 and AhR3'DT-1 identified in this study are labeled with red solid arrows. Enzymatic reactions confirmed in peanut are marked with black solid arrow, while other proposed reactions are labeled in black arrows with dashed lines. *: Pinosylvin, 3-methyl-2-butenyl-3'-resveratrol and the prenylation product of piceatannol by AhR3'DT-1 have not been reported in peanut tissue.

Figure 42:
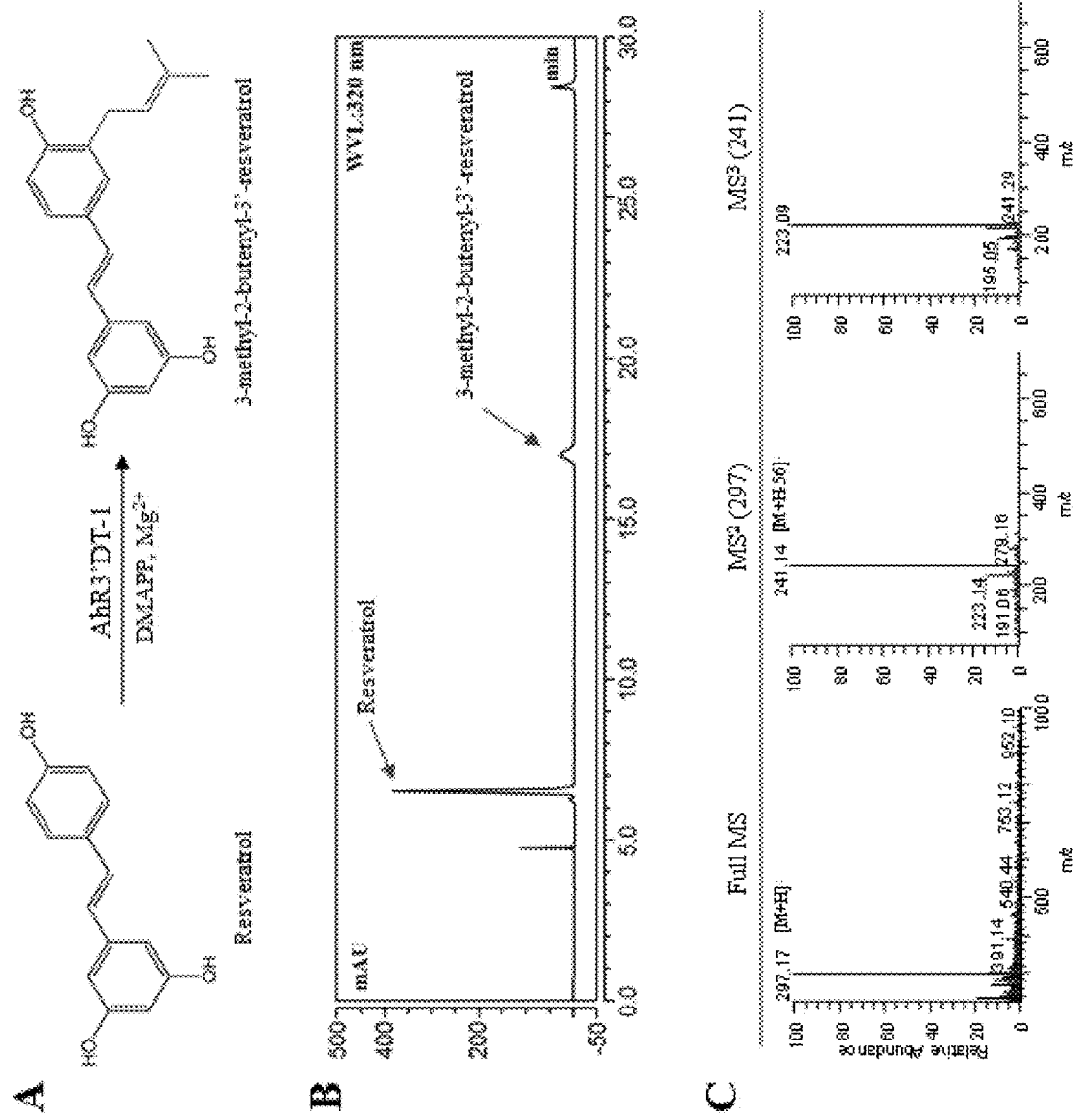

FIG. 42 shows the prenylation of resveratrol by AhR3'DT-1. Prenyltransferase activity of AhR3'DT-1 in microsomal fraction of *Nicotiana benthamiana* leaf after vacuum infiltration with *Agrobacterium tumefaciens* LBA4404 harboring pBIB-Kan-AhR3'DT-1 was confirmed by HPLC and LC-MS$^n$ analysis.

(A) Chemical structures of resveratrol and its prenylated product, 3-methyl-2-butenyl-3'-resveratrol.

(B) HPLC chromatograms (UV 320 nm) of ethyl acetate extraction of reaction mixtures contained 100 μM resveratrol, 300 μM DMAPP, 10 mM $MgCl_2$, 5 mM DTT and 30 microsomal fraction in a pH 9.0 Tris-HCl buffer for 40 min.

(C) HPLC-PAD-ESI-MS$^3$ analysis of prenylated product, 3-methyl-2-butenyl-3'-resveratrol.

FIG. 43 shows NMR spectra of the 1 mM 3-methyl-2-butenyl-3'-resveratrol isolated from a large-scale enzymatic assay.

1D $^1$H NMR (A), 1D $^{13}$C NMR spectrum (B), 2D $^1$H-$^{13}$C HMBC (C) and 2D $^1$H-$^{13}$C HSQC (D) spectra obtained on 700 MHz Bruker Avance spectrometer dissolved in d6-Acetone at 298K. The peaks circled in red are consistent in both 1D and 2D experiments which represent protons on the specific locations of the scaffold.

Figure 44:
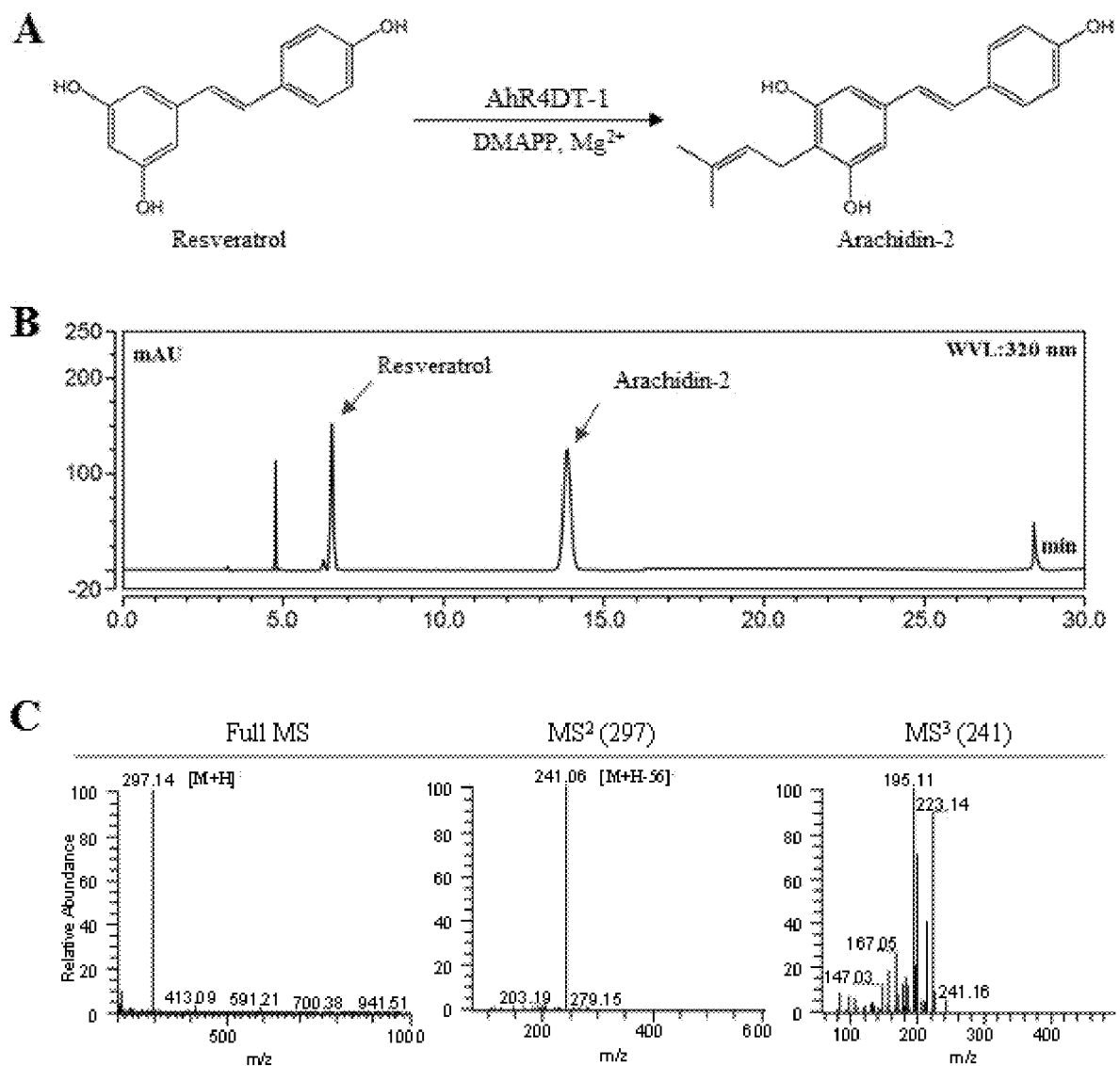

FIG. 44 shows Prenylation of resveratrol by AhR4DT-1. Prenyltransferase activity of AhR4DT-1 in microsomal fraction of *Nicotiana benthamiana* leaf after vacuum infiltration with *Agrobacterium tumefaciens* LBA4404 harboring pBIB-Kan-AhR4DT-1 was confirmed by HPLC and LC-MS$^n$ analysis.

(A) Chemical structures of resveratrol and its prenylated product, arachidin-2.

(B) HPLC chromatograms (UV 320 nm) of ethyl acetate extraction of reaction mixtures contained 100 μM resveratrol, 300 μM DMAPP, 10 mM $MgCl_2$, 5 mM DTT and 30 microsomal fraction in a pH 9.0 Tris-HCl buffer for 40 min.

(C) HPLC-PAD-ESI-MS$^3$ analysis of prenylated product, arachidin-2.

Figure 45:
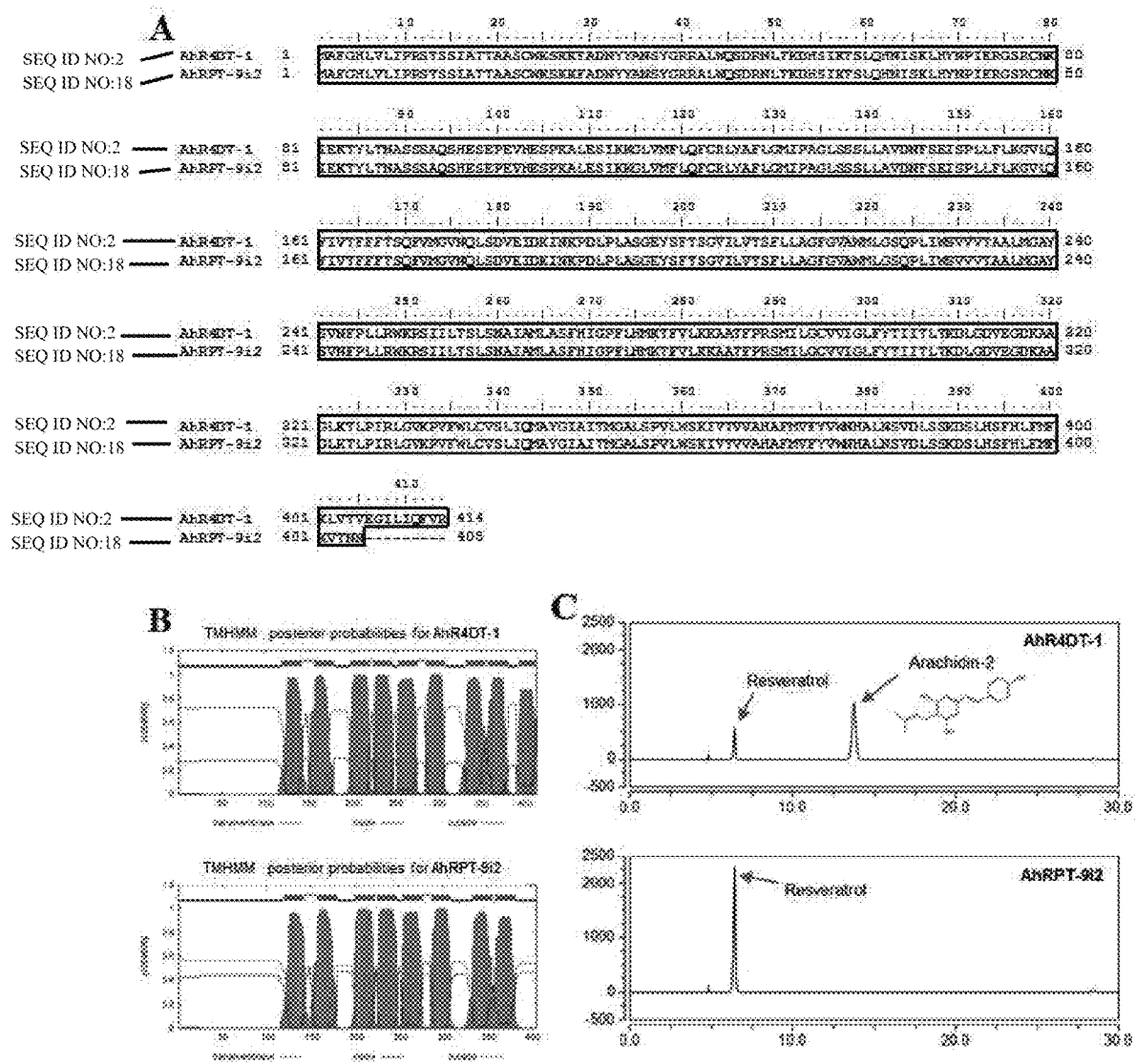

FIG. 45 shows the Comparison of AhR4DT-1 and AhRPT-9i2.

(A) Alignment of AhR4DT-1 with AhRPT-9i2 was performed using ClustalX.

(B) Potential transmembrane domains of AhR4DT-1 and AhRPT-9i2 were predicted by TMHMM.

(C) Resveratrol prenylation activity of AhR4DT-1 and AhRPT-9i2 were analyzed by using HPLC.

Figure 46:
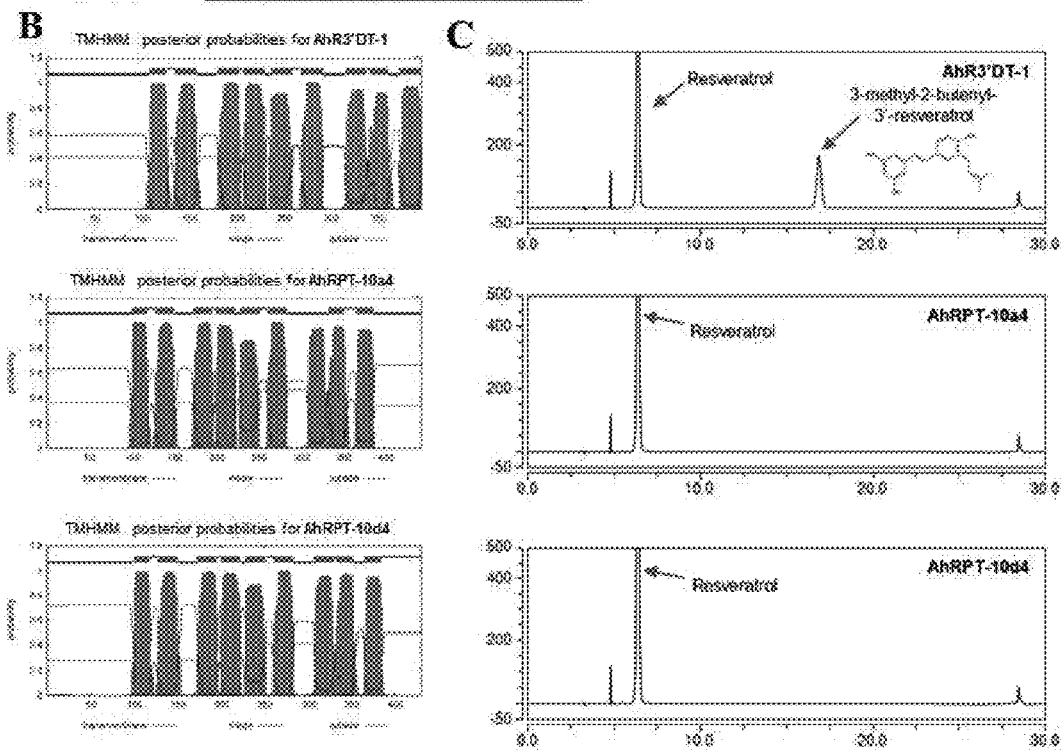

FIG. 46 shows a comparison of AhR3'DT-1, AhRPT-10a4 and AhRPT-10d4.

(A) Alignment of AhR3'DT-1, AhRPT-10a4 and AhRPT-10d4 was performed using ClustalX.

(B) Potential transmembrane domains of AhR3'DT-1, AhRPT-10a4 and AhRPT-10d4 were predicted by TMHMM.

(C) Resveratrol prenylation activity of AhR3'DT-1, AhRPT-10a4 and AhRPT-10d4 were analyzed by using HPLC.

Figure 47:
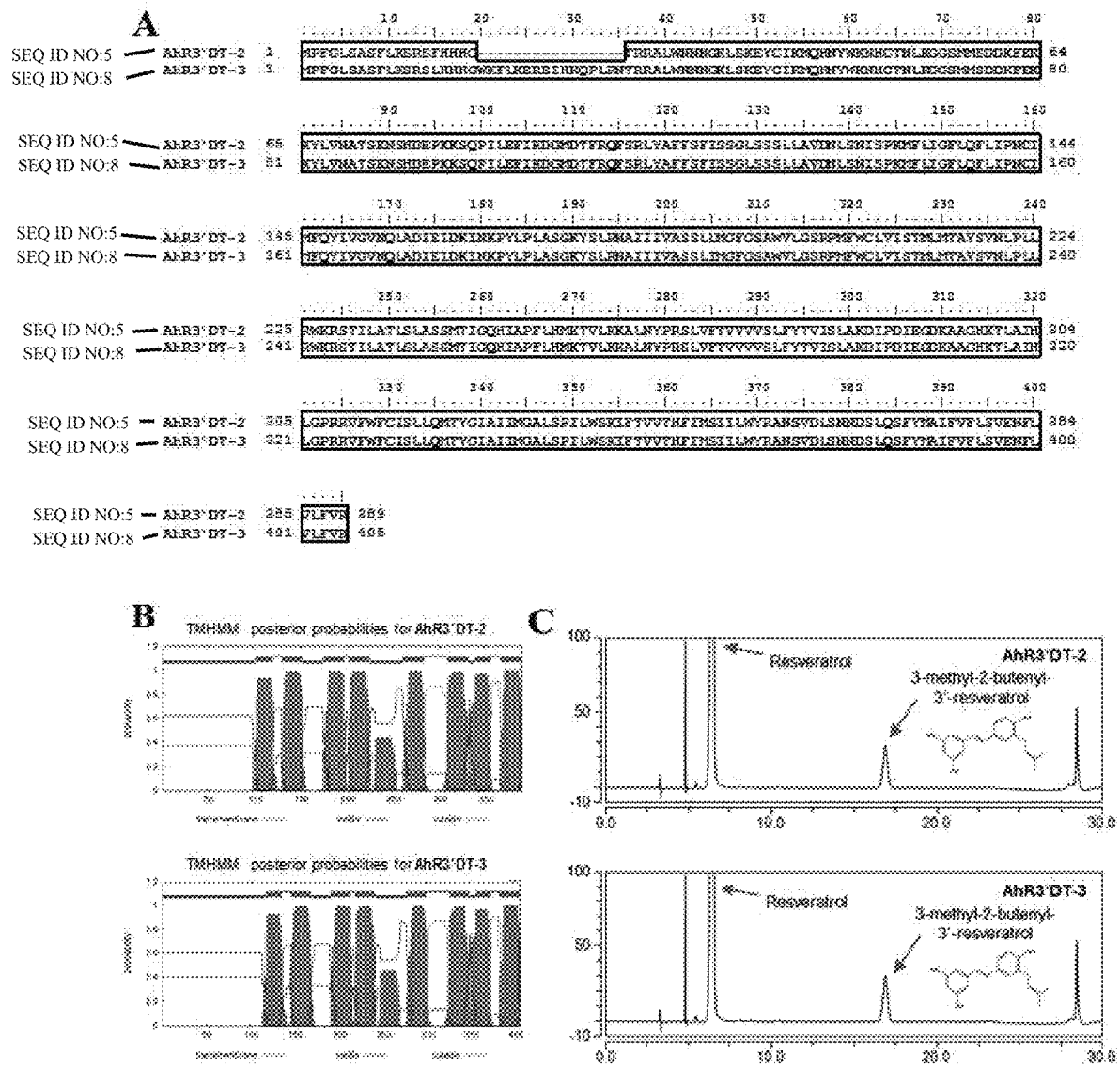

FIG. 47 shows a comparison of AhR3'DT-2 and AhR3'DT-3.

(A) Alignment of AhR3'DT-2 with AhR3'DT-3 was performed using ClustalX.

(B) Potential transmembrane domains of AhR3'DT-2 and AhR3'DT-3 were predicted by TMHMM.

(C) Resveratrol prenylation activity of AhR3'DT-2 and AhR3'DT-3 were analyzed by using HPLC.

Figure 48:
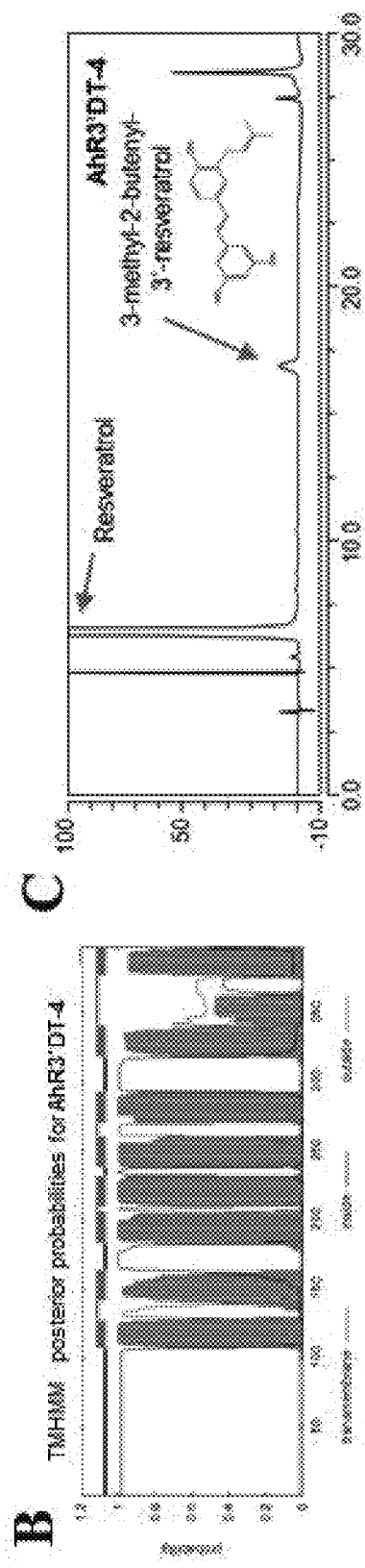

FIG. 48 shows a structural analysis of AhR3'DT-4.

(A) Primary structure of AhR3'DT-4.

(B) Potential transmembrane domains of AhR3'DT-4 was predicted by TMHMM.

(C) Resveratrol prenylation activity of AhR3'DT-4 was analyzed by using HPLC.

FIG. 49 shows a temperature dependency of AhR4DT-1 and AhR3'DT-1 activity. AhR4DT-1 (A) and AhR3'DT-1 (B) activities were measured at various temperature (20, 25, 28, 30, 37, 40 and 50° C.) in 100 mM Tris-HCl buffer (pH 9.0) for 40 mins.

Figure 50:
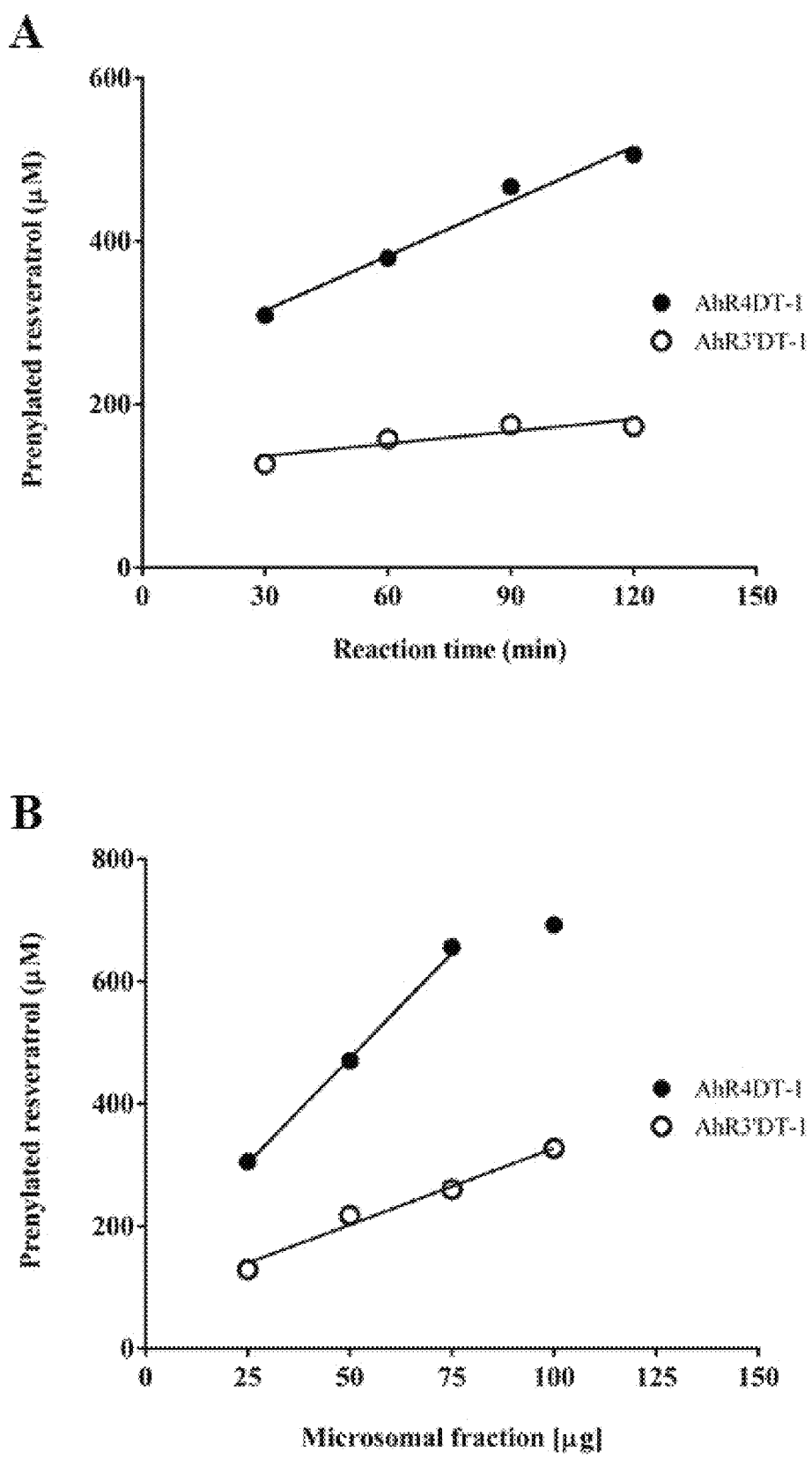

FIG. 50 shows the incubation time and amounts of microsomal fraction dependency of AhR4DT-1 and AhR3'DT-1 activity.

(A) Concentrations of generated prenylated resveratrol from AhR4DT-1 and AhR3'DT-1 reaction mixtures with varying incubation times (30, 60, 90 and 120 min) were quantified by HPLC.

(B) Concentrations of generated prenylated resveratrol from AhR4DT-1 and AhR3'DT-1 reaction mixtures with varying amounts of microsomal fraction (25, 50, 75 and 100 µg) were quantified by HPLC.

FIG. 51 shows a pH dependency of AhR4DT-1 and AhR3'DT-1 activity. AhR4DT-1 (A) and AhR3'DT-1 (B) activities at various pH values were measured in three different buffers: 100 mM Tris-HCl buffer at pH 7.0, 8.0, 8.6 and 9.0; 100 mM Glycine-NaOH buffer at pH 8.6, 9.0, 9.4, 10.0 and 10.6; and 100 mM NaHCO$_3$—Na$_2$CO$_3$ buffer at pH 9.2, 9.7, 10.2 and 10.7. All the reactions were performed at 28° C. for 40 min.

FIG. 52 shows a divalent cation dependency of AhR4DT-1 and AhR3'DT-1 activity. AhR4DT-1 (A) and AhR3'DT-1 (B) activity with various divalent cation were measured with 10 mM MnCl$_2$, FeCl$_2$, CaCl$_2$), CoCl$_2$, ZnCl2, NiCl$_2$, or CuCl$_2$ and the enzyme activity was compared with the reaction of 10 mM MgCl$_2$. Reactions without divalent cation and 10 mM EDTA instead of MgCl$_2$ were used as controls. All the reactions were performed in 100 mM Tris-HCl buffer (pH 9.0) at 28° C. for 40 min. (t.a., trace amount (<0.5%), n.d., Not detected). Means and the standard deviation (error bars) were calculated from three replicates.

Figure 53:
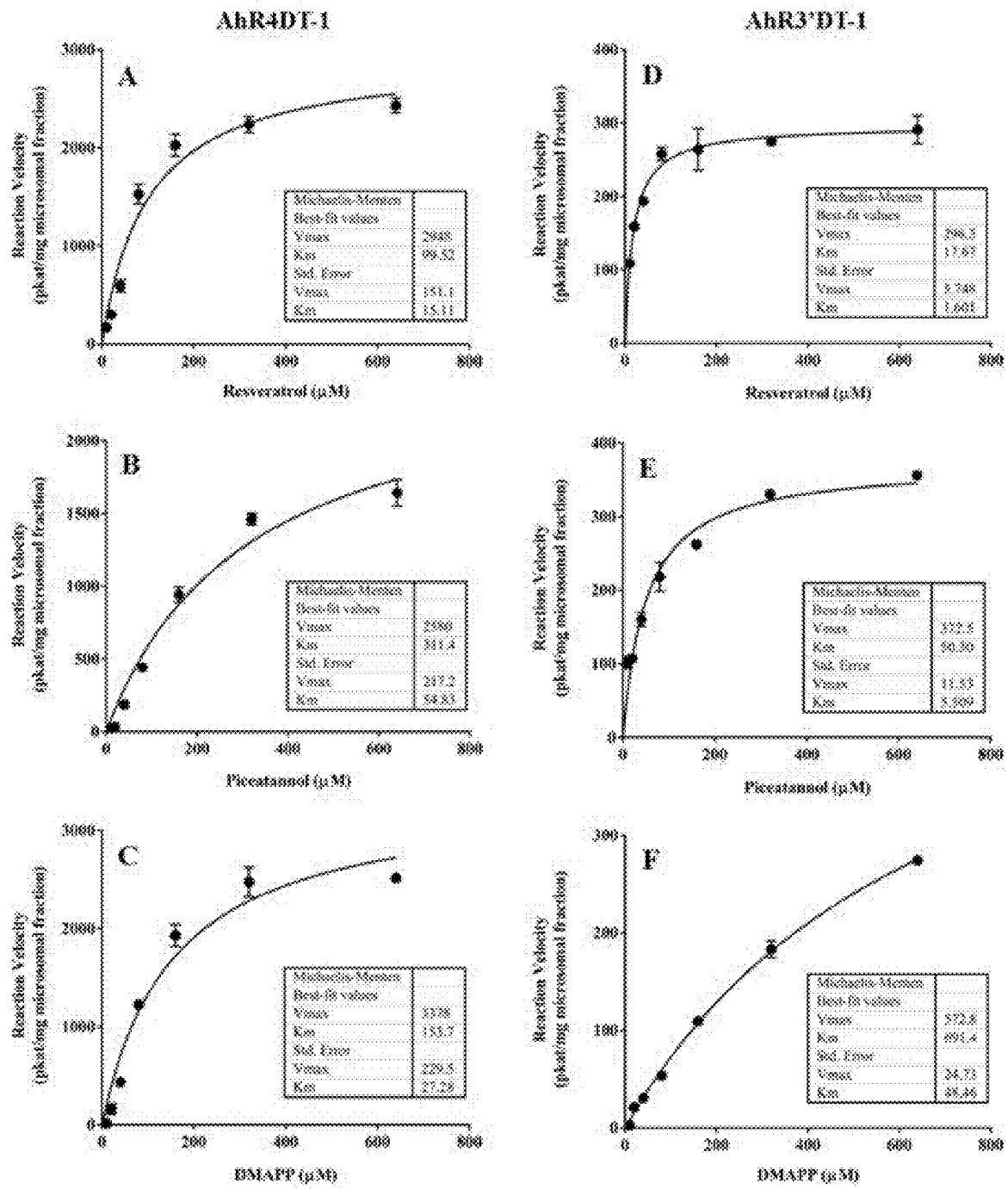

FIG. 53 shows the kinetic values of AhR4DT-1 and AhR3'DT-1. Dependency of AhR4DT-1 (left) and AhR3'DT-1 (right) on the concentration of resveratrol (A&D), piceatannol (B&E) and DMAPP (C&F) measured with a microsomal fraction from leaves of *Nicotiana benthamiana*. The apparent K$_m$ and V$_{max}$ values for resveratrol and piceatannol were determined with varying concentrations (10~640 µM) using 640 µM DMAPP as prenyl donor, while that for DMAPP were determined with varying concentrations (10~640 µM) using 640 µM resveratrol as prenyl acceptor. All the values were calculated from nonlinear regression analysis with Michaelis-Menten equation by Graphpad Prism 6 software. Means and the standard deviation (error bars) were calculated from three replicates.

Figure 54:
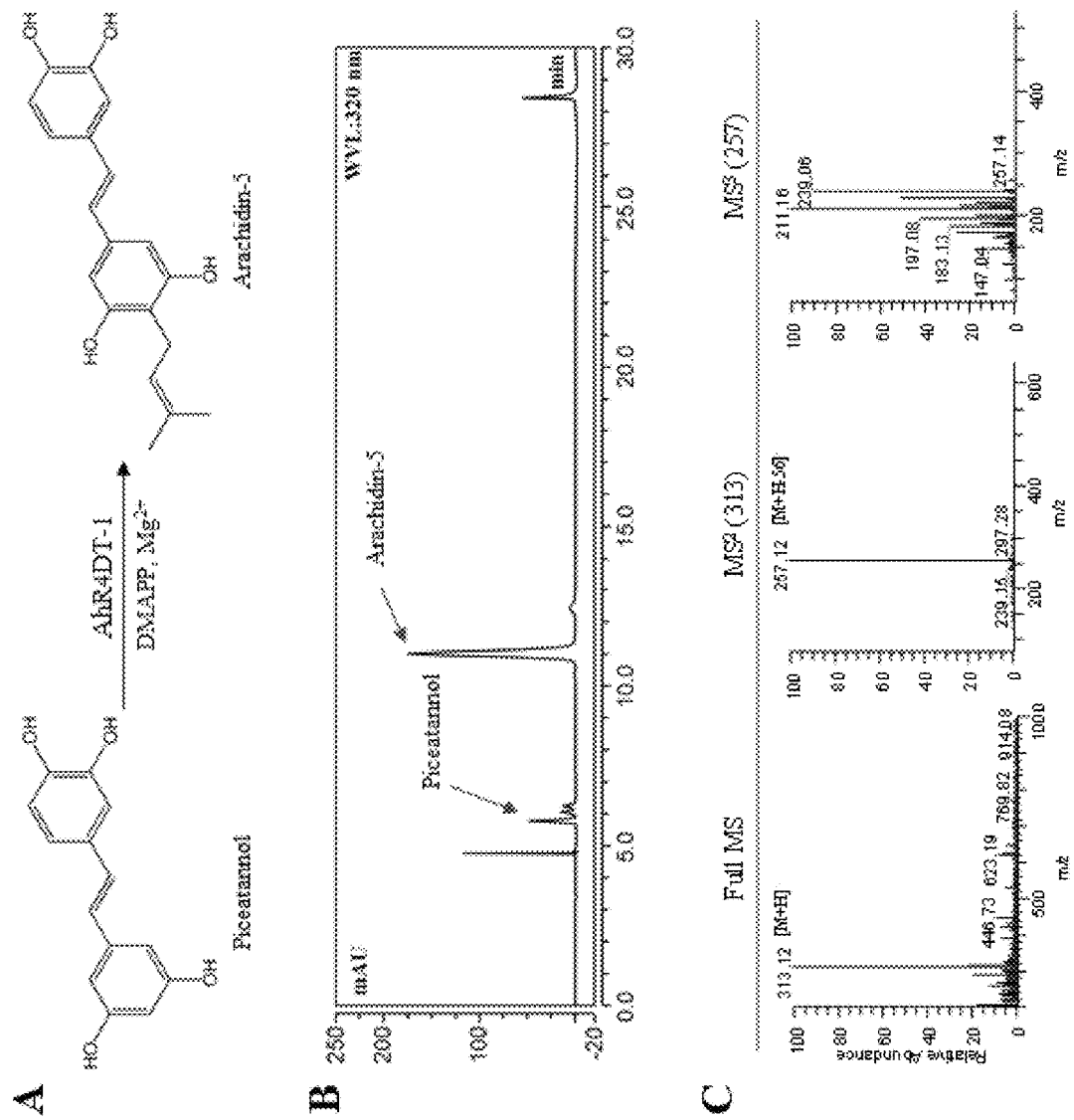

FIG. 54 shows the prenylation of piceatannol by AhR4DT-1. Substrate specificity of AhR4DT-1 in microsomal fraction of *Nicotiana benthamiana* leaf after vacuum infiltration with *Agrobacterium tumefaciens* LBA4404 harboring pBIB-Kan-AhR4DT-1 was analyzed by HPLC and LC-MS$^n$.

(A) Chemical structures of resveratrol and its prenylated product.

(B) HPLC chromatograms (UV 320 nm) of ethyl acetate extraction of reaction mixtures contained 100 µM piceatannol, 300 µM DMAPP, 10 mM MgCl$_2$, 5 mM DTT and 30 µg microsomal fraction in a pH 9.0 Tris-HCl buffer for 40 min.

(C) HPLC-PAD-ESI-MS$^3$ analysis of prenylated product, arachidin-5.

Figure 55:
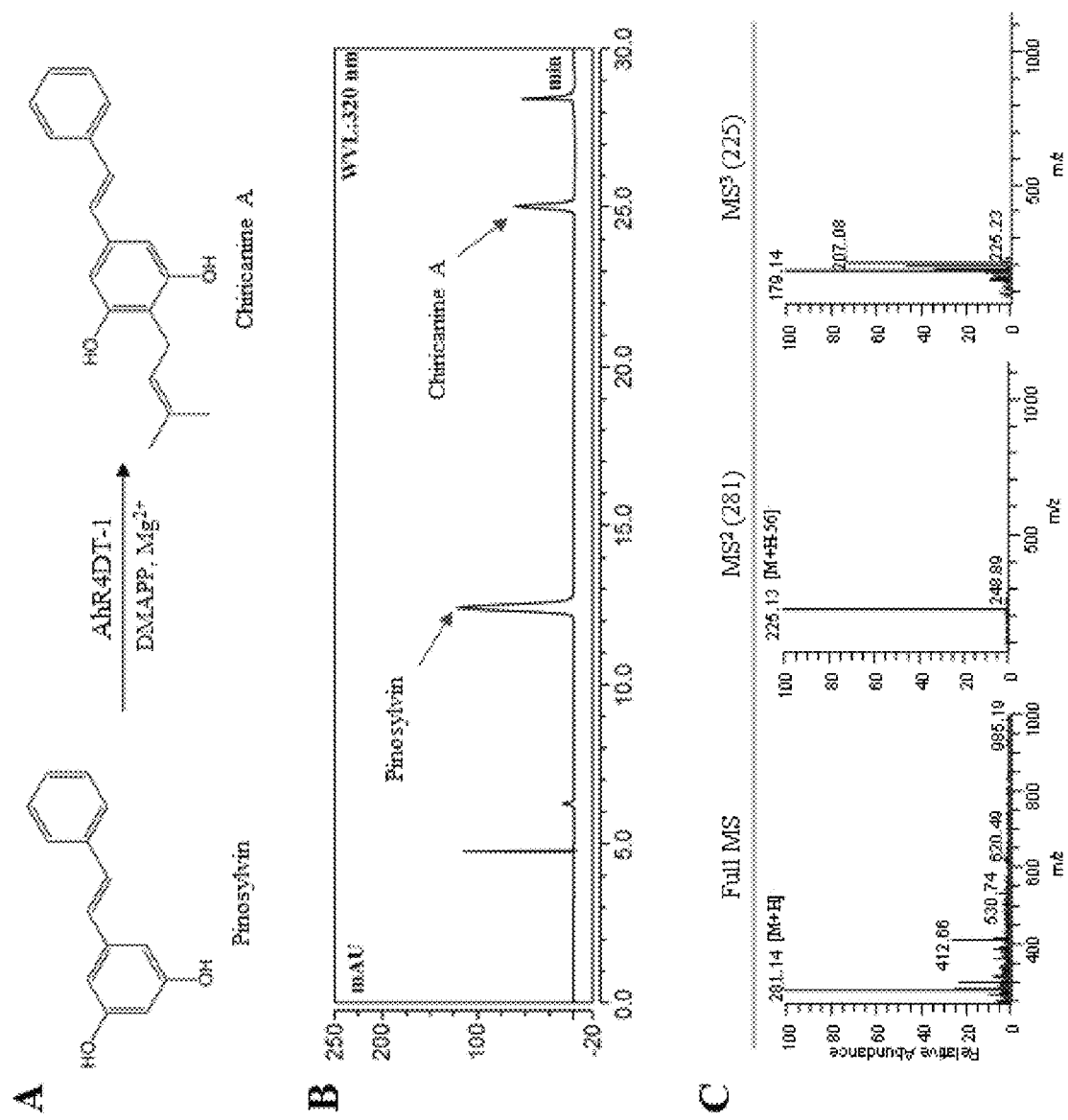

FIG. 55 shows the prenylation of pinosylvin by AhR4DT-1.

Substrate specificity of AhR4DT-1 in microsomal fraction of *Nicotiana benthamiana* leaf after vacuum infiltration with *Agrobacterium tumefaciens* LBA4404 harboring pBIB-Kan-AhR4DT-1 was analyzed by HPLC and LC-MS$^n$.

(A) Chemical structures of resveratrol and its prenylated product.

(B) HPLC chromatograms (UV 320 nm) of ethyl acetate extraction of reaction mixtures contained 100 µM pinosylvin, 300 µM DMAPP, 10 mM MgCl$_2$, 5 mM DTT and 30 µg microsomal fraction in a pH 9.0 Tris-HCl buffer for 40 min.

(C) HPLC-PAD-ESI-MS$^3$ analysis of prenylated product, chiricanine A.

Figure 56:
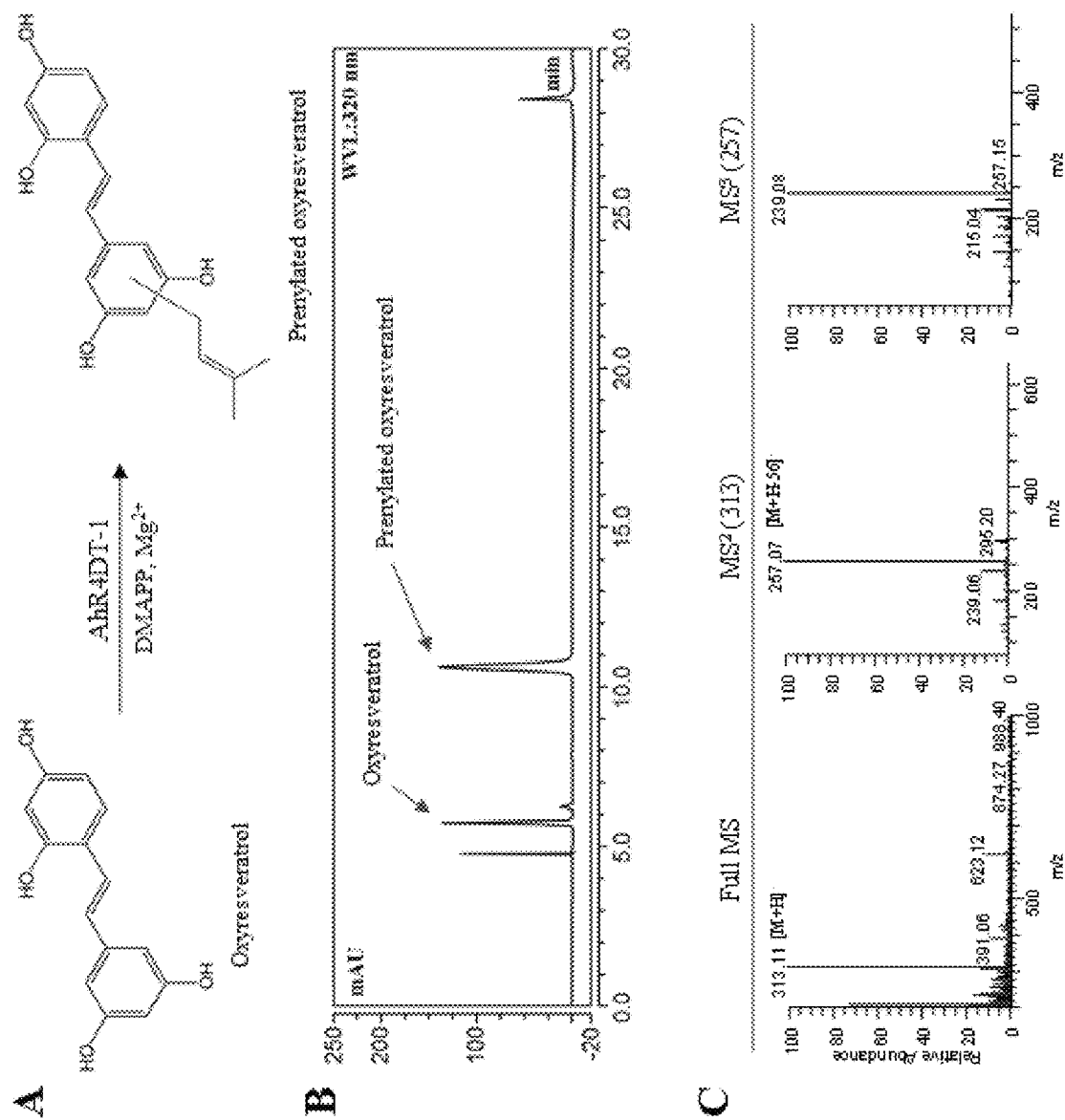

FIG. 56 shows the prenylation of oxyresveratrol by AhR4DT-1.

Substrate specificity of AhR4DT-1 in microsomal fraction of *Nicotiana benthamiana* leaf after vacuum infiltration with *Agrobacterium tumefaciens* LBA4404 harboring pBIB-Kan-AhR4DT-1 was analyzed by HPLC and LC-MS$^n$.

(A) Chemical structures of resveratrol and its prenylated product.

(B) HPLC chromatograms (UV 320 nm) of ethyl acetate extraction of reaction mixtures contained 100 µM oxyresveratrol, 300 µM DMAPP, 10 mM MgCl$_2$, 5 mM DTT and 30 µg microsomal fraction in a pH 9.0 Tris-HCl buffer for 40 min.

(C) HPLC-PAD-ESI-MS$^3$ analysis of prenylated product.

Figure 57:
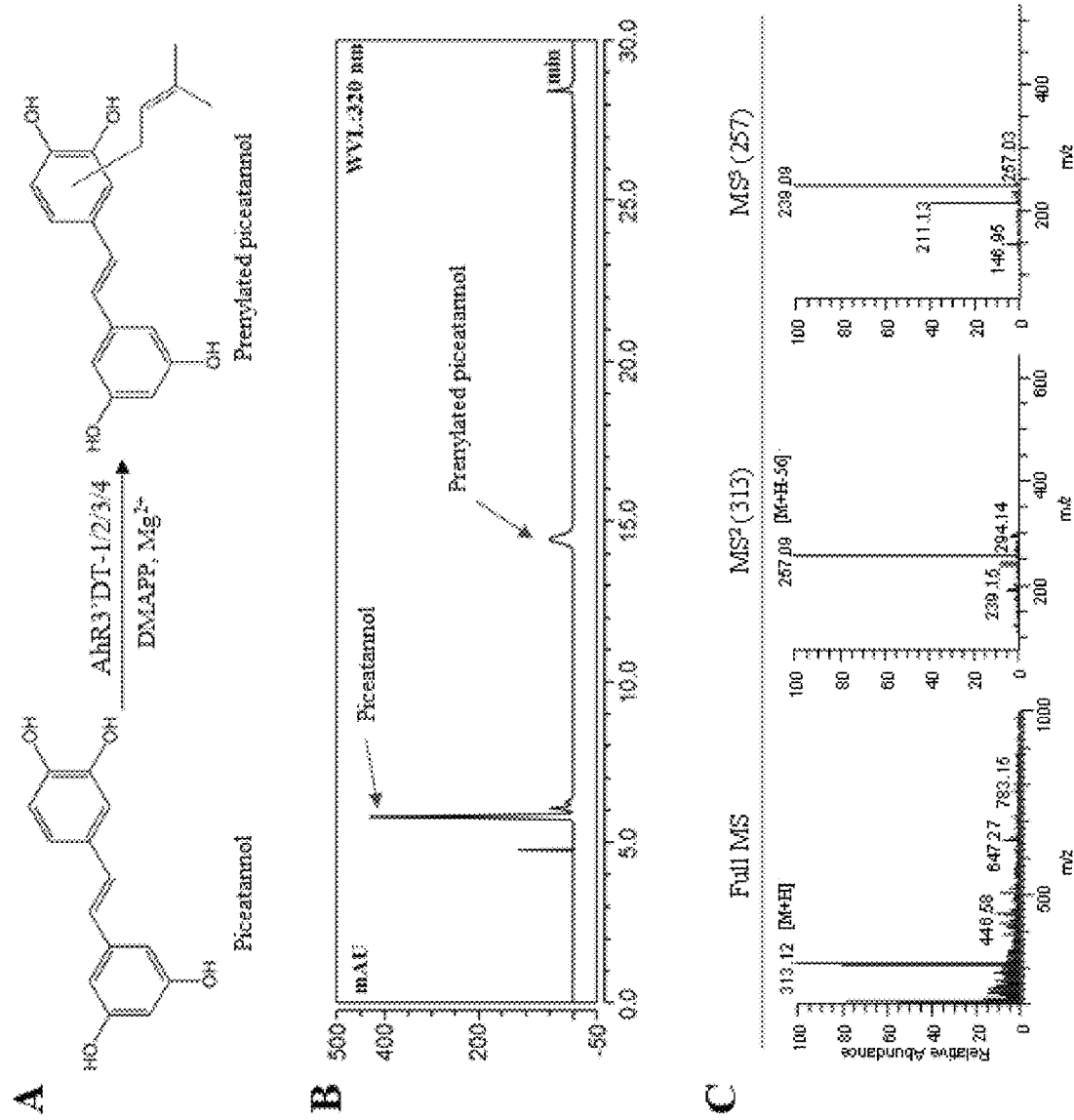

FIG. 57 shows the prenylation of piceatannol by AhR3'DT-1.

Substrate specificity of AhR3'DT-1 in microsomal fraction of *Nicotiana benthamiana* leaf after vacuum infiltration with *Agrobacterium tumefaciens* LBA4404 harboring pBIB-Kan-AhR3'DT-1 was analyzed by HPLC and LC-MS$^n$.

(A) Chemical structures of resveratrol and its prenylated product, arachidin-2.

(B), HPLC chromatograms (UV 320 nm) of ethyl acetate extraction of reaction mixtures contained 100 µM piceatannol, 300 µM DMAPP, 10 mM MgCl$_2$, 5 mM DTT and 30 µg microsomal fraction in a pH 9.0 Tris-HCl buffer for 40 min.

(C) HPLC-PAD-ESI-MS$^3$ analysis of prenylated product.

Figure 58:
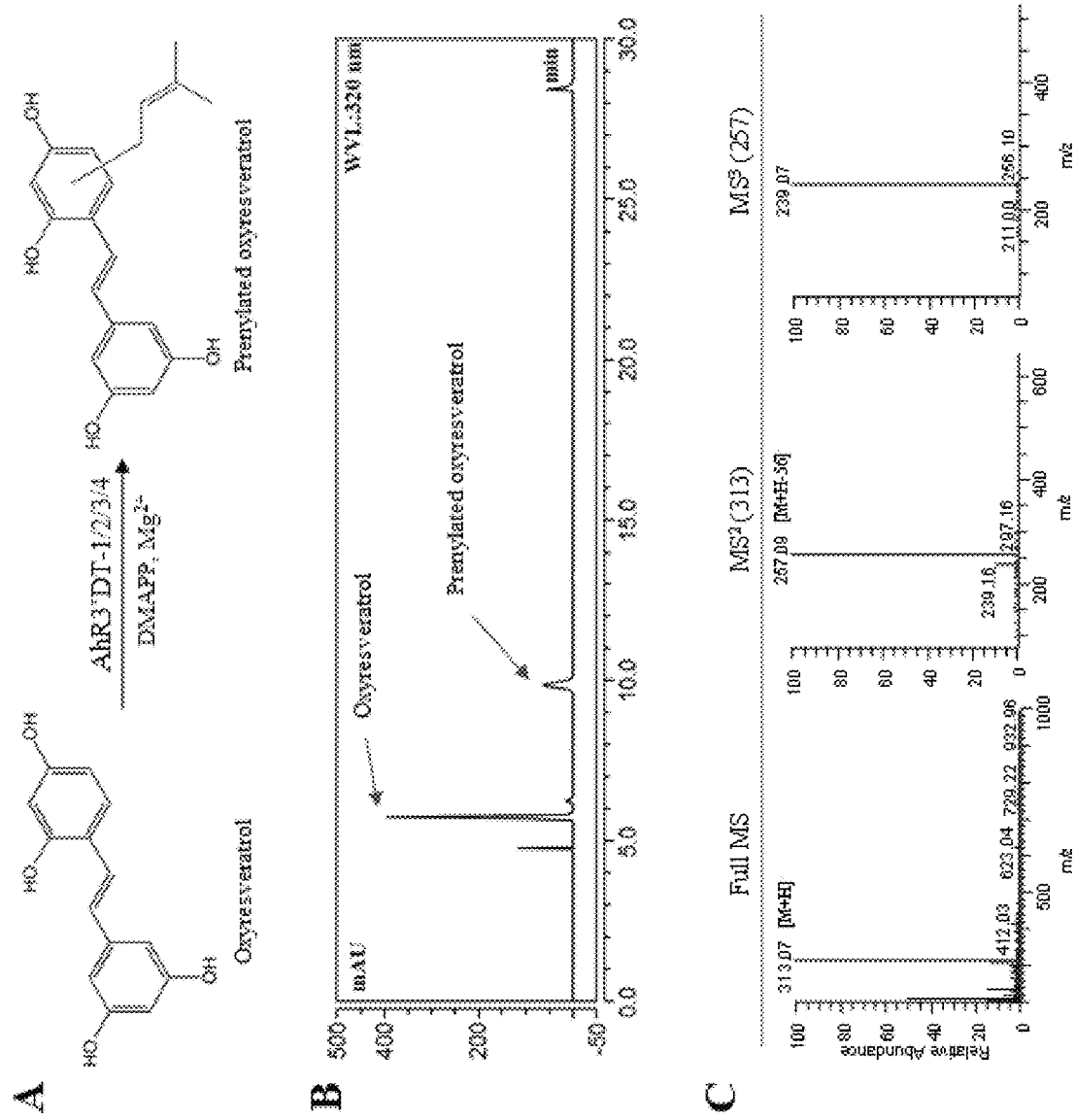

FIG. 58 shows the prenylation of oxyresveratrol by AhR3'DT-1.

Substrate specificity of AhR3'DT-1 in microsomal fraction of Nicotiana benthamiana leaf after vacuum infiltration with Agrobacterium tumefaciens LBA4404 harboring pBIB-Kan-AhR3'DT-1 was analyzed by HPLC and LC-MS".

(A) Chemical structures of resveratrol and its prenylated product, arachidin-2.

(B) HPLC chromatograms (UV 320 nm) of ethyl acetate extraction of reaction mixtures contained 100 µM oxyresveratrol, 300 µM DMAPP, 10 mM MgCl$_2$, 5 mM DTT and 30 µg microsomal fraction in a pH 9.0 Tris-HCl buffer for 40 min.

(C) HPLC-PAD-ESI-MS$^3$ analysis of prenylated product.

FIGS. 59, 59A, 59B, 59C, 59D, 59E, 59F, and 59G show the cloning strategy of binary vectors for peanut prenyltransferase genes screening.

FIGS. 60, 60A, 60B, 60C, 60D, 60E, 60F, and 60G show the cloning strategy of binary vectors for subcellular localization of AhR4DT-1 or AhR3'DT-1.

FIGS. 61, 61A, 61B, 61C, 61D, 61E, 61F, and 61G show the cloning strategy of binary vectors containing GFP for subcellular localization control.

Figure 62:
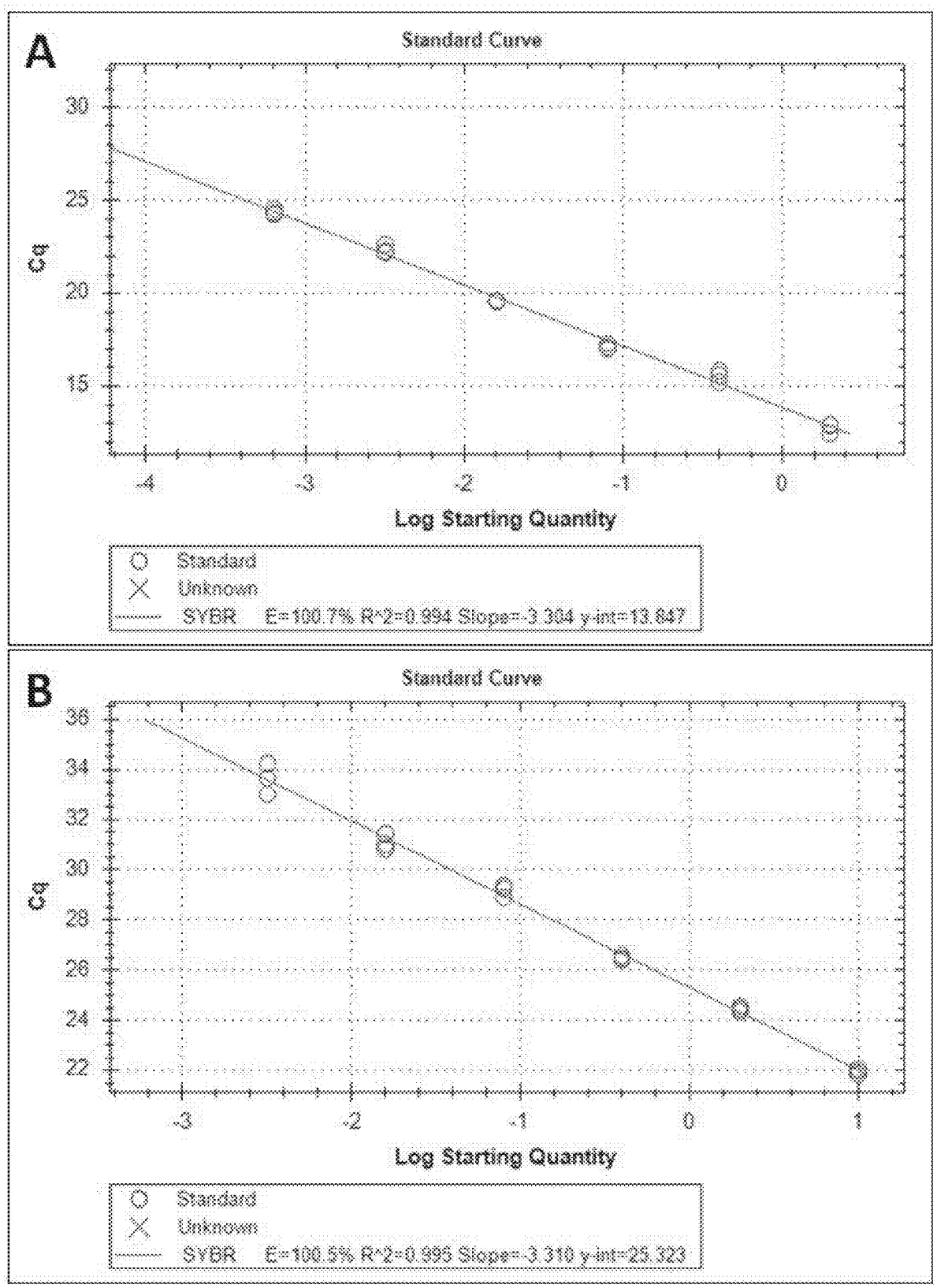

FIG. 62 shows the primer efficiencies for real-time qPCR.

The efficiency of AhR4DT-1 (A) was tested in 5× serial dilutions of peanut hairy root cDNA (range of 2 to 0.00032 ng). The efficiencies of AhR3'DT-1 (B) was calculated in the range of 10 to 0.0064 ng cDNA, and that of ATC7 (C) and EFα1 (D) were performed with 10 to 0.00032 ng cDNA.

FIG. 63 shows a table of Prenyltransferase transcripts described in this application. Activities of expressed protein products and loci of best alignment in diploid Arachis reference genomes are shown.

FIG. 64 shows a table of AhR4DT-1 and AhR3'DT-1 activity from N. benthamiana leaves fractions. The preparation of fractions and the resveratrol prenyltransferase assay are described in "Materials and Methods." Values are the mean±standard deviation for three replicates.

FIG. 65 shows a table of comparison of kinetic values of AhR4DT-1, AhR3'DT-1 and prenyltransferase activity identified from peanut hairy root. The apparent K$_m$ and V$_{max}$ values of AhR4DT-1 and AhR3'DT-1 for resveratrol, piceatannol and DMAPP were measured using the microsomal fraction of N. benthamiana leaves transiently expressing these two enzymes. Values are the mean±standard deviation of three replicates. The apparent K$_m$ and V$_{max}$ values of prenyltransferase activity identified from the microsomal fraction of peanut hairy root for resveratrol and DMAPP were previously reported by Yang et al. (2016).

FIGS. 66A-66B show a list of primers used in this study. The restriction site on each primer is underlined. (SEQ ID NOs:21-51)

FIG. 67 shows substrates used for specificity assay and the prenylated products from reaction mixtures catalyzed by AhR4DT-1 or AhR3'DT-1. Analysis was done by HPLC-PDA-electrospray ionization-MS3.

FIG. 68 shows a list of plasmids used in this study. For details of the binary vectors, see Materials and Methods.

FIGS. 69A-69B show accession numbers of proteins used for phylogenetic analysis.

Figure 70:
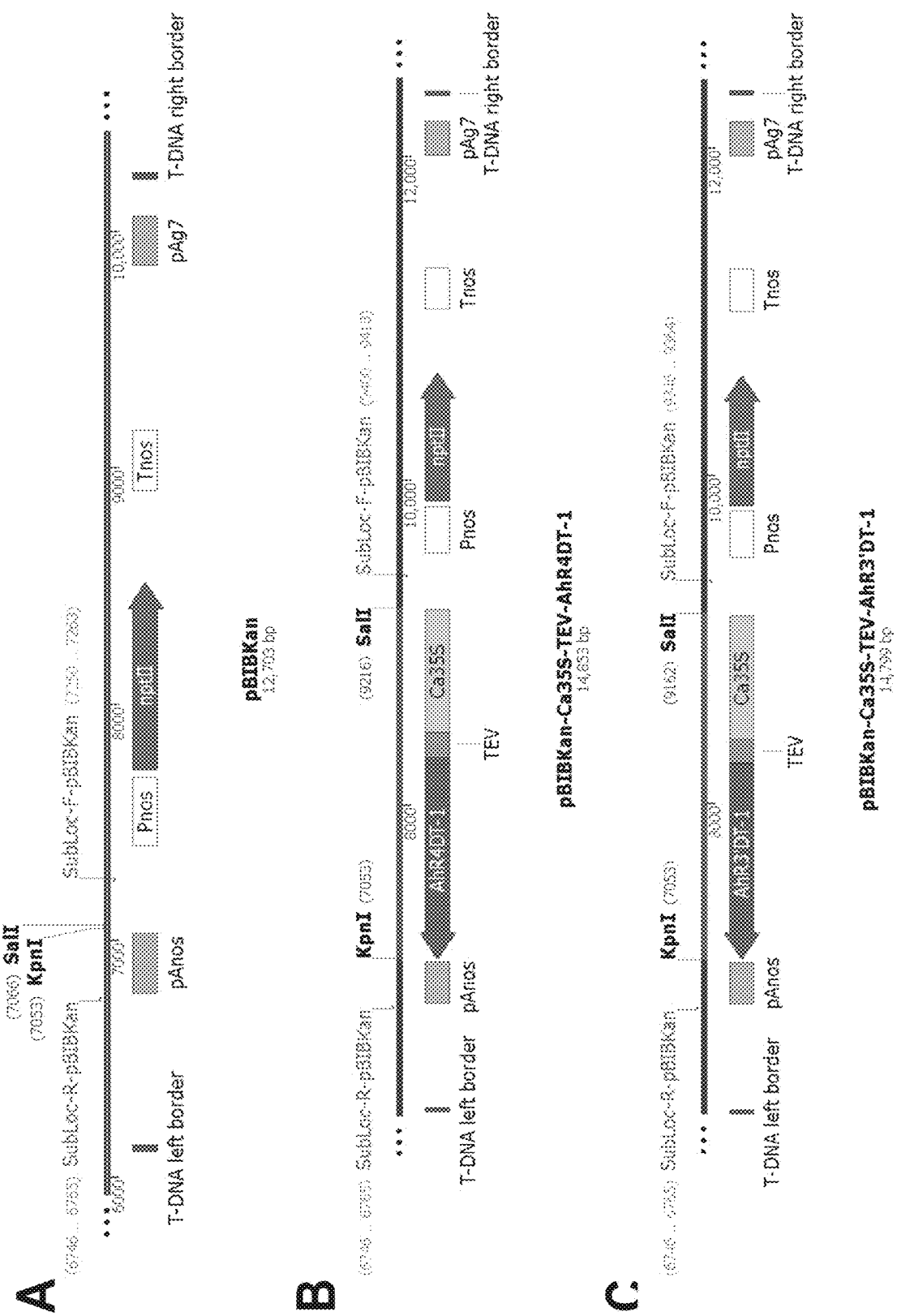

FIG. 70 shows a primer design for analysis of transgenic plants expressing peanut stilbenoid-specific prenyltransferases (AhR4DT-1 and AhR3'DT-1). Targeting position of primers, SubLoc-F-pBIBKan and SubLoc-R-pBIBKan on (A) pBIBKan, (B) pBIB-Kan-AhR4DT-1 and (C) pBIB-Kan-AhR3'DT-1.

Figure 71:
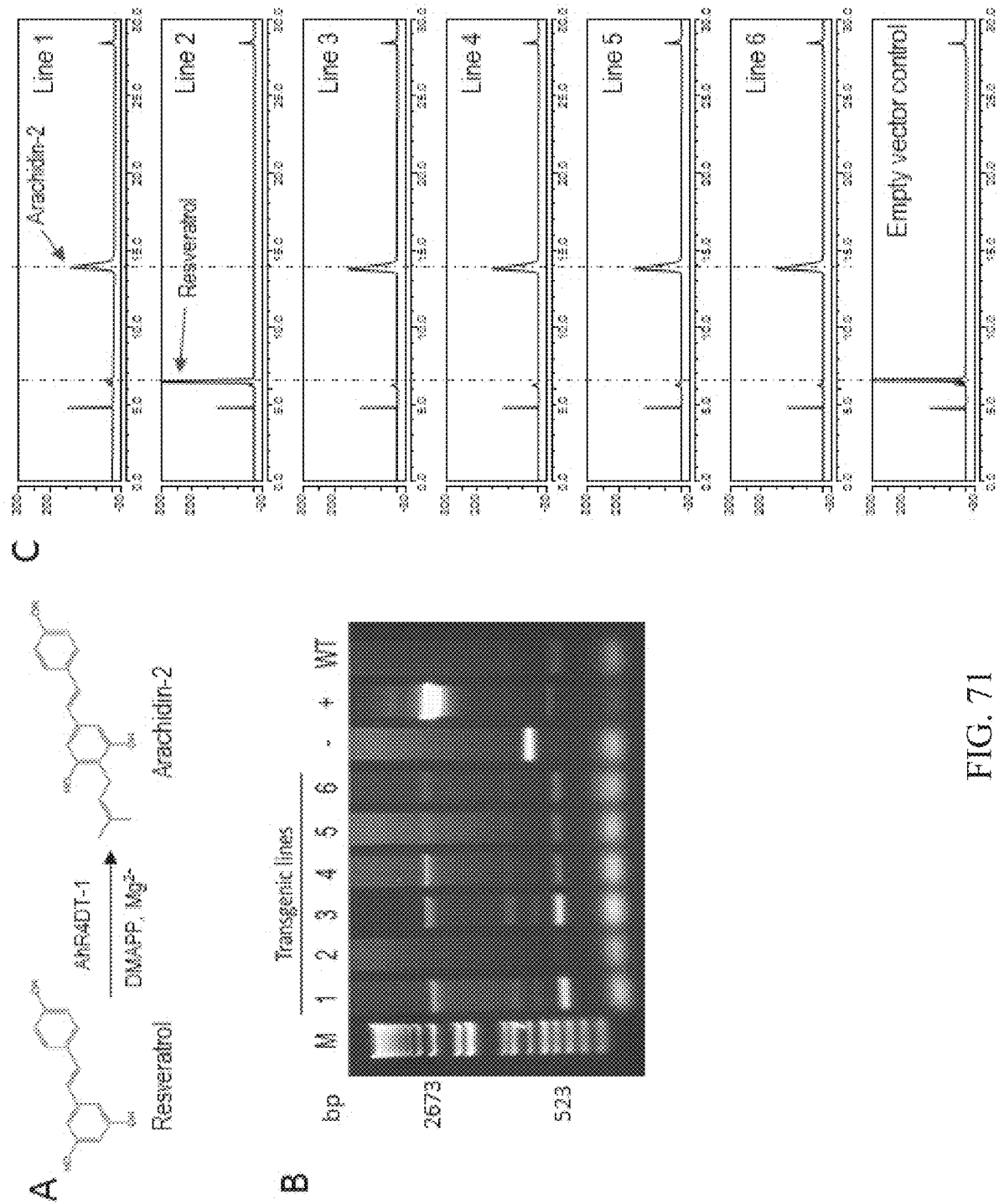

FIG. 71 shows a characterization of transgenic tobacco plants expressing peanut stilbenoid prenyltransferase AhR4DT-1 gene.

(A) AhR4DT-1 from peanut catalyzes the 4-C prenylation of resveratrol.

(B) PCR Analyses of transgenic tobacco plants expressing AhR4DT-1 gene. Genomic DNA was isolated from transgenic lines 1, 2, 3, 4, 5 and 6. Plasmid pBIB-Kan-AhR4DT-1 was used as positive control (+). Genomic DNAs of the transgenic plant transformed with pBIB-Kan empty vector and wild type plant were used as empty vector control (−) and negative control, respectively. Positive amplicon (2673 bp); negative amplicon (523 bp).

(C) Enzymatic characterization of AhR4DT-1 activity in the leaf of transgenic tobacco plants. HPLC chromatograms of ethyl acetate extract of 1 mL reaction mixture of 100 resveratrol, 300 µM DMAPP, 10 mM MgCl$_2$ and 5 mM DTT incubated with 50 µl of crude protein (approximately 75 µg) from the leaf of transgenic tobacco plants in a pH 9.0 Tris-HCl buffer for 40 min. The crude protein from the leaf of transgenic plant transformed with pBIB-Kan vector was used as empty vector control.

Figure 72:
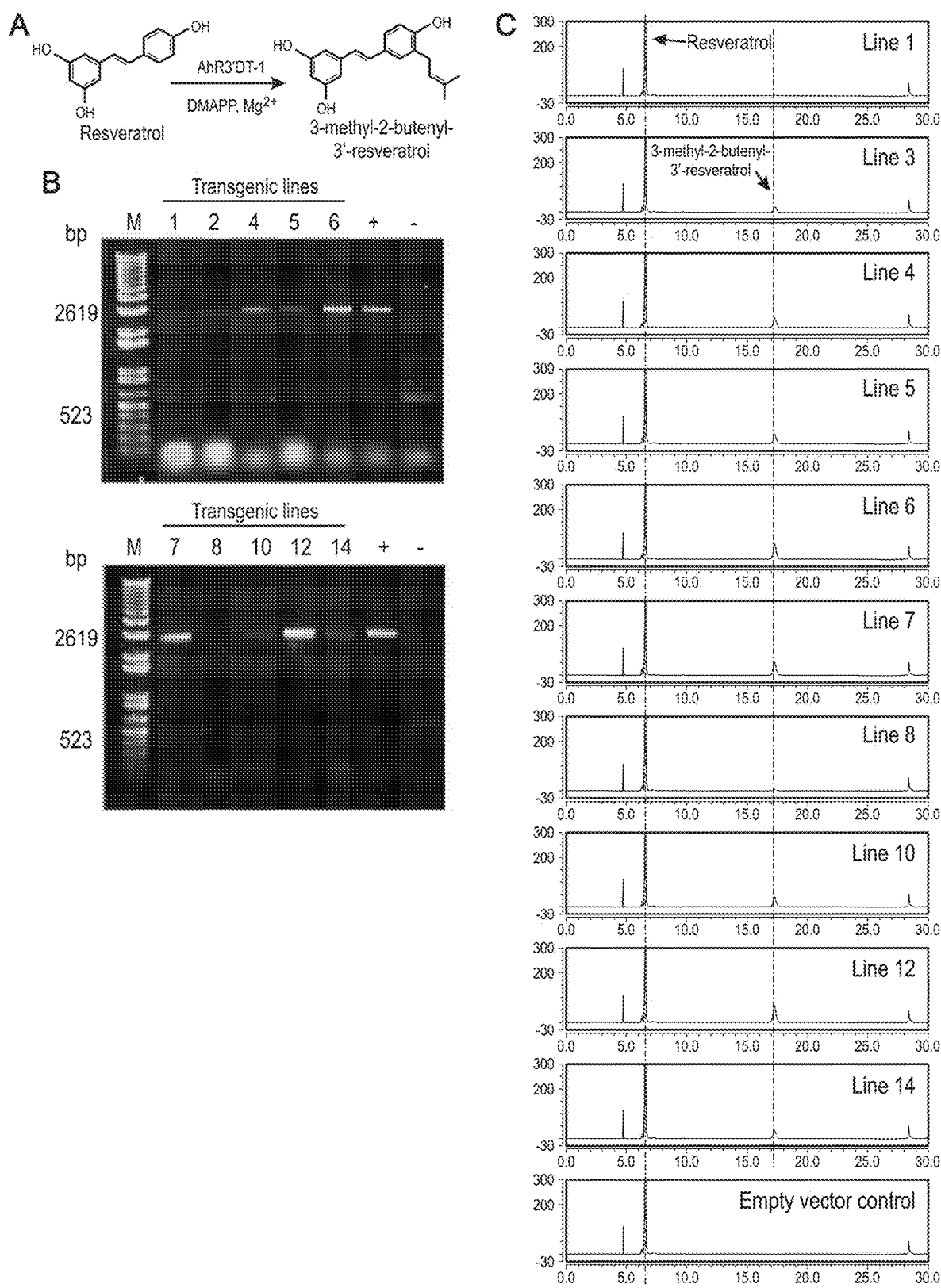

FIG. 72 shows a characterization of transgenic tobacco plants expressing peanut stilbenoid prenyltransferase AhR3'DT-1 gene.

(A) AhR3'DT-1 from peanut catalyzes the 3'-C prenylation of resveratrol.

(B) PCR Analyses of transgenic tobacco plants expressing AhR3'DT-1 gene. Genomic DNA was isolated from transgenic lines 1, 3, 4, 5, 6, 7, 8, 10, 12 and 14. Plasmid pBIB-Kan-AhR3'DT-1 was used as positive control (+). Genomic DNAs of the transgenic plant transformed with pBIB-Kan vector was used as empty vector control (−). Positive amplicon (2619 bp); negative amplicon (523 bp).

(C) Enzymatic characterization of AhR3'DT-1 activity in the leaf of transgenic tobacco lines. HPLC chromatograms of ethyl acetate extract of 1 mL reaction mixture of 200 µm resveratrol, 300 µM DMAPP, 10 mM MgCl$_2$ and 5 mM DTT incubated with 50 µl (approximately 75 µg) of crude protein from the leaf of transgenic tobacco lines in a pH 9.0 Tris-HCl buffer for 120 min. The crude protein from the leaf of transgenic plant transformed with pBIB-Kan vector was used as empty vector control.

Figure 73:
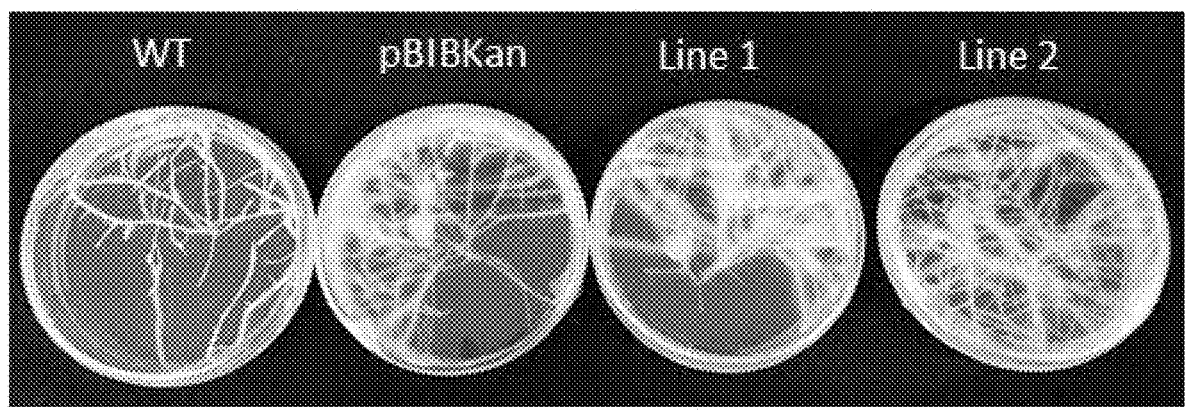

FIG. 73 shows a phenotype of transgenic hairy roots of tobacco expressing peanut stilbenoid prenyltransferase AhR3'DT-1.

From left to right, hairy root lines developed from wild type of tobacco (WT), transgenic tobacco transformed with pBIB-Kan vector (pBIBKan-control), and AhR3'DT-1-expressing line 12 (Line 1 and Line 2). Hairy roots were developed via Agrobacterium rhizogenes-mediated transformation.

DETAILED DESCRIPTION

A substantial part of non-host defense responses in many plants is the pathogen-induced production of secondary metabolites, generally termed phytoalexins, that locally restrict disease progression due to bioactivities toxic to the pathogen (reviewed in Ahuja et al., 2012). Peanut or groundnut (Arachis hypogaea) tissues mount a defense against infection by the soil fungus Aspergillus flavus and other pathogens by overproducing stilbene derivatives around sites of wounding and elicitor perception (Sobolev, 2013).

Resveratrol (3,5,4'-trihydroxy-stilbene), one of the most studied phytoalexin stilbenoids, has attracted great attention because of its bioactive properties shown through in vitro and in vivo assays to benefit human health. These include anti-inflammatory (Das and Das, 2007) and antioxidant properties, as well as antitumor and favorable cardiovascular effects (Gambini et al., 2015). However, the limited oral bioavailability of resveratrol due to its rapid absorption and metabolism restricts the future of this potentially valuable drug in clinical trials (Tome-Carneiro et al., 2013; Gambini et al., 2015).

Prenylated stilbenoids naturally produced as phytoalexins in the peanut plant possess one or two isoprenyl moieties bound to the aromatic ring of the stilbene molecule (FIG. 1). When compared to resveratrol, these compounds exhibit similar or enhanced bioactivity in in vitro experiments. For instance, arachidin-1 and resveratrol showed similar anti-inflammatory activity in lipid polysaccharide-treated RAW 264.7 macrophages and this correlated with the inhibition of prostaglandin $E_2$ production (Chang et al., 2006; Djoko et al., 2007). Arachidin-1, arachidin-2 and arachidin-3, also applied to macrophages, were more effective than resveratrol in inhibiting inducible nitric oxide production (Sobolev et al., 2011). In other antioxidant activity assays, arachidin-1 inhibited lipid oxidation more effectively than resveratrol (Abbott et al., 2010), and arachidin-2 and arachidin-3 showed greater potency over resveratrol in inhibiting production of intracellular reactive oxygen species (Sobolev et al., 2011). Arachidin-1 further showed higher cytotoxicity than resveratrol to leukemia HL-60 cells (Huang et al., 2010) and other cancer cells (SK-MEL, KB, BT-549, and SK-OV-3) (Sobolev et al., 2011). Interestingly, arachidin-1 and arachidin-3 were shown to bind to human cannabinoid receptors 2 (hCBR2s), while the affinity of their non-prenylated analogous, piceatannol and resveratrol for hCB2Rs was 5- to 10-fold lower. Molecular modeling studies with hCBR2s indicated that the prenyl moiety of the arachidins improved the binding affinity to the receptors (Brents et al., 2012).

In addition to the above-mentioned stilbenoids (arachidin-1, arachidin-2 and arachidin-3), more than 20 other prenylated stilbenoids have been described in peanut tissues (Sobolev et al., 2006; Wu et al., 2011; Sobolev, 2013; Sobolev et al., 2016). The biosynthesis of stilbenoids derives from both the phenylpropanoid and acetate pathways. These merge to produce resveratrol by the action of resveratrol synthase which catalyzes the cyclization of 4-coumaroyl-CoA and malonyl-CoA (Schöppner and Kindl, 1984). The prenylation step, in which either of two prenyl patterns (3,3-dimethylallyl or 3-methyl-but-1-enyl) are introduced to various positions of the stilbene backbone (FIG. 1), along with the oxidation, methylation and cyclization steps plays a major role in the diversification of peanut prenylated stilbenoids. Although the enzymes involved in resveratrol biosynthesis have been elucidated (Chong et al., 2009), the enzymes involved in the prenylation steps of resveratrol or any other stilbenoid have not been described.

For other prenylated aromatic compounds, a prenyltransferase was found to be the critical activity for coupling the aromatic compound biosynthesis and terpenoid biosynthesis, the latter leading to the formation of the prenyl unit (Yazaki et al., 2009). Two pathways are known for the biosynthesis of prenylated compounds in plants, the mevalonic acid (MVA) pathway in the cytosol and the 2-C-methyl-D-erythritol-4-phosphate (MEP) pathway in the plastid (Lohr et al., 2012). Many studies have shown that dimethylallyl pyrophosphate (DMAPP) derived from the MEP pathway is used as prenyl donor to form prenylated flavonoids or prenylated isoflavonoids in the plastid (Yamamoto et al., 2000; Yazaki et al., 2009). To determine the biosynthetic origin of these terpenoids, distinct metabolic inhibitors were applied to inhibit the key rate limiting enzymes involved in either the MVA or MEP pathway. For instance, mevastatin, an inhibitor of 3-hydroxy-3-methyl-glutaryl-coenzyme A reductase involved in the MVA pathway was used in hairy root cultures of ginseng to study the biosynthesis of ginsenosides (Zhao et al., 2014); while clomazone, a herbicide that inhibits 1-deoxy-D-xylulose-5-phosphate synthase (DXS) during early steps of DMAPP biosynthesis in the plastid was used to investigate the synthesis of monoterpenes in Catharanthus roseus (Han et al., 2013).

In order to elucidate the biosynthesis of peanut prenylated stilbenoids, we established hairy root cultures of peanut (Condon et al., 2010) and recently demonstrated that a sustainable production of the prenylated stilbenoids arachidin-1 and arachidin-3 can be achieved upon co-treatment of these cultures with methyl jasmonate (MeJA) and cyclodextrin (CD) (Yang et al., 2015a). In the current study, we took advantage of this bioproduction system and produced arachidin-2 and a new prenylated stilbenoid, named arachidin-5, as the prenylated products of the hairy root microsomal fraction using resveratrol and piceatannol as substrates, respectively. To determine the biosynthetic origin of the prenyl moiety of these prenylated stilbenoids, two metabolic inhibitors, mevastatin and clomazone were selected and applied to peanut hairy root cultures co-treated with MeJA and CD as elicitors. In the process, we identified and characterized a resveratrol 4-dimethylallyltransferase (AhR4DT) from the microsomal fraction of elicited peanut hairy roots. To our knowledge, this enzyme is the first stilbenoid-specific prenyltransferase that prenylates resveratrol and other specific stilbenoids at the 4-C position of the aromatic ring (FIG. 1).

Results
Purification and Structural Elucidation of a New Prenylated Stilbenoid from Peanut Hairy Root Culture Hairy roots of peanut have the capability to produce and secrete resveratrol (3,5,4'-trihydroxy-trans-stilbene), piceatannol (3,5,3',4'-tetrahydroxy-trans-stilbene) and their prenylated analogs, arachidin-3 and arachidin-1, in the medium upon co-treatment with MeJA and CD as elicitors (Yang et al., 2015a). In addition, in the current study we also identified arachidin-2 in the ethyl acetate extract of the culture medium by comparing with the HPLC retention time, characteristic UV spectrum ($\lambda_{max}$=323 mn) (FIG. 2) and mass spectrometric analysis of the purified arachidin-2 isolated from fungus-infected peanut seeds. The structure of arachidin-2 purified from peanut hairy root culture was subsequently confirmed by $^1$H- and $^{13}$C-NMR spectra (data not shown).

A new prenylated stilbenoid with $\lambda_{max}$ 327 nm in the HPLC mobile phase was also isolated from the peanut hairy root culture medium (FIG. 2). We named it arachidin-5. Mass spectrometry analysis (Table 1 shown in FIG. 7) of arachidin-5 (m/z 313 [M+H]$^+$) gave a main fragment with a m/z 257 [M+H-56]$^+$ in MS$^2$ which suggested the presence of a prenyl moiety. Arachidin-5 and arachidin-1 share very similar MS, MS$^2$ and MS$^3$ spectra (Table 1 shown in FIG. 7) indicating that the structural difference between these two compounds might be only in the position of olefinic bond on their prenylated moieties.

The structure of the prenylated moiety on the arachidin-5 was further determined by $^1$H- and $^{13}$C-NMR. The presence of a five-carbon unit of the 3,3-dimethylallyl stricture was evident from the peak at 5.30 ppm (t, 7.1 Hz) that is coupled to the peak at 3.36 ppm (d, 7.1), as well as the peaks at 1.77 and 1.65 ppm for the two methyl groups (H-5" and H-4", respectively) (FIG. 17). These proton resonances are the same as those published for arachidin-2 (Park et al., 2011). The 3,3-dimethylallyl structure is also supported by the presence of a quaternary carbon peak at 130.9 (C-3") in the $^{13}$C-NMR, spectrum, as well as peaks at 124.4 (C-2"), 26.0 (C-4"), 23.1 (C-1") and 17.9 (C-5") (FIG. 18). These resonances are in agreement with published resonances for the isoprene tail of arachidin-2 (Park et al 2011). The NMR results showed that arachidin-5 has the same 3,3-dimethylallyl moiety as arachidin-2 but an additional hydroxyl group at the 3' position, while arachidin-1 and arachidin-3 have the 3-methyl-but-1-enyl moieties instead.

In addition to arachidin-5, arachidin-1, arachidin-2 and arachidin-3, HPLC analysis of the culture medium showed the presence of 2 other compounds with similar characteristic of arachidin-5 and arachidin-2 based on UV and MS, MS$^2$ and MS$^3$ spectra (FIG. 2 and Table 1 shown in FIG. 7). These compounds were later designated as arachidin-5 derivative and arachidin-2 derivative respectively.

Effects of Metabolic Inhibitors on Yield of Prenylated Stilbenoids in Peanut Hairy Root Culture As expected for peanut phytoalexins, non-prenylated and prenylated stilbenoids were only present in the peanut hairy root cultures after elicitor treatment (Medina-Bolivar et al., 2007; Yang et al., 2015a). To study the metabolic origin of the prenyl moiety of the prenylated stilbenoids, mevastatin or clomazone was added to 9-day peanut hairy root cultures co-treated with 100 µM MeJA and 9 g/L CD. In preliminary experiments we found that mevastatin at 1, 10, or 100 µM did not affect the levels of prenylated stilbenoids (FIG. 19). On the other hand, the effects on the accumulation of resveratrol and inhibition of prenylated stilbenoids accumulation were increased with the concentration of clomazone (1 µM to 100 µM) (FIG. 20). Hence, to quantify these effects, we determined yields of resveratrol and prenylated stilbenoids after 48 h and 72 h of elicitor treatment together with mevastatin (10 µM), or clomazone (10 µM and 100 µM). The yields of stilbenoids were expressed in micromoles to assess the molar contribution of resveratrol as a precursor of the prenylated stilbenoids.

Mevastatin had no significant effect on the yields of resveratrol, piceatannol and prenylated stilbenoids with the exception of arachidin-5 and arachidin-1, which showed a 27% and 41% increase in yield, respectively, after a 72-h treatment (FIG. 3). During the 24-h interval between 48 and 72-h treatments, non-inhibitor and mevastatin treated groups had significant increases in the yields of arachidin-5, arachidin-1, arachidin-2, and arachidin-3 indicating that mevastatin did not inhibit the accumulation of these prenylated stilbenoids (FIG. 3).

With an inherent limited production (about hundred fold lower than that of resveratrol) upon elicitor treatment, piceatannol concentration increased only slightly in the 100 µM clomazone group after 72 h of treatment (FIG. 3). However, in both 10 µM and 100 µM clomazone treated groups, there were significantly higher yields of resveratrol and significantly lower yields of prenylated stilbenoids when compared to the non-inhibitor group. In particular, the accumulation of arachidin-5 and arachidin-1 was almost completely inhibited and only trace amounts were observed in the 48-hour treated groups containing 100 µM clomazone (FIG. 3). There were no significant increases in the levels of all prenylated stilbenoids during the 24-h interval between the 48- and 72-h time points indicating that clomazone has an inhibitory effect on the accumulation of prenylated stilbenoids in peanut hairy root cultures. Since each of the inhibitors was applied to 9-day-old hairy root cultures together with elicitors, DMAPP or IPP might have been already synthesized and stored in the tissue prior to the inhibition. Thus, even if the biosynthesis of DMAPP and IPP was blocked when clomazone was added into the medium, small amounts of arachidin-2 and arachidin-3 could be detected in the 48- and 72-h clomazone treated samples (FIG. 3). Moreover, when different concentrations of clomazone were applied to the peanut hairy root culture without elicitors, none of these stilbenoids was detected in the ethyl acetate extracts of the culture medium suggesting that clomazone was not able to induce the production of stilbenoids by itself (FIG. 21). However, in the co-treated group of 100 clomazone with elicitors, the yield of resveratrol reached up to 830.73±25.83 µM after 72 h which was 6.3 fold higher than that in the non-inhibitor group. The micromolar increase of resveratrol was about 1.54 fold greater than the overall decrease in the accumulation of arachidin-5, arachidin-1, arachidin-2, and arachidin-3, suggesting that these prenylated stilbenoids may have been derived from resveratrol.

Degradation of Exogenous Resveratrol in Peanut Hairy Roots

Upon co-treatment of peanut hairy root cultures with MeJA and CD as elicitors, most of the total resveratrol and prenylated stilbenoids produced were secreted into the culture medium and only trace amounts were found in the ethyl acetate extracts of the root tissue (FIG. 22). Based on previous observations regarding loss of resveratrol accumulation in medium of non-elicited peanut hairy root cultures (Yang et al., 2015a), we speculated that resveratrol could be taken up by the hairy roots and metabolized by one or multiple enzymatic mechanisms in the roots.

To confirm this hypothesis, 1 mM resveratrol was co-incubated with a crude cell-free extract from non-elicited peanut hairy roots. After 30-min incubation, the concentration of resveratrol declined to 53% of that in the control group co-incubated with heat-denatured crude cell-free extract. Meanwhile, piceatannol and other unidentified compound with $\lambda_{max}$ 327 nm referred to as a resveratrol derivative, were detected as reaction products (FIG. 4a and FIG. 4d). In fact, according to our preliminary experiments, not only was resveratrol metabolized, but the accumulation of prenylated stilbenoids like arachidin-2 was likewise affected. Consequently, after 120-min incubation, neither resveratrol nor its prenylation product, arachidin-2 was detected in the ethyl acetate extracts of the reaction mixtures (FIG. 23). To prevent the oxidation of resveratrol, dithiothreitol (DTT) as reducing agent was added to the reaction mixture of the crude cell-free extract from non-elicited peanut hairy root using 1 mM resveratrol as substrate. After 120-min co-incubation with 5 mM DTT, more than 95% of the amount of resveratrol remained and no piceatannol was detected in the mixture (FIG. 4c), suggesting that DTT was able to prevent the oxidation of resveratrol.

Detection of Resveratrol Prenyltransferase (AhR4DT) Activity in Peanut Hairy Roots All flavonoid-specific prenyltransferases reported to date from other legume plants have been localized to plastid membranes, and results described above indicate that the accumulation of prenylated stilbenoids in our hairy root culture system can be blocked in the presence of plastid MEP pathway inhibitor. We therefore hypothesized that the stilbenoid-specific prenyltransferase(s) in peanut might also be membrane localized and use DMAPP or IPP originating from the MEP pathway as the prenyl donor. Furthermore, our clomazone inhibitor experiments suggested resveratrol as a prenyl acceptor and a precursor of prenylated stilbenoids. We therefore prepared a microsomal fraction using ultracentrifugation from 48-h elicited peanut hairy root treated with resveratrol, DMAPP, along with DTT to reduce the degradation of resveratrol and its prenylated product. Two enzymatic products were synthesized in the reaction mixture; the predominant one was identified as arachidin-2 by comparison of its retention time, UV spectrum, mass spectra and fragmentation patterns obtained by tandem mass spectrometry ($MS^2$ and $MS^3$), each of which were identical to that of arachidin-2 purified from peanut hairy root culture (FIG. 5b). Another product (FIG. 5b) shared identical retention time, UV spectrum, mass spectra, MS' and $MS^3$ with that of unidentified compound found in peanut hairy root culture (Table 1 shown in FIG. 7). Due to the presence in the enzymatic reaction with 100 μM arachidin-2 and crude cell-free extract (FIG. 24), this product is considered as an enzymatic derivative of arachidin-2. None of the prenylated products were detected in the sample incubated with the microsomal fraction from non-elicited hairy root tissue (FIG. 28), indicating the inducibility of this resveratrol prenyltransferase in peanut hairy roots. Moreover, the specific activity of resveratrol prenyltransferase in the microsomal fraction (421.16±16.25 pkat·$mg^{-1}$ of protein, based on the production of arachidin-2) was 9.3-fold higher than that in the crude cell-free extracts, suggesting that resveratrol prenyltransferase in peanut was bound to the membrane fraction of the root cells (Table 2 shown in FIG. 8).

Biochemical Characterization of Resveratrol Prenyltransferase AhR4DT

In the resveratrol prenyltransferase reaction, the accumulation of the prenylated product arachidin-2 followed a linear relationship with input between 30 μg and 120 μg of microsomal protein. The reaction was also linear over the 120 min incubation time (FIG. 25). The optimum pH for this prenyltransferase was 9.2 in a Tris-HCl buffer (FIG. 26), which was close to the optimum pH values of 9-10 for flavonoid specific prenyltransferases (Yamamoto et al., 2000). Divalent cations were absolutely required for resveratrol prenyltransferase activity and $Mg^{2+}$ was the most effective these (100%), followed by $Mn^{2+}$ (71.8%), $Fe^{2+}$ (14.6%) and $Ca^{2+}$ (0.9%) (FIG. 27). No prenyltransferase activity was detected when a divalent cation was absent from the reaction (FIG. 28). Isoprenoid precursor isopentenyl diphosphate (IPP) was tested as a prenyl donor for the prenyltransferase with resveratrol as the prenyl acceptor and no activity was detected in the assay (FIG. 28). The apparent $k_m$ values for resveratrol and DMAPP were calculated as 111.1±40.44 μM and 91.89±7.032 μM, respectively (FIG. 29).

Substrate Specificity of Resveratrol Prenyltransferase AhR4DT

To analyze the substrate specificity of the resveratrol prenyltransferase from peanut hairy root, stilbenoids (piceatannol, pinosylvin, pterostilbene and oxyresveratrol), flavanone (naringenin), flavone (apigenin) and isoflavone (genistein) were incubated with a microsomal fraction using DMAPP as a prenyl donor. When piceatannol was used as a prenyl acceptor, the microsomal fraction catalyzed the synthesis of arachidin-5 as the predominant prenylated product (FIG. 30). Similar to the arachidin-2 derivative, another product considered as an enzymatic derivative of arachidin-5, was also detected in the reaction (FIG. 31). In addition, the microsomal fraction catalyzed pinosylvin into chiricanine A, confirmed by comparison of its retention time, UV spectrum, mass spectra and fragmentation patterns with those of chiricanine-A standard purified from fungus-challenged peanut seeds (FIG. 6 and FIG. 30). Using this microsomal fraction, an isoprene unit was also transferred to oxyresveratrol. Mass spectroscopic analysis of its reaction product (m/z 313 $[M+H]^+$) showed a main fragment with a m/z 257 $[M+H-56]^+$ in $MS^2$ which suggested the presence of a prenyl moiety (FIG. 32). However, the position of the prenyl moiety on this prenylated oxyresveratrol remains undetermined due to the insufficient amount of compound for further structure elucidation.

Interestingly, pterostilbene which has methoxy groups at C-3 and C-5 positions, respectively, did not produce any product within the microsomal fraction (FIG. 6 and FIG. 30), suggesting that the additional methyl group on its structure might block prenylation and that either or both of the hydroxyl groups at C-3 and C-5 position might be required for the prenylation reaction. Furthermore, neither prenylated flavanone, prenylated flavone nor prenylated isoflavone was detected in the reaction mixtures (FIG. 6 and FIG. 30), indicating that this peanut prenyltransferase may be a stilbenoid-specific prenyltransferase.

Discussion

AhR4DT, a Membrane-Bound Prenyltransferase Specific for Stilbenoids from Peanut Hairy Root As the limiting enzyme involved in the biosynthesis of prenylated flavonoids, flavonoid prenyltransferases have been a focus of previous research particularly in plants of the Leguminosae family known to accumulate these type of specialized metabolites. The first flavonoid prenyltransferase, SfN8DT, was identified in *Sophora flavescens* cell cultures by Sasaki et al. in 2008. Subsequently, SfG6DT and SfiLDT, which prenylate genistein to produce wighteone (6-dimethylallylgenistein) and isoliquiritigenin to dimethyllylisoliquiritigenin respectively, were identified in the same species (Sasaki et al., 2011). While SfG6DT prenylates genistein on the A-ring of the isoflavone, LaPT1 isolated from another legume, white lupin (*Lupinus albus*), catalyzes the prenylation of the B-ring of genistein and 2'-hydroxygenistein to form isowighteone (3'-dimethylallylgeni stein) and luteone (2'-hydroxy-3'-dimethylallyl-genistein), respectively (Shen et al., 2012). As a crucial prenyltransferase involved in glyceollin biosynthesis, GmG4DT was identified and characterized in soybean (*Glycine max*). This enzyme catalyzes the dimethylallylation of glycinol at position 4 to produce the precursor of the phytoalexin, glyceollin I (Akashi et al., 2008). More recently, GuA6DT, a flavone prenyltransferase was identified in another legume species, liquorice (*Glycyrrhiza uralensis*) (Li et al., 2014).

In this study, we have described the first plant stilbenoid prenyltransferase activity, and named this enzyme as resveratrol 4-dimethylallyltransferase (AhR4DT). AhR4DT catalyzes the dimethylallylation of resveratrol at C-4 and is derived from the microsomal fraction of elicited peanut hairy roots. AhR4DT shows several common features with other prenyltransferases, such as those described above. For instance, all prenylation activities mentioned above and demonstrated here require a divalent cation as cofactor and a basic buffer for optimal reaction rate (except for GmG4DT which reaction rate optimum is pH 7.5 buffer for the reaction, (Akashi et al., 2008). Because the activity of AhR4DT was concentrated in the microsomal fraction and the accumulation of prenylated stilbenoid in peanut hairy roots was inhibited by clomazone, we suggest that this peanut resveratrol prenyltransferase is a membrane-bound protein located in the plastid. This further suggests that the DMAPP used in the prenylation reaction was derived from the MEP plastidic pathway. Our hypothesis is in agreement with the plastidic subcellular location of flavonoid prenyltransferases identified in other legume species.

During the biosynthesis of stilbenoids and flavonoids, both resveratrol synthase and chalcone synthase use 4-coumaroyl-CoA as a substrate and perform three condensation reactions with malonyl-CoA to form a linear tetraketide, which is later folded into new ring structures. These two enzymes are distinguished by a special property of stilbene synthases, which looses the terminal carboxyl group as $CO_2$, resulting in release of 4 $CO_2$. In contrast, each reaction catalyzed by chalcone synthase releases 3 $CO_2$ molecules. It has been suggested that stilbene synthase may have developed from chalcone synthase via gene duplication and mutation rendering new and improved functions (Tropf et al., 1994).

Among the prenylation products of resveratrol, piceatannol, pinosylvin, and oxyresveratrol catalyzed by the microsomal fraction containing AhR4DT, only arachidin-2 and arachidin-5 were detected in the spent medium of peanut hairy root cultures co-treated with MeJA and CD. Interestingly, oxyresveratrol and prenylated oxyresveratrol reported in the bark of *Artocarpus dadah* (Su et al., 2002) along with pinosylvin isolated from pine hardwood, have not been identified in any peanut tissue, while the prenylated product of pinosylvin, chiricanine A that was first described in the roots of *Lonchocarpus chiricanus* (Ioset et al., 2001), has been described in peanut seeds after infection with the fungus *Aspergillus flavus* (Sobolev et al., 2009).

Biosynthesis of Prenylated Stilbenoids in Peanut Hairy Root Cultures

The use of abiotic elicitors to induce the biosynthesis of stilbenoid in hairy root cultures provides for an axenic sustainable and controlled production platform for these specialized metabolites which can be leveraged to study their biosynthetic pathway. The metabolic steps to produce resveratrol from phenylalanine including phenylalanine ammonia-lyase (PAL), cinnamate-4-hydroxylase (C4H), 4-coumarate:coenzyme A ligase (4CL), and resveratrol synthase (RS) have already been elucidated (Watts et al., 2006). In the current study, a stilbenoid prenyltransferase, AhR4DT, which prenylates resveratrol to form arachidin-2 was characterized from the microsomal faction of elicited peanut hairy roots. Since resveratrol accumulated in the medium while clomazone blocked the plastid MEP pathway in our inhibitor feeding experiments, it may be that prenylated stilbenoids in addition to arachidin-2 also derive from resveratrol. A study of phytoalexins induced in peanut kernels by soil fungal exposures also suggests that resveratrol might be the precursor for other prenylated stilbenoids in peanut (Sobolev, 2008).

The main prenylated stilbenoids produced by peanut hairy root can be categorized into two groups according to the structure of their prenyl side chains. One group includes arachidin-2 and arachidin-5 (identified in this study) having a 3,3-dimethylallyl moiety. This is the most common type of prenylation found in prenylated stilbenoids from various plant families. For instance, longistylines C, longistylines D and chiricanine A found in *Lonchocarpus chiricanus* (Leguminosae) (Ioset et al., 2001) also have the same dimethylallyl moiety. Artoindonesianin N with one dimethylallyl moiety and 4-dimethylallyl-oxystilbene were reported in *Artocarpus integer* (Moraceae) (Boonlaksiri et al., 2000) and *A. gomezianus* (Moraceae) (Hakim et al., 2002) respectively. Mappain found in *Macaranga mappa* (Euphorbiaceae) (Van Der Kaaden et al., 2001) has one dimethylallyl moiety and one geranyl moiety, while schweinfurthin C with two geranyl moieties was isolated from *M. alnifolia* (Euphorbiaceae) (Yoder et al., 2007). Moreover, the dimethylallyl moiety is also the most common prenylation pattern present in prenylated flavonoids, which are mostly found in the following families: Cannabaceae, Guttiferae, Leguminosae, Moraceae, Rutaceae, and Umbelliferae. The longer form of the dimethylallyl moiety, geranyl and lavandulyl moiety, has also been reported in prenylated flavonoids (Botta et al., 2005; Yang et al., 2015b). During the biosynthesis of these prenylated stilbenoids and prenylated flavonoids, prenyltransferases are responsible for these dimethylallylation and geranylation attaching DMAPP and GPP, respectively, to different positions of the stilbenoid and flavonoid skeletons.

One major group of prenylated stilbenoids in peanut hairy roots is represented by arachidin-1 and arachidin-3 which harbor a 3-methyl-but-1-enyl moiety. When compared with the dimethylallyl moieties commonly present in other prenylated stilbenoids and flavonoids, this unique prenylated form has been reported in peanut and very few other species. To our knowledge, the 3-methyl-but-1-enyl-oxystilbene isolated from *A. integer* (Moraceae) (Boonlaksiri et al., 2000) is the only prenylated stilbenoid with this moiety reported in a species other than peanut. Due to the difference in the position of the olefinic bond on the prenylated moieties, 3-methyl-but-1-enyl stilbenoids such arachidin-3 and arachidin-1 have higher lipophilicity as evident from a later retention time in reverse-phase HPLC chromatograms when compared with their 3,3-dimethylallyl analogs, arachidin-2 and arachidin-5 respectively. The $\lambda_{max}$ of UV absorbance of 3-methyl-but-1-enyl stilbenoids has an apparent shift to 335~340 nm when compared with that shown at 323~327 nm for 3,3-dimethylallyl stilbenoids (Table 1 shown in FIG. 7). However, the effects of these two moieties on the bioactivity of peanut stilbenoids is still unclear because arachidin-1 and arachidin-3 are not commercially available limiting their studies and the relatively low yields of arachidin-2 and arachidin-5 produced in peanut hairy roots.

The yields of arachidin-1 and arachidin-3 in our peanut hairy root culture system were much higher than those of their dimethylallyl analogs, arachidin-2 and arachidin-5. As described in the activity assays above, both arachidin-2 and arachidin-5 were further modified to other derivatives, suggesting that dimethylallyl stilbenoids are important intermediates for the biosynthesis of other peanut prenylated stilbenoids. As a substrate recognized by AhR4DT, piceatannol was considered to be the putative precursor of arachidin-5 in peanut. However, the yield of piceatannol in our peanut hairy root culture is very limited and far less than that of resveratrol. Even after blocking the biosynthesis of the prenylated moiety by 100 μM clomazone, the cultures only produced 9.02 μM of piceatannol compared with 845.7 μM of resveratrol (FIG. 3). These observations suggests that arachidin-5 and arachidin-1 might not be synthesized from piceatannol due to its limited amounts, instead arachidin-1 may derive from arachidin-3, which is relatively abundant in the medium, by hydroxylation at C-3' position.

Metabolism of Prenylated Stilbenoids in Peanut Hairy Root

Under treatment with MeJA and CD, arachidin-1, arachidin-2, arachidin-3, and arachidin-5, are the major prenylated stilbenoids secreted and accumulated in the spent culture together with resveratrol. When CD is not added in the hairy root cultures, only limited amounts of resveratrol and stilbenoids are detected in the medium. These observations were reported previously when peanut hairy roots were treated with NaOAc, $H_2O_2$ or MeJA alone as elicitors (Yang et al., 2015a). Importantly, when resveratrol was added in non-elicited peanut hairy root cultures, 47% and 97% reductions of the initial resveratrol concentration in the culture medium were observed after 0.5 h and 1 h co-incubation, respectively (Yang et al., 2015a). In the current study, we confirmed that the degradation of extrinsic resveratrol in peanut hairy root culture occurs due to activities of the root tissue. Unlike resveratrol synthase, which is induced and involved in stilbenoid biosynthesis, the enzymes involved in the degradation of resveratrol appear to be constitutively expressed in non-elicited root tissue, leading to the dramatic decline of extrinsic resveratrol. Results from experiments described here suggest that peanut enzymes present initiate this process by oxidizing resveratrol into piceatannol and then secondly by converting this into other derivatives. This enzymatic degradation process may also apply to other prenylated stilbenoids, such as arachidin-2 (FIG. 23), and may explain the observation that only trace amounts of stilbenoids are detected in ethyl acetate extracts of root tissue (FIG. 22). The constitutive degradation of stilbenoids may provide the plant with the ability to manage potential toxic effect of stilbenoids when they accumulate at high levels within the cell. Interestingly, other species such as grape accumulate resveratrol as glucosides (i.e. piceid). However, this conjugate was not identified in the peanut hairy roots and has not been described in fungal elicited peanut kernels. Altogether, these findings suggest that peanut may have evolved a distinct mechanism to metabolize resveratrol-type phytoalexins after they are produced.

Conclusion of Arachidin-5 Production

Harnessing the inducible bioproduction capabilities of the peanut hairy root culture system, we have newly produced a prenylated stilbenoid, i.e., arachidin-5, and have demonstrated that the prenyl moiety on peanut prenylated stilbenoids is derived from a plastidic biosynthesis pathway. We have characterized for the first time a plant membrane-bound stilbenoid-specific prenyltransferase, i.e., AhR4DT, from the microsomal fraction of peanut hairy roots. The characteristics of AhR4DT provide important information for subsequent cloning and comprehensive definition of the prenyltransferase gene(s) of peanut. Moreover, we have observed the enzymatic degradation of exogenous resveratrol by peanut hairy root tissue, an observation that will lead to elucidation of further mechanisms governing phytoalexin accumulation in plants.

Materials and Methods

Chemical Reagents

Authentic standards of resveratrol and piceatannol were obtained from Biophysica and Axxora, respectively; arachidin-1, arachidin-2, arachidin-3, and arachidin-5 standards were purified from elicited peanut hairy root as described below. Pinosylvin, oxyresveratrol, pterostilbene, naringenin, apigenin, and genistein used in this study were purchased from Sigma-Aldrich. Chiricanine-A was purified from fungal-challenged peanut seeds as described below. DMAPP was obtained from Isoprenoids, LC. Stock solutions of inhibitors, mevastatin (100 mM, Sigma-Aldrich) and clomazone (100 mM, Sigma-Aldrich), were prepared in ethanol and stored at 4° C.

Isolation and Purification of Chiricanine-A from Fungal Challenged Peanut Seeds

One kg of seeds of the 31-1314 peanut runner breeding line from the National Peanut Research Laboratory (Dawson, Ga.), stored at 4° C. for two years after harvest, were allowed to imbibe distilled water for 18 h at 4° C. They were then chopped with a custom-made hand cutter into 3-6 mm pieces, thoroughly washed with distilled water, blotted with a paper towel, air-dried to the condition where sliced peanuts did not leave water spots on filter paper, and placed on aluminum trays so that the thickness of the layer did not exceed 1 cm. The trays were evenly sprayed with the fungal spores of $Aspergillus\ caelatus$ NRRL 25528 ($10^5$/mL), placed into autoclave bags, and incubated at 30° C. for 96 h. The bags were opened every 24 h to allow fresh air to the peanuts and growing fungus.

The incubated peanut seeds were extracted with 3.0 L of MeOH overnight at room temperature without agitation. This procedure was repeated two more times. The combined mixture was filtered through a paper filter in a Buchner type funnel under reduced pressure. The combined filtrates were defatted three times with 0.5 L of n-hexane. The MeOH layer was evaporated to dryness. The residue was redissolved in $CHCl_3$ and applied to a chromatographic column (34 mm i.d.) packed with silica gel (silica gel 60, 0.063-0.200 mm; EM Science, Gibbstown, N.J.)
to the height of 400 mm. The column was subsequently eluted with 0.5 L of $CHCl_3$, 1.0 L of EtOAc, 1.0 L of acetone, and 1.0 L of MeOH (all solvents were purchased from Fisher). Eight fractions were collected from the column and analyzed by HPLC. Fractions containing chiricanine A were combined, evaporated to dryness with a rotary evaporator, and subjected to further purification on a similar silica gel column. The column was subsequently eluted with 0.4 L of $CHCl_3$, 1.5 L of $CHCl_3$/EtOAc (1:1), 1.3 L of EtOAc, and 1.0 L of acetone. Twenty four fractions were collected. Combined fractions containing chiricanine A were evaporated to dryness on a rotary evaporator, redissolved in MeOH, filtered, and subjected to final purification with a preparative 100 mm×19 mm i.d., 5 μm XTerra Prep RP18 OBD HPLC column (Waters). The flow rate was 9.5 mL/min, and column temperature was maintained at 40° C. The following mobile phase was used: 73% $CH_3CN$, 3% of 1% HCOOH in $H_2O$, and 24% of $H_2O$. Pure fractions of chiricanine A obtained from HPLC were evaporated with a rotary evaporator to a point where almost all of the organic solvent was removed. Then the target compound was extracted four times with EtOAc ($H_2O$/EtOAc ratio 1:1, v/v). The combined EtOAc layers were evaporated nearly to dryness with a rotary evaporator. The residue was transferred into a 15 mL vial with EtOAc and evaporated nearly to dryness with a stream of $N_2$. The residue was redissolved in EtOAc, filtered, and transferred into 4 mL vials and evaporated to dryness with a stream of $N_2$. Then the vial was placed into a lyophilizer for 2 h at room temperature to remove traces of the solvents. Chiricanine A was obtained as a slightly yellowish oil (6.5 mg).

Analyses of Stilbenoids from Peanut Hairy Root Cultures

Hairy root cultures of peanut ($Arachis\ hypogaea$) cv. Hull line 3 established by the Medina-Bolivar laboratory (Condori et al., 2010) were maintained in 50 mL modified Murashige and Skoog medium (MSV) (Condori et al., 2010) with 3% sucrose in 250 ml flasks. In order to induce synthesis and secretion of stilbenoids, the spent medium of nine-day-old hairy root cultures was discarded and replaced with 50 mL fresh MSV medium containing 3% sucrose with 100 μM methyl jasmonate (MeJA) and 9 g/L methyl-β-cyclodextrin (CD; Cavasol™) as elicitors and incubated in the dark at 28° C. for an additional 72 hours as previously described (Yang et al., 2015a). After elicitation period, one milliliter spent medium was partitioned with ethyl acetate twice. The combined organic phase was evaporated under nitrogen gas and dissolved in methanol for subsequent HPLC and mass spectrometry analyses.

Quantitative analysis of stilbenoids in peanut hairy root culture extracts was performed in an UltiMate 3000 LC system (Dionex, Thermo Scientific), equipped with a photodiode array detector. The separation was performed on a SunFire™ $C_{18}$, 5 µm, 4.6×250 mm column (Waters) at 40° C. with a flow rate at 1.0 ml/min. The mobile phase consisted of 2% formic acid in water (A) and methanol (B). The column was initially equilibrated with 100% A for 1 min. Then a linear gradient was performed from 40% A and 60% B to 35% A and 65% B (1 to 20 min), followed by a linear gradient from 35% A and 65% B to 100% B (20 to 25 min). Then the column was washed with 100% A for 5 min (25 to 30 min). Calibration curves of various stilbenoids were established using absorbance at 320 nm for resveratrol, piceatannol, arachidin-2 and arachidin-5 and at 340 nm for arachidin-1 and arachidin-3.

For LC-mass spectrometry qualitative analysis of stilbenoids, an UltiMate 3000 rapid separation LC system (Dionex, Thermo Scientific) was used for the chromatographic separation. The separation method was similar to the HPLC conditions described above with the following modification, 0.02% formic acid in water was used instead 2% in the mobile phase A. The LTQ XL™ linear ion trap mass spectrometer (Thermo Scientific) with an electrospray ionization (ESI) source was used to obtain structural information of stilbenoids and followed the method described previously (Marsh et al., 2014). Briefly, all mass spectra were performed in the positive ion mode with ion spray voltage at 4 kV, sheath gas (high purity nitrogen) at 45 arbitrary units (AU), auxiliary gas (high purity nitrogen) at 15 AU, capillary voltage at 9 V, capillary temperature at 300° C., and tube lens offset at 45 V. Full mass scan was recorded in the range m/z 100-2000. Ultrahigh pure helium (He) was used as the collision gas and 35% of collision energy was applied in collision-induced dissociation (CID). The data were recorded and analyzed by Xcalibur software (Thermo Scientific).

Purification and Characterization of Arachidin-5 from Peanut Hairy Root Cultures For purification of arachidin-5 and other prenylated stilbenoids, one liter of spent medium obtained from a pool of about 20 flasks of 72 h-elicited peanut hairy root cultures was collected and extracted with an equal volume of ethyl acetate twice in a 2 L separatory funnel. The organic phase was recovered and dried in a rotavapor (Buchi) and the crude extract (~800 mg) was stored at 4° C. for subsequent high performance counter current chromatography (HPCCC) fractionation. A two-phase HPCCC solvent system (hexane: ethyl acetate: methanol: water (4:5:3:3, v/v/v/v) was equilibrated at room temperature in a 2 L separatory funnel. The upper phase of this solvent mixture was used as stationary phase and the lower one was used as mobile phase for preparative HPCCC (Dynamic Extractions) system. The multilayer coil was filled with the stationary phase at a flow rate of 8 mL/min while spinning at 1600 rpm. Then the hydrodynamic equilibrium was established by pumping 6 mL/min of mobile phase into the column until a clear mobile phase was eluted at the outlet. Crude extract (300 mg) was dissolved in 5 mL of the two-phase solvent and manually injected. The effluent was monitored at UV 340 nm. The fractions were collected every 30 s, dried in a SpeedVac, and analyzed by HPLC as described above. According to the HPLC profiles, the fractions collected between 27 to 32 min contained arachidin-1 and arachidin-5, whereas those collected between 53 to 62 min contained arachidin-2 and arachidin-3. Fractions containing arachidin-1 and arachidin-5 were combined as one sample, whereas those containing arachidin-2 and arachidin-3 were combined as a separate sample. Then, the organic solvent in the samples was removed using rotavapor. The remaining aqueous mixtures containing the target compounds were extracted with ethyl acetate (1:1, v/v), evaporated nearly to dryness with a rotavapor and redissolved in methanol. Then these combined fractions were applied to TLC plates (TLC silica gel 60 RP-18 $F_{254}s$, Millipore) and separated using as developing solvent a solvent system composed of methanol:water:acetic acid (15:45:40, v/v/v). After separation, the purified prenylated stilbenoids on the adsorbent were scraped off, re-dissolved in methanol and dried under nitrogen gas for subsequent $^1H$ and $^{13}C$ NMR spectra analysis. In summary, 4.6 mg of arachidin-5, 20.3 mg of arachidin-1, 5.2 mg of arachidin-2 and 17.8 mg of arachidin-3 were purified from the peanut hairy root culture medium using the HPCCC and preparative TLC method.

For NMR analysis of purified arachidin-5 and arachidin-2, $^1H$ NMR was recorded at 400 MHz, $^{13}C$ NMR was recorded at 100 MHz in acetone-$d_6$ on a Bruker AV-400 NMR spectrometer.

Inhibitor Feeding Experiment

Nine-day-old peanut hairy root cultures were used in the inhibitor feeding experiment. Prior to treatment, the spent medium from each culture was removed and replaced with 50 mL fresh MSV medium containing 3% sucrose and 100 µM MeJA and 9 g/L CD as elicitors. Then, mevastatin (10 µM) or clomazone (10 µM and 100 µM) was applied to the culture medium. For the control group, 50 µL of absolute ethanol (solvent of mevastatin and clomazone) was added to the medium. All treatments were performed at 28° C. and continuous darkness with three biological replicates per treatment. One milliliter of spent medium was collected from each treatment at 48 h and 72 h after treatment. The 1 mL medium aliquots were extracted with 1 mL ethyl acetate, and then the organic phase was collected and dried under nitrogen gas and re-dissolved in methanol for HPLC analysis as described above.

Enzyme Preparation

Enzyme solutions from peanut hairy roots for prenyltransferase assay were prepared using nine-day-old roots elicited with 100 µM MeJA and 9 g/L CD for 48 h. Ten grams (fresh weight) of elicited hairy root tissues were grinded and homogenized in 20 mL of extraction buffer composed of 100 mM Tris-HCL buffer (pH 7.6), 10 mM dithiothreitol (DTT) and 2.5% (w/v) polyvinylpyrrolidone (average mol wt 40,000; PVP-40, Sigma) using a mortar and pestle. The homogenate was centrifuged at 12,000×g for 15 min at 4° C. to remove the cell debris. Crude cell-free extracts were obtained by passing 2.5 mL of the 12,000×g supernatant through a PD-10 desalting column (GE Healthcare), using 100 mM Tris-HCL (pH 9.2) containing 10 mM DTT as equilibration buffer. About 13.5 mL of the remaining 12,000×g supernatant were subsequently centrifuged at 156,000×g for 45 min at 4° C. The 156,000×g supernatant was collected and cleaned up through a PD-10 desalting column (GE Healthcare) equilibrated with 100 mM Tris-HCl buffer (pH 9.2) containing 10 mM DTT. The microsomal pellet was resuspended in 100 mM Tris-HCl buffer (pH 9.2) containing 10 mM DTT, re-centrifugated (156,000×g for 45 min), and finally resuspended in 1 mL of the same buffer for subsequent enzyme reaction.

For the degradation of resveratrol assay, crude cell-free extract was prepared from 12-day-old non-elicited peanut hairy roots following a similar procedure to that described for elicited roots above except that no DTT was included in the extraction and equilibration buffers.

Protein Quantification

Protein contents in the various enzyme solutions were determined using the Coomassie protein assay (Thermo Scientific) using bovine serum albumin as standard.

Degradation of Resveratrol Assay

The standard assay condition contained 1 mM resveratrol with 50 µg crude cell-free extract from 12-day-old non-elicited peanut hairy root in 500 µL of 100 mM Tris-HCl buffer (pH 7.6). To study the effect of reducing agent on the degradation of resveratrol, additional 5 mM DTT was added to the standard assay mixture. After 30 min incubation at 28° C., the reaction mixture was extracted with 500 µL ethyl acetate and the amount of resveratrol remaining in the mixture was analyzed by HPLC. In the control group, crude cell-free extract was heated at 99° C. for 20 min.

Prenyltransferase Assay

The standard assay was performed in a total volume of 500 µL containing 100 µM resveratrol, 300 µM DMAPP as a prenyl donor, 10 mM $MgCl_2$, 5 mM DTT and 30 µg microsomal fractions in 100 mM Tris-HCl buffer (pH 9.2). After 60 min incubation at 28° C., the reaction mixture was terminated by adding 20 µL of 6 M HCl and extracted with 500 µL of ethyl acetate. The extracts were dried under nitrogen gas, dissolved in methanol and the reaction product was quantified by HPLC analysis. The prenylation activity for each reaction was quantified by the molar concentration of generated prenylated product per second with one milligram microsomal fractions (kat/mg).

In the linearity study, the prenyltransferase activities under varying incubation times (30, 60, 90 and 120 min) with 30 µg microsomal fraction and varying mount of microsomal faction (30, 60, 90 and 120 µg) incubated for 60 min were measured. For pH dependency study, the activities of prenyltransferase were measured using 100 mM Tris-HCl buffer at pH 7.0, 8.0, 8.4, 8.6, 8.8, 9.0, 9.2, 9.4, 9.6, and 10.0. For divalent cation dependency study, 10 mM $MnCl_2$, $FeCl_2$, $CaCl_2$), $CoCl_2$, $ZnCl_2$, $NiCl_2$ or $CuCl_2$ was added to the reaction mixture instead of $MgCl_2$ as described above, and the enzyme activity was compared with that reaction containing $MgCl_2$. For kinetic studies, varying concentration (10, 20, 40, 80, 160, 320, and 640 µM) of resveratrol with a fixed concentration of DMAPP (640 µM) and varying concentration (10, 20, 40, 80, 160, 320, and 640 µM) of DMAPP with a fixed concentration of resveratrol (640 µM) were incubated with microsomal fractions of peanut hairy root in a total volume of 250 µL at 28° C. for 60 min. These reactions were used to calculate $V_m$ and $K_m$ values using nonlinear regression analysis of Michaelis-Menten equation using Graphpad Prism 6 software. For substrate specificity assay, 100 µM stilbenoids (resveratrol, piceatannol, pinosylvin, pterostilbene, and oxyresveratrol), flavanone (naringenin), flavone (apigenin), and isoflavone (genistein) with 300 µM DMAPP as a prenyl donor were incubated with microsomal fractions of peanut hairy root in a total volume of 250 µL at 28° C. for 60 min. Arachidin-2 and arachidin-5 purified from peanut hairy root culture and chiricanine-A purified from fungus-challenged peanut seed were diluted to various concentration and calibration curves of their absorbance at 320 nm were used for quantitative analysis.

Identification of Resveratrol Prenyltransferase Activities from the A. hypogaea Hairy Root Transcriptome The first flavonoid-specific prenyltransferase, SfN8DT-1, was cloned from a cDNA (EST) library of Sophora flavescens cell cultures and its enzymatic activity was characterized using the microsomal fraction of recombinant yeast (Sasaki et al., 2008). Sequence homology to SfN8DT-1 was the basis for discovery of several other flavonoid prenyltransferases, such as SfiLDT and SfG6DT in S. flavescens (Sasaki et al., 2011) and LaPT1 in Lupinus albus (Shen et al., 2012). Our previous work had indicated that resveratrol prenyltransferase(s) in peanut are membrane-bound proteins that utilize DMAPP from the plastidic terpenoid pathway as the prenyl donor (Yang et al., 2016). These two key features are also observed in flavonoid-specific prenyltransferases identified from other legume species (Sasaki et al., 2008; Akashi et al., 2008; Sasaki et al., 2011; Shen et al., 2012; Li et al., 2014; Chen et al., 2013), suggesting that the sequence of stilbenoid prenyltransferase(s) may share similarity with flavonoid prenyltransferases genes.

To discover and clone peanut prenyltransferase genes, therefore, we first built a transcript sequence reference from RNA of our elicited hairy root culture system, and annotated likely candidate stilbenoid prenyltransferase transcripts by alignment to well-characterized flavonoid prenyltransferases. An RNA sequencing experiment was designed to capture mRNA temporally associated with stilbene accumulation in the hairy root cultures. We assembled and evaluated a variety of transcript sequences from RNA-Seq (Mortazavi et al., 2008) reads sets (see Methods) and initially considered any whose translated product aligned to characterized flavonoid prenyltransferase sequences listed above. 224 transcripts from our set of 2,591,753 transcript assemblies encoded full-length protein sequences of 101 to 432 amino acid residues that aligned to the set of flavonoid prenyltransferase sequences over a length of at least 100, with >80% sequence identity. As derived from a tetraploid, we anticipated that these sequences would represent transcripts of unique enzyme genes, as well as homeologs, alleles and potential assembly errors. The cultivated peanut genome is allotetraploid thought to have been formed as the result of a single hybridization between two closely-related diploid species, Arachis duranensis and Arachis ipaensis. Reference sequence assemblies of the latter diploid genomes were reported recently (Bertioli et al., 2016), and these provided a draft proxy reference we used to evaluate and potentially reduce our transcriptome to unique genic loci.

Our previous work had implicated prenyltransferase activities of interest occurred in the plastid (Yang et al., 2016). We therefore reduced the candidate transcript sequences to ten whose encoded proteins contain predicted chloroplast targeting peptide sequences according to analyses with both ChloroP (Emanuelsson et al., 1999) and iPSORT (Bannai et al., 2002). All ten transcripts showed expression in the 9-hour elicitor-treated hairy root transcriptome, and therefore we used 9-hour elicited hairy roots to clone their cDNAs. PCR using primers designed against the assembled transcript sequences resulted in amplification of three full-length cDNAs (AhR3'DT-1, AhRPT-10a4 and AhRPT-10d4) encoding stilbenoid prenyltransferase candidates (FIG. 63). We subcloned these candidates into yeast expression vector pPICZ, for heterogeneous expression in Pichia pastoris. The microsomal fractions of the yeast cultures were employed for prenyltransferase assays. However, prenylation activity using resveratrol as substrate was not detected in any of the recombinant yeast cultures assayed (data not shown). In previous studies, researchers failed to detect flavonoid prenyltransferase activity when the full-length open reading frame (ORF) of GmG4DT was expressed in yeast, while the truncated form of GmG4DT without its N-terminus transit peptide showed genistein prenyltransferase activity (Yazaki et al., 2009). Likewise, the microsomal fraction of yeast expressing a truncated form of LaPT1, in which the first 44 amino acids were deleted, showed 6-fold higher activity than that of the full-length protein (Shen et al., 2012). Reasons for these observations may be low tolerance of plant transit peptides in yeast, correlated with incorrect folding and decreased stability of the prenyltransferases, resulting in low enzymatic activity. Rather than removing N-terminal putative transit peptide sequences and reexamining the yeast expression system as in the flavonoid prenyltransferase studies mentioned, we shifted to a heterologous plant expression system. We subcloned the full length cDNAs of the three candidate stilbenoid prenyltransferase into binary vectors under the control of CaMV35S-TEV promoter and transiently expressed these by Agrobacterium-infiltration of Nicotiana benthamiana leaves. The crude cell extract of N. benthamiana leaves was incubated with DMAPP and resveratrol to test prenyltransferase activities. One of the cDNA products (amplified with primers PT-10-FW-NotI/PT-k-RV-KpnI, FIG. 66) showed resveratrol dimethylallyltransferase activity (FIG. 35). No activity was observed in the crude cell extract of N. benthamiana control leaves that were infiltrated with Agrobacterium harboring an empty binary vector (FIG. 35). Mass spectrometry analysis of the reaction product (m/z 297 [M+H]$^+$) gave a primary fragment with a m/z 241 [M+H-56]$^+$ in MS$^2$ which suggested the presence of a prenyl moiety (FIG. 42; FIG. 67). After recovery of the reaction product from a large-scale enzymatic assay, it was purified by semi-preparative HPLC and its structure was further elucidated by NMR analysis.

Because the purified compound was available in extremely low quantities, we continued performing each experiment ($^1$H-$^{13}$C HMBC & HSQC) over longer time intervals with an increased number of scans. Data obtained showed well-resolved peaks, forming the basis for our unambiguous assignment of both $^1$H and $^{13}$C chemical shifts. In both the $^1$H and $^{13}$C spectra, peaks assigned were in agreement with the original scaffold of resveratrol. To determine the position of the prenyl group on the resveratrol scaffold, NMR predict tool was used to generate multiple $^1$H and $^{13}$C spectra for with various combinations of prenyl positions, with reference to the 4-hydroxyphenyl ring (Banfi and Patiny, 2008; Castillo et al., 2011). Two possible prenyl positions appear to be of highest probability and matched with the experimentally obtained $^1$H and $^{13}$C NMR spectra (FIGS. 43A and 43B). We further narrowed down to the final conformation by examining the $^1$H signals at 6.12 ppm, 6.38 ppm, 6.95 ppm, 7.04 ppm, 7.25 ppm, 7.49 ppm and were found to be consistent with the resveratrol scaffold. 1H peaks at 3.21 ppm and 5.75 ppm with matched well with the prenyl side chain. (FIG. 43A). The experimental NMR data strongly support the predicted location of the prenyl at the ortho position of the 4-hydroxyphenyl ring. The conformation of resveratrol is further corroborated by the 2D NMR data which show $^{13}$C peaks at 104.5 ppm, 122.8 ppm and 129.0 ppm (FIG. 43B). From the $^1$H-$^{13}$C HSQC and $^1$H-$^{13}$C HMBC spectrum, the $^1$H signal at 7.25 ppm, 6.95 ppm and 6.38 ppm correlate with protons at the ortho position on 1,3-benzenediol, ethenyl proton and ortho-positioned proton on 4-hydroxyphenyl ring, respectively. Their corresponding $^{13}$C signals were at 127.0, 124.2 ppm, and 125.3 ppm, respectively (FIGS. 43C and 43D). Analysis of the NMR data suggest that the prenyl moiety is attached to the C-3' position of the resveratrol backbone to produce 3-methyl-2-butenyl-3'-resveratrol. Thus, the enzyme that catalyzed this reaction was named as AhR3'DT-1 (A. hypogaea resveratrol-3'-dimethylallyltransferase).

Interestingly, this prenylated resveratrol was not the arachidin-2 we had expected, given our previous work identifying prenylated products in the reaction using microsomal fraction of elicited peanut hairy root (Yang et al., 2016). Moreover, the 3-methyl-2-butenyl-3'-resveratrol reaction product described here was not observed in the elicited hairy root culture of peanut. Our results indicate then that there are other prenyltransferase(s) responsible for prenylating resveratrol to arachidin-2 in peanut. To further search for additional resveratrol prenyltransferase(s) from the peanut hairy root transcriptome, other primer pairs were designed based on the alignment of the putative prenyltransferase transcripts (FIG. 66). Using this approach, additional PCR amplicons were amplified from the cDNA of 9-hour-elicited peanut hairy roots and five were subsequently subcloned into binary vectors and transiently expressed in N. benthamiana leaves for prenyltransferase activity assays using DMAPP and resveratrol as substrates. Four additional cDNAs were identified as resveratrol prenyltransferase genes. One cDNA clone (amplified with primers PT-9-FW-NotI/PT-b-RV-KpnI, FIG. 66) showed a clear dimethylallyltransferase activity for resveratrol and prenylated it at the C-4 position to form arachidin-2 (FIG. 35). This product was confirmed by comparison of its retention time, UV light spectrum, mass spectra, and fragmentation patterns obtained by tandem mass spectrometry (MS$^2$ and MS$^3$) with arachidin-2 purified from peanut hairy root culture (FIG. 44). Hence, this enzyme was designated as AhR4DT-1 (A. hypogaea resveratrol-4-dimethylallyltransferase). The other three cDNA clones (two amplified with primers PT-4-FW-NotI/PT-e-RV-KpnI and one amplified with primers PT-5-FW-NotI/PT-m-RV-KpnI, FIG. 66) exhibited the same catalytic activities as AhR3'DT-1, converting resveratrol into 3-methyl-2-butenyl-3'-resveratrol using DMAPP as prenyl donor. Hence, we named these AhR3'DT-2, AhR3'DT-3 and AhR3'DT-4. Among these four isoenzymes, AhR3'DT-1 exhibited the highest activity. AhR3'DT-2 and AhR3'DT-3 exhibited activity levels that were 18% and 17% of AhR3'DT-1 respectively, while AhR3'DT-4 reached only 5% that of AhR3'DT-1 (FIG. 35).

Genomic and Phylogenetic Relationships of the Prenyltransferases

We report here five active resveratrol prenyltransferases identified from biochemical analyses of eight peanut transcripts. Transcripts assembled from RNA-Seq reads and cloned as cDNAs each independently evidence that these encode polypeptides of 389-414 amino acids (FIG. 36). All possess nine transmembrane α-helices as predicted by TMHMM 2.0 (Krogh et al., 2001) (FIGS. 4 to 7), as well as two aspartate-rich motifs, NQXXDXXXD in loop 2 and KD(I/L)XDX(E/D)GD in loop 6, that are also conserved in flavonoid prenyltransferases (FIG. 36).

The gene structure of peanut prenyltransferases was estimated by aligning the transcripts to available Arachis diploid progenitor genome sequence references (Bertioli et al., 2016). Four loci in each became apparent as candidate origins. Three of these were on pseudochromosome 8 in each genome, contained within a span containing notable gaps and described by Bertioli et al. (2016) as effected by a genomic reduction during polyploidization. Only AhR3'DT-4 aligned completely to pseudochromosome 1 (FIG. 63). Eliminating poor alignments in either progenitor, we estimated two loci in A. duranensis and two in A. ipaensis could explain the origin of the set of prenyltransferases characterized in this study (FIG. 63). Transcript alignments showed that AhR3'DT-2 and -3 differ by a deletion in AhR3'DT-2 that encodes 16 amino acid residues in AhR3'DT-3 (FIG. 36). Although the genomic reference contained gaps in this region that prevented gene structure validation, we expect that these two transcripts may be expressed from the same gene in *A. hypogaea* as alternatively spliced forms (FIG. 63).

Among the eight peanut transcripts tested in *N. benthamiana* transient assays, three cDNAs failed to show resveratrol prenyltransferase activity. One appears to be alternative splice form or allele of AhR4DT-1, and two of AhR3'DT-1. Observed variation among these may provide preliminary insights into structural requirements for the active forms characterized here. Interestingly, each of the three inactive cDNAs vary in length and sequence at the C-terminal end (45 and 46). A nine amino acid residue deletion at the C-terminus of the inactive AhR4DT-1 transcript, AhRPT-9i2 likely reduces its encoded protein structure to eight transmembrane spans (FIG. 45), suggesting that the integrity of the nine transmembrane domains in AhR4DT-1 are essential for its activity. Two inactive transcripts of AhR3'DT-1 encode a C-terminal extension that does not appear to have transmembrane properties (FIG. 46). Each furthermore harbors several coding SNPs and an eight amino acid residue deletion (Δ41-48) that disrupts a region conserved in both active AhR4DT-1 and AhR3'DT-1 (FIG. 36). Interestingly, although not fully deleted in AhR3'DT-2, -3 and -4, this sequence is highly variable in these three less active forms, suggesting this uncharacterized region may play a role in influencing the prenyltransferase active site.

Phylogenetic analysis of these characterized prenyltransferase enzymes together showed that the peanut stilbenoid prenyltransferases form their own monophyletic group (FIG. 37). This Glade is notably distinct from the flavonoid prenyltransferases, as well as from homogentisate (HG) prenyltransferases involved in ubiquinone and shikonin biosynthesis, and p-hydroxybenzoate (PHB) prenyltransferases involved in the tocotrienol, tocopherol and plastoquinone biosynthetic pathways (FIG. 37).

Biochemical Characterization of AhR4DT-1 and AhR3'DT-1

AhR3'DT-1, the enzyme with the highest activity among its group, along with AhR4DT-1 were selected for further biochemical characterization. Similar to the previous resveratrol prenyltransferase activity characterized from peanut hairy roots (Yang et al., 2016), the specific activity in the microsomal fraction of *N. benthamiana* leaves expressing AhR4DT-1 or AhR3'DT-1 were 8.9-fold and 13.9-fold higher than that in the crude cell-free extracts, respectively (FIG. 64). Therefore, we used the microsomal fraction enriched with AhR4DT-1 or AhR3'DT-1 for subsequent enzymatic assays. Reactions were incubated with resveratrol, DMAPP and $Mg^{2+}$ as cofactor. Although the optimum activities of AhR4DT-1 and AhR3'DT-1 were observed at 37° C. and 30° C., respectively, in the microsomal fraction of *N. benthamina*, all further prenylation assays were performed at 28° C. which corresponds to the culture temperature of peanut hairy roots in order to observe the actual behavior of AhR4DT-1 and AhR3'DT-1 during the elicitor-induced production of prenylated stilbenoids (FIG. 49). The accumulation of the prenylated product produced by AhR4DT-1 or AhR3'DT-1 showed a linear relationship with the amount of the microsomal fraction (25~75 µg) and with incubation time (30~120 min) (FIG. 50).

The effects of pH on AhR4DT-1 and AhR3'DT-1 activities were investigated using three buffers which spanned a pH range from 7.0 to 10.7. The optimum pH of AhR4DT-1 activity was 9.4 in Glycine-NaOH buffer (relative activity of each prenyltransferase, 100%), 9.0 in Tris-HCl buffer (99.8%) and 9.7 (92.1%) in $NaHCO_3$—$Na_2CO_3$ buffer (FIG. 51A). AhR3'DT-1 exhibited optimal activities at pH 9.0 in both Tris-HCl (relative activity, 100%) and Glycine-NaOH (92.8%) buffers, but at pH 9.7 in $NaHCO_3$—$Na_2CO_3$ buffer (50.6%) (FIG. 51B). In summary, for these two prenyltransferases, the optimum pH was approximately 9.0, which is consistent with the basic pH of the stroma (Hauser et al., 1995). Therefore 100 mM of Tris-HCl (pH 9.0) was used as a standard reaction buffer in subsequent prenyltransferase reactions.

A variety of divalent cations other than $Mg^{2+}$ were tested to determine their effects on AhR4DT-1 and AhR3'DT-1 activities. $Mg^{2+}$ was the most effective (100%) for AhR4DT-1, followed by $Mn^{2+}$ (83.9%) and $Fe^{2+}$ (6.4%) (FIG. 52A). Interestingly, in AhR3'DT-1 reactions, $Mn^{2+}$ (210.3%) provided 2.1-fold higher efficiency than $Mg^{2+}$ (100%). $Mg^{2+}$ forms a bidentate complex with DMAPP which gets stabilized for an efficient transferase reaction. A possible reason why $Mn^{2+}$ exhibited a higher efficiency could be due to the larger ionic radius facilitating a stronger interaction with the pyrophosphate and the neighboring residues in the DMAPP binding pocket. $Fe^{2+}$ (34.8%) also appeared to contribute to AhR3'DT-1 activity (FIG. 52B). Trace amounts of AhR4DT-1 and AhR3'DT-1 activities (<0.5%) were also detected with all other divalent cations ($Ca^{2+}$, $Co^{2+}$, $Zn^{2+}$, $Ni^{2+}$, and $Cu^{2+}$) and in the control group in which no divalent cation was added, while no activity was detected in the EDTA treated group (FIG. 52). The trace activities observed are likely due to presence of low levels of $Mg^{2+}$ in the leaf microsomal fractions, released from chlorophyll-containing plastids.

The apparent $K_m$ values of AhR4DT-1 for both resveratrol (99.52±15.11 µM) and DMAPP (153.7±27.28 µM) were somewhat similar, and comparable with those of resveratrol prenyltransferase identified from peanut hairy root (FIG. 65). In contrast, AhR3'DT-1 exhibited a notably lower $K_m$ for resveratrol (17.67±1.601 but a much higher $K_m$ for DMAPP (691.4±48.46 µM) (FIG. 65; FIG. 53). Piceatannol, a compound detected in peanut hairy root culture as another putative substrate for peanut prenyltransferase, provided another contrast. The AhR4DT-1 $K_m$ for piceatannol was 311.4±54.83 while that of AhR3'DT-1 was 50.3±5.509 µM 153.7±27.28 µM (FIG. 65; FIG. 53). Importantly, AhR4DT-1 and AhR3'DT-1 each exhibited a higher $V_{max}/K_m$ value for resveratrol than piceatannol, suggesting that both of these prenyltransferases prefer resveratrol over piceatannol as substrate.

Substrate Specificity of AhR4DT-1 and AhR3'DT-1

In addition to resveratrol, various other stilbenoids (piceatannol, oxyresveratrol, pinosylvin, pterostilbene and piceid) and flavonoids (naringenin, apigenin and genistein) were used as potential substrates to analyze the prenyl acceptor specificity of AhR4DT-1 and AhR3'DT-1. The results (FIG. 38; FIGS. 54 to 58; FIG. 67) showed that AhR4DT-1 can selectively catalyze piceatannol, pinosylvin and oxyresveratrol into arachidin-5, chiricanine A and prenylated oxyresveratrol (the position of the prenyl moiety on the prenylated oxyresveratrol remains undetermined), respectively. In the reactions of AhR3'DT-1, the prenylated products of piceatannol and prenylated oxyresveratrol were identified by HPLC-PDA/ESI-MS" analysis (FIGS. 57 to 58; FIG. 67), although the positions of their prenyl moiety have not been confirmed due to the insufficient amount of these products for further structural elucidation. Pterostilbene which has two methoxy groups at the C-3 and C-5 positions along with piceid, a resveratrol glucoside with a glycosidic group at C-3 position, were not prenylated by either AhR4DT-1 or AhR3'DT-1 (FIG. 38), suggesting that either or both hydroxyl groups on the C-3 and C-5 of stilbene backbone might be crucial for substrate recognition by AhR4DT-1 and AhR3'DT-1. Interestingly, no prenylated pinosylvin was produced in the AhR3'DT-1 reaction (FIG. 38C), suggesting that other than the necessary 3- and 5-hydroxyl groups, a hydroxyl group at C-4' position might be an additional requirement for AhR3'DT-1 activity. Moreover, neither prenylated flavanone, prenylated flavone, nor prenylated isoflavone was detected in either AhR4DT-1 or AhR3'DT-1 reactions when flavonoid was used as substrate, indicating that both of these peanut prenyltransferases may be stilbenoid-specific prenyltransferases.

To address the prenyl donor specificity of AhR4DT-1 and AhR3'DT-1, in addition to DMAPP, other prenyl diphosphates, including isopentenyl pyrophosphate (IPP), geranyl pyrophosphate (GPP), farnesyl pyrophosphate (FPP) and geranylgeranyl pyrophosphate (GGPP) were examined with resveratrol as a prenyl acceptor. Neither AhR4DT-1 nor AhR3'DT-1 showed any detectable activity when these prenyl diphosphates were used as prenyl donor, suggesting that both of these prenyltransferases had strict specificity for DMAPP (FIGS. 4D and 4E).

Subcellular Localization of AhR4DT-1 and AhR3'DT-1

In evaluating primary structures using available software, we found conflicting predictions for the subcellular localization of these enzymes. The iPSORT program predicted a chloroplast transit peptide (cTP) in AhR4DT-1 and a mitochondrial targeting peptide (mTP) in AhR3'DT-1. However, ChloroP and TargetP predictions suggested AhR4DT-1 contained neither cTP nor mTP, while AhR3'DT-1 contained an N-terminal cTP. To confirm their subcellular localizations experimentally, AhR4DT-1-GFP and AhR3'DT-1-GFP gene fusion constructs driven by the CaMV35S-TEV promoter were expressed transiently in onion epidermal cells via particle bombardment. As a positive control for plastid localization, we co-expressed a construct created by Nelson et al. (2007) that features the transit peptide (first 79 amino acids) of tobacco RuBisCO small subunit fused to red fluorescent protein (RS-TP-mCherry). The green fluorescence signals of AhR4DT-1-GFP and AhR3'DT-1-GFP appeared in punctate patterns against organelles in the onion epidermal cells (FIG. 39), patterns highly similar to that of the red fluorescence derived from RS-TP-mCherry (FIG. 39). In contrast, control GFP driven by the Ca35S-TEV promoter was localized throughout the cytosol and nucleus (FIG. 39). These results strongly suggest that AhR4DT-1 and AhR3'DT-1 are localized to plastids, similar to flavonoid prenyltransferases such as SfN8DT-1, GmG4DT and LaPT1 characterized in other plant species (Yazaki et al., 2009; Shen et al., 2012; Sasaki et al., 2008).

Expression of AhR4DT-1 and AhR3'DT-1 in Peanut Hairy Roots During Elicitation

Our previous studies have shown that the accumulation of prenylated stilbenoids in peanut hairy root culture and the prenyltransferase activities from crude cell-free extracts of peanut hairy roots were upregulated by elicitor treatments and increased with incubation time (Yang et al., 2015, 2016). We therefore hypothesized that the mRNA of enzymes involved in the prenylation of stilbenoids, i.e. AhR4DT-1 and AhR3'DT-1, may accumulate upon elicitation in peanut hairy roots. To test this hypothesis, transcript levels of AhR4DT-1 and AhR3'DT-1 during co-treatment of hairy root cultures with MeJA and CD were quantified using real-time PCR. A rapid up-regulation of AhR4DT-1 was observed after 0.5-hour post-elicitation, and its expression pattern was consistent with the prenyltransferase activities assayed in the same system (FIGS. 40A and 40B). Despite an apparent delay in accumulation as compared to AhR4DT-1, levels of AhR3'DT-1 mRNA increased as well, after 48-hour of elicitation in these experiments (FIG. 40C). Whereas qPCR detects a short, sequence-unique portion of the target mRNA, comparative mapping of RNA-Seq reads can provide a more complete picture of differential expression. Assessment of differential expression of individual transcripts in this case is however confounded by the complexity of this tetraploid transcriptome, the large target enzyme family, and lack of A. hypogaea genome sequence reference. Employing available sequence references of the peanut diploid progenitors (above), we mapped all assembled A. hypogaea transcripts, both to confirm singularity of genomic loci and to select transcript sequence of each prenyltransferase that is most sequence-inclusive to use as reference for quantification (FIG. 65). FIGS. 6D-G represent sample-normalized counts of reads that mapped unambiguously to these transcript references. Not surprisingly, mock treatments (assayed at 9 h and 72 h) that mechanically stimulate the hairy root cultures resulted in increases in all transcripts. AhR4DT-1 mRNA stood out, however, as accumulating to 2-3× over control levels early in response to addition of MeJA+CD (FIG. 40D). AhR3'DT-1, on the other hand, among treatments assayed, reached its highest levels only 72 h post-elicitation (FIG. 40E). AhR3'DT-2/3 and -4 transcripts were clearly detectable by RNA-Seq across the time course, but did not appear to change in response to elicitation (FIG. 40F-G). These results indicate the activation of AhR4DT-1 and AhR3'DT-1 genes correlates with stress elicitation in peanut hairy root tissue, and that the accumulation of mRNA encoding these two enzymes correlates temporally with their prenyltransferase activities observed and with their catalyzed product accumulation. In contrast, mRNA of similar enzymes we show to exhibit activities that are not relevant, or less relevant, to arachidin-2 and 3-methyl-2-butenyl-3'-resveratrol production in peanut are not noticeably transcriptionally responsive to the elicitation. As products attributable to AhR4DT-1 and AhR3'DT-1 activities do not accumulate in peanut hairy root cultures in response to the control treatments used here (Yang et al., 2015), protein expression and/or localization are likely to be controlled by mechanisms beyond the transcript accumulation observed.

Discussion

Stilbenoid-Specific Prenyltransferases from Peanut

Prenylation of aromatic compounds plays an important role in the diversification of plant secondary metabolites and contributes to the enhancement of the biological activity of these polyphenolic compounds (Yazaki et al., 2009). To date only a few flavonoid prenyltransferase genes have been identified, including SfN8DT-1, SfiLDT, SfG6DT, SfFPT, GmG4DT, GuA6DT and LaPT1 cloned from legume species (Sasaki et al., 2008, 2011; Chen et al., 2013; Yazaki et al., 2009; Li et al., 2014; Shen et al., 2012), along with MaIDT and CtIDT from non-legume species Morus alba and Cudrania tricuspidata, respectively (Wang et al., 2014). In the study reported here, we tested eight potential resveratrol prenyltransferase transcripts and five of them encoded enzymes with two distinct prenylation activities. The eight transcripts derived from four or more genes expressed in peanut hairy root cultures. Two of these, AhR4DT-1 and AhR3'DT-1, were characterized as stilbenoid-specific prenyltransferases.

The stilbenoid prenyltransferases described in this study share several common features with flavonoid prenyltransferases. First, each of these enzymes is a membrane-bound protein containing several putative transmembrane α-helices. The subcellular localization of the two stilbenoid prenyltransferases described here are primarily or exclusively in the plastid, as are the five flavonoid prenyltransferases previously characterized. Secondly, each enzyme contains two conserved aspartate-rich motifs. The observed divalent cation dependency of our prenylation reactions corroborates the proposed role of this structure in the active site, where the divalent cation and the prenyl diphosphate bind (Huang et al., 2014). Interestingly, with the exception of AhR3'DT-1 in which $Mn^{2+}$ is most effective, all other flavonoid enzymes and the stilbenoid enzyme AhR4DT-1 show highest activity in the present of $Mg^{2+}$. Lastly, most flavonoid prenyltransferases and the stilbenoid prenyltransferases identified in this study exhibit strict substrate specificity with respect to their prenyl acceptor and prenyl donor, a feature that contrasts sharply with the catalytically promiscuous aromatic prenyltransferases of fungi and bacteria.

Despite sharing key features with flavonoid prenyltransferases, the stilbenoid prenyltransferases are monophyletic to other plant prenyltransferases accepting aromatic substrates (FIG. 40).

Involvement of AhR4DT-1 and AhR3'DT-1 in the Biosynthesis of Prenylated Stilbenoids in Peanut AhR4DT-1 specifically transfers a 3,3-dimethylallyl group to the A-ring at the C-4 position of resveratrol, piceatannol and pinosylvin. This enzyme exhibits biochemical properties that match well with the prenyltransferase activity identified from elicited peanut hairy roots (Yang et al., 2016), including Km values of resveratrol/DMAPP and identical preferences for prenyl acceptors and divalent cations. The consistency of all biochemical characteristics, along with our demonstration of transcript accumulation that is temporally correlated with C-4 prenylated stilbenoid (arachidin-1, arachidin-2, arachidin-3 and arachidin-5) accumulation, lead us to propose AhR4DT-1 is responsible for the prenylation activity in the microsomal fraction of peanut hairy roots identified in our previous study (Yang et al., 2016).

The second stilbenoid specific prenyltransferase characterized here was AhR3'DT-1, that recognizes 3,5,4'-trihydroxystilbene and adds a 3,3-dimethylallyl group to C-3' of the B-ring. Notably, none of the prenylation products of resveratrol and piceatannol catalyzed by AhR3'DT-1 were detected in peanut hairy root culture or peanut hairy root tissue. When compared to AhR4DT-1, AhR3'DT-1 showed a lower Km for resveratrol and piceatannol, indicating a higher affinity for these prenyl acceptor substrates. In contrast, its affinity for DMAPP was much lower than that of AhR4DT-1. Furthermore, the $V_{max}$ values of resveratrol, piceatannol and DMAPP for AhR4DT-1 were 9.9-fold, 6.9-fold and 5.8-fold higher than that of AhR3'DT-1, respectively (FIG. 65), indicating that the catalytic efficiency of AhR4DT-1, especially for utilizing DMAPP, is much higher than that in AhR3'DT-1. This might be a reason that no prenylation product of AhR3'DT-1 was found in the peanut hairy root culture, even when the substrate for AhR3'DT-1 was present.

Under the co-treatment of 100 µM MeJA and 9 g/L CD for 72 hours, the peanut hairy root cultures secrete into the medium large amounts of resveratrol (44.64±10.26 mg/L), arachidin-1 (77.85±21.47 mg/L) and arachidin-3 (184.65±22.29 mg/L), relatively moderate levels of arachidin-5 (15.54±5.58 mg/L) and arachidin-2 (25.57±2.98 mg/L), and even less piceatannol (4.02±0.67 mg/L) (Yang et al., 2015, 2016). These observations suggest that arachidin-1 and arachidin-3 may be end products during the tested period of elicitation. Differing from arachidin-5, arachidin-2, and most other prenylated flavonoids which harbor a 3,3-dimethylallyl moiety, arachidin-1 and arachidin-3 have a unique 3-methyl-but-1-enyl moiety (FIG. 41). Until now, the biosynthesis pathway(s) of arachidin-1 and arachidin-3 have not been fully elucidated, however several biosynthetic routes leading to their production could be proposed when considering results from our previous and current studies.

In our previous study, it was demonstrated that exogenous resveratrol could be oxidized to piceatannol by an extract from the peanut hairy root tissue through a very efficient enzymatic reaction (Yang et al., 2016). With the abundance of resveratrol in the culture medium of peanut hairy root, piceatannol generated from the oxidation of resveratrol could serve as a precursor, alternative to resveratrol, for prenylated stilbenoids in peanut. It appeared that this compound could be further metabolized into other derivatives, resulting in a relative low yield of piceatannol in the peanut hairy root culture.

AhR4DT-1 identified here initiates the first step in the biosynthesis of prenylated stilbenoids in peanut by catalyzing the prenylation of resveratrol and piceatannol to form arachidin-2 and arachidin-5, respectively. Other than derived that from the prenylation of piceatannol, which is limited in the culture medium, it remains possible that arachidin-5 is also formed via hydroxylation of arachidin-2 by a stilbenoid monooxygenase (P450). Flavonoid 3'-monooxygenases, for example, are known to catalyze 3'-hydroxylation of the flavonoid backbone (Tanaka and Brugliera, 2013). Similarly, arachidin-3 might be hydroxylated by a monooxygenase to produce arachidin-1 (FIG. 41). Further enzyme discovery and testing are needed to explore these possibilities.

In the reactions with peanut hairy root microsomes, arachidin-2 and arachidin-5 prenylated from resveratrol and piceatannol, respectively, could be further converted into derivatives of arachidin-2 derivative and arachidin-5 that were detected in the medium upon the elicitor treatment (Yang et al., 2016). Nonetheless, these derivatives were not detected in the AhR4DT-1 reactions (FIG. 41), indicating other enzyme(s) that modify arachidin-2 and arachidin-5 are present downstream of AhR4DT-1.

In one proposed pathway for arachidin-1 and arachidin-3, arachidin-2 and arachidin-5 might be directly converted to arachidin-3 and arachidin-1 by an isomerase which could shift the olefinic bond position on their prenylated moieties (FIG. 41). Alternatively, arachidin-2 or arachidin-5 might be converted into an intermediate product which is further modified into arachidin-3 or arachidin-1 through multiple enzymatic steps (FIG. 41). It is still unclear whether arachidin-2 derivative and arachidin-5 derivative found in the peanut hairy root culture were one of these intermediates involved in the biosynthesis of arachidin-3 and arachidin-1, which are the predominant compounds in the culture (FIG. 41). Alternatively, it may still be a slight possibility that arachidin-3 and arachidin-1 were directly synthesized from resveratrol and piceatannol catalyzed by AhR4DT-1 or another specific prenyltransferase utilizing 3-methyl-but-1-enyl pyrophosphate as prenyl donor. Although, as far as we know, this kind pyrophosphate has never been described in plants.

To date, over 45 prenylated stilbenoids and derivatives, including monomers and dimers, have been identified in peanut. Many of these chemical structures have been confirmed by NMR (FIG. 41) or predicted by mass spectrometry. Interestingly, all these stilbenoids can be divided into two groups, one showing a prenyl unit or a derivative at the C-4 and a second group showing a prenyl unit or derivative at the C-3' position (FIG. 41). These observations strongly suggest that the prenyltransferases encoded by AhR4DT-1 and AhR3'DT-1 act in the first committed steps that channel the diversification of non-prenylated stilbenoids into prenylated stilbenoids. As the first stilbenoid-specific prenylated transferases identified in a plant, these findings advance our understanding of this specialized gene family and the biosynthesis of important bioactive compounds in plant stress responses.

Methods

Plant Materials and Chemical Reagents

Hairy root of peanut cv. Hull line 3 was previously established by transforming peanut cotyledonary leaves with *Agrobacterium rhizogenes* strain ATCC 15834 and maintained in modified Murashige and Skoog (MSV) medium under continuous darkness at 28° C. as described before (Condori et al., 2010). The procedure of elicitation for stilbenoids production in peanut hairy root culture was performed according to Yang et al., (2015).

Authentic standards of resveratrol and piceatannol were obtained from Biophysica and Axxoram, respectively. Arachidin-1, arachidin-2, arachidin-3 and arachidin-5 standards were purified from elicited peanut hairy root cultures as described previously (Yang et al., 2016). Pinosylvin, oxyresveratrol, pterostilbene, naringenin, apigenin, genistein, and IPP, GPP, FPP and GGPP were purchased from Sigma-Aldrich. DMAPP used in this study was obtained from Isoprenoids.

RNA Preparation

A co-treatment time-course of 100 μM methyl jasmonate (MeJA; sigma) and 9 g/L (6.87 mM) methyl-β-cyclodextrin (CD; Cavasal W7M) was applied to nine-day-old peanut hairy roots to induce the expression of genes involved in the biosynthesis of stilbenoids. Total RNA was extracted from elicited root tissue at 0.5, 3, 9, 18, 24 and 72 hours using TRIzol reagent (Life Technologies), according to the manufacturer's instructions. For controls, RNA was likewise extracted from cultures prior to treatment (t=0) and from non-elicited cultures, collected 9 and 72 hours after mock treatment, being refreshed with fresh MSV medium.

Transcript Sequencing and Assembly

Strand-aware, polyA-enriched RNA libraries were prepared using Illumina TruSeq Stranded mRNA Sample Preparation reagents with sequence-indexed adaptors, with inputs of 4 micrograms total RNA per sample. Average insert size of indexed libraries was 300 bp according to Bioanalyzer (Agilent) evaluation. Libraries were sent to the Roy J. Carver Biotechnology Center/W.M. Keck Center at the University of Illinois at Urbana-Champaign, where they were quantified by qPCR and pooled together for sequencing of 2×101 paired cycles on an Illumina HiSeq2500 using TruSeq SBS sequencing kits version 3. Number of read pairs ranged from 34.8 to 58.9 M per sample. Data were processed and demultiplexed using Casava 1.8.2 (Illumina).

Reads were trimmed using Trimmomatic v 0.32 (Bolger et al., 2014) with headcrop 12, sliding window 5, minimum quality 25. Parallel assemblies of each sample-specific reads set as well as a combination of all reads were generated using Trinity v 2013-11-10 (Haas et al., 2013), TransABySS 1.5.5 (Robertson et al., 2010), Velvet-Oases 1.2.10 (Schulz et al., 2012) and SOAPtrans 1.03 (Li et al., 2009), yielding a total of 2.6 M putative complete and partial transcript sequences. Coding sequences (CDS) were predicted and translated using CD-Hit (Li and Godzik, 2006) through scripts of the Evigenes pipeline (Don Gilbert, Indiana University) to build the transcriptome BlastP and BLASTN databases.

Using GMAP 2016-04-04 (Wu and Watanabe, 2005), transcript assemblies were aligned independently to the *Arachis duranensis* and *Arachis ipaensis* genomes available in PeanutBase (www.peanutbase.org and Bertioli et al., 2016), which confirmed clustering of highly similar forms and allowed us to approximate a reduced *A. hypogaea* sequence reference against which we could quantify reads coverage attributable to the enzyme transcripts under study. Reads mapped to the resulting four genomic loci were then isolated using Samtools 1.3.1 (Li et al., 2009b) and remapped to *A. hypogaea* transcript references determined here. Mapping of RNA-Seq reads was performed using Tophat2, v 2.0.7 (Kim et al., 2013) using the genome guided option. Uniquely mapped read counts from each sample were assessed using HTSeq v 0.6.1p1 (Anders et al., 2015).

Cloning of AhR4DT-1 and AhR3'DT-1 cDNA

The amino acid sequences of flavonoid prenyltransferases SfN8DT-1 (accession number: BAG12671.1), SfG6DT (BAK52291.1), SfFPT (AHA36633.1), GmG4DT (BAH22520.1), GuA6DT (AIT11912.1) and LaPT1 (AER35706.1) were used as input to run BlastP (Altschul et al., 1990) against our translated peanut hairy root transcriptome sequence database. Predictions of chloroplast transit peptides (cTP) were made using both ChloroP (http://www.cbs.dtu.dk/services/ChloroP/) and iPSORT (http://ipsort.hgc.jp/). To clone the full-length cDNA of these candidates, RNA of 9-hour-elicited peanut hairy roots was prepareded by TRIzol reagent and the cDNA was synthesized using iScript™ Select cDNA Synthesis kit (Bio-Rad) using oligo (dT) primer. One N-terminal primer and three C-terminal primers were synthesized with flanking NotI and KpnI restriction sites, respectively (FIG. 66) and PCR using these primers was performed with ExTaq DNA Polymerase (Takara) following the program below: initial denaturation (3 min, 94° C.); 30 cycles (30 s, 94° C.; 30 s, 52° C.; 1 min 30 s, 72° C.); and a final extension step (10 min, 72° C.). Three amplicons (including AhR3'DT-1) were subcloned into a pGEM-T vector (Promega) and multiple clones from each amplicon were sequenced at University of Chicago Comprehensive Cancer Center (UCCCC). In the second screening, according to all the 108 candidate sequences, four N-terminal primers and five C-terminal primers with NotI/KpnI flanking restriction sites (FIG. 66) were designed for prenyltransferase cloning and another four amplicons (including AhR4DT-1) obtained from the same cDNA template were cloned into pGEM-T vector for sequencing validation.

Phylogenetic Analysis

Protein sequences were aligned using MUSCLE (Edgar 2004), and a neighbor-joining phylogenetic tree computed with PhyML (Guindon and Gascuel 2003) using the Dayhoff substitution model and 100 bootstrapped replicates.

Construction of Binary Vectors

Figure 59:
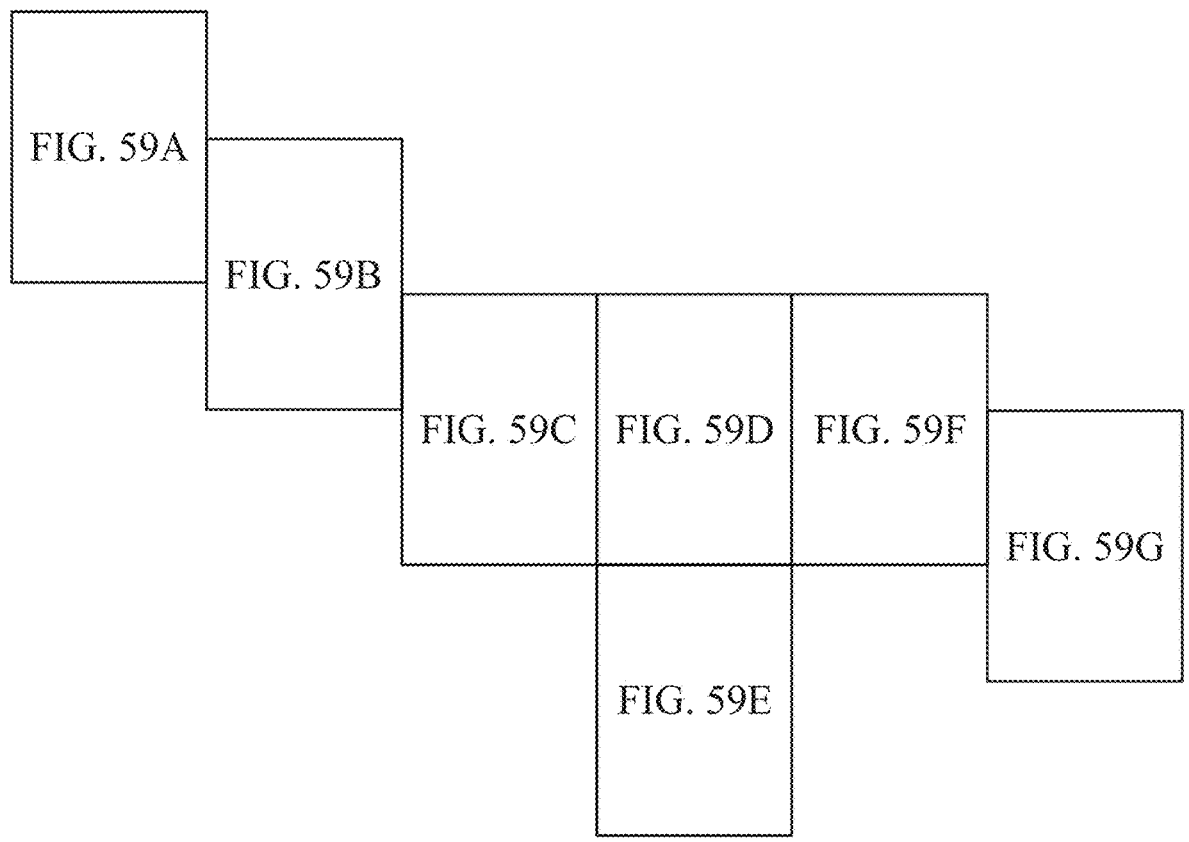
Figure 59C:
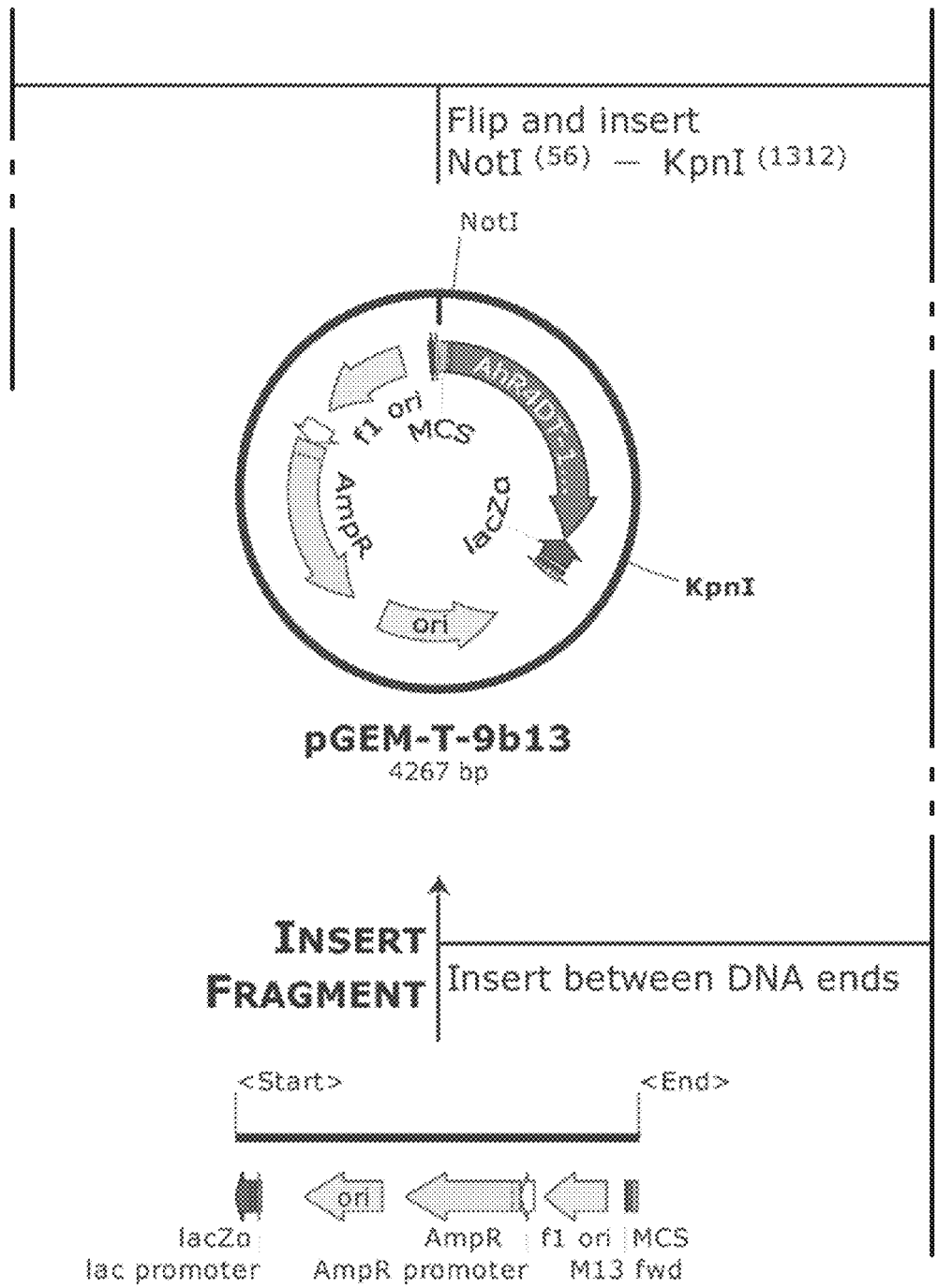
Figure 59D:
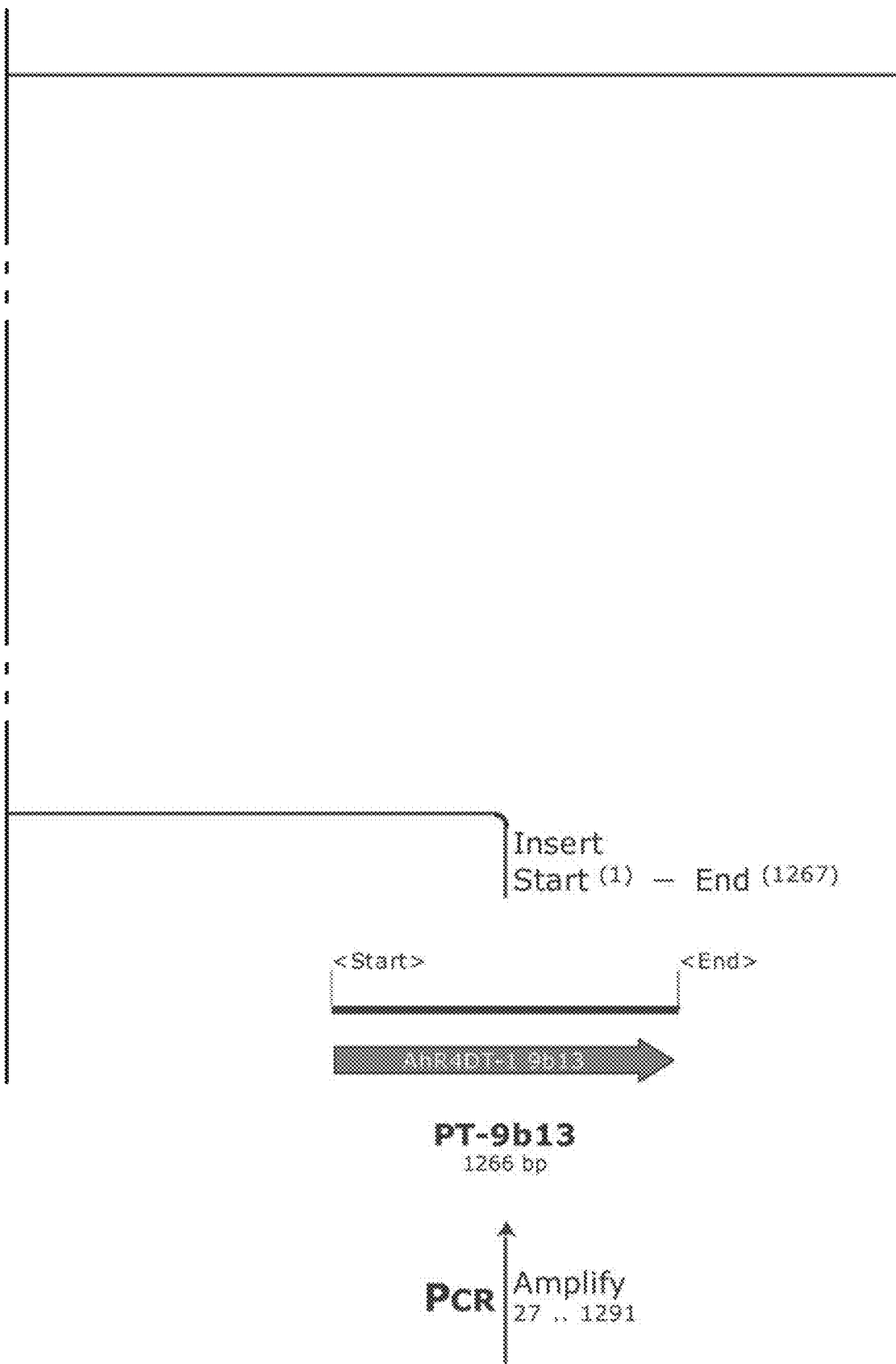
Figure 59E:
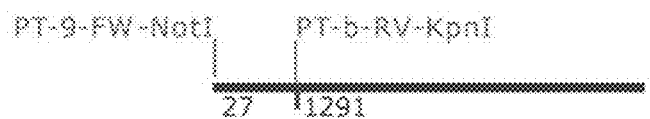
Figure 60:
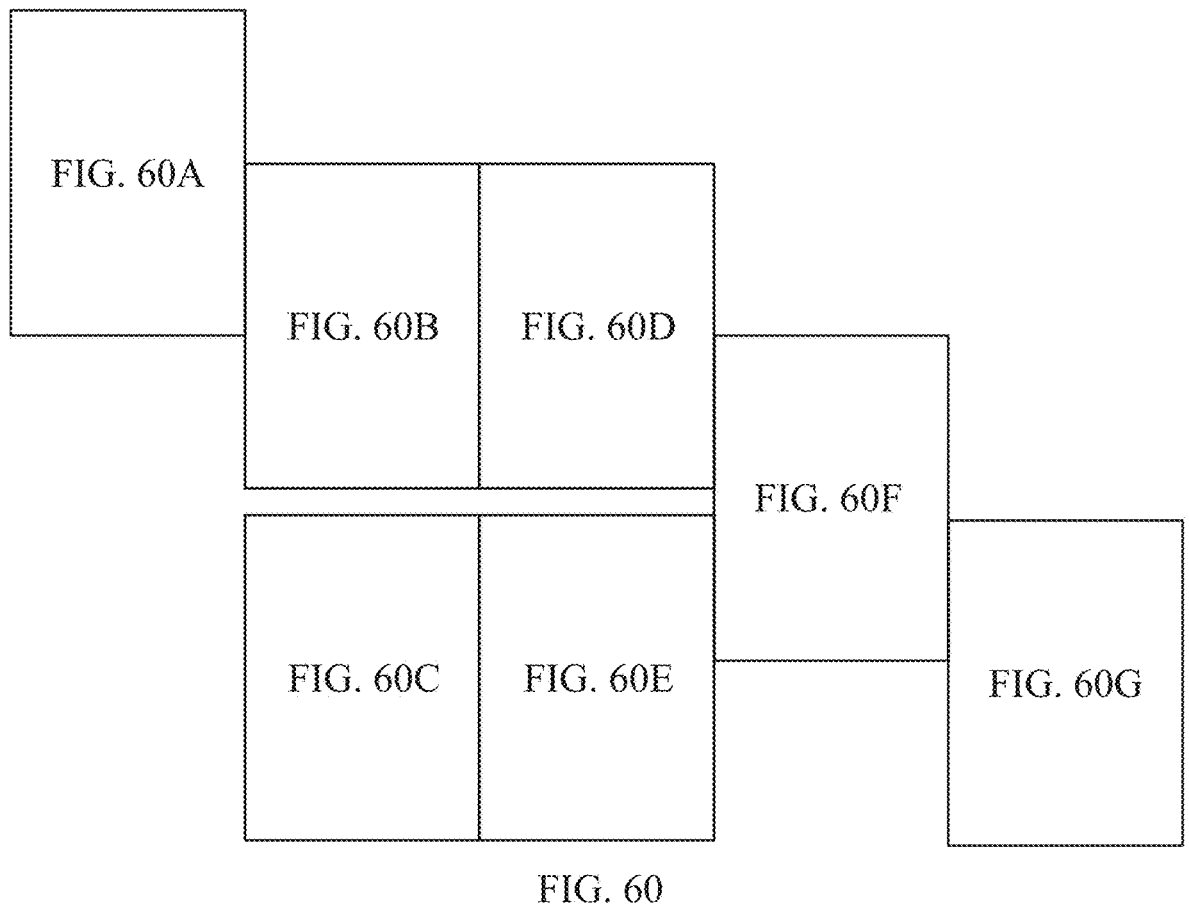
Figure 60A:
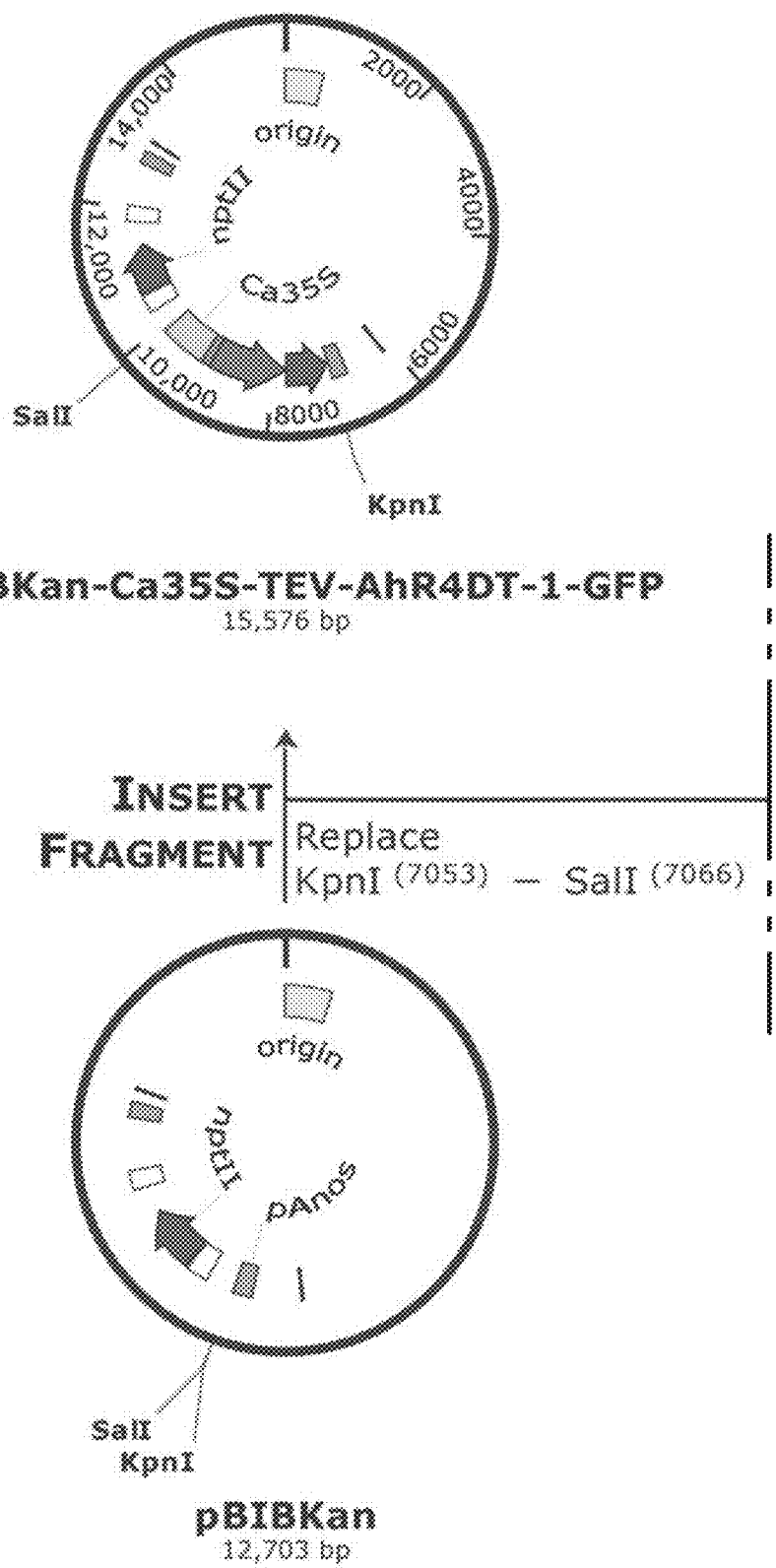
Figure 60C:
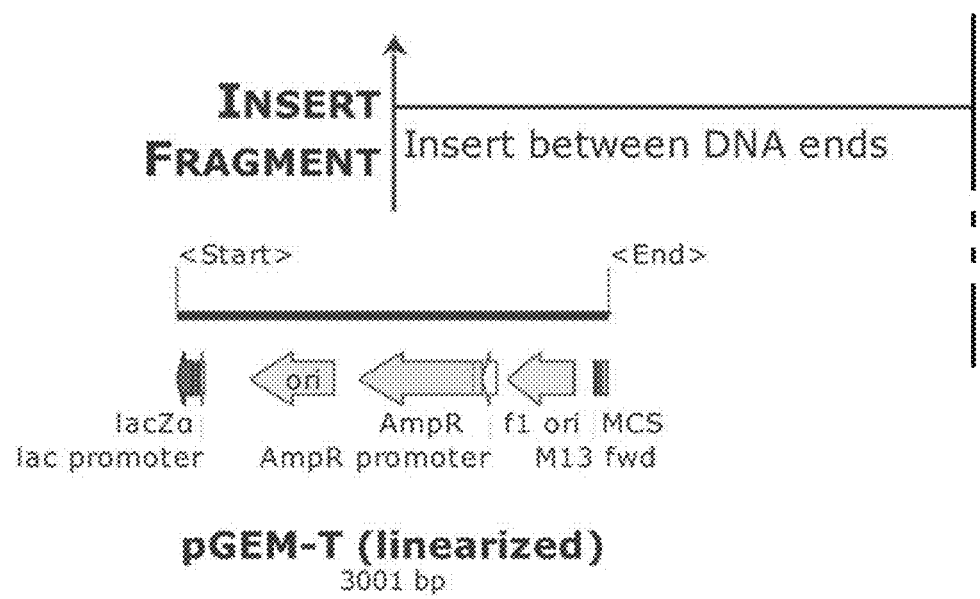
Figure 60D:
Figure 60E:
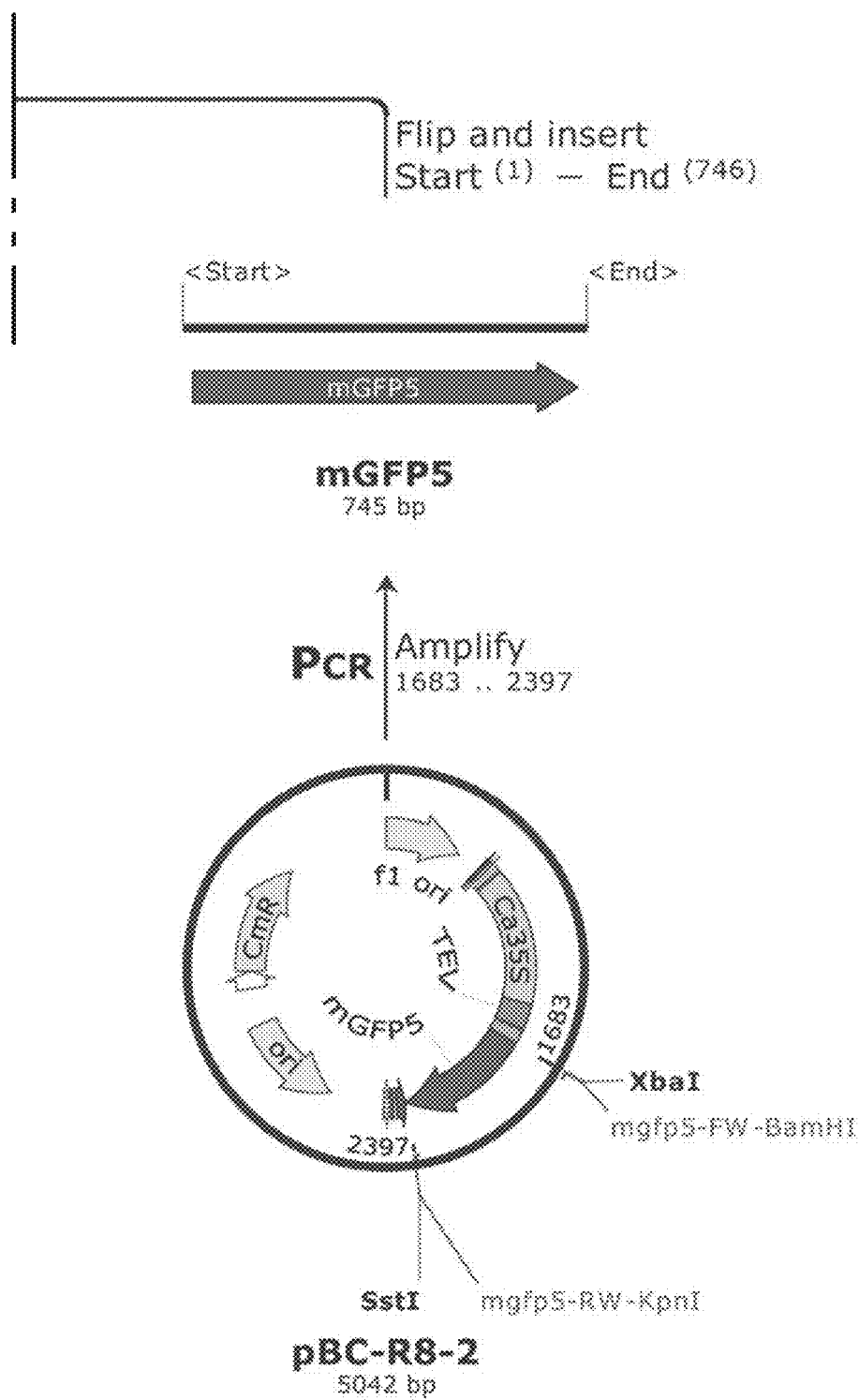
Figure 60G:
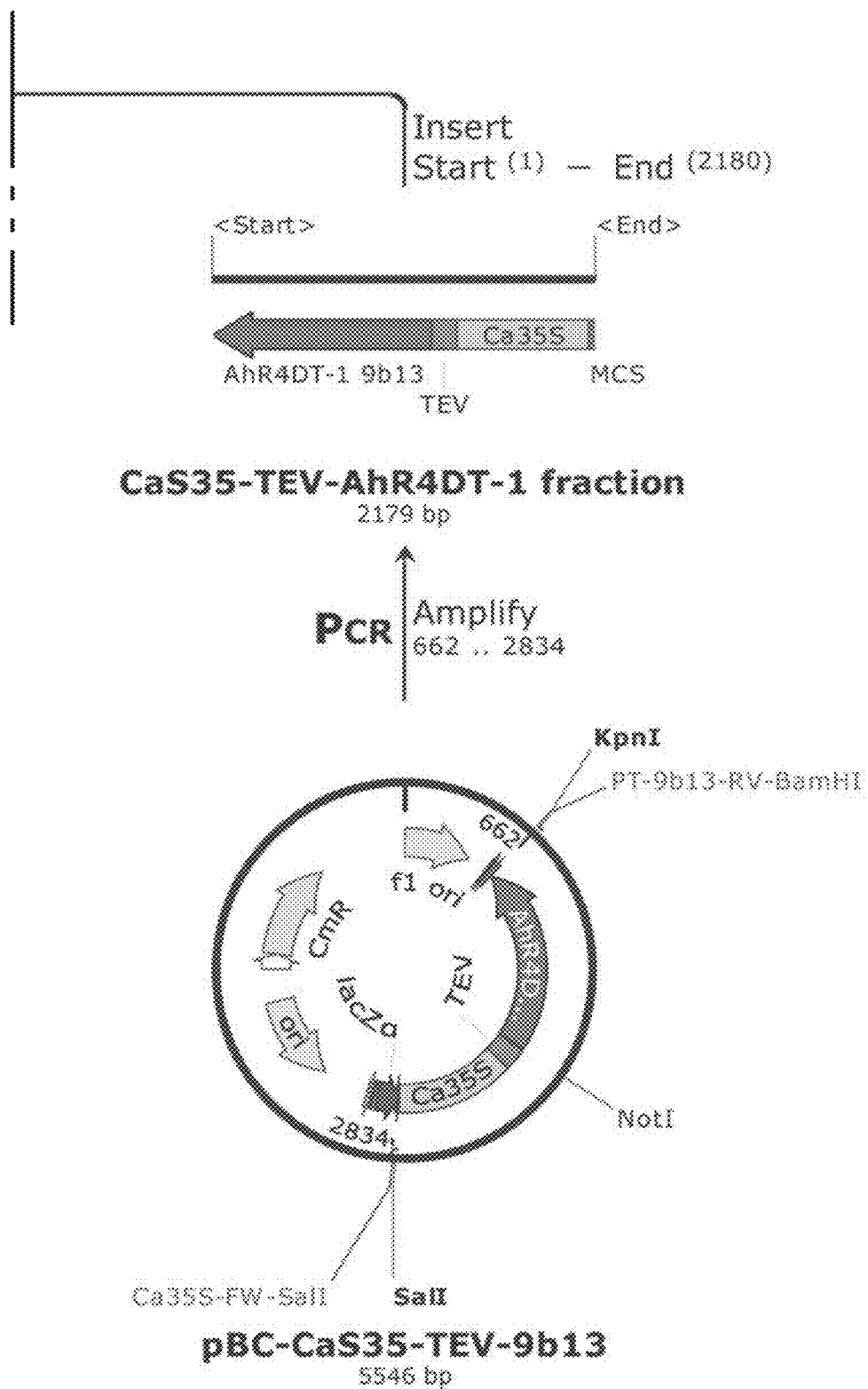

The cloning strategy of binary vectors is showed in FIG. 59. In detail, the sequence of the double enhanced cauliflower mosaic virus 35S promoter (CaMV35S) fused to the translational enhancer from tobacco etch virus (TEV) was amplified from plasmid pR8-2 (constructed by Medina-Bolivar and Cramer, 2004) and subcloned into pGEM-T vector using Ca35S-FW-SalI-1/TEV-RW-NotI primers (FIG. 66) with SalI/NotI flanking restriction sites. After validation of the sequences, the pGEM-CaMV35S-TEV and pGEM-T vectors containing putative prenyltransferase gene (PT) were digested with SalI/NotI and NotI/KpnI, respectively. A high copy number vector, pBC KS(−) digested with KpnI/SalI was used as a transition vector. Two fragments of full-length cDNA and CaMV35 S-TEV promoter were ligated into the transition vector in a 16° C. overnight reaction with T4 ligase (NEB). Then the fragment of CaMV35S-TEV-PT from the transition vector digested by KpnI/SalI was subcloned into a binary vector, pBIB-Kan which was created by Becker (1990). Eventually, the constructed binary vector with the putative prenyltransferase gene under the control of CaMV35S-TEV chimeric promoter and three prime untranslated region (3'-UTR) of nopaline synthase from the original pBIB-Kan vector was transformed into *A. tumefaciens* LBA4404 for stilbenoid prenylation activity screening.

Screening for Stilbenoid Prenylation Activity

The engineered *A. tumefaciens* was grown in 5 mL of YEP medium, containing 50 mg/L of kanamycin (Sigma-Aldrich) and 30 mg/L of streptomycin (Sigma-Aldrich) for antibiotic selection, at 28° C. on an orbital shaker at 200 rpm. After cultivation for 2 days, 5 mL of bacterial suspension was inoculated into 50 mL of fresh YEP medium containing the antibiotics and allowed to grow for one additional day under the same conditions. Bacteria were pelleted by centrifugation, resuspended in 500 mL of induction medium containing 10 mM $MgCl_2$ with 1 mM acetosyringone and incubated for 4 h at 28° C. under 200 rpm orbital shaking until their $OD_{600}$ reached to a range from 0.5 to 0.6. Before the infiltration, 0.005% of Tween-20, 0.005% of Triton 100 and 0.005% of Silwet L-77 were added to bacterial cultures to enhance the efficiency of transformation in *N. benthamiana* leaves. *Agrobacterium*-mediated vacuum infiltration was performed on 4-week-old *N. benthamiana* following the methodology described previously (Medrano et al., 2009).

After 48 hours of post-infiltration, the "middle tier" of *N. benthamiana* leaves were harvested for prenylation activity screening. Five grams of leaf tissue (fresh weight) were grounded and homogenized using a mortar with pestle in 10 mL of extraction buffer containing 100 mM Tris-HCl (pH 7.6) and 10 mM dithiothreitol (DTT). After removing the cell debris by centrifugation at 12,000×g for 20 min at 4° C., the crude cell-free extract was obtained by passing the 12,000×g supernatant through a PD-10 desalting column (GE Healthcare) equilibrated with 100 mM Tris-HCl (pH 9.0) containing 10 mM DTT. The total protein concentration was determined by coomassie protein assay (Thermo Scientific) using bovine serum albumin as standard.

The prenylation reactions contained resveratrol (100 DMAPP (300 $MgCl_2$ (10 mM) and DTT (5 mM) in a Tris-HCl buffer (100 mM, pH 9.0). After incubation (28° C., 40 min) with the crude cell-free extract of *N. benthamiana* leaves (5 mg of total protein) in a total volume of 1 mL, the enzyme reaction was terminated by addition of HCl (6 M, 20 μL) and then the reaction mixture was extracted with ethyl acetate (1 mL). The ethyl acetate extract was dried under nitrogen gas and dissolved in 300 μL of methanol. The reaction product was identified and quantified using HPLC/ESI-MS$^n$ analysis as previously described (Yang et al., 2016). The reaction of crude cell-free extract of *N. benthamiana* leaves infiltrated with *A. tumefaciens* harboring the empty pBIB-Kan vector was used as control.

Enzymatic Characterization of AhR4DT-1 and AhR3'DT-1

In preliminary experiments focused to study the effect of post-infiltration period on the prenylation activity in *N. benthamiana*, leaf tissues of plants which transiently expressed AhR4D-1 were harvested 24, 48, 72 and 96 hours post-infiltration. Among these reactions, the AhR4D-1 activity in the crude cell-free extract of *N. benthamiana* leaves increased with the post-infiltration period from 24 to 72 hours, while the activity in the leaves harvested from 96 hours post-infiltration was similar to 72 hours (data not shown). In addition, since both AhR4DT-1 and AhR3'DT-1 were predicted as membrane bound proteins by TMHMM 2.0, the microsomal fraction of *N. benthamiana* leaves at 72 hours post-infiltration was used to study the biochemical properties of AhR4DT-1 or AhR3'DT-1. Ten grams of fresh leaves were homogenized using a mortar with pestle in a 20 mL of extraction buffer (100 mM Tris-HCL pH 7.6 containing 10 mM DTT). The homogenate was centrifuged at 12,000×g for 20 min at 4° C., and about 13.2 mL of the supernatant was centrifuged at 156,000×g for 45 min at 4° C. to pellet the microsomal fraction, while the 156,000×g supernatant was prepared by using a PD-10 desalting column (GE Healthcare) equilibrated with Tris-HCl buffer (100 mM, pH 9.0) containing DTT (10 mM). The microsomal fraction was washed twice with Tris-HCl buffer (100 mM, pH 9.0) containing DTT (10 mM) and resuspended in 1 mL of the same buffer.

The basic reaction and measurement for AhR4DT-1 and AhR3'DT-1 activity were the same as that for prenylation activity screening with exception of using 30 μg of microsomal fraction of *N. benthamiana* leaves as enzyme instead of crude cell-free extract of *N. benthamiana* leaves in a 500 μL of reaction. To investigate the optimal pH, the enzymatic reactions were performed in Tris-HCl buffer (100 mM, pH 7.0 to 9.0), glycine-NaOH buffer (100 mM pH 8.6 to 10.6) and $NaHCO_3$—$Na_2CO_3$ buffer (100 mM, pH 9.2 to 10.7). The optimal reaction temperatures for AhR4DT-1 and AhR3'DT-1 were tested at 20, 25, 28, 30, 37, 40, and 50° C. in Tris-HCl buffer (100 mM, pH 9.0). For the divalent cation dependency study, 10 mM $MnCl_2$, $FeCl_2$, $CaCl_2$), $CoCl_2$, $ZnCl_2$, $NiCl_2$, or $CuCl_2$ was added to the reaction mixture instead of $MgCl_2$, and the enzyme activity was compared with the reaction containing $MgCl_2$. The reactions without divalent cation and 10 mM EDTA instead of $MgCl_2$ were used as controls.

For the kinetic study, varying concentrations (10, 20, 40, 80, 160, 320, and 640 μM) of resveratrol or piceatannol with a fixed concentration of DMAPP (640 μM) and varying concentrations (10, 20, 40, 80, 160, 320, and 640 μM) of DMAPP with a fixed concentration of resveratrol (640 μM) were incubated with 30 μg of microsomal fractions of *N. benthamiana* leaves expressing AhR4DT-1 or AhR3'DT-1 to calculate the apparent $K_m$ and $V_{max}$ values by nonlinear regression analysis of the Michaelis-Menten equation using GraphPad Prism 6 software. The prenyl acceptor specificity of AhR4DT-1 and AhR3'DT-1 were tested using 100 of each stilbenoid (resveratrol, piceatannol, oxyresveratrol, pinosylvin, pterostilbene and piceid), flavanone (naringenin), flavone (apigenin), and isoflavone (genistein) with 300 DMAPP as a prenyl donor, while the prenyl donor specificities of these two enzymes were tested using 300 μM prenyl diphosphates (DMAPP, IPP, GPP, FPP, GGPP) with 100 μM resveratrol as a prenyl acceptor. All these reactions were performed in a total volume of 500 μL with 100 mM Tris-HCl buffer (pH 9.0) at 28° C. for 40 min.

NMR Spectra

Figure 61:
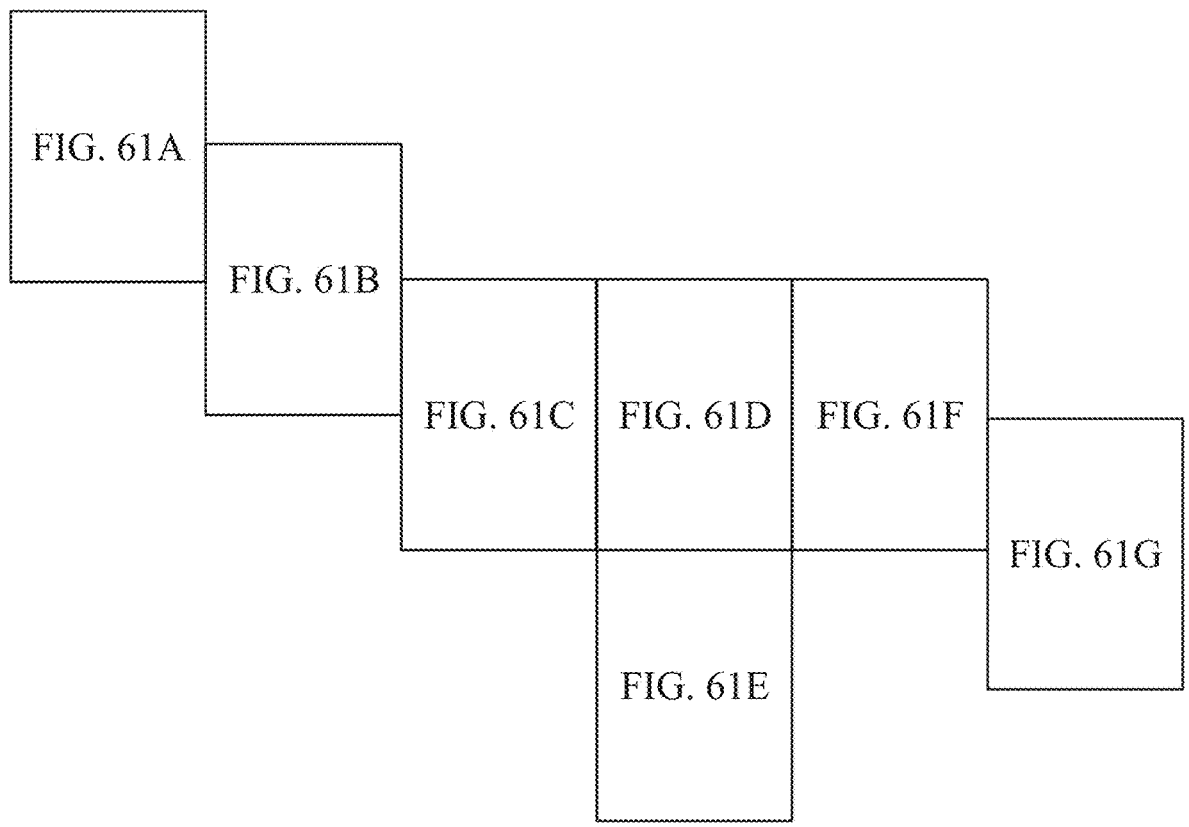
Figure 61C:
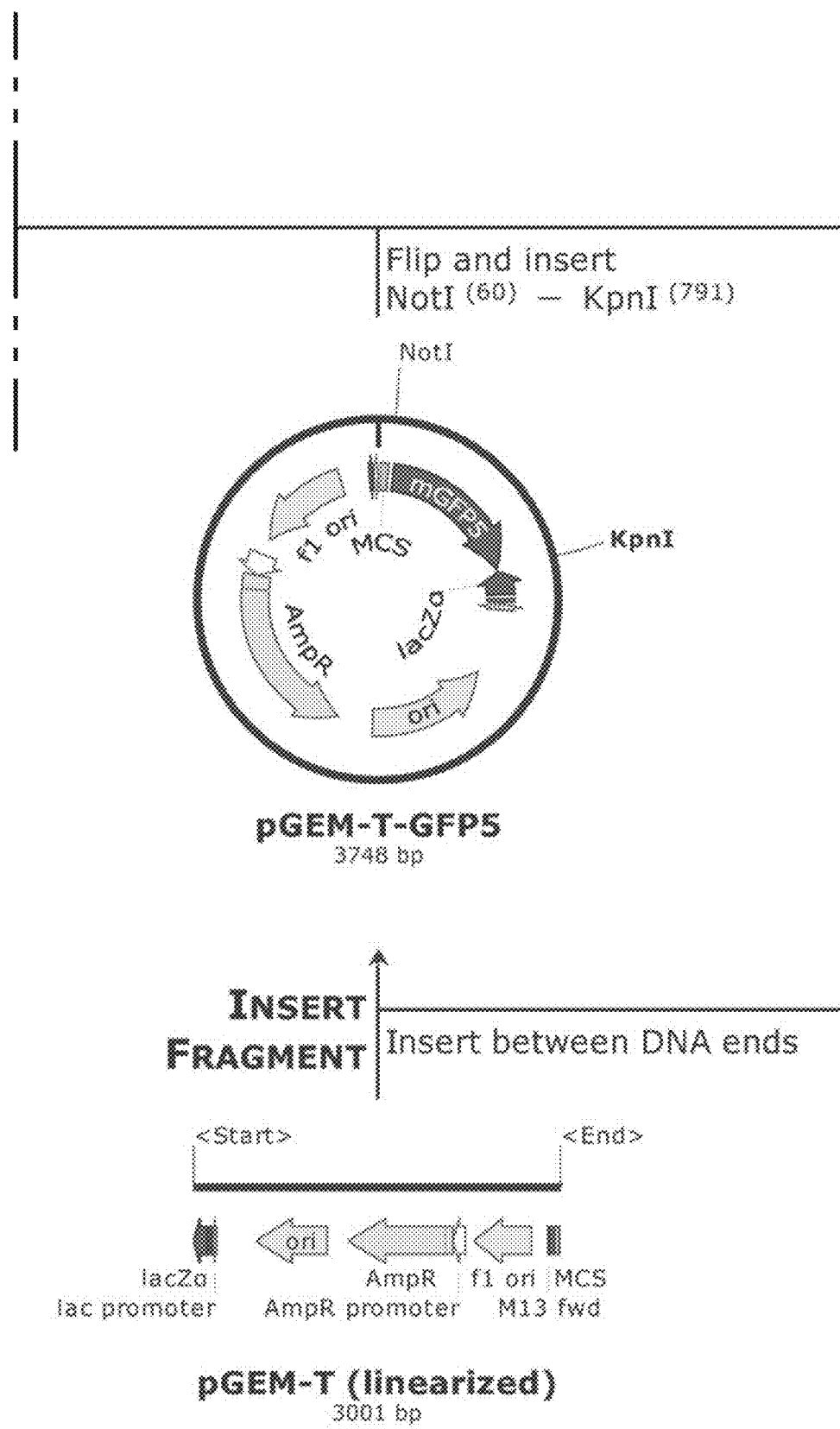
Figure 61D:
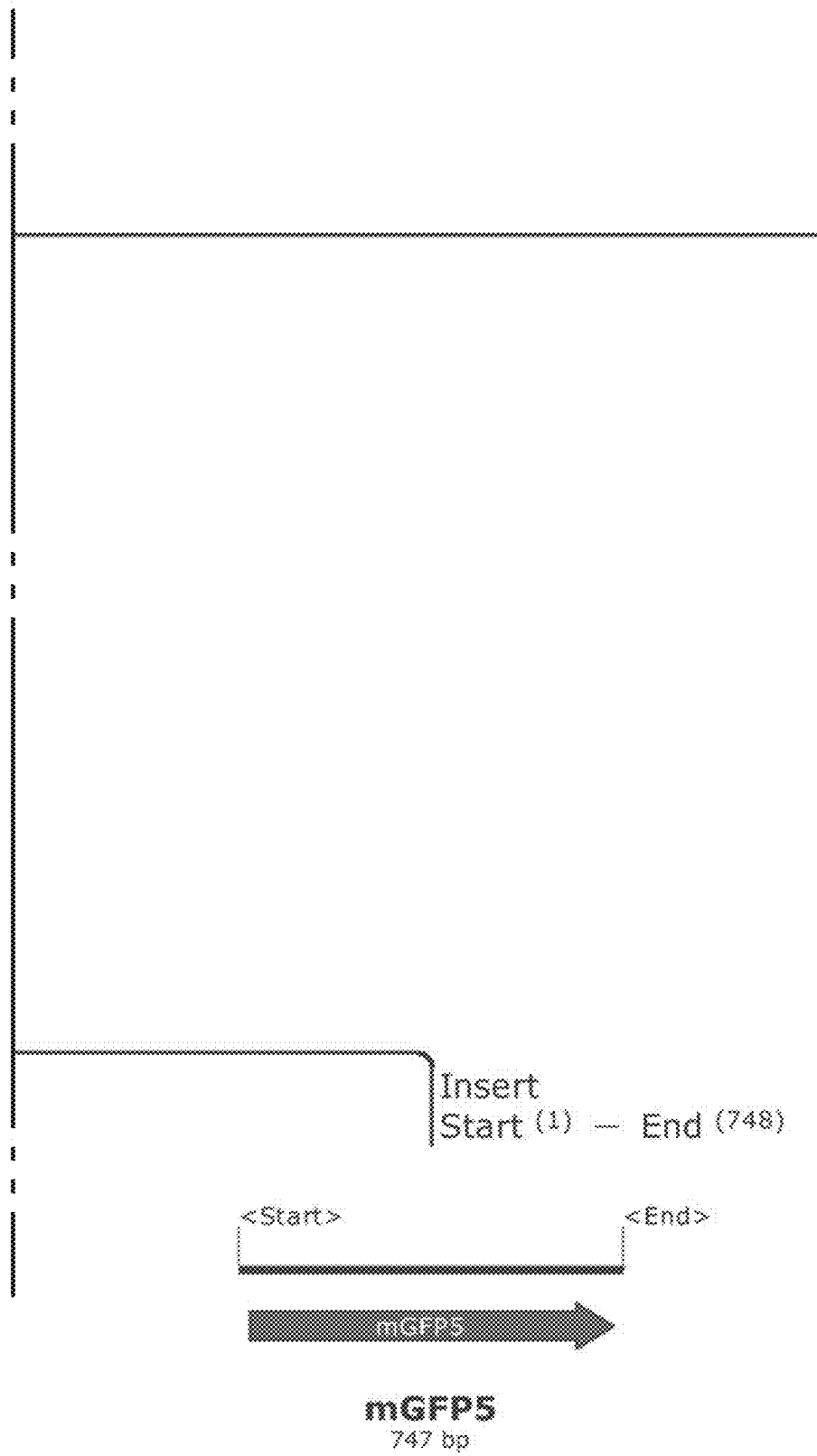
Figure 61E:
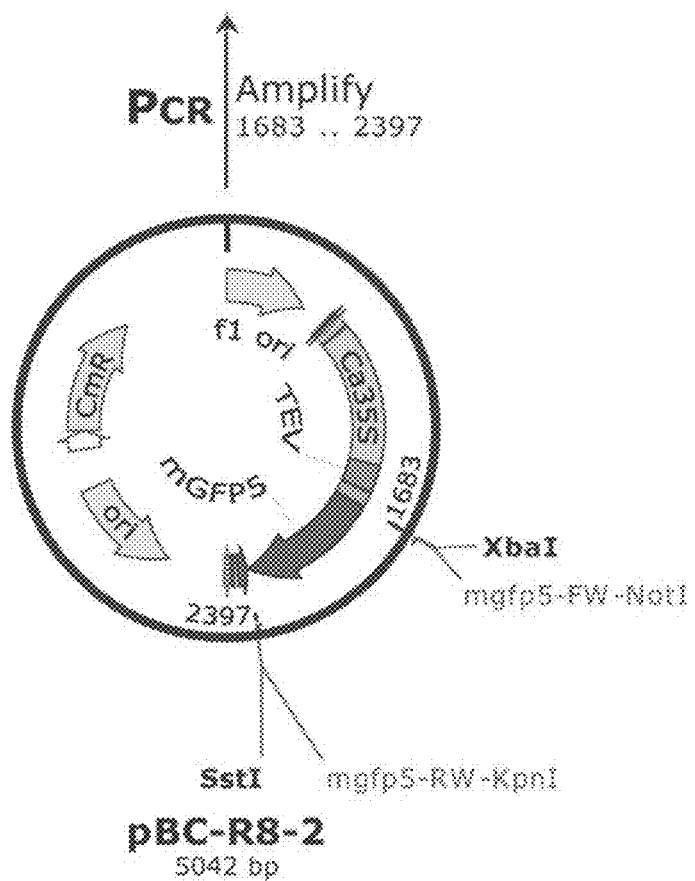
Figure 61F:
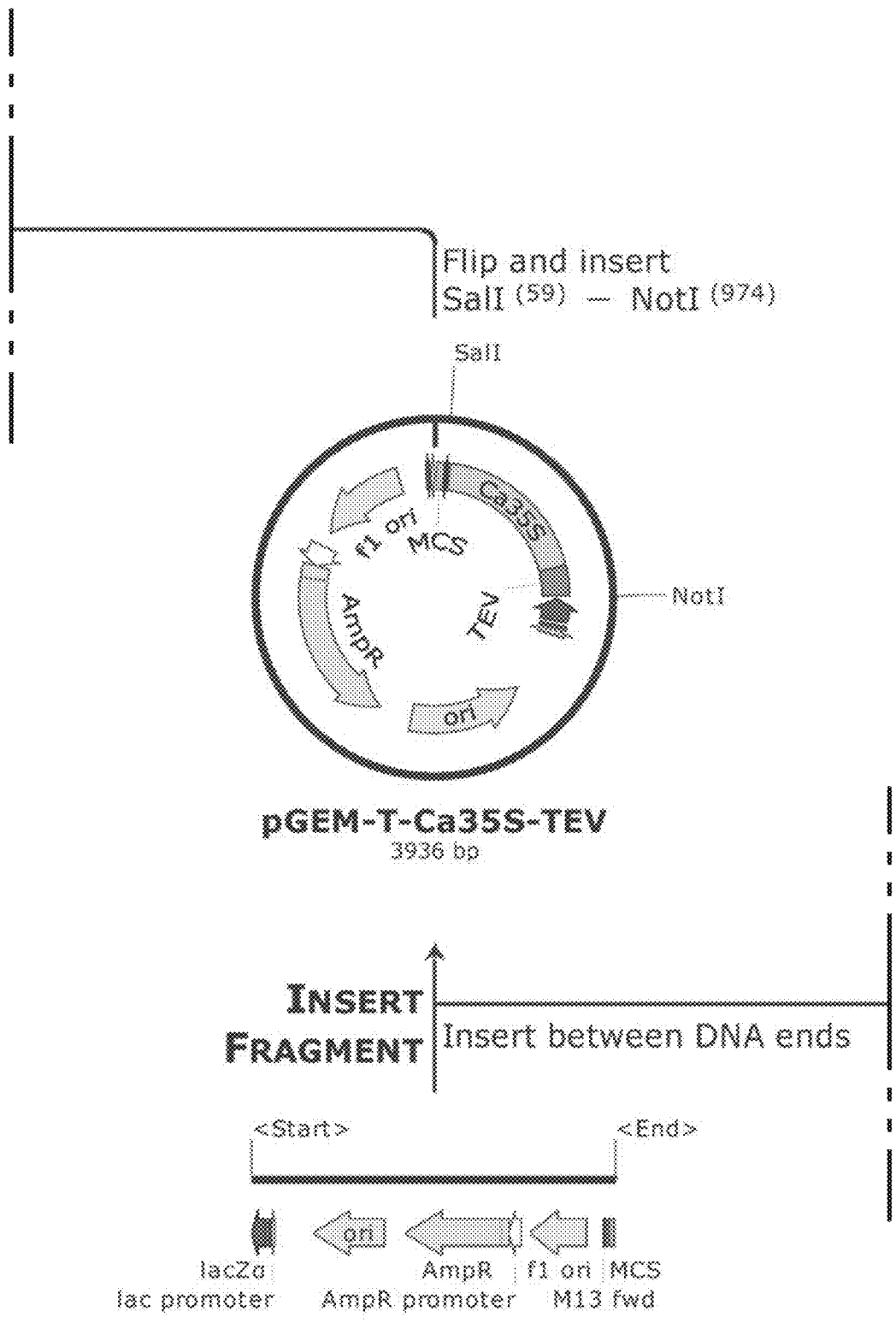

All NMR measurements were performed on a Bruker Avance 700 MHz and spectrometers at 298 K. The $^1H$-$^{13}C$ HMBC and $^1H$-$^{13}C$ HSQC spectra were collected in $d_6$-acetone. The concentration of the sample was ~1 mM. For $^1H$ NMR analysis, 16 transients were acquired with a 1 second relaxation delay using 32 K data points. The 90° pulse was 9.7 μs with a spectral width of 16 ppm. 1D $^{13}C$ NMR spectra were obtained with a spectral width of 30 ppm collected with 64 K data points. Two-dimensional spectra were acquired with 2048 data points for t2 and 256 for t1 increments. All NMR data were analyzed using Topspin v 2.0 and SPARKY v 3.0 software. Peaks were integrated and overlaid with the simulated spectra for different versions of the prenyl chain attached on the resveratrol compound Construction of GFP Fusion Proteins The nucleotide sequence of modified green fluorescence protein (mGFP5) was amplified from pR8-2 (Medina-Bolivar and Cramer, 2004) using primers mgfp5-FW-BamHI/mgfp5-RW-KpnI (FIG. 66) and cloned into pGEM-T vector to give pGEM-mGFP5-1. PT-9b13-RV-BamHI or PT-10k1-RV-BamHI reverse primer with Ca35S-FW-SalI-2 forward primer were used to amplify the full-length of AhR4DT-1 or AhR3'DT-1 with CaMV35S-TEV promoter region from pBC-CaMV35S-TEV-9b13 and pBC-CaMV35S-TEV-10k1 vector, which were created during the construction of the binary vector (FIG. 60; FIG. 68). The PCR products were then cloned into pGEM-T vector for sequencing validation. After SalI/BamHI digestion, CaMV35S-TEV-AhR4DT-1 and CaMV735S-TEV-AhR3'DT-1 fragments were isolated and inserted into pGEM-mGFP5-1 to yield pGEM-CaMV35S-TEV-AhR4DT-1-GFP and pGEM-CaMV35S-TEV-AhR3'DT-1-GFP, respectively. Lastly, the fragments of CaMV35S-TEV-AhR4DT-1-GFP and CaMV735S-TEV-AhR3'DT-1-GFP were excised with SalI/KpnI and ligated into binary vector pBIB-Kan to yield pBIBKan-AhR4DT-1-GFP and pBIBKan-AhR3'DT-1-GFP, respectively (FIG. 61). For the GFP control construct, mGFP5 gene was amplified from pR8-2 using primers mgfp5-FW-NotI/mgfp5-RW-KpnI and cloned into pGEM-T vector to give pGEM-mGFP5-2. Two fragments CaMV35S-TEV digested from pGEM-CaMV35S-TEV by SalI/NotI and mGFP5 digested from pGEM-mGFP5-2 by NotI/KpnI were inserted into pBC KS(−) vector to form pBC-CaMV35S-TEV-GFP. The fragment of CaMV735S-TEV-GFP was eventually subcloned into binary vector pBIB-Kan to form pBIB-Kan-GFP (FIG. 61).

Particle Bombardment and Microscopy

To investigate the subcellular localization of AhR4DT-1 and AhR3'DT-1, pBIB-Kan-AhR4DT-1-GFP, pBIB-Kan-AhR3'DT-1-GFP and pBIB-Kan-GFP were co-bombarded with binary vector pt-rk (ABRC stock numbers: CD3-999, Nelson et al., 2007) containing a plastid marker fused with red fluorescent protein into the onion epidermal peel cells by PDS-1000/He™ systems (Bio-Rad) following the manufacturer's recommendations. In brief, 5 µg of target plasmid and 5 µg of pt-rk plasmid were together coated on 50 µL of 60 mg/mL tungsten particles (M17, 1 µm; Bio-Rad) in the presence of 1 M $CaCl_2$) and 15 mM spermidine. After several ethanol washes, plasmid-coated particles were dried on plastic discs and accelerated with a helium burst at 1100 psi in a bombardment chamber. Bombarded onion epidermal peels were kept on plates containing MS medium for 60 hours in the dark. The localization of the expressed proteins in the transformed cell was visualized with a Nikon Eclipse E800 microscope with a 20×/0.5 W Fluor water immersion objective. Confocal fluorescence images were obtained by using Nikon digital eclipse C1 microscope system with 488 nm laser illumination and 525/50 nm filter for GFP fluorescence and 543 nm laser with 595/50 nm filter for RFP fluorescence.

Quantitative Real-Time PCR of AhR4DT-1 and AhR3'DT-1

Total RNA was isolated from 100 µM MeJA and 9 g/L CD co-treated peanut hairy roots at 0.5, 3, 9, 18, 24 and 72 hours using TRIzol reagent, and cDNA was synthesized using iScript™ Select cDNASynthesis Kit (Bio-Rad) with oligo (dt) primers following the manufacturer's instructions. Primers for AhR4DT-1 and AhR3'DT-1 were designed using Allele ID (PREMIER Biosoft). Two reference genes, ACTT (encoding actin 7) and EFα1 (encoding elongation factor α1) were selected previously (Condon et al., 2011) and used to normalize the expression of AhR4DT-1 and AhR3'DT-1 in peanut hairy roots. Efficiencies of primers for these targets are shown in FIG. 62. Quantitative real-time PCR (qPCR) reactions were carried out using iQ SYBR Green Supermix (Bio-Rad) as previously described (Yang et al., 2015) and the expression of AhR4DT-1 and AhR3'DT-1 were analyzed by qbase+ (Biogazelle).

Accession Numbers

The nucleotide sequences of AhR4DT-1, AhR3'DT-1, AhR3'DT-2, AhR3'DT-3, AhR3'DT-4 have been deposited in the GenBank™ database under the accession numbers KY565244, KY565245, KY565246, KY565247 and KY565248, respectively.

Stable Expression of Peanut Stilbenoid-Specific Prenyltransferase in Tobacco Plants and Hairy Roots.

To establish transgenic tobacco (Nicotiana tabacum) plants expressing peanut stilbenoid prenyltransferase genes, pBIB-Kan binary vectors containing either the AhR4DT-1 or AhR3'DT-1 cDNA under the control of the constitutive 35S promoter were transformed into Agrobacterium tumefaciens LBA4404. Leaf blade, petiole and stem explants of N. tabacum were wounded and inoculated with above engineered A. tumefaciens. After 48 hours of inoculation, explants were placed in regeneration medium (modified MS medium containing 1 mg/L BAL and 0.1 mg/L NAA), 600 mg/L cefotaxime and 200 mg/L kanamycin for selection of transgenic plants. After 2-3 weeks, transgenic callus that developed at the inoculation site were harvested and transferred to medium containing 600 mg/l cefotaxime and 200 mg/L kanamycin, and maintained at 24° C. for another 2 weeks for shoot development. Newly developed shoots were transferred to antibiotic-free medium for roots of whole plants (FIG. 11).

To confirm that the prenyltransferase gene was integrated into the plant genome, genomic DNA was isolated from transgenic lines using DNeasy Plant Mini Kit (QIAGEN). Primer pairs that targeted the outside of prenyltransferase gene on pBIB-Kan vectors were used for molecular characterization of transgenic lines. The transgenic plants transformed with empty pBIB-Kan vector showed an amplicon of 523 bp, while the AhR4DT-1 and AhR3'DT-1 transgenic lines gave amplicons of 2673 bp and 2619 bp, respectively. The AhR4DT-1 or AhR3'DT-1 activity in these transgenic lines was further confirmed via enzymatic assay (FIGS. 71C and 72C). In summary, five AhR4DT-1-expressing tobacco plants and nine AhR3'DT-1-expressing tobacco plants of N. tabacum were established (FIGS. 71 and 72).

Two hairy root lines, line 1 and line 2, were developed from the AhR3'DT-1-expressing tobacco plant #12 via Agrobacterium rhizogenes 15834 infection and the activity of the AhR3'DT-1 was detected from both of these transgenic hairy root lines (FIG. 73).

These results indicate that the peanut stilbenoid-specific transferases (AhR4DT-1 or AhR3'DT-1) were actively functional in the transgenic tobacco plants and hairy roots.

Statistical Analysis

Two-way ANOVA with multiple-comparisons tests was conducted for the data in FIG. 3. Analyses were done with GraphPad Prism 6, version 6.02 software.

LITERATURE CITED

References disclosing relevant information are disclosed below. These references are hereby expressly incorporated by reference in their entirety.

Abbott J A, Medina-Bolivar F, Martin E M, Engelberth A S, Villagarcia H, Clausen E C, Carrier D J (2010) Purification of resveratrol, arachidin-1, and arachidin-3 from hairy root cultures of peanut (*Arachis hypogaea*) and determination of their antioxidant activity and cytotoxicity. Biotechnol Prog 26: 1344-1351

Aguamah, G. E., Langcake, P., Leworthy, D. P., Page, J. A., Pryce, R. J., and Strange, R. N. (1981). Two novel stilbene phytoalexins from *Arachis hypogaea*. Phytochemistry 20: 1381-1383.

Ahuja I, Kissen R, Bones A M (2012) Phytoalexins in defense against pathogens. Trends Plant Sci 17: 73-90

Akashi T, Sasaki K, Aoki T, Ayabe S, Yazaki K (2008) Molecular cloning and characterization of a cDNA for pterocarpan 4-dimethylallyltransferase catalyzing the key prenylation step in the biosynthesis of glyceollin, a soybean phytoalexin. Plant Physiol 149: 683-693

Altschul, S. F., Gish, W., Miller, W., Myers, E. W., and Lipman, D. J. (1990). Basic local alignment search tool. J. Mol. Biol. 215: 403-10.

Anders, S., Pyl, P. T., and Huber, W. (2015). HTSeq-A Python framework to work with high-throughput sequencing data. Bioinformatics 31: 166-169.

Ball, J. M. et al. (2015). Investigation of stilbenoids as potential therapeutic agents for Rotavirus gastroenteritis. Adv. Virol. 2015: 1-10.

Banfi, D., Patiny, L. (2008). Resurrecting and processing NMR spectra on-line. *Chimia* 62: 280-281.

Bannai, H., Tamada, Y., Maruyama, O., Nakai, K., and Miyano, S. (2002). Extensive feature detection of N-terminal protein sorting signals. Bioinformatics 18: 298-305.

Baur, J. A. and Sinclair, D. A. (2006). Therapeutic potential of resveratrol: the in vivo evidence. Nat. Rev. Drug Discov. 5: 493-506.

Becker, D. (1990). Binary vectors which allow the exchange of plant selectable markers and reporter genes. Nucleic Acids Res. 18: 203.

Bertioli, D. J. et al. (2016). The genome sequences of *Arachis duranensis* and *Arachis ipaensis*, the diploid ancestors of cultivated peanut. Nat Genet 48: 438-446.

Bolger, A. M., Lohse, M., and Usadel, B. (2014). Trimmomatic: A flexible trimmer for Illumina sequence data. Bioinformatics 30: 2114-2120.

Boonlaksiri C, Oonanant W, Kongsaeree P, Kittakoop P, Tanticharoen M, Thebtaranonth Y (2000) An antimalarial stilbene from *Artocarpus integer*. Phytochemistry 54: 415-7

Botta B, Vitali A, Menendez P, Misiti D, Delle Monache G (2005) Prenylated flavonoids: pharmacology and biotechnology. Curr Med Chem 12: 717-739

Brents L K, Medina-Bolivar F, Seely K A, Nair V, Bratton S M, Ñopo-Olazabal L, Patel R Y, Liu H, Doerksen R J, Prather P L, et al (2012) Natural prenylated resveratrol analogs arachidin-1 and -3 demonstrate improved glucuronidation profiles and have affinity for cannabinoid receptors. Xenobiotica 42: 139-156

Castillo, A. M., Patiny, L., and Wist, J. (2011). Fast and accurate algorithm for the simulation of NMR spectra of large spin systems. J Magn Reson 209: 123-130.

Chang J-C, Lai Y-H, Djoko B, Wu P-L, Liu C-D, Liu Y-W, Chiou R Y-Y (2006) Biosynthesis enhancement and antioxidant and anti-inflammatory activities of peanut (*Arachis hypogaea* L.) arachidin-1, arachidin-3, and isopentadienylresveratrol. J Agric Food Chem 54: 10281-10287

Chen, R., Liu, X., Zou, J., Yin, Y., Ou, B., Li, J., Wang, R., Xie, D., Zhang, P., and Dai, J. (2013). Regio- and stereospecific prenylation of flavonoids by *Sophora flavescens* prenyltransferase. Adv. Synth. Catal. 355: 1817-1828.

Chong J, Poutaraud A, Hugueney P (2009) Metabolism and roles of stilbenes in plants. Plant Sci 177: 143-155

Condori, J., Nopo-Olazabal, C., Medrano, G., and Medina-Bolivar, F. (2011). Selection of reference genes for qPCR in hairy root cultures of peanut. BMC Res. Notes 4: 392.

Condori J, Sivakumar G, Hubstenberger J, Dolan M C, Sobolev V S, Medina-Bolivar F (2010) Induced biosynthesis of resveratrol and the prenylated stilbenoids arachidin-1 and arachidin-3 in hairy root cultures of peanut: Effects of culture medium and growth stage. Plant Physiol Biochem 48: 310-318

Cooksey, C., Garratt, P., and Richards, S. (1988). A dienyl stilbene phytoalexin from *Arachis hypogaea*. Phytochemistry 27: 1015-1016.

Das S, Das D K (2007) Anti-inflammatory responses of resveratrol. Inflamm Allergy Drug Targets 6: 168-73

Djoko B, Chiou R Y-Y, Shee J-J, Liu Y-W (2007) Characterization of immunological activities of peanut stilbenoids, arachidin-1, piceatannol, and resveratrol on lipopolysaccharide-induced inflammation of RAW 264.7 macrophages. J Agric Food Chem 55: 2376-2383

Edgar, R. C. (2004) MUSCLE: multiple sequence alignment with high accuracy and high throughput. Nucleic Acids Res 32: 1792-1797.

Emanuelsson, O., Nielsen, H., and von Heijne, G. (1999). ChloroP, a neural network-based method for predicting chloroplast transit peptides and their cleavage sites. Protein Sci. 8: 978-984.

Gambini J, Inglés M, Olaso G, Lopez-Grueso R, Bonet-Costa V, Gimeno-Mallench L, Mas-Bargues C, Abdelaziz K M, Gomez-Cabrera M C, Vina J, et al (2015) Properties of resveratrol: In vitro and In vivo studies about metabolism, bioavailability, and biological effects in animal models and humans. Oxid Med Cell Longev 2015: 837042

Guindon, S. and Gascuel, O. (2003) A simple, fast, and accurate algorithm to estimate large phylogenies by maximum likelihood. Syst Biol 52: 696-704.

Haas, B. J. et al. (2013). De novo transcript sequence reconstruction from RNA-seq using the Trinity platform for reference generation and analysis. Nat. Protoc. 8: 1494-1512.

Hakim E H, Ulinnuha U Z, Syah Y M, Ghisalberti E L (2002) Artoindonesianins N and O, new prenylated stilbene and prenylated arylbenzofuran derivatives from *Artocarpus gomezianus*. Fitoterapia 73: 597-603

Han M, Heppel S C, Su T, Bogs J, Zu Y, An Z, Rausch T (2013) Enzyme inhibitor studies reveal complex control of methyl-D-erythritol 4-phosphate (MEP) pathway enzyme expression in *Catharanthus roseus*. PLoS One 8: e62467

Hauser, M., Eichelmann, H., Oja, V., Heber, U., and Laisk, A. (1995). Stimulation by light of rapid pH regulation in the chloroplast stroma in vivo as indicated by $CO_2$ solubilization in leaves. Plant Physiol. 108:1059-1066.

Huang C-P, Au L-C, Chiou R Y-Y, Chung P-C, Chen S-Y, Tang W-C, Chang C-L, Fang W-H, Lin S-B (2010) Arachidin-1, a peanut stilbenoid, induces programmed cell death in human leukemia HL-60 cells. J Agric Food Chem 12123-12129

Huang, H., Levin, E. J., Liu, S., Bai, Y., Lockless, S. W., and Zhou, M. (2014). Structure of a membrane-embedded prenyltransferase homologous to UBIAD1. PLoS Biol. 12: e1001911.

Ioset J-R, Marston A, Gupta M P, Hostettmann K (2001) Five new prenylated stilbenes from the root bark of *Lonchocarpus chiricanus*. J Nat Prod 64: 710-715

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol. 14: R36.

Krogh, A., Larsson, B., von Heijne, G. and Sonnhammer, E. L. L. (2001) Predicting transmembrane protein topology with a hidden markov model: application to complete genomes. J Mol Biol 305: 567-580.

Li J, Chen R, Wang R, Liu X, Xie D, Zou J, Dai J (2014) GuA6DT, a regiospecific prenyltransferase from *Glycyrrhiza uralensis*, catalyzes the 6-prenylation of flavones. ChemBioChem 15: 1673-1681

Li, R., Yu, C., Li, Y., Lam, T. W., Yiu, S. M., Kristiansen, K., and Wang, J. (2009). SOAP2: An improved ultrafast tool for short read alignment. Bioinformatics 25: 1966-1967.

Li, H., Handsaker, B., Wysoker, A., Fennell, T., Ruan, J., Homer, N., Marth, G., Abecasis, G., Durbin, R. and 1000 Genome Project Data Processing Subgroup. (2009). The Sequence alignment/map (SAM) format and SAMtools. Bioinformatics 25: 2078-2079.

Li, W. and Godzik, A. (2006). Cd-hit: A fast program for clustering and comparing large sets of protein or nucleotide sequences. Bioinformatics 22: 1658-1659.

Lohr M, Schwender J, Polle J E (2012) Isoprenoid biosynthesis in eukaryotic phototrophs: A spotlight on algae. Plant Sci 185-186: 9-22

Marsh Z, Yang T, Nopo-Olazabal L, Wu S, Ingle T, Joshee N, Medina-Bolivar F (2014) Effect of light, methyl jasmonate and cyclodextrin on production of phenolic compounds in hairy root cultures of *Scutellaria lateriflora*. Phytochemistry 107: 50-60

Medina-Bolivar F, Condori J, Rimando A M, Hubstenberger J, Shelton K, O'Keefe S F, Bennett S, Dolan M C (2007) Production and secretion of resveratrol in hairy root cultures of peanut. Phytochemistry 68: 1992-2003

Medina-Bolivar, F. and Cramer, C. (2004). Production of recombinant proteins by hairy roots cultured in plastic sleeve bioreactors. Methods Mol. Biol. 267: 351-63.

Medrano, G., Reidy, M. J., Liu, J., Ayala, J., Dolan, M. C., and Cramer, C. L. (2009). Rapid system for evaluating bioproduction capacity of complex pharmaceutical proteins in plants. Methods Mol. Biol. 483: 51-67.

Mortazavi, A., Williams, B. A., McCue, K., Schaeffer, L., and Wold, B. (2008). Mapping and quantifying mammalian transcriptomes by RNA-Seq. Nat. Methods 5: 621-628.

Nelson, B. K., Cai, X., and Nebenführ, A. (2007). A multicolored set of in vivo organelle markers for co-localization studies in *Arabidopsis* and other plants. Plant J. 51: 1126-1136.

Park B H, Lee H J, Lee Y R (2011) Total Synthesis of chiricanine A, arahypin-1, trans-arachidin-2, trans-arachidin-3, and arahypin-5 from peanut seeds. J Nat Prod 74: 644-649

Robertson, G. et al. (2010). De novo assembly and analysis of RNA-seq data. Nat. Methods 7: 909-12.

Sasaki, K., Mito, K., Ohara, K., Yamamoto, H., and Yazaki, K. (2008). Cloning and characterization of naringenin 8-prenyltransferase, a flavonoid-specific prenyltransferase of *Sophora flavescens*. Plant Physiol. 146: 1075-1084.

Sasaki K, Tsurumaru Y, Yamamoto H, Yazaki K (2011) Molecular characterization of a membrane-bound prenyltransferase specific for isoflavone from *Sophora flavescens*. J Biol Chem 286: 24125-24134

Schöppner A, Kindl H (1984) Purification and properties of a stilbene synthase from induced cell suspension cultures of peanut. J Biol Chem 259: 6806-6811

Schulz, M. H., Zerbino, D. R., Vingron, M., and Birney, E. (2012). Oases: Robust de novo RNA-seq assembly across the dynamic range of expression levels. Bioinformatics 28: 1086-1092.

Shen G, Huhman D, Lei Z, Snyder J, Sumner L W, Dixon R A (2012) Characterization of an Isoflavonoid-specific prenyltransferase from *Lupinus albus*. Plant Physiol 159: 70-80

Sobolev V S (2008) Localized production of phytoalexins by peanut (*Arachis hypogaea*) kernels in response to invasion by *Aspergillus* species. J Agric Food Chem 56: 1949-1954

Sobolev V S (2013) Production of phytoalexins in peanut (*Arachis hypogaea*) seed elicited by selected microorganisms. J Agric Food Chem 61: 1850-1858

Sobolev V S, Khan S I, Tabanca N, Wedge D E, Manly S P, Cutler S J, Coy M R, Becnel J J, Neff S A, Gloer J B (2011) Biological activity of peanut (*Arachis hypogaea*) phytoalexins and selected natural and synthetic stilbenoids. J Agric Food Chem 59: 1673-1682

Sobolev V S, Krausert N M, Gloer J B (2016) New monomeric stilbenoids from peanut (*Arachis hypogaea*) seeds challenged by an *Aspergillus flavus* strain. doi: 10.1021/acs.jafc.5b04753

Sobolev, V. S., Krausert, N. M., and Gloer, J. B. (2016). New monomeric stilbenoids from peanut (*Arachis hypogaea*) seeds challenged by an *Aspergillus flavus* strain. J. Agric. Food Chem. 64: 579-584.

Sobolev, V. S., Neff, S. A., and Gloer, J. B. (2010). New dimeric stilbenoids from fungal-Challenged peanut (*Arachis hypogaea*) seeds. J. Agric. Food Chem. 58: 875-881.

Sobolev V S, Neff S A, Gloer J B (2009) New stilbenoids from peanut (*Arachis hypogaea*) seeds challenged by an *Aspergillus caelatus* strain. J Agric Food Chem 57: 62-68

Sobolev V S, Potter T L, Horn B W (2006) Prenylated stilbenes from peanut root mucilage. Phytochem Anal 17: 312-322

Su B-N, Cuendet M, Hawthorne M E, Kardono L B S, Riswan S, Fong H H S, Mehta R G, Pezzuto J M, Kinghorn A D (2002) Constituents of the bark and twigs of *Artocarpus dadah* with cyclooxygenase inhibitory activity. J Nat Prod 65: 163-169

Tanaka, Y. and Brugliera, F. (2013). Flower colour and cytochromes P450. Philos. Trans. R. Soc. B Biol. Sci. 368: 20120432-20120432.

Tomé-Carneiro J, Larrosa M, González-Sarrias A, Tomás-Barberán F A, García-Conesa M T, Espín J C (2013) Resveratrol and clinical trials: the crossroad from in vitro studies to human evidence. Curr Pharm Des 19: 6064-6093

Tropf S, Lanz T, Rensing S A, Schröder J, Schröder G (1994) Evidence that stilbene synthases have developed from chalcone synthases several times in the course of evolution. J Mol Evol 38: 610-618

Van Der Kaaden J E, Hemscheidt T K, Mooberry S L (2001) Mappain, a new cytotoxic prenylated stilbene from *Macaranga mappa*. J Nat Prod 64: 103-105

Wang, R., Chen, R., Li, J., Liu, X., Xie, K., Chen, D., Yin, Y., Tao, X., Xie, D., Zou, J., Yang, L., and Dai, J. (2014). Molecular characterization and phylogenetic analysis of two novel regio-specific flavonoid prenyltransferases from *Morus alba* and *Cudrania tricuspidata*. J. Biol. Chem. 289: 35815-35825.

Watts K, Lee P, Schmidt-Dannert C (2006) Biosynthesis of plant-specific stilbene polyketides in metabolically engineered *Escherichia coli*. BMC Biotechnol 6: 22

Wu, T. D. and Watanabe, C. K. (2005). GMAP: A genomic mapping and alignment program for mRNA and EST sequences. Bioinformatics 21: 1859-1875.

Wu Z, Song L, Huang D (2011) Food grade fungal stress on germinating peanut seeds induced phytoalexins and enhanced polyphenolic antioxidants. J Agric Food Chem 59: 5993-6003

Yamamoto H, Senda M, Inoue K (2000) Flavanone 8-dimethylallyltransferase in *Sophora flavescens* cell suspension cultures. Phytochemistry 54: 649-655

Yang T, Fang L, Nopo-Olazabal C, Condori J, Nopo-Olazabal L, Balmaceda C, Medina-Bolivar F (2015a) Enhanced production of resveratrol, piceatannol, arachidin-1, and arachidin-3 in hairy root cultures of peanut co-treated with methyl jasmonate and cyclodextrin. J Agric Food Chem 63: 3942-3950

Yang, T., Fang, L., Rimando, A. M. A. M., Sobolev, V., Mockaitis, K., and Medina-Bolivar, F. (2016). A stilbenoid-specific prenyltransferase utilizes dimethylallyl pyrophosphate from the plastidic terpenoid pathway. Plant Physiol. 171: 2483-98.

Yang X, Jiang Y, Yang J, He J, Sun J, Chen F, Zhang M, Yang B (2015b) Prenylated flavonoids, promising nutraceuticals with impressive biological activities. Trends Food Sci Technol 44: 93-104

Yazaki K, Sasaki K, Tsurumaru Y (2009) Prenylation of aromatic compounds, a key diversification of plant secondary metabolites. Phytochemistry 70: 1739-1745

Yoder B J, Cao S, Norris A, Miller J S, Ratovoson F, Razafitsalama J, Andriantsiferana R, Rasamison V E, Kingston D G I (2007) Antiproliferative prenylated stilbenes and flavonoids from *Macaranga alnifolia* from the Madagascar rainforest. J Nat Prod 70: 342-346

Zhao S, Wang L, Liu L, Liang Y, Sun Y, Wu J (2014) Both the mevalonate and the non-mevalonate pathways are involved in ginsenoside biosynthesis. Plant Cell Rep 33: 393-400

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A method of producing a prenylated stilbenoid in a transgenic organism, cell or tissue, the method comprising:
   generating the transgenic organism, cell, or tissue comprising a transgene encoding a polypeptide comprising an amino acid sequence comprising the sequence as set forth in SEQ ID NO: 14 having stilbenoid prenyltransferase activity;
   wherein the transgenic organism, cell, or tissue is transgenic for the nucleic acid molecule comprising a sequence that encodes the polypeptide having prenyltransferase activity;
   adding a dimethylallyl pyrophosphate to the C-3' position of a stilbenoid as the prenyltransferase activity to produce the prenylated stilbenoid in the transgenic organism, cell, or tissue.

2. The method of claim 1 wherein the stilbenoid is resveratrol.

3. A method of producing a prenylated stilbenoid in a transgenic organism, cell or tissue, the method comprising:
   cultivating or culturing the transgenic organism, cell or tissue;
   wherein the transgenic organism, cell, or tissue is transgenic for a nucleic acid molecule comprising the sequence as set forth in SEQ ID NO: 15,
   wherein a dimethylallyl pyrophosphate is added to the C-3' position of a stilbenoid as prenyltransferase activity to produce the prenylated stilbenoid in the transgenic organism, cell, or tissue.

4. A method for expressing a nucleic acid molecule that encodes a polypeptide having stilbenoid prenyltransferase activity in a transgenic organism, cell or tissue, the method comprising:
   generating a transgenic organism, cell, or tissue comprising a transgene comprising a nucleic acid molecule comprising the sequence as set forth in SEQ ID NO: 15 that encodes a polypeptide having stilbenoid prenyltransferase activity, and expressing the nucleic acid molecule.

5. The method of claim 4, wherein the tissue is hairy root.

6. The method of claim 4, wherein the organism is grape.

7. The method of claim 4, wherein the organism is yeast.

8. The method of claim 4, wherein the organism is capable of making resveratrol.

9. A method for expressing a polypeptide having stilbenoid prenyltransferase activity in a transgenic organism, cell or tissue, the method comprising:
   generating a transgenic organism, cell, or tissue comprising a transgene encoding a polypeptide comprising an amino acid sequence comprising the sequence as set forth in SEQ ID NO: 14 having stilbenoid prenyltransferase activity, and expressing the polypeptide.

10. The method of claim 9, wherein the tissue is hairy root.

11. The method of claim 9, wherein the organism is grape.

12. The method of claim 9, wherein the organism is yeast.

13. The method of claim 9, wherein the organism is capable of making resveratrol.

14. A method of producing a prenylated stilbenoid in a transgenic organism, cell or tissue, the method comprising:
   generating a transgenic organism, cell, or tissue comprising a transgene comprising a nucleic acid molecule comprising the sequence as set forth in SEQ ID NO: 15;
   adding a dimethylallyl pyrophosphate to the C-3' position of a stilbenoid as the prenyltransferase activity to produce the prenylated stilbenoid in the transgenic organism, cell, or tissue.

15. The method of claim 14, wherein the stilbenoid is resveratrol.

16. The method of claim 14, wherein the tissue is hairy root.

17. The method of claim 14, wherein the organism is grape.

18. The method of claim 14, wherein the organism is yeast.

19. The method of claim 14, wherein the organism is capable of making resveratrol.

20. The method of claim 3, wherein the stilbenoid is resveratrol.

* * * * *

SEQUENCE LISTING

```
<160> NUMBER OF SEQ ID NOS: 51

<210> SEQ ID NO 1
<211> LENGTH: 1245
<212> TYPE: DNA
<213> ORGANISM: Arachis hypogaea
<220> FEATURE:
<221> NAME/KEY: CDS
<222> LOCATION: (1)..(1245)
<223> OTHER INFORMATION: resveratrol 4-dimethylallyltransferase
      (AhR4DT-1)

<400> SEQUENCE: 1 atg gct ttt ggg cat ttg gtg tta att ccc aga tca act tct tcc att      48
Met Ala Phe Gly His Leu Val Leu Ile Pro Arg Ser Thr Ser Ser Ile
1               5                   10                  15 gcc act act gct gca agc tgc tgg aag agt aaa aaa ttc gcc gac aat      96
Ala Thr Thr Ala Ala Ser Cys Trp Lys Ser Lys Lys Phe Ala Asp Asn
                20                  25                  30 tac tat gca aat tct tat gga aga aga gct tta tgg cag agt gat agg     144
Tyr Tyr Ala Asn Ser Tyr Gly Arg Arg Ala Leu Trp Gln Ser Asp Arg
            35                  40                  45 aat ctc aca aaa gat cac agc atc aag aca tct ttg cag cac aac att     192
Asn Leu Thr Lys Asp His Ser Ile Lys Thr Ser Leu Gln His Asn Ile
        50                  55                  60 tca aag ctt cat tac aat ccc att gaa aga gga tct aga tgc aat aaa     240
Ser Lys Leu His Tyr Asn Pro Ile Glu Arg Gly Ser Arg Cys Asn Lys
65                  70                  75                  80 att gag aaa aca tac tta aca aat gca tca tct tct gca caa tca cat     288
Ile Glu Lys Thr Tyr Leu Thr Asn Ala Ser Ser Ser Ala Gln Ser His
                85                  90                  95 gaa tct gaa cca gaa gtg cat gaa tca cca aaa gct tta gag tct att     336
Glu Ser Glu Pro Glu Val His Glu Ser Pro Lys Ala Leu Glu Ser Ile
                100                 105                 110 aaa aag gga ctc gtt atg ttt ctc caa ttt tgc aga ctt tat gca ttc     384
Lys Lys Gly Leu Val Met Phe Leu Gln Phe Cys Arg Leu Tyr Ala Phe
            115                 120                 125
```

-continued

| | | |
|---|---|---|
| ctt ggc atg ata cca gca gga ctt tct tca tca ctt ctt gcc gta gat<br>Leu Gly Met Ile Pro Ala Gly Leu Ser Ser Ser Leu Leu Ala Val Asp<br>130                          135                          140 | | 432 |
| aat ttt tca gaa ata tct cca tta tta ttt tta aaa gga gtc ttg cag<br>Asn Phe Ser Glu Ile Ser Pro Leu Leu Phe Leu Lys Gly Val Leu Gln<br>145                          150                          155                          160 | | 480 |
| tat ata gta act ttc ttc ttc acg tct caa ttt gtt atg gga gtg aat<br>Tyr Ile Val Thr Phe Phe Phe Thr Ser Gln Phe Val Met Gly Val Asn<br>                         165                          170                          175 | | 528 |
| caa tta tcc gat gtg gaa ata gac aag att aat aag cca gat ctt cct<br>Gln Leu Ser Asp Val Glu Ile Asp Lys Ile Asn Lys Pro Asp Leu Pro<br>                         180                          185                          190 | | 576 |
| ttg gca tcc gga gaa tat tcc ttc act tct gga gtt ata ctt gtg aca<br>Leu Ala Ser Gly Glu Tyr Ser Phe Thr Ser Gly Val Ile Leu Val Thr<br>                         195                          200                          205 | | 624 |
| tcg ttt tta ctt gcg ggt ttt gga gtt gca tgg atg tta gga tca caa<br>Ser Phe Leu Leu Ala Gly Phe Gly Val Ala Trp Met Leu Gly Ser Gln<br>        210                          215                          220 | | 672 |
| cca tta att tgg agt gtt gtt gtt act gct gcg cta atg gga gca tat<br>Pro Leu Ile Trp Ser Val Val Val Thr Ala Ala Leu Met Gly Ala Tyr<br>225                          230                          235                          240 | | 720 |
| tca gtt aat ttc cct tta tta aga tgg aag aga tct ata atc ctc aca<br>Ser Val Asn Phe Pro Leu Leu Arg Trp Lys Arg Ser Ile Ile Leu Thr<br>                         245                          250                          255 | | 768 |
| tca cta tct aat gca att gct atg ttg gca tca ttt cat ata gga cct<br>Ser Leu Ser Asn Ala Ile Ala Met Leu Ala Ser Phe His Ile Gly Pro<br>                         260                          265                          270 | | 816 |
| ttt ctt cac atg aag acc ttt gtg cta aaa aag gca gct acc ttt cca<br>Phe Leu His Met Lys Thr Phe Val Leu Lys Lys Ala Ala Thr Phe Pro<br>        275                          280                          285 | | 864 |
| aga tct atg att ctt ggt tgt gtg gtc ata ggt ttg ttc tac aca ata<br>Arg Ser Met Ile Leu Gly Cys Val Val Ile Gly Leu Phe Tyr Thr Ile<br>                         290                          295                          300 | | 912 |
| ata aca tta aca aag gat tta ggg gat gtt gaa gga gac aaa gca gca<br>Ile Thr Leu Thr Lys Asp Leu Gly Asp Val Glu Gly Asp Lys Ala Ala<br>305                          310                          315                          320 | | 960 |
| ggt ttg aaa act ttg cca ata cgc ttg ggt gtt aag ccg gta ttt tgg<br>Gly Leu Lys Thr Leu Pro Ile Arg Leu Gly Val Lys Pro Val Phe Trp<br>                         325                          330                          335 | | 1008 |
| tta tgt gta tca ctt att caa atg gct tat gga att gct att aca atg<br>Leu Cys Val Ser Leu Ile Gln Met Ala Tyr Gly Ile Ala Ile Thr Met<br>                         340                          345                          350 | | 1056 |
| gga gca tta tct cct gtt cta tgg agc aaa att gtt acg gtt gtg gca<br>Gly Ala Leu Ser Pro Val Leu Trp Ser Lys Ile Val Thr Val Val Ala<br>                         355                          360                          365 | | 1104 |
| cat gcc ttc atg gtt ttc tac gtg tgg aac cat gct ctt aat tca gta<br>His Ala Phe Met Val Phe Tyr Val Trp Asn His Ala Leu Asn Ser Val<br>        370                          375                          380 | | 1152 |
| gac tta tca agc aaa gat tcg tta cat tcc ttt cat ttg ttt atg ttt<br>Asp Leu Ser Ser Lys Asp Ser Leu His Ser Phe His Leu Phe Met Phe<br>385                          390                          395                          400 | | 1200 |
| aag ctt gta act gtg gaa ggc atc ctt ata caa ttt gtt cgt tga<br>Lys Leu Val Thr Val Glu Gly Ile Leu Ile Gln Phe Val Arg<br>                         405                          410 | | 1245 |

<210> SEQ ID NO 2
<211> LENGTH: 414
<212> TYPE: PRT
<213> ORGANISM: Arachis hypogaea

<400> SEQUENCE: 2

```
Met Ala Phe Gly His Leu Val Leu Ile Pro Arg Ser Thr Ser Ser Ile
1               5                   10                  15

Ala Thr Thr Ala Ala Ser Cys Trp Lys Ser Lys Lys Phe Ala Asp Asn
            20                  25                  30

Tyr Tyr Ala Asn Ser Tyr Gly Arg Arg Ala Leu Trp Gln Ser Asp Arg
        35                  40                  45

Asn Leu Thr Lys Asp His Ser Ile Lys Thr Ser Leu Gln His Asn Ile
    50                  55                  60

Ser Lys Leu His Tyr Asn Pro Ile Glu Arg Gly Ser Arg Cys Asn Lys
65                  70                  75                  80

Ile Glu Lys Thr Tyr Leu Thr Asn Ala Ser Ser Ala Gln Ser His
                85                  90                  95

Glu Ser Glu Pro Glu Val His Glu Ser Pro Lys Ala Leu Glu Ser Ile
                100                 105                 110

Lys Lys Gly Leu Val Met Phe Leu Gln Phe Cys Arg Leu Tyr Ala Phe
            115                 120                 125

Leu Gly Met Ile Pro Ala Gly Leu Ser Ser Ser Leu Leu Ala Val Asp
        130                 135                 140

Asn Phe Ser Glu Ile Ser Pro Leu Leu Phe Leu Lys Gly Val Leu Gln
145                 150                 155                 160

Tyr Ile Val Thr Phe Phe Phe Thr Ser Gln Phe Val Met Gly Val Asn
                165                 170                 175

Gln Leu Ser Asp Val Glu Ile Asp Lys Ile Asn Lys Pro Asp Leu Pro
            180                 185                 190

Leu Ala Ser Gly Glu Tyr Ser Phe Thr Ser Gly Val Ile Leu Val Thr
        195                 200                 205

Ser Phe Leu Leu Ala Gly Phe Gly Val Ala Trp Met Leu Gly Ser Gln
210                 215                 220

Pro Leu Ile Trp Ser Val Val Thr Ala Ala Leu Met Gly Ala Tyr
225                 230                 235                 240

Ser Val Asn Phe Pro Leu Leu Arg Trp Lys Arg Ser Ile Ile Leu Thr
                245                 250                 255

Ser Leu Ser Asn Ala Ile Ala Met Leu Ala Ser Phe His Ile Gly Pro
            260                 265                 270

Phe Leu His Met Lys Thr Phe Val Leu Lys Lys Ala Ala Thr Phe Pro
        275                 280                 285

Arg Ser Met Ile Leu Gly Cys Val Val Ile Gly Leu Phe Tyr Thr Ile
290                 295                 300

Ile Thr Leu Thr Lys Asp Leu Gly Asp Val Glu Gly Asp Lys Ala Ala
305                 310                 315                 320

Gly Leu Lys Thr Leu Pro Ile Arg Leu Gly Val Lys Pro Val Phe Trp
                325                 330                 335

Leu Cys Val Ser Leu Ile Gln Met Ala Tyr Gly Ile Ala Ile Thr Met
            340                 345                 350

Gly Ala Leu Ser Pro Val Leu Trp Ser Lys Ile Val Thr Val Val Ala
        355                 360                 365

His Ala Phe Met Val Phe Tyr Val Trp Asn His Ala Leu Asn Ser Val
    370                 375                 380

Asp Leu Ser Ser Lys Asp Ser Leu His Ser Phe His Leu Phe Met Phe
385                 390                 395                 400

Lys Leu Val Thr Val Glu Gly Ile Leu Ile Gln Phe Val Arg
                405                 410
```

<210> SEQ ID NO 3
<211> LENGTH: 1245
<212> TYPE: DNA
<213> ORGANISM: Arachis hypogaea

<400> SEQUENCE: 3

```
atggcttttg gcatttggt gttaattccc agatcaactt cttccattgc cactactgct      60
gcaagctgct ggaagagtaa aaaattcgcc gacaattact atgcaaattc ttatggaaga    120
agagctttat ggcagagtga taggaatctc acaaaagatc acagcatcaa gacatctttg    180
cagcacaaca tttcaaagct tcattacaat cccattgaaa aggatctag atgcaataaa     240 attgagaaaa catacttaac aaatgcatca tcttctgcac aatcacatga atctgaacca    300
gaagtgcatg aatcaccaaa agctttagag tctattaaaa agggactcgt tatgtttctc    360
caattttgca gactttatgc attccttggc atgataccag caggactttc ttcatcactt    420
cttgccgtag ataattttc agaaatatct ccattattat ttttaaaagg agtcttgcag    480
tatatagtaa ctttcttctt cacgtctcaa tttgttatgg gagtgaatca attatccgat    540
gtggaaatag acaagattaa taagccagat cttcctttgg catccggaga atattccttc    600
acttctggag ttatacttgt gacatcgttt ttacttgcgg ttttggagt tgcatggatg    660 ttaggatcac aaccattaat ttggagtgtt gttgttactg ctgcgctaat gggagcatat    720
tcagttaatt tcccttatt aagatggaag agatctataa tcctcacatc actatctaat    780
gcaattgcta tgttggcatc atttcatata ggaccttttc ttcacatgaa gacctttgtg    840
ctaaaaaagg cagctaccct tccaagatct atgattcttg ttgtgtggt cataggtttg    900 ttctacacaa taataacatt aacaaaggat ttagggatg ttgaaggaga caaagcagca    960
ggtttgaaaa ctttgccaat acgcttgggt gttaagccgg tattttggtt atgtgtatca   1020
cttattcaaa tggcttatgg aattgctatt acaatgggag cattatctcc tgttctatgg   1080
agcaaaattg ttacggttgt ggcacatgcc ttcatggttt tctacgtgtg gaaccatgct   1140
cttaattcag tagacttatc aagcaaagat tcgttacatt cctttcattt gtttatgttt   1200
aagcttgtaa ctgtggaagg catccttata caatttgttc gttga                   1245
```

<210> SEQ ID NO 4
<211> LENGTH: 1170
<212> TYPE: DNA
<213> ORGANISM: Arachis hypogaea
<220> FEATURE:
<221> NAME/KEY: CDS
<222> LOCATION: (1)..(1170)
<223> OTHER INFORMATION: resveratrol 3'-dimethylallyltransferase
      (AhR3'DT-2)

<400> SEQUENCE: 4

```
atg cct ttc gga ctc tcc gcc tca ttt ctc aaa tct cgc tcc ttc cac        48
Met Pro Phe Gly Leu Ser Ala Ser Phe Leu Lys Ser Arg Ser Phe His
1               5                   10                  15 cac cac ggt aca aga aga gcc tta tgg aac aac aat ggg aaa cta tca        96
His His Gly Thr Arg Arg Ala Leu Trp Asn Asn Asn Gly Lys Leu Ser
                20                  25                  30 aaa gaa tat tgt atc aag atg cag cat aat tat tgg aag aat cat tgc       144
Lys Glu Tyr Cys Ile Lys Met Gln His Asn Tyr Trp Lys Asn His Cys
            35                  40                  45 acc aac ctt aaa gga gga tct atg atg agt gat gat aaa ttt gag aaa       192
Thr Asn Leu Lys Gly Gly Ser Met Met Ser Asp Asp Lys Phe Glu Lys
        50                  55                  60
```

-continued

| | |
|---|---|
| aaa tac ttg gtg aat gca acc tca aaa aat tca cat gat gaa cca aaa<br>Lys Tyr Leu Val Asn Ala Thr Ser Lys Asn Ser His Asp Glu Pro Lys<br>65                    70                    75                    80 | 240 |
| aaa tca caa cct att ttg gag ttt atc aaa gat ggc atg gat act ttt<br>Lys Ser Gln Pro Ile Leu Glu Phe Ile Lys Asp Gly Met Asp Thr Phe<br>                    85                    90                    95 | 288 |
| cgc cag ttt tcc aga tta tac gca ttc ttt agc ttc ata tca agt gga<br>Arg Gln Phe Ser Arg Leu Tyr Ala Phe Phe Ser Phe Ile Ser Ser Gly<br>          100                    105                  110 | 336 |
| ctt tct tca tca ctc ctt gcg gtg gac aat tta tca aat ata tct cca<br>Leu Ser Ser Ser Leu Leu Ala Val Asp Asn Leu Ser Asn Ile Ser Pro<br>          115                    120                  125 | 384 |
| aaa atg ttc tta ata ggc ttc ttg cag ttt ctg ata cct aac tgc atc<br>Lys Met Phe Leu Ile Gly Phe Leu Gln Phe Leu Ile Pro Asn Cys Ile<br>130                    135                    140 | 432 |
| atg ttt caa tat att gtt ggt gtg aat caa tta gcc gat att gaa ata<br>Met Phe Gln Tyr Ile Val Gly Val Asn Gln Leu Ala Asp Ile Glu Ile<br>145                    150                    155                    160 | 480 |
| gac aag att aac aaa cca tat ctt cca ttg gca tcc ggg aaa tat tcc<br>Asp Lys Ile Asn Lys Pro Tyr Leu Pro Leu Ala Ser Gly Lys Tyr Ser<br>                    165                    170                  175 | 528 |
| tta aga aat gca ata ata att gtc gca tca tct ctt cta atg ggc ttt<br>Leu Arg Asn Ala Ile Ile Ile Val Ala Ser Ser Leu Leu Met Gly Phe<br>          180                    185                  190 | 576 |
| gga tct gcg tgg gtg tta gga tca agg cca atg ttt tgg tgt tta gtc<br>Gly Ser Ala Trp Val Leu Gly Ser Arg Pro Met Phe Trp Cys Leu Val<br>          195                    200                  205 | 624 |
| atc agt act atg ctc atg act gct tat tca gtt aat ttg ccc ttg ttg<br>Ile Ser Thr Met Leu Met Thr Ala Tyr Ser Val Asn Leu Pro Leu Leu<br>210                    215                    220 | 672 |
| aga tgg aaa aga tcc aca atc ctt gca aca tta tct ctt gca agt tct<br>Arg Trp Lys Arg Ser Thr Ile Leu Ala Thr Leu Ser Leu Ala Ser Ser<br>225                    230                    235                    240 | 720 |
| atg aca att gga caa cat att gca cca ttt ctt cac atg aag act gtg<br>Met Thr Ile Gly Gln His Ile Ala Pro Phe Leu His Met Lys Thr Val<br>                    245                    250                  255 | 768 |
| ctc aag aag gca ctt aac tat ccg aga tca cta gtt ttt act gtt gtg<br>Leu Lys Lys Ala Leu Asn Tyr Pro Arg Ser Leu Val Phe Thr Val Val<br>          260                    265                  270 | 816 |
| gtc gtc agc ctt ttc tat aca gtt ata tcc ttg gca aag gat ata cct<br>Val Val Ser Leu Phe Tyr Thr Val Ile Ser Leu Ala Lys Asp Ile Pro<br>          275                    280                  285 | 864 |
| gac att gaa gga gat aaa gca gca ggt cac aaa acc ttg gca ata cat<br>Asp Ile Glu Gly Asp Lys Ala Ala Gly His Lys Thr Leu Ala Ile His<br>290                    295                    300 | 912 |
| ttg ggt cct aga cga gta ttt tgg ttt tgc att tcg ctc ctt caa atg<br>Leu Gly Pro Arg Arg Val Phe Trp Phe Cys Ile Ser Leu Leu Gln Met<br>305                    310                    315                    320 | 960 |
| aca tat gga att gct att ata atg gga gca tta tct cct atc cta tgg<br>Thr Tyr Gly Ile Ala Ile Ile Met Gly Ala Leu Ser Pro Ile Leu Trp<br>                    325                    330                  335 | 1008 |
| agc aaa att ttt acg gtt gtg aca cat ttc atc atg tcc ata atc ctt<br>Ser Lys Ile Phe Thr Val Val Thr His Phe Ile Met Ser Ile Ile Leu<br>          340                    345                  350 | 1056 |
| tgg tat cgt gca aat tcc gta gat tta tcg aac aat gat tcg tta caa<br>Trp Tyr Arg Ala Asn Ser Val Asp Leu Ser Asn Asn Asp Ser Leu Gln<br>          355                    360                  365 | 1104 |

```
tcc ttt tat atg gct atc ttt gtg ttt ctt tct gtg gaa aac ttc ctt      1152
Ser Phe Tyr Met Ala Ile Phe Val Phe Leu Ser Val Glu Asn Phe Leu
370                 375                 380 gta ctt ttt gtt cga tga                                              1170
Val Leu Phe Val Arg
385
```

<210> SEQ ID NO 5
<211> LENGTH: 389
<212> TYPE: PRT
<213> ORGANISM: Arachis hypogaea

<400> SEQUENCE: 5

```
Met Pro Phe Gly Leu Ser Ala Ser Phe Leu Lys Ser Arg Ser Phe His
1               5                   10                  15

His His Gly Thr Arg Arg Ala Leu Trp Asn Asn Asn Gly Lys Leu Ser
            20                  25                  30

Lys Glu Tyr Cys Ile Lys Met Gln His Asn Tyr Trp Lys Asn His Cys
        35                  40                  45

Thr Asn Leu Lys Gly Gly Ser Met Met Ser Asp Asp Lys Phe Glu Lys
    50                  55                  60

Lys Tyr Leu Val Asn Ala Thr Ser Lys Asn Ser His Asp Glu Pro Lys
65                  70                  75                  80

Lys Ser Gln Pro Ile Leu Glu Phe Ile Lys Asp Gly Met Asp Thr Phe
                85                  90                  95

Arg Gln Phe Ser Arg Leu Tyr Ala Phe Phe Ser Phe Ile Ser Ser Gly
            100                 105                 110

Leu Ser Ser Ser Leu Leu Ala Val Asp Asn Leu Ser Asn Ile Ser Pro
        115                 120                 125

Lys Met Phe Leu Ile Gly Phe Leu Gln Phe Leu Ile Pro Asn Cys Ile
    130                 135                 140

Met Phe Gln Tyr Ile Val Gly Val Asn Gln Leu Ala Asp Ile Glu Ile
145                 150                 155                 160

Asp Lys Ile Asn Lys Pro Tyr Leu Pro Leu Ala Ser Gly Lys Tyr Ser
                165                 170                 175

Leu Arg Asn Ala Ile Ile Val Ala Ser Ser Leu Leu Met Gly Phe
            180                 185                 190

Gly Ser Ala Trp Val Leu Gly Ser Arg Pro Met Phe Trp Cys Leu Val
        195                 200                 205

Ile Ser Thr Met Leu Met Thr Ala Tyr Ser Val Asn Leu Pro Leu Leu
    210                 215                 220

Arg Trp Lys Arg Ser Thr Ile Leu Ala Thr Leu Ser Leu Ala Ser Ser
225                 230                 235                 240

Met Thr Ile Gly Gln His Ile Ala Pro Phe Leu His Met Lys Thr Val
                245                 250                 255

Leu Lys Lys Ala Leu Asn Tyr Pro Arg Ser Leu Val Phe Thr Val Val
            260                 265                 270

Val Val Ser Leu Phe Tyr Thr Val Ile Ser Leu Ala Lys Asp Ile Pro
        275                 280                 285

Asp Ile Glu Gly Asp Lys Ala Ala Gly His Lys Thr Leu Ala Ile His
    290                 295                 300

Leu Gly Pro Arg Arg Val Phe Trp Phe Cys Ile Ser Leu Leu Gln Met
305                 310                 315                 320

Thr Tyr Gly Ile Ala Ile Met Gly Ala Leu Ser Pro Ile Leu Trp
                325                 330                 335
```

Ser Lys Ile Phe Thr Val Val Thr His Phe Ile Met Ser Ile Ile Leu
              340                 345                 350

Trp Tyr Arg Ala Asn Ser Val Asp Leu Ser Asn Asn Asp Ser Leu Gln
              355                 360                 365

Ser Phe Tyr Met Ala Ile Phe Val Phe Leu Ser Val Glu Asn Phe Leu
              370                 375                 380

Val Leu Phe Val Arg
385

<210> SEQ ID NO 6
<211> LENGTH: 1170
<212> TYPE: DNA
<213> ORGANISM: Arachis hypogaea

<400> SEQUENCE: 6

```
atgcctttcg gactctccgc ctcatttctc aaatctcgct ccttccacca ccacggtaca      60
agaagagcct atggaacaa caatgggaaa ctatcaaaag aatattgtat caagatgcag     120
cataattatt ggaagaatca ttgcaccaac cttaaaggag gatctatgat gagtgatgat     180
aaatttgaga aaaatactt ggtgaatgca acctcaaaaa attcacatga tgaaccaaaa     240
aaatcacaac ctattttgga gtttatcaaa gatggcatgg atacttttcg ccagttttcc     300
agattatacg cattctttag cttcatatca agtggacttt cttcatcact ccttgcggtg     360
gacaatttat caaatatatc tccaaaaatg ttcttaatag gcttcttgca gtttctgata     420
cctaactgca tcatgtttca atatattgtt ggtgtgaatc aattagccga tattgaaata     480
gacaagatta caaaaccata tcttccattg gcatccggga atattccttt aagaaatgca     540
ataataattg tcgcatcatc tcttctaatg ggctttggat ctgcgtgggt gttaggatca     600
aggccaatgt tttggtgttt agtcatcagt actatgctca tgactgctta ttcagttaat     660
ttgcccttgt tgagatggaa aagatccaca atccttgcaa cattatctct tgcaagttct     720
atgacaattg gacaacatat tgcaccattt cttcacatga agactgtgct caagaaggca     780
cttaactatc cgagatcact agttttttact gttgtggtcg tcagccttttt ctatacagtt     840
atatccttgg caaaggatat acctgacatt gaaggagata agcagcagg tcacaaaacc     900
ttggcaatac atttgggtcc tagacgagta ttttggtttt gcatttcgct ccttcaaatg     960
acatatggaa ttgctattat aatgggagca ttatctccta tcctatgag caaaattttt    1020
acggttgtga cacatttcat catgtccata atcctttggt atcgtgcaaa ttccgtagat    1080
ttatcgaaca atgattcgtt acaatccttt tatatggcta tctttgtgtt tctttctgtg    1140
gaaaacttcc ttgtacttttt tgttcgatga                                     1170
```

<210> SEQ ID NO 7
<211> LENGTH: 1218
<212> TYPE: DNA
<213> ORGANISM: Arachis hypogaea
<220> FEATURE:
<221> NAME/KEY: CDS
<222> LOCATION: (1)..(1218)
<223> OTHER INFORMATION: resveratrol 3'-dimethylallyltransferase
      (AhR3'DT-3)

<400> SEQUENCE: 7

```
atg cct ttc gga ctc tcc gcc tca ttt ctc aaa tct cgc tcc ctc cac      48
Met Pro Phe Gly Leu Ser Ala Ser Phe Leu Lys Ser Arg Ser Leu His
1               5                   10                  15
```

-continued

| | | |
|---|---|---|
| cac cac ggg tgg aag ttt ctg aaa gag cga gaa att cac aaa caa cca<br>His His Gly Trp Lys Phe Leu Lys Glu Arg Glu Ile His Lys Gln Pro<br>           20                       25                       30 | 96 | |
| cta cgc aat aca aga aga gcc tta tgg aac aac aat ggg aaa cta tca<br>Leu Arg Asn Thr Arg Arg Ala Leu Trp Asn Asn Asn Gly Lys Leu Ser<br>           35                       40                       45 | 144 | |
| aaa gaa tat tgt atc aag atg cag cat aat tat tgg aag aat cat tgc<br>Lys Glu Tyr Cys Ile Lys Met Gln His Asn Tyr Trp Lys Asn His Cys<br>50                       55                       60 | 192 | |
| acc aac ctt aaa gga gga tct atg atg agt gat gat aaa ttt gag aaa<br>Thr Asn Leu Lys Gly Gly Ser Met Met Ser Asp Asp Lys Phe Glu Lys<br>65                     70                       75                    80 | 240 | |
| aaa tac ttg gtg aat gca acc tca aaa aat tca cat gat gaa cca aaa<br>Lys Tyr Leu Val Asn Ala Thr Ser Lys Asn Ser His Asp Glu Pro Lys<br>                   85                      90                    95 | 288 | |
| aaa tca caa cct att ttg gag ttt atc aaa gat ggc atg gat act ttt<br>Lys Ser Gln Pro Ile Leu Glu Phe Ile Lys Asp Gly Met Asp Thr Phe<br>                  100                     105                  110 | 336 | |
| cgc cag ttt tcc aga tta tac gca ttc ttt agc ttc ata tca agt gga<br>Arg Gln Phe Ser Arg Leu Tyr Ala Phe Phe Ser Phe Ile Ser Ser Gly<br>             115                     120                    125 | 384 | |
| ctt tct tca tca ctc ctt gcg gtg gac aat tta tca aat ata tct cca<br>Leu Ser Ser Ser Leu Leu Ala Val Asp Asn Leu Ser Asn Ile Ser Pro<br>130                    135                     140 | 432 | |
| aaa atg ttc tta ata ggc ttc ttg cag ttt ctg ata cct aac tgc atc<br>Lys Met Phe Leu Ile Gly Phe Leu Gln Phe Leu Ile Pro Asn Cys Ile<br>145                    150                    155                  160 | 480 | |
| atg ttt caa tat att gtt ggt gtg aat caa tta gcc gat att gaa ata<br>Met Phe Gln Tyr Ile Val Gly Val Asn Gln Leu Ala Asp Ile Glu Ile<br>                  165                     170                  175 | 528 | |
| gac aag att aac aaa cca tat ctt cca ttg gca tcc ggg aaa tat tcc<br>Asp Lys Ile Asn Lys Pro Tyr Leu Pro Leu Ala Ser Gly Lys Tyr Ser<br>180                    185                     190 | 576 | |
| tta aga aat gca ata ata att gtc gca tca tct ctt ata atg ggc ttt<br>Leu Arg Asn Ala Ile Ile Ile Val Ala Ser Ser Leu Ile Met Gly Phe<br>             195                     200                    205 | 624 | |
| gga tct gcg tgg gtg tta gga tca agg cca atg ttt tgg tgt tta gtc<br>Gly Ser Ala Trp Val Leu Gly Ser Arg Pro Met Phe Trp Cys Leu Val<br>210                    215                    220 | 672 | |
| atc agt act atg ctc atg act gct tat tca gtt aat ttg ccc ttg ttg<br>Ile Ser Thr Met Leu Met Thr Ala Tyr Ser Val Asn Leu Pro Leu Leu<br>225                    230                    235                  240 | 720 | |
| aga tgg aaa aga tcc aca atc ctt gca aca tta tct ctt gca agt tct<br>Arg Trp Lys Arg Ser Thr Ile Leu Ala Thr Leu Ser Leu Ala Ser Ser<br>                  245                     250                  255 | 768 | |
| atg aca att gga caa cat att gca cca ttt ctt cac atg aag act gtg<br>Met Thr Ile Gly Gln His Ile Ala Pro Phe Leu His Met Lys Thr Val<br>260                    265                     270 | 816 | |
| ctc aag aag gca ctt aac tat ccg aga tca cta gtt ttt act gtt gtg<br>Leu Lys Lys Ala Leu Asn Tyr Pro Arg Ser Leu Val Phe Thr Val Val<br>             275                     280                    285 | 864 | |
| gtc gtc agc ctt ttc tat aca gtt ata tcc ttg gca aag gat ata cct<br>Val Val Ser Leu Phe Tyr Thr Val Ile Ser Leu Ala Lys Asp Ile Pro<br>290                    295                    300 | 912 | |
| gac att gaa gga gat aaa gca gca ggt cac aaa acc ttg gca ata cat<br>Asp Ile Glu Gly Asp Lys Ala Ala Gly His Lys Thr Leu Ala Ile His<br>305                    310                    315                  320 | 960 | |
| ttg ggt cct aga cga gta ttt tgg ttt tgc att tcg ctc ctt caa atg<br>Leu Gly Pro Arg Arg Val Phe Trp Phe Cys Ile Ser Leu Leu Gln Met<br>             325                     330                    335 | 1008 | |

```
aca tat gga att gct att ata atg gga gca tta tct cct atc cta tgg    1056
Thr Tyr Gly Ile Ala Ile Ile Met Gly Ala Leu Ser Pro Ile Leu Trp
            340                 345                 350 agc aaa att ttt acg gtt gtg aca cat ttc atc atg tcc ata atc ctt    1104
Ser Lys Ile Phe Thr Val Val Thr His Phe Ile Met Ser Ile Ile Leu
            355                 360                 365 tgg tat cgt gca aat tcc gta gat tta tcg aac aat gat tcg tta caa    1152
Trp Tyr Arg Ala Asn Ser Val Asp Leu Ser Asn Asn Asp Ser Leu Gln
    370                 375                 380 tcc ttt tat atg gct atc ttt gtg ttt ctt tct gtg gaa aac ttc ctt    1200
Ser Phe Tyr Met Ala Ile Phe Val Phe Leu Ser Val Glu Asn Phe Leu
385                 390                 395                 400 gta ctt ttt gtt cga tga                                            1218
Val Leu Phe Val Arg
                405
```

<210> SEQ ID NO 8
<211> LENGTH: 405
<212> TYPE: PRT
<213> ORGANISM: Arachis hypogaea

<400> SEQUENCE: 8

```
Met Pro Phe Gly Leu Ser Ala Ser Phe Leu Lys Ser Arg Ser Leu His
1               5                   10                  15

His His Gly Trp Lys Phe Leu Lys Glu Arg Glu Ile His Lys Gln Pro
            20                  25                  30

Leu Arg Asn Thr Arg Arg Ala Leu Trp Asn Asn Gly Lys Leu Ser
        35                  40                  45

Lys Glu Tyr Cys Ile Lys Met Gln His Asn Tyr Trp Lys Asn His Cys
50                  55                  60

Thr Asn Leu Lys Gly Gly Ser Met Met Ser Asp Asp Lys Phe Glu Lys
65                  70                  75                  80

Lys Tyr Leu Val Asn Ala Thr Ser Lys Asn Ser His Asp Glu Pro Lys
                85                  90                  95

Lys Ser Gln Pro Ile Leu Glu Phe Ile Lys Asp Gly Met Asp Thr Phe
            100                 105                 110

Arg Gln Phe Ser Arg Leu Tyr Ala Phe Phe Ser Phe Ile Ser Ser Gly
        115                 120                 125

Leu Ser Ser Ser Leu Leu Ala Val Asp Asn Leu Ser Asn Ile Ser Pro
130                 135                 140

Lys Met Phe Leu Ile Gly Phe Leu Gln Phe Leu Ile Pro Asn Cys Ile
145                 150                 155                 160

Met Phe Gln Tyr Ile Val Gly Val Asn Gln Leu Ala Asp Ile Glu Ile
                165                 170                 175

Asp Lys Ile Asn Lys Pro Tyr Leu Pro Leu Ala Ser Gly Lys Tyr Ser
            180                 185                 190

Leu Arg Asn Ala Ile Ile Val Ala Ser Ser Leu Ile Met Gly Phe
        195                 200                 205

Gly Ser Ala Trp Val Leu Gly Ser Arg Pro Met Phe Trp Cys Leu Val
210                 215                 220

Ile Ser Thr Met Leu Met Thr Ala Tyr Ser Val Asn Leu Pro Leu Leu
225                 230                 235                 240

Arg Trp Lys Arg Ser Thr Ile Leu Ala Thr Leu Ser Leu Ala Ser Ser
                245                 250                 255

Met Thr Ile Gly Gln His Ile Ala Pro Phe Leu His Met Lys Thr Val
            260                 265                 270
```

```
Leu Lys Lys Ala Leu Asn Tyr Pro Arg Ser Leu Val Phe Thr Val Val
            275                 280                 285

Val Val Ser Leu Phe Tyr Thr Val Ile Ser Leu Ala Lys Asp Ile Pro
        290                 295                 300

Asp Ile Glu Gly Asp Lys Ala Ala Gly His Lys Thr Leu Ala Ile His
305                 310                 315                 320

Leu Gly Pro Arg Arg Val Phe Trp Phe Cys Ile Ser Leu Leu Gln Met
                325                 330                 335

Thr Tyr Gly Ile Ala Ile Ile Met Gly Ala Leu Ser Pro Ile Leu Trp
            340                 345                 350

Ser Lys Ile Phe Thr Val Val Thr His Phe Ile Met Ser Ile Ile Leu
        355                 360                 365

Trp Tyr Arg Ala Asn Ser Val Asp Leu Ser Asn Asn Asp Ser Leu Gln
370                 375                 380

Ser Phe Tyr Met Ala Ile Phe Val Phe Leu Ser Val Glu Asn Phe Leu
385                 390                 395                 400

Val Leu Phe Val Arg
            405

<210> SEQ ID NO 9
<211> LENGTH: 1218
<212> TYPE: DNA
<213> ORGANISM: Arachis hypogaea

<400> SEQUENCE: 9
```

| | | | | | |
|---|---|---|---|---|---|
| atgcctttcg | gactctccgc | ctcatttctc | aaatctcgct | ccctccacca | ccacgggtgg | 60 |
| aagtttctga | agagcgaga | aattcacaaa | caaccactac | gcaatacaag | aagagcctta | 120 |
| tggaacaaca | atgggaaact | atcaaaagaa | tattgtatca | agatgcagca | taattattgg | 180 |
| aagaatcatt | gcaccaacct | aaaggagga | tctatgatga | gtgatgataa | atttgagaaa | 240 |
| aaatacttgg | tgaatgcaac | ctcaaaaaat | tcacatgatg | aaccaaaaaa | atcacaacct | 300 |
| attttggagt | ttatcaaaga | tggcatggat | acttttcgcc | agttttccag | attatacgca | 360 |
| ttctttagct | tcatatcaag | tggactttct | tcatcactcc | ttgcggtgga | caatttatca | 420 |
| aatatatctc | caaaaatgtt | cttaataggc | ttcttgcagt | ttctgatacc | taactgcatc | 480 |
| atgtttcaat | atattgttgg | tgtgaatcaa | ttagccgata | ttgaaataga | caagattaac | 540 |
| aaaccatatc | ttccattggc | atccgggaaa | tattccttaa | gaaatgcaat | aataattgtc | 600 |
| gcatcatctc | ttataatggg | ctttggatct | gcgtgggtgt | taggatcaag | gccaatgttt | 660 |
| tggtgtttag | tcatcagtac | tatgctcatg | actgcttatt | cagttaattt | gcccttgttg | 720 |
| agatggaaaa | gatccacaat | ccttgcaaca | ttatctcttg | caagttctat | gacaattgga | 780 |
| caacatattg | caccatttct | tcacatgaag | actgtgctca | agaaggcact | taactatccg | 840 |
| agatcactag | tttttactgt | tgtggtcgtc | agccttttct | atacagttat | atccttggca | 900 |
| aaggatatac | ctgacattga | aggagataaa | gcagcaggtc | acaaaacctt | ggcaatacat | 960 |
| ttgggtccta | gacgagtatt | tggttttgc | atttcgctcc | ttcaaatgac | atatggaatt | 1020 |
| gctattataa | tgggagcatt | atctcctatc | ctatggagca | aaattttac | ggttgtgaca | 1080 |
| catttcatca | tgtccataat | cctttggtat | cgtgcaaatt | ccgtagattt | atcgaacaat | 1140 |
| gattcgttac | aatcctttta | tatggctatc | tttgtgtttc | tttctgtgga | aaacttcctt | 1200 |
| gtacttttg | ttcgatga | | | | | 1218 |

```
<210> SEQ ID NO 10
<211> LENGTH: 1197
<212> TYPE: DNA
<213> ORGANISM: Arachis hypogaea
<220> FEATURE:
<221> NAME/KEY: CDS
<222> LOCATION: (1)..(1197)
<223> OTHER INFORMATION: resveratrol 3'-dimethylallyltransferase
      (AhR3'DT-4)

<400> SEQUENCE: 10 atg gct tcc act tcc agg ctg ctg ctt cat gcc tca ttg cct cct ccc      48
Met Ala Ser Thr Ser Arg Leu Leu Leu His Ala Ser Leu Pro Pro Pro
1               5                   10                  15 act aca tcc att tcc aaa acc aat tct ggt tca cat gca gtg atc aga      96
Thr Thr Ser Ile Ser Lys Thr Asn Ser Gly Ser His Ala Val Ile Arg
            20                  25                  30 agc ata tgg cat aat aat ggg aaa tat cca aaa gaa aaa act tgc att     144
Ser Ile Trp His Asn Asn Gly Lys Tyr Pro Lys Glu Lys Thr Cys Ile
        35                  40                  45 gag acg cca tta tta ttg cag cat aat cag aag cat cat tat aca tgt     192
Glu Thr Pro Leu Leu Leu Gln His Asn Gln Lys His His Tyr Thr Cys
    50                  55                  60 gat caa att aag aga aaa cac ttt gtg aaa gca act cat gca caa tcg     240
Asp Gln Ile Lys Arg Lys His Phe Val Lys Ala Thr His Ala Gln Ser
65                  70                  75                  80 aag aat gaa cct gaa ccg caa gct gat tct gca aaa ccc att tgg aat     288
Lys Asn Glu Pro Glu Pro Gln Ala Asp Ser Ala Lys Pro Ile Trp Asn
                85                  90                  95 tct atc aaa gat gtt atg cat act atc caa aag ttt agc gta ttc tat     336
Ser Ile Lys Asp Val Met His Thr Ile Gln Lys Phe Ser Val Phe Tyr
            100                 105                 110 gcg tta att ggc ctg tta tcg ggc ata ctt tct tca ctc ctt gca         384
Ala Leu Ile Gly Leu Leu Ser Gly Ile Leu Ser Ser Ser Leu Leu Ala
        115                 120                 125 gta gaa aaa tta tca gat tta tct cca aca ttt ttt att tcc atg tta     432
Val Glu Lys Leu Ser Asp Leu Ser Pro Thr Phe Phe Ile Ser Met Leu
    130                 135                 140 cag ttt atg gca gct tat agc tct atg caa ttg tat act act ggc gtg     480
Gln Phe Met Ala Ala Tyr Ser Ser Met Gln Leu Tyr Thr Thr Gly Val
145                 150                 155                 160 aat caa tta gcc gat att gaa ata gac aag att aat aag cca tac cgt     528
Asn Gln Leu Ala Asp Ile Glu Ile Asp Lys Ile Asn Lys Pro Tyr Arg
                165                 170                 175 cca ttg gca tca tcg aaa att tct ttt gga ggt gga ctc gct att gtt     576
Pro Leu Ala Ser Ser Lys Ile Ser Phe Gly Gly Gly Leu Ala Ile Val
            180                 185                 190 gca gca tct tta ttt atg agc ttt gga ctt gcg ctg atg ata gga tca     624
Ala Ala Ser Leu Phe Met Ser Phe Gly Leu Ala Leu Met Ile Gly Ser
        195                 200                 205 aag cct ttg ctt tgg ggt ctc ata tta att ttt ata ctg atg act gct     672
Lys Pro Leu Leu Trp Gly Leu Ile Leu Ile Phe Ile Leu Met Thr Ala
    210                 215                 220 tat tca gtg aac tta ccc ttt tta aga tgg aag aaa tct aca att ctt     720
Tyr Ser Val Asn Leu Pro Phe Leu Arg Trp Lys Lys Ser Thr Ile Leu
225                 230                 235                 240 aca tta ctg tct ggc gta cca act att ctc act gca tat aat ttg gca     768
Thr Leu Leu Ser Gly Val Pro Thr Ile Leu Thr Ala Tyr Asn Leu Ala
                245                 250                 255 cca tat ctt cac atg aag acc ttt gtg ctg aag aag cca ttt ata ttt     816
Pro Tyr Leu His Met Lys Thr Phe Val Leu Lys Lys Pro Phe Ile Phe
            260                 265                 270
```

| | | |
|---|---|---|
| aca aga tca cta gct ttt acc act gtg gtc atg acc ttc ttc tat gta<br>Thr Arg Ser Leu Ala Phe Thr Thr Val Val Met Thr Phe Phe Tyr Val<br>    275                              280                      285 | | 864 |
| gtt ata tca ttg ttc aag gac att ccc gac att gaa gga gat aaa aaa<br>Val Ile Ser Leu Phe Lys Asp Ile Pro Asp Ile Glu Gly Asp Lys Lys<br>290                            295                            300 | | 912 |
| gaa ggt ctt caa act ttg tct att cgc ttg ggt cct aaa cga gta ttt<br>Glu Gly Leu Gln Thr Leu Ser Ile Arg Leu Gly Pro Lys Arg Val Phe<br>305                            310                          315              320 | | 960 |
| tgg ttg tgt att tca ctt ctt gag atg act tat gga att gcc att ata<br>Trp Leu Cys Ile Ser Leu Leu Glu Met Thr Tyr Gly Ile Ala Ile Ile<br>                          325                          330                        335 | | 1008 |
| atg gga tta aca tct cca ttc cta tgg agc aaa atc ttc acg gtt atg<br>Met Gly Leu Thr Ser Pro Phe Leu Trp Ser Lys Ile Phe Thr Val Met<br>                  340                          345                        350 | | 1056 |
| gca cat gcc atc aat gct tgg att ttg tgg ttt cgt gct aat tct gta<br>Ala His Ala Ile Asn Ala Trp Ile Leu Trp Phe Arg Ala Asn Ser Val<br>                        355                          360                        365 | | 1104 |
| gat tta aag agc aaa gaa gat ttc caa tcc ttt tat atg ttt atc ttt<br>Asp Leu Lys Ser Lys Glu Asp Phe Gln Ser Phe Tyr Met Phe Ile Phe<br>370                            375                            380 | | 1152 |
| aag ctc ctt tac ttg gag aat gtc ctt gtg ctt ttt gtg aga taa<br>Lys Leu Leu Tyr Leu Glu Asn Val Leu Val Leu Phe Val Arg<br>385                            390                            395 | | 1197 |

<210> SEQ ID NO 11
<211> LENGTH: 398
<212> TYPE: PRT
<213> ORGANISM: Arachis hypogaea

<400> SEQUENCE: 11

Met Ala Ser Thr Ser Arg Leu Leu Leu His Ala Ser Leu Pro Pro
1               5                   10                  15

Thr Thr Ser Ile Ser Lys Thr Asn Ser Gly Ser His Ala Val Ile Arg
            20                  25                  30

Ser Ile Trp His Asn Asn Gly Lys Tyr Pro Lys Glu Lys Thr Cys Ile
        35                  40                  45

Glu Thr Pro Leu Leu Leu Gln His Asn Gln Lys His His Tyr Thr Cys
    50                  55                  60

Asp Gln Ile Lys Arg Lys His Phe Val Lys Ala Thr His Ala Gln Ser
65                  70                  75                  80

Lys Asn Glu Pro Glu Pro Gln Ala Asp Ser Ala Lys Pro Ile Trp Asn
                85                  90                  95

Ser Ile Lys Asp Val Met His Thr Ile Gln Lys Phe Ser Val Phe Tyr
            100                 105                 110

Ala Leu Ile Gly Leu Leu Ser Gly Ile Leu Ser Ser Leu Leu Ala
        115                 120                 125

Val Glu Lys Leu Ser Asp Leu Ser Pro Thr Phe Phe Ile Ser Met Leu
    130                 135                 140

Gln Phe Met Ala Ala Tyr Ser Ser Met Gln Leu Tyr Thr Thr Gly Val
145                 150                 155                 160

Asn Gln Leu Ala Asp Ile Glu Ile Asp Lys Ile Asn Lys Pro Tyr Arg
                165                 170                 175

Pro Leu Ala Ser Ser Lys Ile Ser Phe Gly Gly Leu Ala Ile Val
            180                 185                 190

Ala Ala Ser Leu Phe Met Ser Phe Gly Leu Ala Leu Met Ile Gly Ser
        195                 200                 205

| Lys | Pro | Leu | Leu | Trp | Gly | Leu | Ile | Leu | Ile | Phe | Ile | Leu | Met | Thr | Ala |
|-----|-----|-----|-----|-----|-----|-----|-----|-----|-----|-----|-----|-----|-----|-----|-----|
| 210 |     |     |     |     | 215 |     |     |     |     | 220 |     |     |     |     |     |

| Tyr | Ser | Val | Asn | Leu | Pro | Phe | Leu | Arg | Trp | Lys | Lys | Ser | Thr | Ile | Leu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Thr | Leu | Leu | Ser | Gly | Val | Pro | Thr | Ile | Leu | Thr | Ala | Tyr | Asn | Leu | Ala |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Pro | Tyr | Leu | His | Met | Lys | Thr | Phe | Val | Leu | Lys | Lys | Pro | Phe | Ile | Phe |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Thr | Arg | Ser | Leu | Ala | Phe | Thr | Thr | Val | Val | Met | Thr | Phe | Phe | Tyr | Val |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Val | Ile | Ser | Leu | Phe | Lys | Asp | Ile | Pro | Asp | Ile | Glu | Gly | Asp | Lys | Lys |
|-----|-----|-----|-----|-----|-----|-----|-----|-----|-----|-----|-----|-----|-----|-----|-----|
| 290 |     |     |     |     | 295 |     |     |     |     | 300 |     |     |     |     |     |

| Glu | Gly | Leu | Gln | Thr | Leu | Ser | Ile | Arg | Leu | Gly | Pro | Lys | Arg | Val | Phe |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Trp | Leu | Cys | Ile | Ser | Leu | Leu | Glu | Met | Thr | Tyr | Gly | Ile | Ala | Ile | Ile |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Met | Gly | Leu | Thr | Ser | Pro | Phe | Leu | Trp | Ser | Lys | Ile | Phe | Thr | Val | Met |
|-----|-----|-----|-----|-----|-----|-----|-----|-----|-----|-----|-----|-----|-----|-----|-----|
|     |     |     |     | 340 |     |     |     |     | 345 |     |     |     |     | 350 |     |

| Ala | His | Ala | Ile | Asn | Ala | Trp | Ile | Leu | Trp | Phe | Arg | Ala | Asn | Ser | Val |
|-----|-----|-----|-----|-----|-----|-----|-----|-----|-----|-----|-----|-----|-----|-----|-----|
|     | 355 |     |     |     |     | 360 |     |     |     |     | 365 |     |     |     |     |

| Asp | Leu | Lys | Ser | Lys | Glu | Asp | Phe | Gln | Ser | Phe | Tyr | Met | Phe | Ile | Phe |
|-----|-----|-----|-----|-----|-----|-----|-----|-----|-----|-----|-----|-----|-----|-----|-----|
| 370 |     |     |     |     | 375 |     |     |     |     | 380 |     |     |     |     |     |

| Lys | Leu | Leu | Tyr | Leu | Glu | Asn | Val | Leu | Val | Leu | Phe | Val | Arg |
|-----|-----|-----|-----|-----|-----|-----|-----|-----|-----|-----|-----|-----|-----|
| 385 |     |     |     |     | 390 |     |     |     |     | 395 |     |     |     |

<210> SEQ ID NO 12
<211> LENGTH: 1197
<212> TYPE: DNA
<213> ORGANISM: Arachis hypogaea

<400> SEQUENCE: 12

```
atggcttcca cttccaggct gctgcttcat gcctcattgc ctcctcccac tacatccatt      60
tccaaaacca attctggttc acatgcagtg atcagaagca tatggcataa taatgggaaa     120
tatccaaaag aaaaaacttg cattgagacg ccattattat tgcagcataa tcagaagcat     180
cattatacat gtgatcaaat taagagaaaa cactttgtga agcaactca tgcacaatcg      240
aagaatgaac ctgaaccgca agctgattct gcaaaaccca tttggaattc tatcaaagat     300
gttatgcata ctatccaaaa gtttagcgta ttctatgcgt taattggcct gttatcgggc     360
atactttctt catcactcct tgcagtagaa aaattatcag attatctcc aacatttttt      420
atttccatgt tacagtttat ggcagcttat agctctatgc aattgtatac tactggcgtg     480
aatcaattag ccgatattga aatagacaag attaataagc ataccgtcc attggcatca     540
tcgaaaattt cttttggagg tggactcgct attgttgcag catctttatt tatgagcttt     600
ggacttgcgc tgatgatagg atcaaagcct ttgctttggg gtctcatatt aatttttata     660
ctgatgactg cttattcagt gaacttaccc ttttaagat ggaagaaatc tacaattctt     720
acattactgt ctggcgtacc aactattctc actgcatata atttggcacc atatcttcac     780
atgaagacct ttgtgctgaa gaagccattt atatttacaa gatcactagc ttttaccact     840
gtggtcatga ccttcttcta tgtagttata tcattgttca aggacattcc cgacattgaa     900
ggagataaaa aagaaggtct tcaaactttg tctattcgct gggtcctaa acgagtattt     960
tggttgtgta tttcactct tgagatgact tatggaattg ccattataat gggattaaca    1020
tctccattcc tatggagcaa aatcttcacg gttatggcac atgccatcaa tgcttggatt    1080
```

```
ttgtggtttc gtgctaattc tgtagattta aagagcaaag aagatttcca atcctttat    1140 atgtttatct ttaagctcct ttacttggag aatgtccttg tgcttttgt gagataa      1197

<210> SEQ ID NO 13
<211> LENGTH: 1191
<212> TYPE: DNA
<213> ORGANISM: Arachis hypogaea
<220> FEATURE:
<221> NAME/KEY: CDS
<222> LOCATION: (1)..(1191)
<223> OTHER INFORMATION: resveratrol 3'-dimethylallyltransferase
      (AhR3'DT-1)

<400> SEQUENCE: 13
```

| | | | | | | | | | | | | | | | | |
|---|---|---|---|---|---|---|---|---|---|---|---|---|---|---|---|---|
| atg | gct | ttt | ggt | gtt | gtt | gct | gcc | tca | ttt | tca | aga | gct | ccc | tcc | att | 48 |
| Met | Ala | Phe | Gly | Val | Val | Ala | Ala | Ser | Phe | Ser | Arg | Ala | Pro | Ser | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | acc | acc | aga | ggt | tgt | tat | gta | aca | aga | gct | tca | ttg | cct | aat | aag | 96 |
| Val | Thr | Thr | Arg | Gly | Cys | Tyr | Val | Thr | Arg | Ala | Ser | Leu | Pro | Asn | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| agt | ctc | aaa | ttc | tca | aaa | gaa | tat | aat | ttg | aag | aca | tct | ctg | cag | cat | 144 |
| Ser | Leu | Lys | Phe | Ser | Lys | Glu | Tyr | Asn | Leu | Lys | Thr | Ser | Leu | Gln | His | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | tgg | aag | cac | aat | tcc | aga | agc | att | ttt | gaa | aga | gga | tct | aca | att | 192 |
| Asn | Trp | Lys | His | Asn | Ser | Arg | Ser | Ile | Phe | Glu | Arg | Gly | Ser | Thr | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| aca | aca | tgt | gat | aaa | tat | gat | gaa | aag | aag | tac | ctt | atg | aat | gtg | aca | 240 |
| Thr | Thr | Cys | Asp | Lys | Tyr | Asp | Glu | Lys | Lys | Tyr | Leu | Met | Asn | Val | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| caa | tca | cat | gaa | gct | gaa | cca | cat | tca | caa | agc | atc | ttg | aag | tcc | atc | 288 |
| Gln | Ser | His | Glu | Ala | Glu | Pro | His | Ser | Gln | Ser | Ile | Leu | Lys | Ser | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| att | gat | gct | tta | gat | gct | ttc | cgc | aag | ttt | agc | aga | ttt | tac | gca | ttc | 336 |
| Ile | Asp | Ala | Leu | Asp | Ala | Phe | Arg | Lys | Phe | Ser | Arg | Phe | Tyr | Ala | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| att | gcc | atg | gta | gtg | ggt | tca | ctt | tcc | aca | tcg | ctt | ctt | gca | gtg | gac | 384 |
| Ile | Ala | Met | Val | Val | Gly | Ser | Leu | Ser | Thr | Ser | Leu | Leu | Ala | Val | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| aat | tta | aca | gaa | tta | tat | cca | gca | ttt | ttt | aat | ggc | ttt | ttg | caa | tgt | 432 |
| Asn | Leu | Thr | Glu | Leu | Tyr | Pro | Ala | Phe | Phe | Asn | Gly | Phe | Leu | Gln | Cys | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | gca | gct | tac | ttc | ttc | atg | cat | ttg | tac | att | gtt | gga | ata | aat | caa | 480 |
| Met | Ala | Ala | Tyr | Phe | Phe | Met | His | Leu | Tyr | Ile | Val | Gly | Ile | Asn | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tta | gcg | gat | ctt | gaa | ata | gac | aag | att | aac | aag | cca | tat | ctt | cct | ttg | 528 |
| Leu | Ala | Asp | Leu | Glu | Ile | Asp | Lys | Ile | Asn | Lys | Pro | Tyr | Leu | Pro | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gca | tca | ggg | aac | tat | tcc | ttc | aga | act | gca | gtt | ata | act | gtg | acg | tca | 576 |
| Ala | Ser | Gly | Asn | Tyr | Ser | Phe | Arg | Thr | Ala | Val | Ile | Thr | Val | Thr | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| ttt | tta | ttt | acg | ggc | ttt | gga | att | gca | tgg | atc | ata | gga | tca | aag | ccg | 624 |
| Phe | Leu | Phe | Thr | Gly | Phe | Gly | Ile | Ala | Trp | Ile | Ile | Gly | Ser | Lys | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| ttg | ctt | tgg | act | att | ttt | gcc | agt | ttt | gtt | cta | atg | act | gct | tat | tca | 672 |
| Leu | Leu | Trp | Thr | Ile | Phe | Ala | Ser | Phe | Val | Leu | Met | Thr | Ala | Tyr | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| gtt | aat | ttg | ccc | tta | ttg | aga | tgg | aag | aaa | tct | aca | ata | ctt | aca | gtg | 720 |
| Val | Asn | Leu | Pro | Leu | Leu | Arg | Trp | Lys | Lys | Ser | Thr | Ile | Leu | Thr | Val | |
| 225 | | | | | 230 | | | | | 235 | | | | | 240 | |

```
atg ggt aac aca ctt tct atg gtg ata tca ttt aat ctt ggt ccc ttt    768
Met Gly Asn Thr Leu Ser Met Val Ile Ser Phe Asn Leu Gly Pro Phe
            245                 250                 255 tat cac atg aag act cat gtg ctc aag aag gca gct acc ttt cca aga    816
Tyr His Met Lys Thr His Val Leu Lys Lys Ala Ala Thr Phe Pro Arg
        260                 265                 270 tcc cta ctt ttt gct gtt gtg gtc atg agc atg tac tat atc gtt ata    864
Ser Leu Leu Phe Ala Val Val Val Met Ser Met Tyr Tyr Ile Val Ile
    275                 280                 285 gca ttg aca aag gat ata cct gat atc gaa gga gac aaa gaa gcc ggc    912
Ala Leu Thr Lys Asp Ile Pro Asp Ile Glu Gly Asp Lys Glu Ala Gly
290                 295                 300 ctc caa act ttg gcc ata cgc ttg ggt cct aag acg gta ttt tgg tct    960
Leu Gln Thr Leu Ala Ile Arg Leu Gly Pro Lys Thr Val Phe Trp Ser
305                 310                 315                 320 agt gtt gca ctt ctt gaa atg gct tat gga gct gct att ata att gga   1008
Ser Val Ala Leu Leu Glu Met Ala Tyr Gly Ala Ala Ile Ile Ile Gly
                325                 330                 335 gca tcc tct cct ttt ctt tgg agc aaa atc tct gtg gtt ctt tcc cat   1056
Ala Ser Ser Pro Phe Leu Trp Ser Lys Ile Ser Val Val Leu Ser His
            340                 345                 350 gct atc ttg gct ttg ttc gta tgg tat cgc tcc act ctt gta gat tta   1104
Ala Ile Leu Ala Leu Phe Val Trp Tyr Arg Ser Thr Leu Val Asp Leu
        355                 360                 365 tcc aac aaa gat tca ttg caa gct ttt tat atg ctt atc ttt aag ctt   1152
Ser Asn Lys Asp Ser Leu Gln Ala Phe Tyr Met Leu Ile Phe Lys Leu
    370                 375                 380 ttt tct gtg gaa aat att ctt atg ctt ttt gtt aga tga               1191
Phe Ser Val Glu Asn Ile Leu Met Leu Phe Val Arg
385                 390                 395

<210> SEQ ID NO 14
<211> LENGTH: 396
<212> TYPE: PRT
<213> ORGANISM: Arachis hypogaea

<400> SEQUENCE: 14

Met Ala Phe Gly Val Val Ala Ala Ser Phe Ser Arg Ala Pro Ser Ile
1               5                   10                  15

Val Thr Thr Arg Gly Cys Tyr Val Thr Arg Ala Ser Leu Pro Asn Lys
            20                  25                  30

Ser Leu Lys Phe Ser Lys Glu Tyr Asn Leu Lys Thr Ser Leu Gln His
        35                  40                  45

Asn Trp Lys His Asn Ser Arg Ser Ile Phe Glu Arg Gly Ser Thr Ile
    50                  55                  60

Thr Thr Cys Asp Lys Tyr Asp Glu Lys Lys Tyr Leu Met Asn Val Thr
65                  70                  75                  80

Gln Ser His Glu Ala Glu Pro His Ser Gln Ser Ile Leu Lys Ser Ile
                85                  90                  95

Ile Asp Ala Leu Asp Ala Phe Arg Lys Phe Ser Arg Phe Tyr Ala Phe
            100                 105                 110

Ile Ala Met Val Val Gly Ser Leu Ser Thr Ser Leu Leu Ala Val Asp
        115                 120                 125

Asn Leu Thr Glu Leu Tyr Pro Ala Phe Phe Asn Gly Phe Leu Gln Cys
    130                 135                 140

Met Ala Ala Tyr Phe Phe Met His Leu Tyr Ile Val Gly Ile Asn Gln
145                 150                 155                 160
```

```
Leu Ala Asp Leu Glu Ile Asp Lys Ile Asn Lys Pro Tyr Leu Pro Leu
                165                 170                 175

Ala Ser Gly Asn Tyr Ser Phe Arg Thr Ala Val Ile Thr Val Thr Ser
            180                 185                 190

Phe Leu Phe Thr Gly Phe Gly Ile Ala Trp Ile Ile Gly Ser Lys Pro
        195                 200                 205

Leu Leu Trp Thr Ile Phe Ala Ser Phe Val Leu Met Thr Ala Tyr Ser
    210                 215                 220

Val Asn Leu Pro Leu Leu Arg Trp Lys Lys Ser Thr Ile Leu Thr Val
225                 230                 235                 240

Met Gly Asn Thr Leu Ser Met Val Ile Ser Phe Asn Leu Gly Pro Phe
                245                 250                 255

Tyr His Met Lys Thr His Val Leu Lys Lys Ala Ala Thr Phe Pro Arg
            260                 265                 270

Ser Leu Leu Phe Ala Val Val Met Ser Met Tyr Tyr Ile Val Ile
        275                 280                 285

Ala Leu Thr Lys Asp Ile Pro Asp Ile Glu Gly Asp Lys Glu Ala Gly
    290                 295                 300

Leu Gln Thr Leu Ala Ile Arg Leu Gly Pro Lys Thr Val Phe Trp Ser
305                 310                 315                 320

Ser Val Ala Leu Leu Glu Met Ala Tyr Gly Ala Ala Ile Ile Gly
                325                 330                 335

Ala Ser Ser Pro Phe Leu Trp Ser Lys Ile Ser Val Val Leu Ser His
            340                 345                 350

Ala Ile Leu Ala Leu Phe Val Trp Tyr Arg Ser Thr Leu Val Asp Leu
        355                 360                 365

Ser Asn Lys Asp Ser Leu Gln Ala Phe Tyr Met Leu Ile Phe Lys Leu
    370                 375                 380

Phe Ser Val Glu Asn Ile Leu Met Leu Phe Val Arg
385                 390                 395
```

<210> SEQ ID NO 15
<211> LENGTH: 1191
<212> TYPE: DNA
<213> ORGANISM: Arachis hypogaea

<400> SEQUENCE: 15

```
atggctttg gtgttgttgc tgcctcattt tcaagagctc cctccattgt caccaccaga      60
ggttgttatg taacaagagc ttcattgcct aataagagtc tcaaattctc aaaagaatat     120
aatttgaaga catctctgca gcataattgg aagcacaatt ccagaagcat ttttgaaaga     180
ggatctacaa ttcaacatgt gataaatat gatgaaaaga agtaccttat gaatgtgaca      240
caatcacatg aagctgaacc acattcacaa agcatcttga agtccatcat tgatgcttta     300
gatgctttcc gcaagtttag cagattttac gcattcattg ccatggtagt gggttcactt     360
tccacatcgc ttcttgcagt ggacaattta acagaattat atccagcatt tttaatggc     420
ttttttgcaat gtatggcagc ttacttcttc atgcatttgt acattgttgg aataaatcaa     480
ttagcggatc ttgaaataga caagattaac aagccatatc ttcctttggc atcagggaac     540
tattccttca gaactgcagt tataactgtg acgtcatttt tatttacggg ctttggaatt     600
gcatggatca taggatcaaa gccgttgctt tggactattt tgccagtttt tgttctaatg     660
actgctttat cagttaattt gcccttattg agatggaaga aatctacaat acttacagtg     720
atgggtaaca cactttctat ggtgatatca tttaatcttg gtccttttta tcacatgaag     780
```

```
actcatgtgc tcaagaaggc agctacccttt ccaagatccc tacttttttgc tgttgtggtc    840 atgagcatgt actatatcgt tatagcattg acaaaggata tacctgatat cgaaggagac    900
aaagaagccg gcctccaaac tttggccata cgcttgggtc ctaagacggt attttggtct    960
agtgttgcac ttcttgaaat ggcttatgga gctgctatta taattggagc atcctctcct   1020
tttctttgga gcaaaatctc tgtggttctt tcccatgcta tcttggcttt gttcgtatgg   1080
tatcgctcca ctcttgtaga tttatccaac aaagattcat tgcaagcttt ttatatgctt   1140
atctttaagc ttttttctgt ggaaaatatt cttatgcttt tgttagatg a              1191
```

<210> SEQ ID NO 16
<211> LENGTH: 9
<212> TYPE: PRT
<213> ORGANISM: Arachis hypogaea
<220> FEATURE:
<221> NAME/KEY: MISC_FEATURE
<222> LOCATION: (3)..(4)
<223> OTHER INFORMATION: Xaa, defined as any naturally-occurring amino
      acid.
<220> FEATURE:
<221> NAME/KEY: MISC_FEATURE
<222> LOCATION: (6)..(8)
<223> OTHER INFORMATION: Xaa, defined as any naturally-occurring amino
      acid.

<400> SEQUENCE: 16

Asn Gln Xaa Xaa Asp Xaa Xaa Xaa Asp
1               5

<210> SEQ ID NO 17
<211> LENGTH: 9
<212> TYPE: PRT
<213> ORGANISM: Arachis hypogaea
<220> FEATURE:
<221> NAME/KEY: MISC_FEATURE
<222> LOCATION: (3)..(4)
<223> OTHER INFORMATION: Xaa, defined as any naturally-occurring amino
      acid.
<220> FEATURE:
<221> NAME/KEY: MISC_FEATURE
<222> LOCATION: (6)..(6)
<223> OTHER INFORMATION: Xaa, defined as any naturally-occurring amino
      acid.

<400> SEQUENCE: 17

Lys Asp Xaa Xaa Asp Xaa Glu Gly Asp
1               5

<210> SEQ ID NO 18
<211> LENGTH: 405
<212> TYPE: PRT
<213> ORGANISM: Arachis hypogaea

<400> SEQUENCE: 18

Met Ala Phe Gly His Leu Val Leu Ile Pro Arg Ser Thr Ser Ser Ile
1               5                   10                  15

Ala Thr Thr Ala Ala Ser Cys Trp Lys Ser Lys Lys Phe Ala Asp Asn
            20                  25                  30

Tyr Tyr Ala Asn Ser Tyr Gly Arg Arg Ala Leu Trp Gln Ser Asp Arg
        35                  40                  45

Asn Leu Thr Lys Asp His Ser Ile Lys Thr Ser Leu Gln His Asn Ile
    50                  55                  60

Ser Lys Leu His Tyr Asn Pro Ile Glu Arg Gly Ser Arg Cys Asn Lys
65                  70                  75                  80

Ile Glu Lys Thr Tyr Leu Thr Asn Ala Ser Ser Ala Gln Ser His
                85                  90                  95

Glu Ser Glu Pro Glu Val His Glu Ser Pro Lys Ala Leu Glu Ser Ile
            100                 105                 110

Lys Lys Gly Leu Val Met Phe Leu Gln Phe Cys Arg Leu Tyr Ala Phe
            115                 120                 125

Leu Gly Met Ile Pro Ala Gly Leu Ser Ser Ser Leu Leu Ala Val Asp
            130                 135                 140

Asn Phe Ser Glu Ile Ser Pro Leu Leu Phe Leu Lys Gly Val Leu Gln
145                 150                 155                 160

Tyr Ile Val Thr Phe Phe Thr Ser Gln Phe Val Met Gly Val Asn
                165                 170                 175

Gln Leu Ser Asp Val Glu Ile Asp Lys Ile Asn Lys Pro Asp Leu Pro
            180                 185                 190

Leu Ala Ser Gly Glu Tyr Ser Phe Thr Ser Gly Val Ile Leu Val Thr
            195                 200                 205

Ser Phe Leu Leu Ala Gly Phe Gly Val Ala Trp Met Leu Gly Ser Gln
            210                 215                 220

Pro Leu Ile Trp Ser Val Val Thr Ala Ala Leu Met Gly Ala Tyr
225                 230                 235                 240

Ser Val Asn Phe Pro Leu Leu Arg Trp Lys Arg Ser Ile Ile Leu Thr
                245                 250                 255

Ser Leu Ser Asn Ala Ile Ala Met Leu Ala Ser Phe His Ile Gly Pro
            260                 265                 270

Phe Leu His Met Lys Thr Phe Val Leu Lys Lys Ala Ala Thr Phe Pro
            275                 280                 285

Arg Ser Met Ile Leu Gly Cys Val Val Ile Gly Leu Phe Tyr Thr Ile
            290                 295                 300

Ile Thr Leu Thr Lys Asp Leu Gly Asp Val Glu Gly Asp Lys Ala Ala
305                 310                 315                 320

Gly Leu Lys Thr Leu Pro Ile Arg Leu Gly Val Lys Pro Val Phe Trp
            325                 330                 335

Leu Cys Val Ser Leu Ile Gln Met Ala Tyr Gly Ile Ala Ile Thr Met
            340                 345                 350

Gly Ala Leu Ser Pro Val Leu Trp Ser Lys Ile Val Thr Val Val Ala
            355                 360                 365

His Ala Phe Met Val Phe Tyr Val Trp Asn His Ala Leu Asn Ser Val
            370                 375                 380

Asp Leu Ser Ser Lys Asp Ser Leu His Ser Phe His Leu Phe Met Phe
385                 390                 395                 400

Lys Val Thr Asn Asn
                405

<210> SEQ ID NO 19
<211> LENGTH: 443
<212> TYPE: PRT
<213> ORGANISM: Arachis hypogaea

<400> SEQUENCE: 19

Met Ala Phe Gly Val Val Ala Ala Ser Leu Ser Arg Ala Pro Ser Ile
1               5                   10                  15

Val Thr Thr Arg Gly Cys Tyr Val Thr Arg Ala Ser Leu Pro Asn Lys
            20                  25                  30

Ser Leu Lys Phe Ser Lys Glu Tyr Asn Trp Lys His Asn Ser Arg Ser
        35                  40                  45

```
Ile Phe Glu Arg Gly Ser Thr Ile Thr Thr Cys Lys His Asp Glu
 50                  55                  60

Lys Lys Tyr Leu Met Asn Val Thr Gln Ser His Glu Ala Glu Pro His
 65                  70                  75                  80

Ser Gln Thr Ile Leu Lys Ser Ile Val His Ala Leu Asp Ala Phe Arg
                 85                  90                  95

Lys Phe Ser Arg Phe Tyr Ala Phe Ile Ala Met Val Val Gly Ser Leu
                100                 105                 110

Ser Thr Ser Leu Leu Ala Val Asp Asn Leu Thr Glu Leu Tyr Pro Thr
                115                 120                 125

Phe Phe Asn Gly Phe Leu Gln Cys Met Ala Ala Tyr Phe Phe Met His
130                 135                 140

Leu Tyr Ile Val Gly Ile Asn Gln Leu Ala Asp Leu Glu Ile Asp Lys
145                 150                 155                 160

Ile Asn Lys Pro Tyr Leu Pro Leu Ala Ser Gly Asn Tyr Ser Phe Arg
                165                 170                 175

Thr Ala Val Ile Thr Val Thr Ser Phe Leu Phe Thr Gly Phe Gly Ile
                180                 185                 190

Ala Trp Met Ile Gly Ser Lys Pro Leu Leu Trp Thr Ile Phe Ala Ser
195                 200                 205

Phe Val Leu Met Ser Ala Tyr Ser Val Asn Leu Pro Leu Leu Arg Trp
210                 215                 220

Lys Lys Ser Thr Ile Leu Thr Val Met Gly Asn Thr Leu Ser Met Val
225                 230                 235                 240

Ile Ser Phe Asn Leu Gly Pro Phe Tyr His Met Lys Thr His Val Leu
                245                 250                 255

Lys Lys Ala Ala Thr Phe Pro Arg Ser Leu Leu Phe Ala Val Val Val
                260                 265                 270

Met Ser Met Tyr Tyr Ile Val Ile Ala Leu Thr Lys Asp Ile Pro Asp
                275                 280                 285

Ile Glu Gly Asp Lys Glu Ala Gly Leu Gln Thr Leu Ala Val Arg Leu
                290                 295                 300

Gly Pro Lys Thr Val Phe Trp Ser Ser Val Leu Leu Leu Glu Met Ala
305                 310                 315                 320

Tyr Gly Ala Ala Ile Ile Gly Ala Ser Ser Pro Phe Leu Trp Ser
                325                 330                 335

Lys Ile Phe Val Val Leu Ser His Ala Ile Met Ala Leu Phe Val Trp
                340                 345                 350

Tyr Arg Ser Thr Leu Val Asp Leu Ser Asn Lys Asp Ser Leu Gln Ala
                355                 360                 365

Phe Tyr Met Leu Ile Phe Lys Val Leu Ser Thr Ile Ala Leu Asp Ile
370                 375                 380

Leu Trp Lys Ser Lys Gly Ser Arg Phe Ala Val Arg Val Pro Ser Val
385                 390                 395                 400

Arg Val Ala Lys Glu Ala Ser Lys Ile Asn Pro Asn Pro Asn Arg Lys
                405                 410                 415

Glu Asp Phe Arg Ser Pro Ser Phe Ser Leu Gly Arg Leu Ile Asn Lys
                420                 425                 430

Asn Glu Val Ala Val Lys Lys Leu Leu Lys Lys
                435                 440
```

```
<210> SEQ ID NO 20
<211> LENGTH: 431
<212> TYPE: PRT
<213> ORGANISM: Arachis hypogaea

<400> SEQUENCE: 20

Met Ala Phe Gly Val Val Ala Ala Ser Leu Ser Arg Ala Pro Ser Ile
1               5                   10                  15

Val Thr Thr Arg Gly Cys Tyr Val Thr Arg Ala Ser Leu Pro Asn Lys
            20                  25                  30

Ser Leu Lys Phe Ser Lys Glu Tyr Asn Trp Lys His Asn Ser Arg Ser
        35                  40                  45

Ile Phe Glu Arg Gly Ser Thr Ile Thr Thr Cys Glu Lys His Asp Glu
    50                  55                  60

Lys Lys Tyr Leu Met Asn Val Thr Gln Ser His Glu Ala Glu Pro His
65                  70                  75                  80

Ser Gln Thr Ile Leu Lys Ser Ile Val His Ala Leu Asp Ala Phe Arg
                85                  90                  95

Lys Phe Ser Arg Phe Tyr Ala Phe Ile Ala Met Val Val Gly Ser Leu
            100                 105                 110

Ser Thr Ser Leu Leu Ala Val Asp Asn Leu Thr Glu Leu Tyr Pro Thr
        115                 120                 125

Phe Phe Asn Gly Phe Leu Gln Cys Met Ala Ala Tyr Phe Phe Met His
    130                 135                 140

Leu Tyr Ile Val Gly Ile Asn Gln Leu Ala Asp Leu Glu Ile Asp Lys
145                 150                 155                 160

Ile Asn Lys Pro Tyr Leu Pro Leu Ala Ser Gly Asn Tyr Ser Phe Arg
                165                 170                 175

Thr Ala Val Ile Thr Val Thr Ser Phe Leu Phe Thr Gly Phe Gly Ile
            180                 185                 190

Ala Trp Met Ile Gly Ser Lys Pro Leu Leu Trp Thr Ile Phe Ala Ser
        195                 200                 205

Phe Val Leu Met Ser Ala Tyr Ser Val Asn Leu Pro Leu Leu Arg Trp
    210                 215                 220

Lys Lys Ser Thr Ile Leu Thr Val Met Gly Asn Thr Leu Ser Met Val
225                 230                 235                 240

Ile Ser Phe Asn Leu Gly Pro Phe Tyr His Met Lys Thr His Val Leu
                245                 250                 255

Lys Lys Ala Ala Thr Phe Pro Arg Ser Leu Leu Phe Ala Val Val Val
            260                 265                 270

Met Ser Met Tyr Tyr Ile Val Ile Ala Leu Thr Lys Asp Ile Pro Asp
        275                 280                 285

Ile Glu Gly Asp Lys Glu Ala Gly Leu Gln Thr Leu Ala Val Arg Leu
    290                 295                 300

Gly Pro Lys Thr Val Phe Trp Ser Ser Val Leu Leu Leu Glu Met Ala
305                 310                 315                 320

Tyr Gly Ala Ala Ile Ile Ile Gly Ala Ser Ser Pro Phe Leu Trp Ser
                325                 330                 335

Lys Ile Phe Val Val Leu Ser His Ala Ile Met Ala Leu Phe Val Trp
            340                 345                 350

Tyr Arg Ser Thr Leu Val Asp Leu Ser Asn Lys Asp Ser Leu Gln Ala
        355                 360                 365

Phe Tyr Met Leu Ile Phe Lys Val Leu Ser Thr Ile Ala Leu Asp Ile
    370                 375                 380
```

-continued

Leu Trp Lys Ser Lys Gly Ser Arg Phe Ala Val Arg Val Pro Ser Val
385                 390                 395                 400

Arg Val Ala Lys Glu Ala Ser Lys Ile Asn Pro Asn Pro Asn Arg Lys
                405                 410                 415

Glu Asp Phe Arg Ser Pro Ser Leu Ser Leu Phe Lys Leu Phe Pro
                420                 425                 430

<210> SEQ ID NO 21
<211> LENGTH: 33
<212> TYPE: DNA
<213> ORGANISM: Arachis hypogaea

<400> SEQUENCE: 21
tagcggccgc atggcttttg gtgttgttgc tgc                              33

<210> SEQ ID NO 22
<211> LENGTH: 39
<212> TYPE: DNA
<213> ORGANISM: Arachis hypogaea

<400> SEQUENCE: 22
atcgatggta ccctattttt taagaagttt ttttactgc                        39

<210> SEQ ID NO 23
<211> LENGTH: 39
<212> TYPE: DNA
<213> ORGANISM: Arachis hypogaea

<400> SEQUENCE: 23
atcgatgagg tacctcatgg aaatagtttg aacagagag                        39

<210> SEQ ID NO 24
<211> LENGTH: 40
<212> TYPE: DNA
<213> ORGANISM: Arachis hypogaea

<400> SEQUENCE: 24
cgatggtacc tcatctaaca aaaagcataa gaatattttc                       40

<210> SEQ ID NO 25
<211> LENGTH: 30
<212> TYPE: DNA
<213> ORGANISM: Arachis hypogaea

<400> SEQUENCE: 25
tagcggccgc atgcctttcg gactctccgc                                  30

<210> SEQ ID NO 26
<211> LENGTH: 30
<212> TYPE: DNA
<213> ORGANISM: Arachis hypogaea

<400> SEQUENCE: 26
tagcggccgc atggcttcca cttccaggct                                  30

<210> SEQ ID NO 27
<211> LENGTH: 33
<212> TYPE: DNA
<213> ORGANISM: Arachis hypogaea

<400> SEQUENCE: 27
tagcggccgc atggctttta ggcttctagg atc                              33

```
<210> SEQ ID NO 28
<211> LENGTH: 32
<212> TYPE: DNA
<213> ORGANISM: Arachis hypogaea

<400> SEQUENCE: 28
tagcggccgc atggcttttg ggcatttggt gt                              32

<210> SEQ ID NO 29
<211> LENGTH: 35
<212> TYPE: DNA
<213> ORGANISM: Arachis hypogaea

<400> SEQUENCE: 29
ctgaggtacc tcaacgaaca aattgtataa ggatg                           35

<210> SEQ ID NO 30
<211> LENGTH: 35
<212> TYPE: DNA
<213> ORGANISM: Arachis hypogaea

<400> SEQUENCE: 30
ctgaggtacc ctatctcacg aaaagtataa ggatg                           35

<210> SEQ ID NO 31
<211> LENGTH: 35
<212> TYPE: DNA
<213> ORGANISM: Arachis hypogaea

<400> SEQUENCE: 31
ctgaggtacc tcatcgaaca aaaagtacaa ggaag                           35

<210> SEQ ID NO 32
<211> LENGTH: 35
<212> TYPE: DNA
<213> ORGANISM: Arachis hypogaea

<400> SEQUENCE: 32
ctgaggtacc ttagttattg gttaccttaa acata                           35

<210> SEQ ID NO 33
<211> LENGTH: 35
<212> TYPE: DNA
<213> ORGANISM: Arachis hypogaea

<400> SEQUENCE: 33
ctgaggtacc ttatctcaca aaaagcacaa ggaca                           35

<210> SEQ ID NO 34
<211> LENGTH: 27
<212> TYPE: DNA
<213> ORGANISM: Cauliflower mosaic virus

<400> SEQUENCE: 34
atcgatgtcg acaagcttgc atgcctg                                    27

<210> SEQ ID NO 35
<211> LENGTH: 35
<212> TYPE: DNA
<213> ORGANISM: Tobacco etch virus

<400> SEQUENCE: 35
atcgatgcgg ccgcgctatc gttcgtaaat ggtga                           35
```

<210> SEQ ID NO 36
<211> LENGTH: 39
<212> TYPE: DNA
<213> ORGANISM: Aequorea victoria

<400> SEQUENCE: 36
atcgatggat ccatggctag taaaggagaa gaactttc                    39

<210> SEQ ID NO 37
<211> LENGTH: 40
<212> TYPE: DNA
<213> ORGANISM: Aequorea victoria

<400> SEQUENCE: 37
atcgatgcgg ccgcatggct agtaaaggag aagaactttt                   40

<210> SEQ ID NO 38
<211> LENGTH: 33
<212> TYPE: DNA
<213> ORGANISM: Aequorea victoria

<400> SEQUENCE: 38
atcgatggta cctcatttgt atagttcatc cat                          33

<210> SEQ ID NO 39
<211> LENGTH: 32
<212> TYPE: DNA
<213> ORGANISM: Arachis hypogaea

<400> SEQUENCE: 39
atcgatggat cctctaacaa aaagcataag aa                           32

<210> SEQ ID NO 40
<211> LENGTH: 30
<212> TYPE: DNA
<213> ORGANISM: Arachis hypogaea

<400> SEQUENCE: 40
atggatccac gaacaaattg tataaggatg                              30

<210> SEQ ID NO 41
<211> LENGTH: 23
<212> TYPE: DNA
<213> ORGANISM: Cauliflower mosaic virus

<400> SEQUENCE: 41
gataccgtcg acaagcttgc atg                                     23

<210> SEQ ID NO 42
<211> LENGTH: 21
<212> TYPE: DNA
<213> ORGANISM: Arachis hypogaea

<400> SEQUENCE: 42
acttctggag ttatacttgt g                                       21

<210> SEQ ID NO 43
<211> LENGTH: 24
<212> TYPE: DNA
<213> ORGANISM: Arachis hypogaea

<400> SEQUENCE: 43
tagatagtga tgtgaggatt atag                                    24

```
<210> SEQ ID NO 44
<211> LENGTH: 18
<212> TYPE: DNA
<213> ORGANISM: Arachis hypogaea

<400> SEQUENCE: 44
gcagcataat tggaagca                                              18

<210> SEQ ID NO 45
<211> LENGTH: 20
<212> TYPE: DNA
<213> ORGANISM: Arachis hypogaea

<400> SEQUENCE: 45
ggaaagcatc taaagcatca                                            20

<210> SEQ ID NO 46
<211> LENGTH: 23
<212> TYPE: DNA
<213> ORGANISM: Arachis hypogaea

<400> SEQUENCE: 46
tatgtattta acagaagaaa tac                                        23

<210> SEQ ID NO 47
<211> LENGTH: 22
<212> TYPE: DNA
<213> ORGANISM: Arachis hypogaea

<400> SEQUENCE: 47
agttgcagcc tcttttccaa ct                                         22

<210> SEQ ID NO 48
<211> LENGTH: 19
<212> TYPE: DNA
<213> ORGANISM: Arabidopsis thaliana

<400> SEQUENCE: 48
atgtatgtag ccatccaag                                             19

<210> SEQ ID NO 49
<211> LENGTH: 19
<212> TYPE: DNA
<213> ORGANISM: Arabidopsis thaliana

<400> SEQUENCE: 49
accagagtcc agaacaata                                             19

<210> SEQ ID NO 50
<211> LENGTH: 18
<212> TYPE: DNA
<213> ORGANISM: Arabidopsis thaliana

<400> SEQUENCE: 50
ggtgtcaagc agatgatt                                              18

<210> SEQ ID NO 51
<211> LENGTH: 18
<212> TYPE: DNA
<213> ORGANISM: Arabidopsis thaliana
```

```
<400> SEQUENCE: 51
acttccttca cgatttca                                                          18
```